(12) United States Patent
Sharma

(10) Patent No.: US 12,364,480 B2
(45) Date of Patent: Jul. 22, 2025

(54) MAGNETIC ANASTOMOSIS DEVICE WITH OPPOSING COIL DIRECTIONALITY

(71) Applicant: Virender K. Sharma, Paradise Valley, AZ (US)

(72) Inventor: Virender K. Sharma, Paradise Valley, AZ (US)

(*) Notice: Subject to any disclaimer, the term of this patent is extended or adjusted under 35 U.S.C. 154(b) by 0 days.

(21) Appl. No.: 16/846,173

(22) Filed: Apr. 10, 2020

(65) Prior Publication Data

US 2020/0323530 A1    Oct. 15, 2020

Related U.S. Application Data

(63) Continuation-in-part of application No. 16/171,779, filed on Oct. 26, 2018, now abandoned, which is a continuation of application No. 15/605,286, filed on May 25, 2017, now Pat. No. 10,154,844.

(60) Provisional application No. 62/832,154, filed on Apr. 10, 2019, provisional application No. 62/425,951, filed on Nov. 23, 2016, provisional application No. 62/408,795, filed on Oct. 16, 2016, provisional application No. 62/366,185, filed on Jul. 25, 2016.

(51) Int. Cl.
    *A61B 17/11*       (2006.01)
    *A61M 27/00*    (2006.01)
    *A61B 17/00*      (2006.01)

(52) U.S. Cl.
    CPC .. *A61B 17/1114* (2013.01); *A61B 2017/00867* (2013.01); *A61B 2017/00876* (2013.01); *A61B 2017/1135* (2013.01); *A61B 2017/1139* (2013.01); *A61M 27/002* (2013.01)

(58) Field of Classification Search
None
See application file for complete search history.

(56) References Cited

U.S. PATENT DOCUMENTS

| | | | |
|---|---|---|---|
| 4,401,045 | A | 8/1983 | Russell |
| 4,551,660 | A | 11/1985 | Suzuki |
| 4,698,609 | A | 10/1987 | Goehle |

(Continued)

FOREIGN PATENT DOCUMENTS

| | | |
|---|---|---|
| CN | 1654020 A | 8/2005 |
| CN | 101254127 A | 9/2008 |

(Continued)

OTHER PUBLICATIONS

International Search Report for PCT/US20/27805, Aug. 3, 2020.

(Continued)

*Primary Examiner* — Katherine M Shi
*Assistant Examiner* — Lindsey Bachman
(74) *Attorney, Agent, or Firm* — Novel IP

(57) ABSTRACT

An anastomosis device includes magnets coupled to a wire capable of changing shape from a straight wire into a coil when deployed within a body. The coil exerts compressive force upon layers of tissue caught between loops of the coil. The compressive force is enhanced by attractive forces between magnets coupled with adjacent loops of the coil and causes the coil to cut through the tissue layers, creating an anastomosis. One end of the wire is preferably provided with a connecting member, such as a screw or a nut, for connecting with a delivery device. Positioned on or around the anastomosis device is an expandable drainage mechanism, such as a stent.

22 Claims, 125 Drawing Sheets

(56) References Cited

U.S. PATENT DOCUMENTS

| | | | |
|---|---|---|---|
| 4,899,744 A | 2/1990 | Fujitsuka | |
| 5,595,562 A | 1/1997 | Grier | |
| 5,631,613 A | 5/1997 | Niimi | |
| 5,660,487 A | 8/1997 | Cayzer | |
| 5,690,656 A | 11/1997 | Cope | |
| 5,925,043 A * | 7/1999 | Kumar | A61B 18/1402 606/49 |
| 6,007,544 A | 12/1999 | Kim | |
| 6,171,320 B1 | 1/2001 | Monassevitch | |
| 6,217,339 B1 | 4/2001 | Tsubata | |
| 6,352,543 B1 | 3/2002 | Cole | |
| 6,361,545 B1 | 3/2002 | Macoviak | |
| 6,402,765 B1 | 6/2002 | Monassevitch | |
| 6,517,556 B1 | 2/2003 | Monassevitch | |
| 6,565,581 B1 | 5/2003 | Spence | |
| 6,607,542 B1 | 8/2003 | Wild | |
| 6,652,540 B1 | 11/2003 | Cole | |
| 6,719,768 B1 | 4/2004 | Cole | |
| 6,802,847 B1 | 10/2004 | Carson | |
| 6,884,250 B2 | 4/2005 | Monassevitch | |
| 6,896,684 B2 | 5/2005 | Monassevitch | |
| 6,932,827 B2 | 8/2005 | Cole | |
| 7,094,247 B2 | 8/2006 | Monassevitch | |
| 7,222,428 B2 | 5/2007 | Koike | |
| 7,232,449 B2 | 6/2007 | Sharkawy | |
| 7,241,300 B2 | 7/2007 | Sharkawy | |
| 7,282,057 B2 | 10/2007 | Surti | |
| 7,374,153 B2 | 5/2008 | Huang | |
| 7,393,027 B1 | 7/2008 | Chen | |
| 7,431,727 B2 | 10/2008 | Cole | |
| 7,527,185 B2 | 5/2009 | Harari | |
| 7,618,427 B2 | 11/2009 | Ortiz | |
| 7,635,374 B2 | 12/2009 | Monassevitch | |
| 7,728,707 B2 | 6/2010 | Gilardi | |
| 7,892,244 B2 | 2/2011 | Monassevitch | |
| 7,909,837 B2 | 3/2011 | Crews | |
| 7,938,841 B2 | 5/2011 | Sharkawy | |
| 8,043,290 B2 | 10/2011 | Harrison | |
| 8,118,821 B2 * | 2/2012 | Mouw | A61B 17/1114 606/153 |
| 8,142,454 B2 | 3/2012 | Harrison | |
| 8,205,782 B2 | 6/2012 | Harari | |
| 8,262,680 B2 | 9/2012 | Swain | |
| 8,439,915 B2 | 5/2013 | Harrison | |
| 8,518,062 B2 | 8/2013 | Cole | |
| 8,556,919 B2 | 10/2013 | Aguirre | |
| 8,623,036 B2 | 1/2014 | Harrison | |
| 8,628,548 B2 | 1/2014 | Aguirre | |
| 8,629,572 B1 | 1/2014 | Phillips | |
| 8,679,139 B2 | 3/2014 | Aguirre | |
| 8,685,046 B2 | 4/2014 | Viola | |
| 8,728,105 B2 | 5/2014 | Aguirre | |
| 8,764,773 B2 | 7/2014 | Harari | |
| 8,828,031 B2 | 9/2014 | Fox | |
| 8,828,032 B2 | 9/2014 | McWeeney | |
| 8,833,130 B2 | 9/2014 | Matsunaga | |
| 8,845,663 B2 | 9/2014 | Chmura | |
| 8,864,781 B2 | 10/2014 | Surti | |
| 8,870,898 B2 | 10/2014 | Beisel | |
| 8,870,899 B2 | 10/2014 | Beisel | |
| 8,876,699 B2 | 11/2014 | Sato | |
| 8,910,366 B2 | 12/2014 | Fuse | |
| 8,915,915 B2 | 12/2014 | Harrison | |
| 8,920,446 B2 | 12/2014 | Viola | |
| 8,946,919 B2 | 2/2015 | Phillips | |
| 8,946,920 B2 | 2/2015 | Phillips | |
| 9,168,041 B2 | 10/2015 | Zaritsky | |
| 9,205,236 B2 | 12/2015 | McNamara | |
| 9,226,753 B2 | 1/2016 | Surti | |
| 9,232,997 B2 | 1/2016 | Sugimoto | |
| 9,240,710 B2 | 1/2016 | Kawarai | |
| 9,277,995 B2 | 3/2016 | Celermajer | |
| 9,332,990 B2 | 5/2016 | Requarth | |
| 9,358,371 B2 | 6/2016 | McNamara | |
| 9,364,238 B2 | 6/2016 | Bakos | |
| 9,456,812 B2 | 10/2016 | Finch | |
| 9,492,173 B2 | 11/2016 | McWeeney | |
| 2001/0004699 A1 | 6/2001 | Gittings | |
| 2002/0183768 A1 | 12/2002 | Deem | |
| 2003/0014061 A1 | 1/2003 | Houser | |
| 2003/0153932 A1 | 8/2003 | Spence | |
| 2003/0229363 A1 | 12/2003 | Sharkawy | |
| 2004/0034377 A1 | 2/2004 | Sharkawy | |
| 2004/0059280 A1 | 3/2004 | Makower | |
| 2004/0102794 A1 | 5/2004 | Roy | |
| 2004/0116945 A1 | 6/2004 | Sharkawy | |
| 2004/0215214 A1 | 10/2004 | Crews | |
| 2004/0260393 A1 | 12/2004 | Rahdert | |
| 2005/0080439 A1 | 4/2005 | Carson | |
| 2005/0143763 A1 | 6/2005 | Ortiz | |
| 2005/0165344 A1 | 7/2005 | Dobak, III | |
| 2006/0111733 A1 | 5/2006 | Shriver | |
| 2006/0271107 A1 | 11/2006 | Harrison | |
| 2006/0282106 A1 | 12/2006 | Cole | |
| 2007/0118158 A1 | 5/2007 | Deem | |
| 2007/0213748 A1 | 9/2007 | Deem | |
| 2007/0250084 A1 | 10/2007 | Sharkawy | |
| 2008/0051626 A1 * | 2/2008 | Sato | A61B 1/00179 600/101 |
| 2008/0114384 A1 | 5/2008 | Chang | |
| 2008/0200934 A1 | 8/2008 | Fox | |
| 2008/0208214 A1 * | 8/2008 | Sato | A61B 17/1114 606/139 |
| 2008/0208224 A1 | 8/2008 | Surti | |
| 2008/0300609 A1 | 12/2008 | Tabet | |
| 2009/0048618 A1 | 2/2009 | Harrison | |
| 2009/0125042 A1 | 5/2009 | Mouw | |
| 2009/0227828 A1 | 9/2009 | Swain | |
| 2010/0010508 A1 | 1/2010 | Takahashi | |
| 2010/0010520 A1 * | 1/2010 | Takahashi | A61B 17/064 606/157 |
| 2010/0025605 A1 | 2/2010 | Galtz | |
| 2010/0036399 A1 | 2/2010 | Viola | |
| 2010/0049223 A1 | 2/2010 | Granja Filho | |
| 2010/0179510 A1 | 7/2010 | Fox | |
| 2010/0256659 A1 | 10/2010 | Aguirre | |
| 2010/0292729 A1 | 11/2010 | Aguirre | |
| 2010/0318015 A1 | 12/2010 | Kassab | |
| 2010/0331862 A1 | 12/2010 | Monassevitch | |
| 2011/0054498 A1 | 3/2011 | Monassevitch | |
| 2011/0087252 A1 | 4/2011 | Chmura | |
| 2011/0112559 A1 | 5/2011 | Monassevitch | |
| 2011/0118765 A1 | 5/2011 | Aguirre | |
| 2011/0144560 A1 | 6/2011 | Gagner | |
| 2011/0160752 A1 | 6/2011 | Aguirre | |
| 2011/0184505 A1 | 7/2011 | Sharkawy | |
| 2011/0295285 A1 | 12/2011 | McWeeney | |
| 2012/0029278 A1 | 2/2012 | Sato | |
| 2012/0035628 A1 | 2/2012 | Aguirre | |
| 2012/0150092 A1 | 6/2012 | McAllister | |
| 2012/0172782 A1 | 7/2012 | Thompson | |
| 2012/0197061 A1 | 8/2012 | Requarth | |
| 2012/0197062 A1 | 8/2012 | Requarth | |
| 2012/0215236 A1 * | 8/2012 | Matsunaga | B21F 3/04 606/151 |
| 2012/0259350 A1 | 10/2012 | Gagner | |
| 2012/0324975 A1 | 12/2012 | Anderson | |
| 2012/0330330 A1 | 12/2012 | Gagner | |
| 2013/0110141 A1 | 5/2013 | Chmura | |
| 2013/0226205 A1 | 8/2013 | Zaritsky | |
| 2013/0253548 A1 | 9/2013 | Harrison | |
| 2013/0253550 A1 | 9/2013 | Beisel | |
| 2013/0325042 A1 | 12/2013 | Fabian | |
| 2014/0100423 A1 | 4/2014 | Monassevitch | |
| 2014/0163449 A1 | 6/2014 | Rottenberg | |
| 2014/0236064 A1 | 8/2014 | Binmoeller | |
| 2014/0236200 A1 | 8/2014 | Beisel | |
| 2014/0309669 A1 | 10/2014 | Fabian | |
| 2014/0309670 A1 | 10/2014 | Bakos | |
| 2014/0343583 A1 | 11/2014 | McWeeney | |
| 2014/0364881 A1 | 12/2014 | Meron | |
| 2014/0379011 A1 | 12/2014 | Viola | |
| 2014/0379074 A1 | 12/2014 | Spence | |
| 2015/0057687 A1 | 2/2015 | Gittard | |

(56) References Cited

U.S. PATENT DOCUMENTS

| | | |
|---|---|---|
| 2015/0057688 A1 | 2/2015 | Beisel |
| 2015/0164508 A1 | 6/2015 | Hernandez |
| 2015/0182224 A1 | 7/2015 | Altman |
| 2015/0201943 A1 | 7/2015 | Brooks |
| 2015/0222165 A1 | 8/2015 | Filippa |
| 2015/0313595 A1 | 11/2015 | Houghton |
| 2016/0022266 A1 | 1/2016 | Lukin |
| 2016/0120550 A1 | 5/2016 | McNamara |
| 2016/0262761 A1 | 9/2016 | Beisel |
| 2016/0324523 A1 | 11/2016 | Lukin |
| 2017/0119394 A1 | 5/2017 | McWeeney |
| 2018/0021043 A1 | 1/2018 | Sharma |
| 2019/0015103 A1 | 1/2019 | Sharma |

FOREIGN PATENT DOCUMENTS

| | | |
|---|---|---|
| CN | 101385656 A | 3/2009 |
| CN | 101511282 A | 8/2009 |
| CN | 101511283 A | 8/2009 |
| CN | 101700191 A | 5/2010 |
| CN | 104971390 A | 10/2015 |
| CN | 105142542 A | 12/2015 |
| CN | 105658182 A | 6/2016 |
| EP | 0123359 B1 | 3/1989 |
| EP | 0326757 B1 | 7/1993 |
| EP | 0754434 B1 | 9/1999 |
| EP | 1284660 A1 | 2/2003 |
| EP | 1307144 A1 | 5/2003 |
| EP | 1077047 B1 | 7/2003 |
| EP | 0910298 B1 | 8/2003 |
| EP | 1389984 A1 | 2/2004 |
| EP | 1435824 A2 | 7/2004 |
| EP | 1435856 A1 | 7/2004 |
| EP | 1435872 A2 | 7/2004 |
| EP | 0954248 B1 | 9/2004 |
| EP | 1550415 A2 | 7/2005 |
| EP | 1334696 B1 | 3/2007 |
| EP | 1938009 A1 | 7/2008 |
| EP | 1551313 B1 | 10/2008 |
| EP | 1301129 B1 | 9/2009 |
| EP | 2131752 A1 | 12/2009 |
| EP | 2151199 A1 | 2/2010 |
| EP | 1289428 B1 | 3/2010 |
| EP | 2236242 A1 | 10/2010 |
| EP | 1732473 B1 | 12/2010 |
| EP | 2258317 A2 | 12/2010 |
| EP | 2124759 B1 | 6/2011 |
| EP | 2332473 A1 | 6/2011 |
| EP | 2207488 B1 | 9/2012 |
| EP | 2519164 A1 | 11/2012 |
| EP | 2429625 B1 | 5/2013 |
| EP | 2086426 B1 | 7/2013 |
| EP | 2413813 B1 | 8/2013 |
| EP | 2632346 A2 | 9/2013 |
| EP | 2690767 A1 | 1/2014 |
| EP | 2485657 B1 | 8/2014 |
| EP | 2839796 A1 | 2/2015 |
| EP | 2424472 B1 | 12/2015 |
| EP | 2958527 A1 | 12/2015 |
| EP | 2967867 A1 | 1/2016 |
| EP | 2537490 B1 | 8/2016 |
| KR | 20120085533 A | 8/2012 |
| WO | 1997013463 A1 | 4/1997 |
| WO | 1998016161 A1 | 4/1998 |
| WO | 2001082803 A1 | 11/2001 |
| WO | 2002013704 A1 | 2/2002 |
| WO | 2002096327 A2 | 12/2002 |
| WO | 2003024307 A2 | 3/2003 |
| WO | 2003101311 A1 | 12/2003 |
| WO | 2003103510 A1 | 12/2003 |
| WO | 2004008937 A2 | 1/2004 |
| WO | 2004045383 A2 | 6/2004 |
| WO | 2004105693 A2 | 12/2004 |
| WO | 2005027736 A2 | 3/2005 |
| WO | 2005094334 A2 | 10/2005 |
| WO | 2006127236 A2 | 11/2006 |
| WO | 2007042016 A1 | 4/2007 |
| WO | 2007140557 A2 | 12/2007 |
| WO | 2007140562 A2 | 12/2007 |
| WO | 2008061024 A2 | 5/2008 |
| WO | 2008101077 A1 | 8/2008 |
| WO | 2008106279 A1 | 9/2008 |
| WO | 2008127328 A1 | 10/2008 |
| WO | 2009048954 A1 | 4/2009 |
| WO | 2009081948 A1 | 7/2009 |
| WO | 2010115116 A1 | 10/2010 |
| WO | 2010132356 A1 | 11/2010 |
| WO | 2011008988 A1 | 1/2011 |
| WO | 2011062831 A1 | 5/2011 |
| WO | 2011081988 A1 | 7/2011 |
| WO | 2011085006 A2 | 7/2011 |
| WO | 2012007042 A1 | 1/2012 |
| WO | 2012007052 A1 | 1/2012 |
| WO | 2012009431 A2 | 1/2012 |
| WO | 2012170502 A1 | 12/2012 |
| WO | 2013009886 A1 | 1/2013 |
| WO | 2013143495 A1 | 10/2013 |
| WO | 2013170474 A1 | 11/2013 |
| WO | 2013176993 A1 | 11/2013 |
| WO | 2014055193 A1 | 4/2014 |
| WO | 2014070720 A1 | 5/2014 |
| WO | 2014130850 A1 | 8/2014 |
| WO | 2014172194 A1 | 10/2014 |
| WO | 2015103346 A1 | 7/2015 |
| WO | 2015191859 A2 | 12/2015 |
| WO | 2015192022 A1 | 12/2015 |
| WO | 2016007917 A2 | 1/2016 |
| WO | 2016014644 A1 | 1/2016 |
| WO | 2016014821 A1 | 1/2016 |
| WO | 2018022180 A1 | 2/2018 |
| WO | 2018132549 A1 | 7/2018 |
| WO | 2019025265 A1 | 2/2019 |
| WO | 2020210727 A1 | 10/2020 |

OTHER PUBLICATIONS

Written Opinion of the International Searching Authority for PCT/US20/27805, Aug. 3, 2020.
Cronin et al., "Normal small bowel wall characteristics on MR enterography"; European Journal of Radiology 75 (2010) 207-211.
Mesenas et al., "Duodenal EUS to identify thickening of the extrahepatic biliary tree wall in primary sclerosing cholangitis"; Gastrointestinal Endoscopy vol. 63, No. 3: 2006, pp. 403-408.
Rapaccini, et al., "Gastric Wall Thickness in Normal and Neoplastic Subjects: A Prospective Study Performed by Abdominal Ultrasound"; Gastrointestinal Radiology 13: 197-199 (1998).
Shikata, et al., "Experimental Studies on the Hemodynamics of the Small Intestine Following Increased Intraluminal Pressure"; Surgery, Gynecology & Obstetrics: Feb. 1983, vol. 156, pp. 155-160.
Matcuk et al.; "Ultrasound Measurements of the Bile Ducts and Gallbladder"; Ultrasound Quarterly, vol. 30, No. 1, Mar. 2014, pp. 41-48.
International Search Report for PCT/US2017/034475, Sep. 1, 2017.
"Choledochojejunostomy with an innovative magnetic compressive anastomosis: How to determine optimal pressure?" Fei Xue et al. World J Gastroenterol Feb. 21, 2016; 22(7): 2326-2335.
"Understanding gastric forces calculated from high-resolution pill tracking" Laulicht et al. Proceedings of the National Academy of Scienes of the United States of America, May 4, 2010; vol. 107, No. 18: 8201-8206.
International Search Report for PCT/US18/13285, Apr. 20, 2018.

* cited by examiner

Coil Wires Cutting Through the Organ Wall

Coil Falls off and an Anastomosis is Formed

| Diameter | 1 Loop | 2 Loops | 4 Loops | 8 Loops | 16 Loops |
|---|---|---|---|---|---|
| 0.5 | 1.57 | 3.142857 | 6.285714 | 12.57143 | 25.14286 |
| 1 | 3.14 | 6.285714 | 12.57143 | 25.14286 | 50.28571 |
| 2 | 6.29 | 12.57143 | 25.14286 | 50.28571 | 100.5714 |
| 3 | 9.43 | 18.85714 | 37.71429 | 75.42857 | 150.8571 |
| 4 | 12.57 | 25.14286 | 50.28571 | 100.5714 | 201.1429 |
| 5 | 15.71 | 31.42857 | 62.85714 | 125.7143 | 251.4286 |

Hexagon Coil r = inradius (apothem)
R = circumradius
a = side length
n = number of sides
x = interior angle
y = exterior angle
A = area
P = perimeter a = 5 mm
r = 4.33013 mm
R = 5 mm
A = 64.9519 mm$^2$
P = 30 mm
x = 120°
y = 60°

Octagon Coil r = inradius (apothem)
R = circumradius
a = side length
n = number of sides
x = interior angle
y = exterior angle
A = area
P = perimeter a = 5 mm
r = 6.03553 mm
R = 6.53281 mm
A = 120.711 mm$^2$
P = 40 mm
x = 135°
y = 45°

Decagonal Coil r = inradius (apothem)
R = circumradius
a = side length
n = number of sides
x = interior angle
y = exterior angle
A = area
P = perimeter a = 5 mm
r = 7.69421 mm
R = 8.09017 mm
A = 192.355 mm$^2$
P = 50 mm
x = 144°
y = 36°

Coil Design - Dodecagon
$a = 5$ mm
$r = 9.33013$ mm
$R = 9.65926$ mm
$A = 279.904$ mm$^2$
$P = 60$ mm
$x = 150°$
$y = 30°$
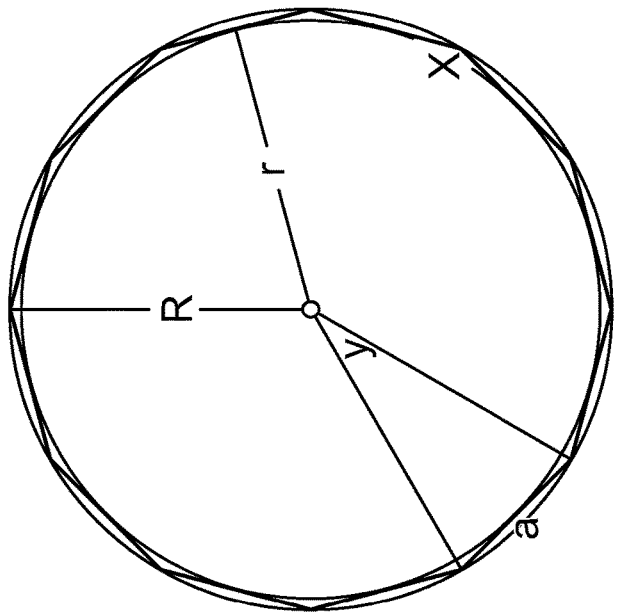
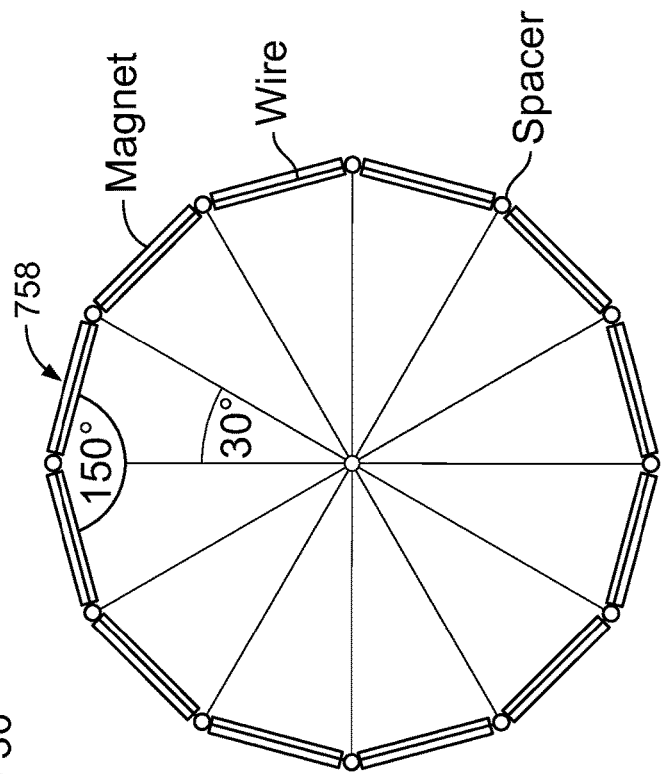
$r$ = inradius (apothem)
$R$ = circumradius
$a$ = side length
$n$ = number of sides
$x$ = interior angle
$y$ = exterior angle
$A$ = area
$P$ = perimeter
FIG. 7J Magnets between the Adjacent Coil Attracting Each Other

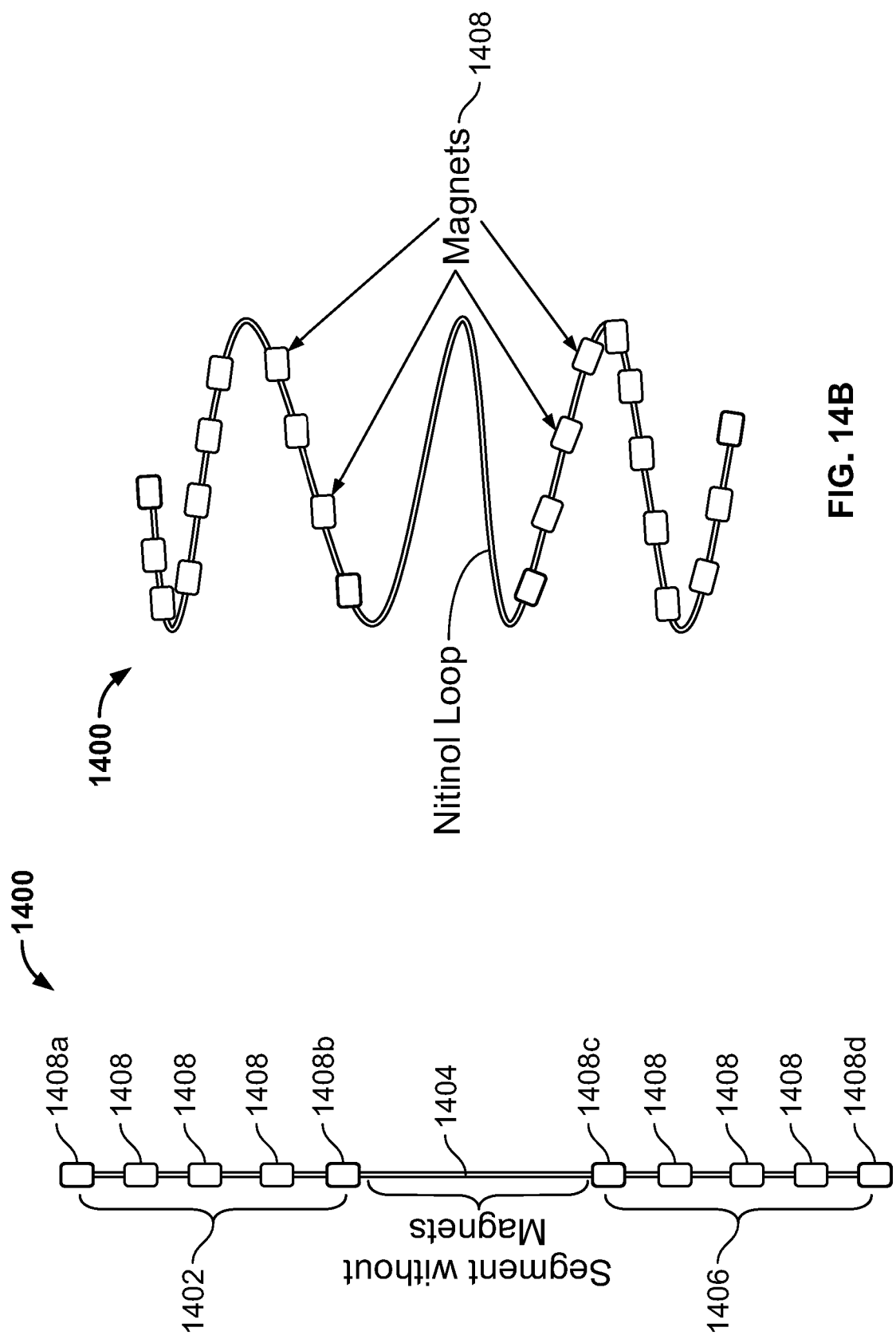

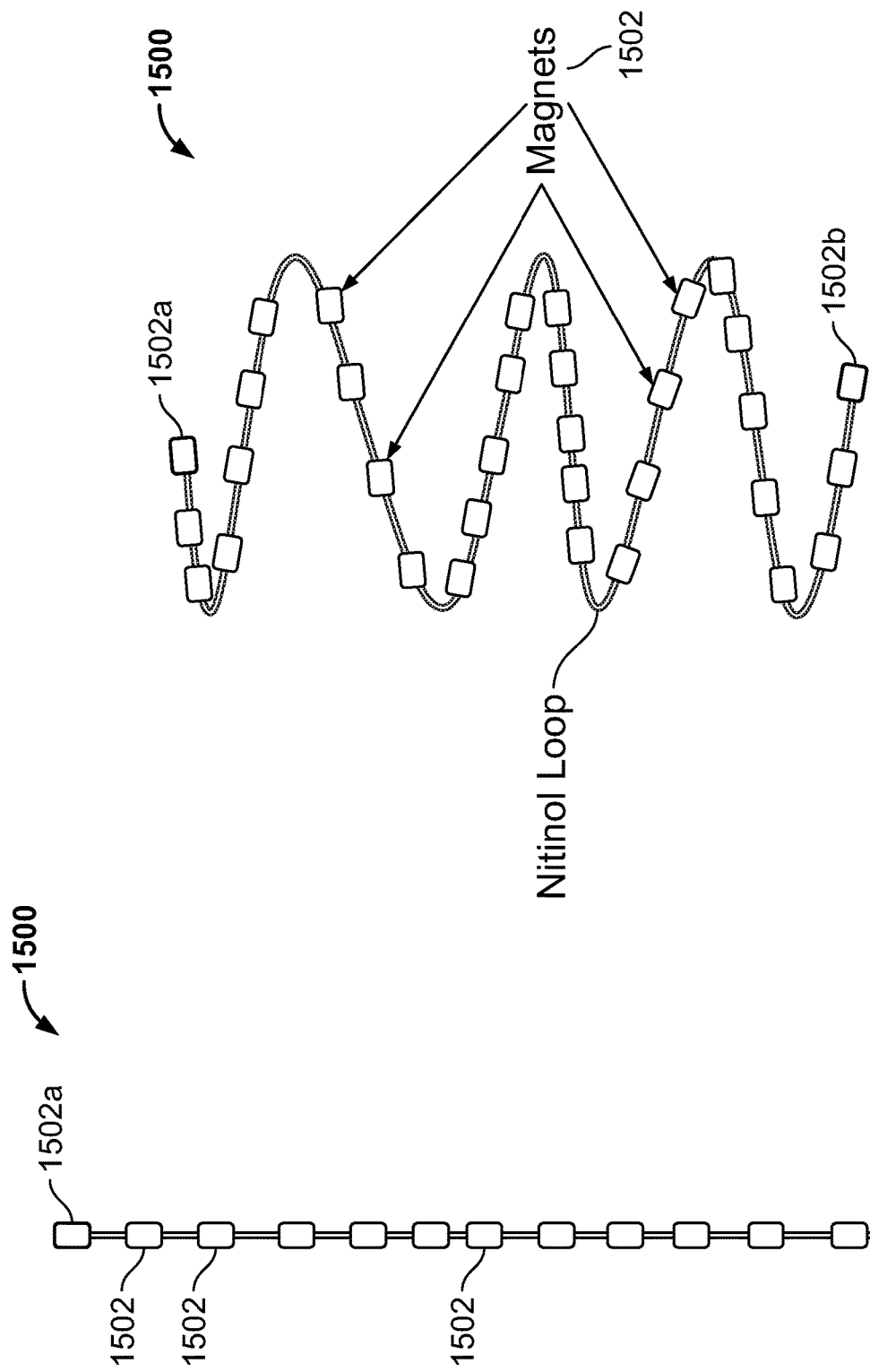

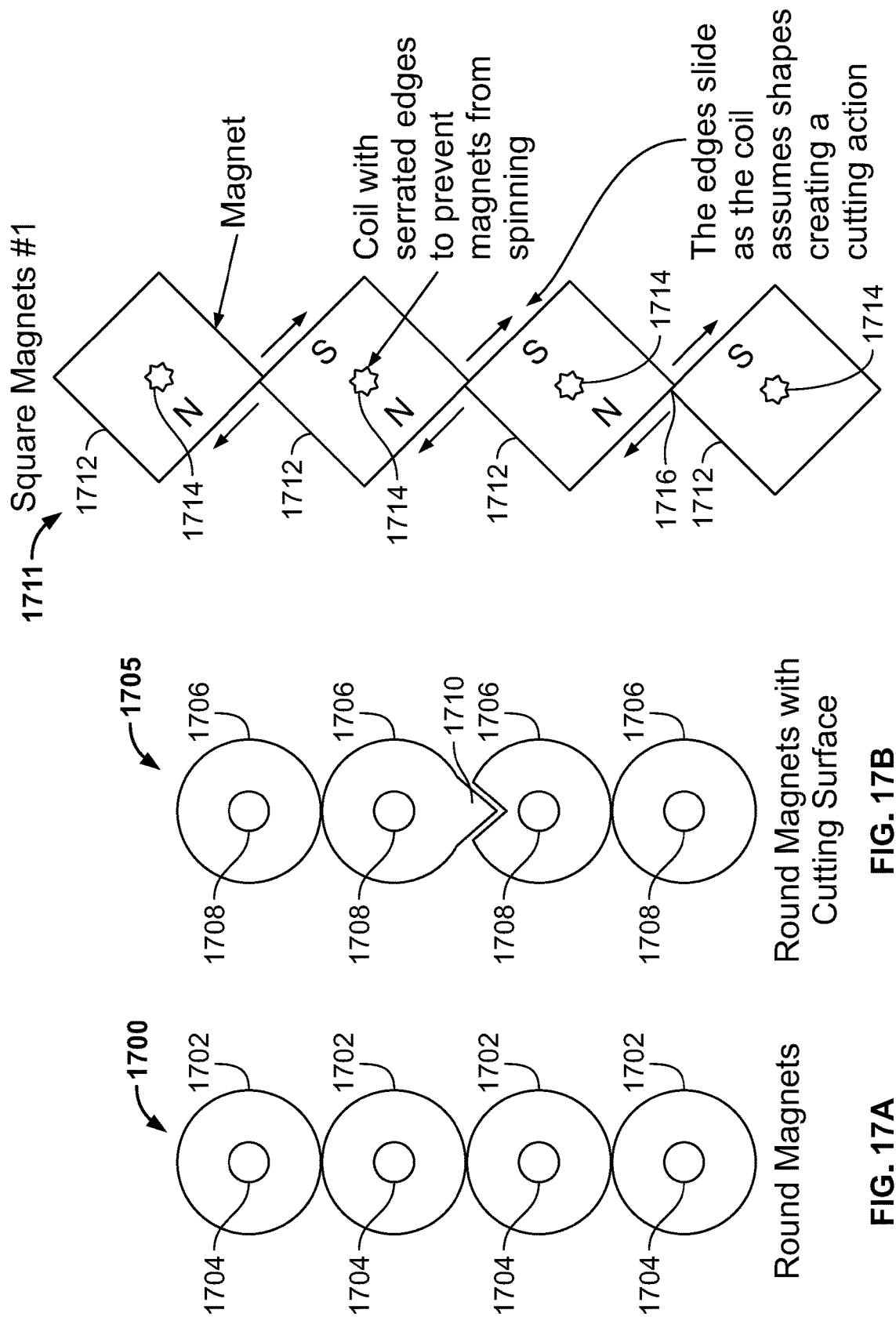

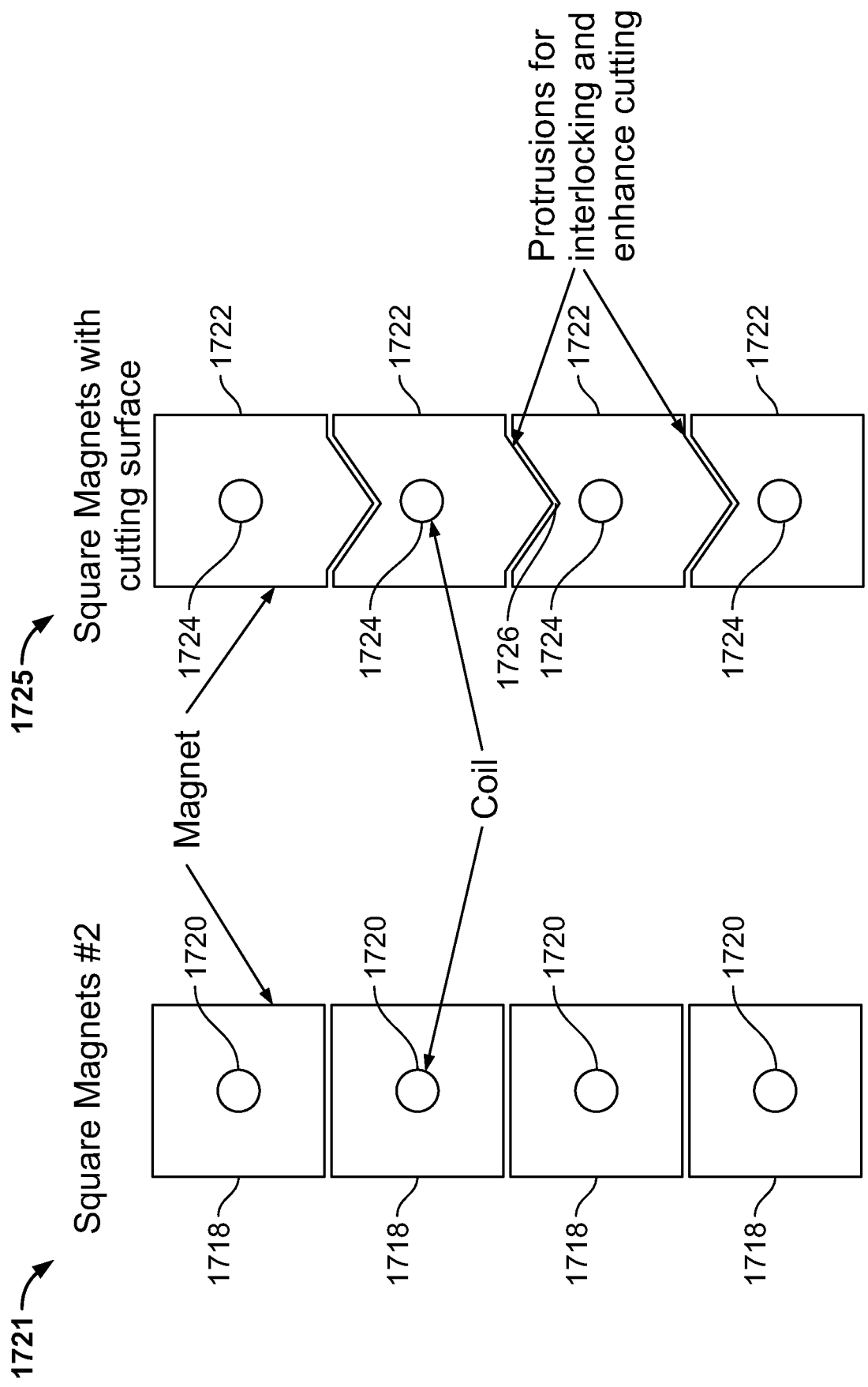

Round Magnets with Cutting Surface

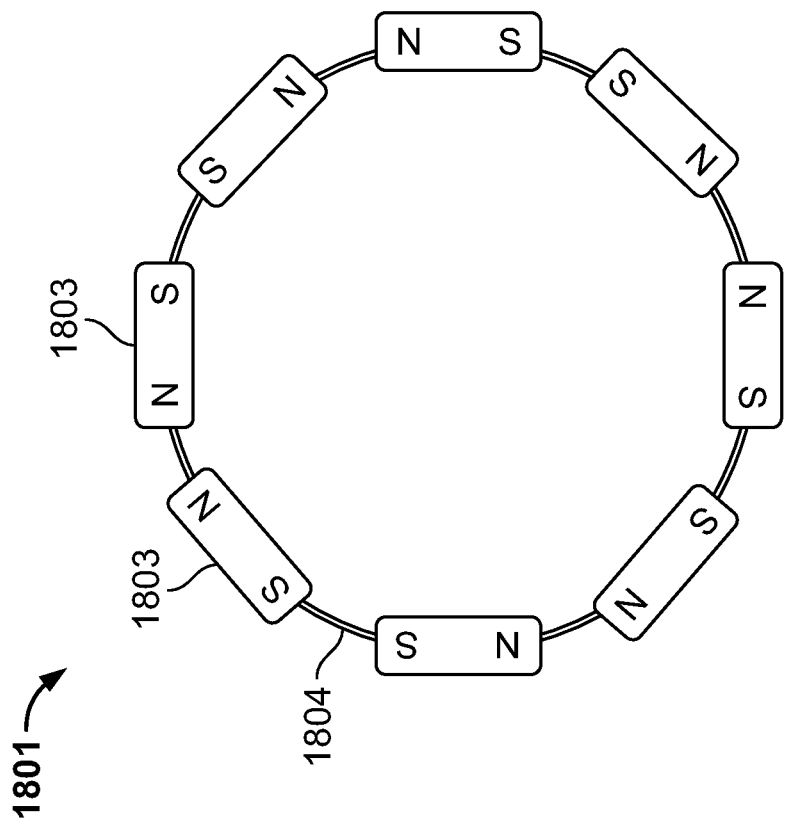
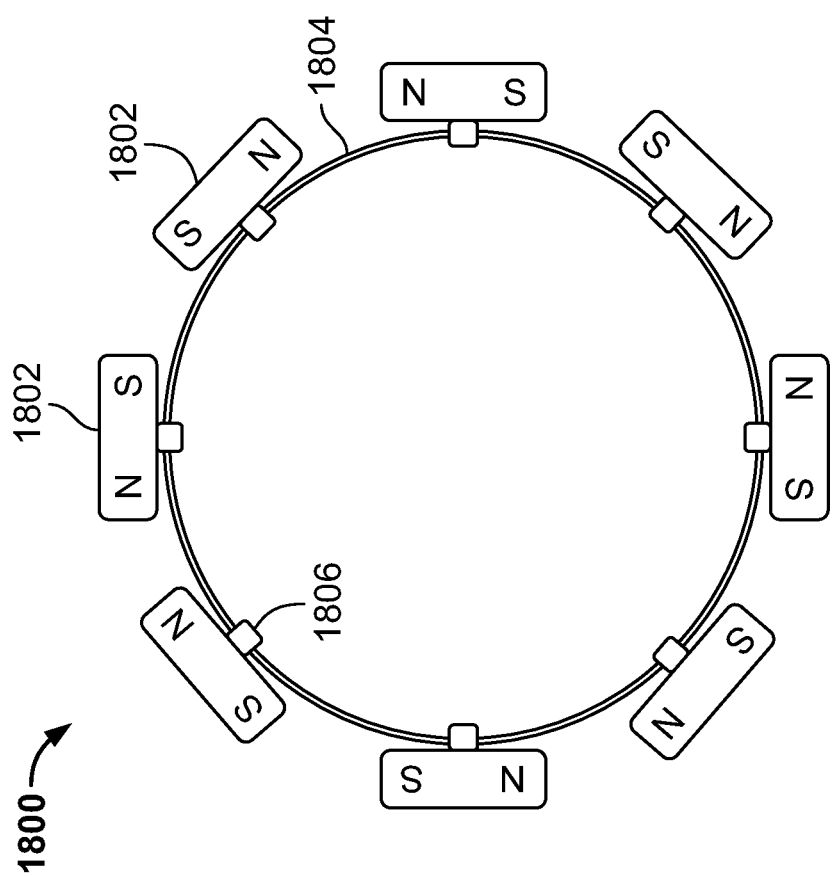
FIG. 18A
FIG. 18B

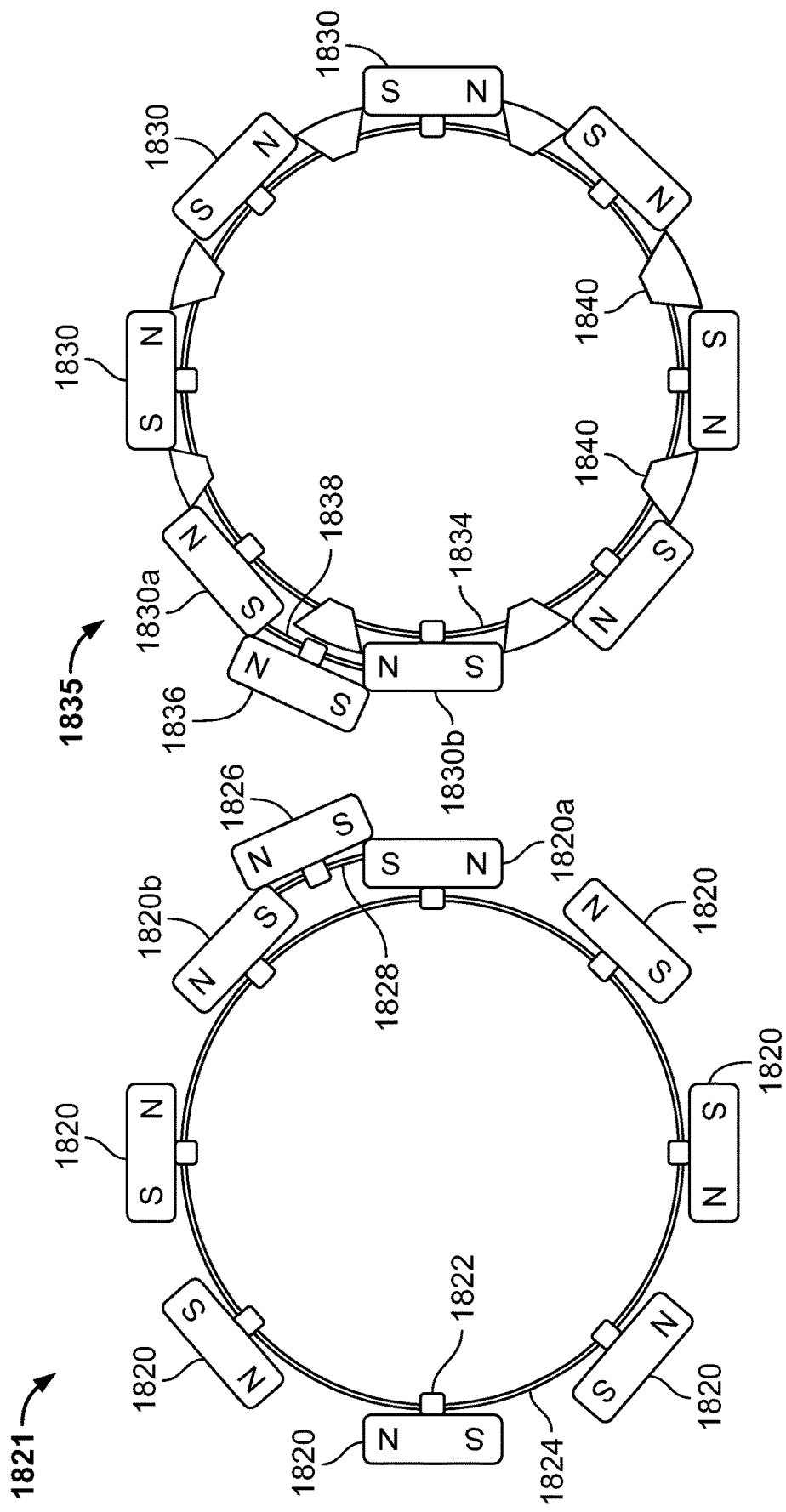

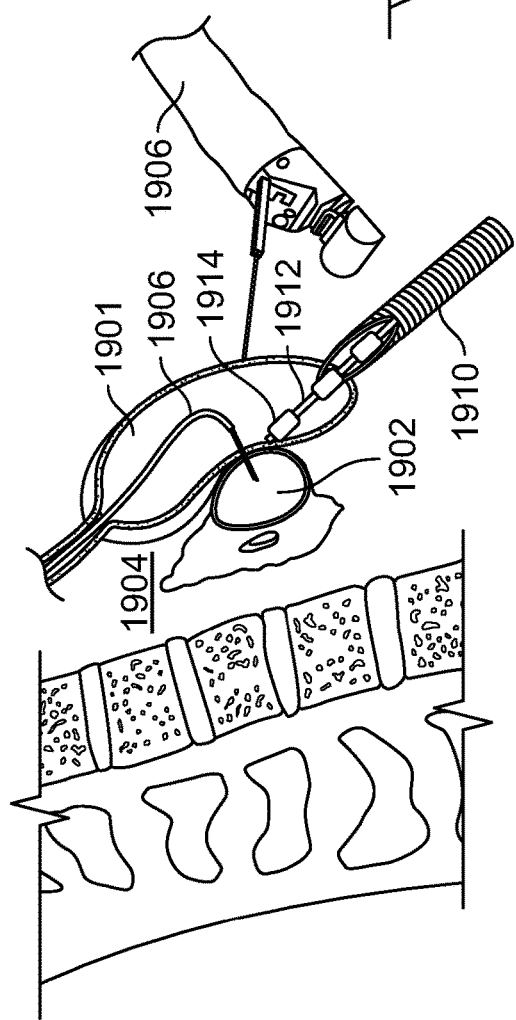
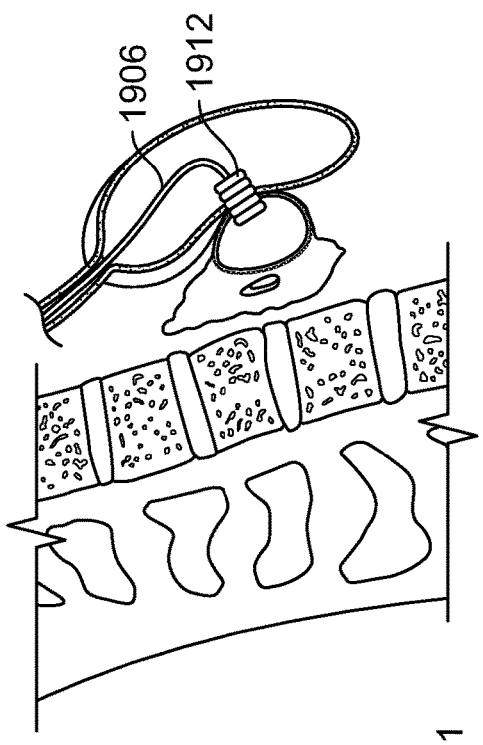
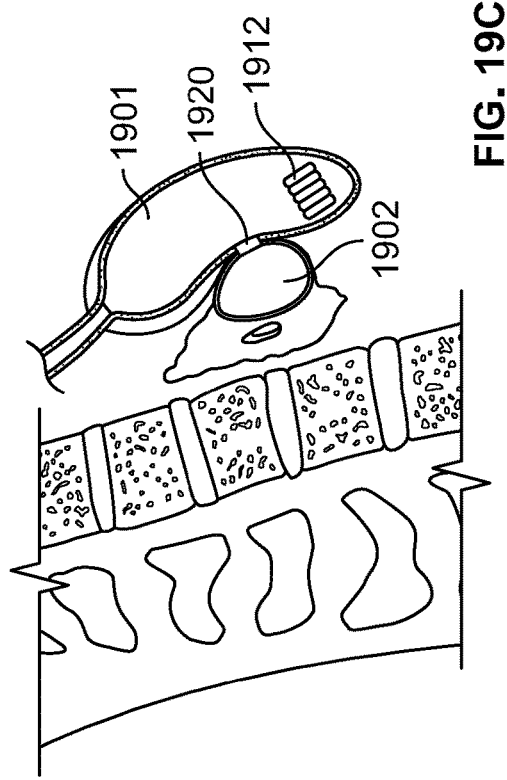
FIG. 19A
FIG. 19B
FIG. 19C

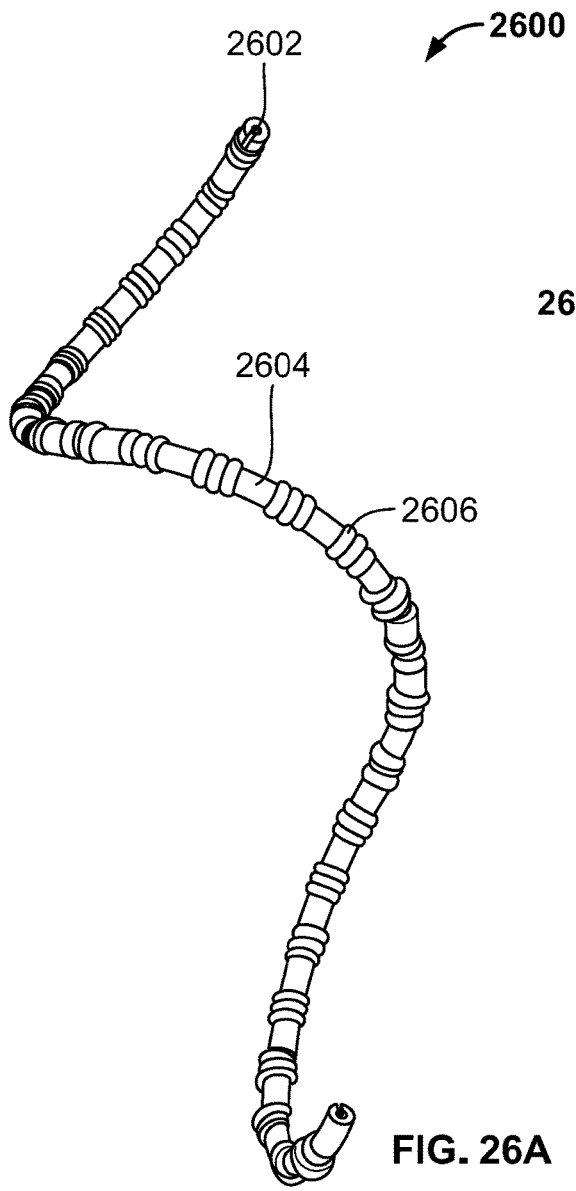
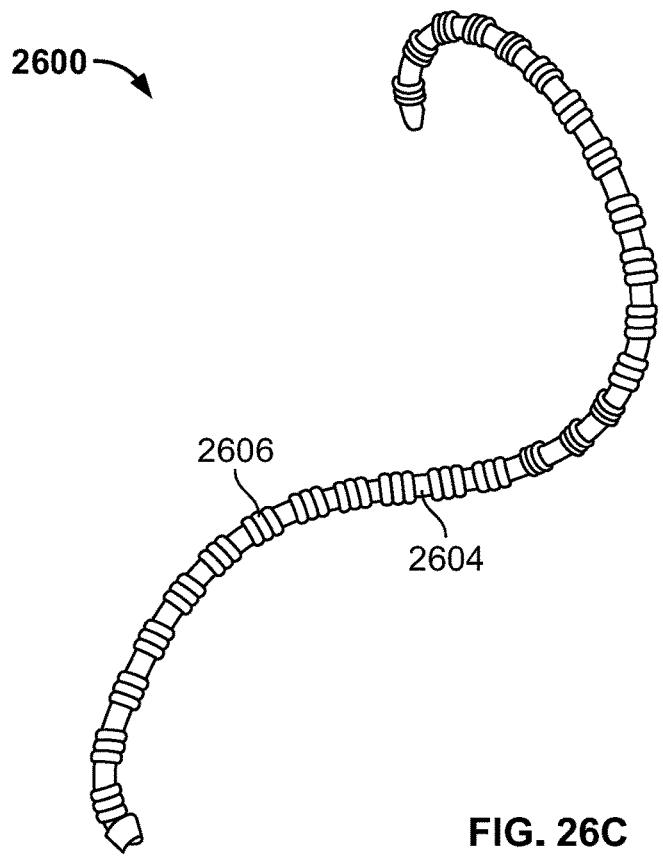
FIG. 26C
FIG. 26A
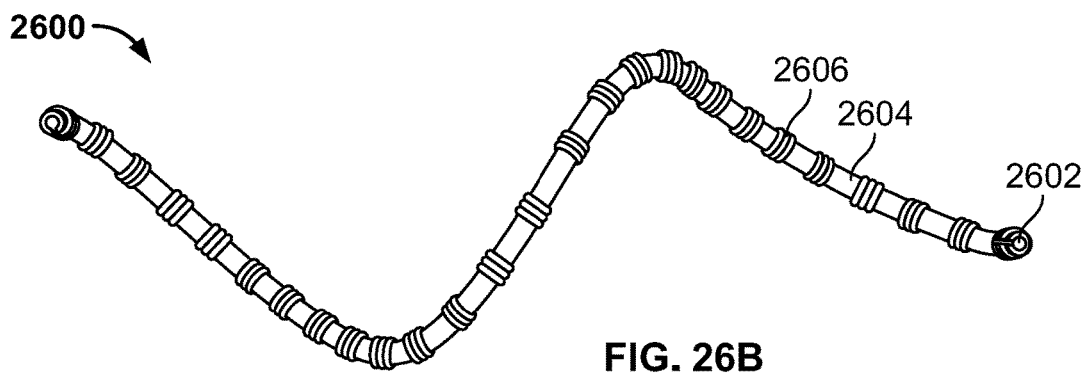
FIG. 26B

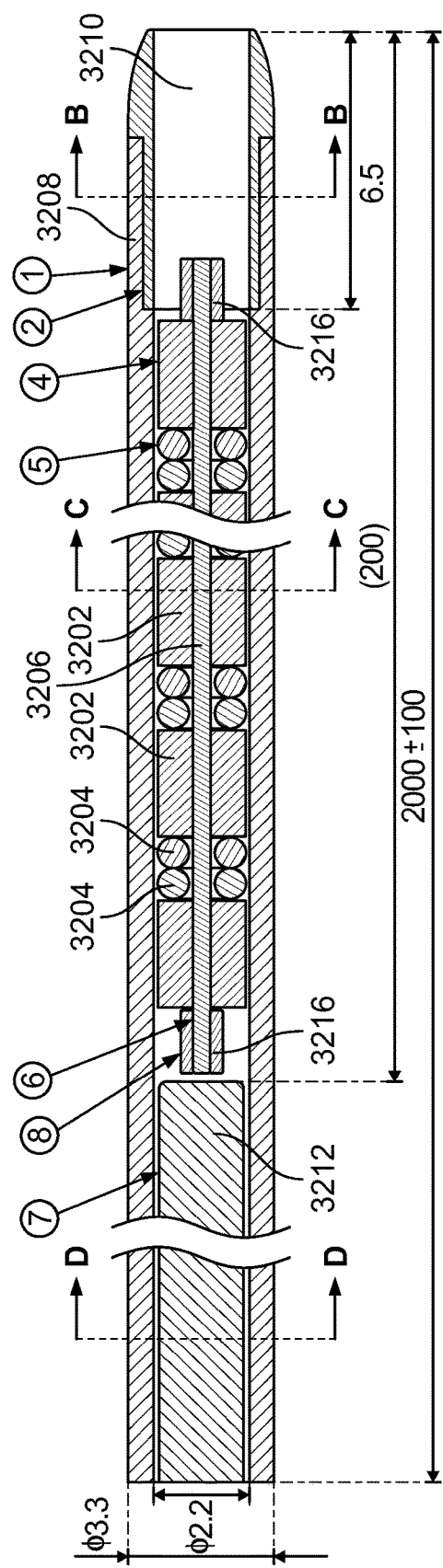
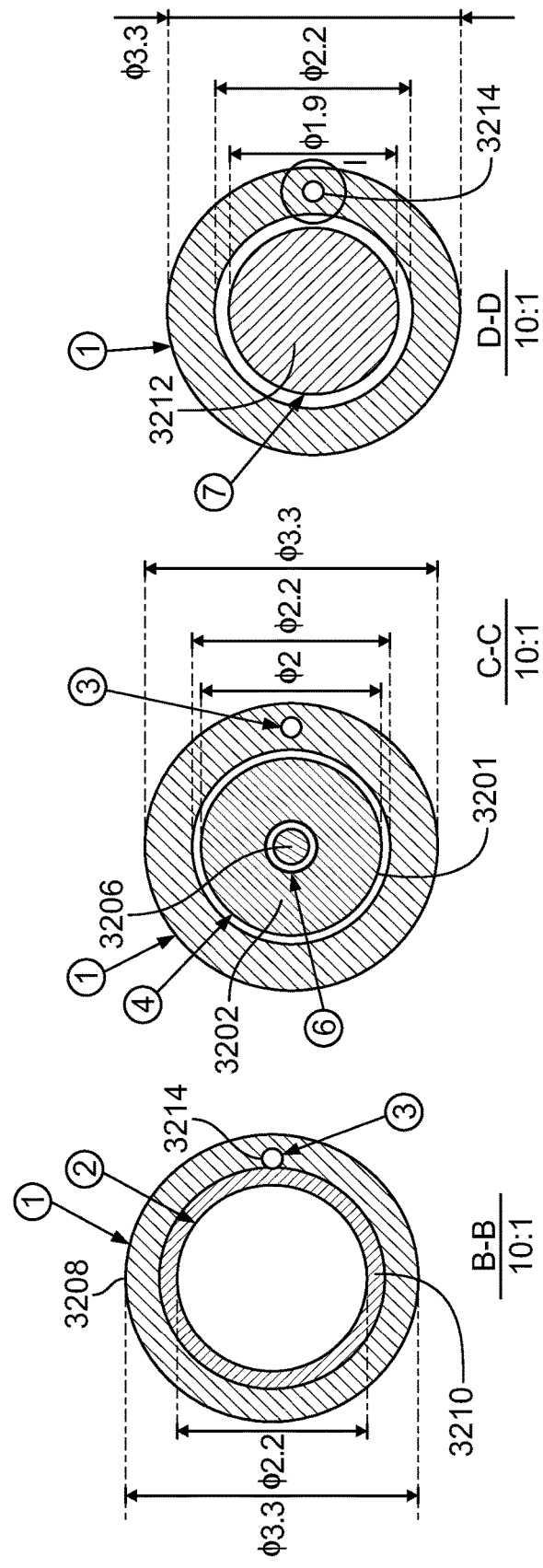
FIG. 32A
FIG. 32B
FIG. 32C
FIG. 32D

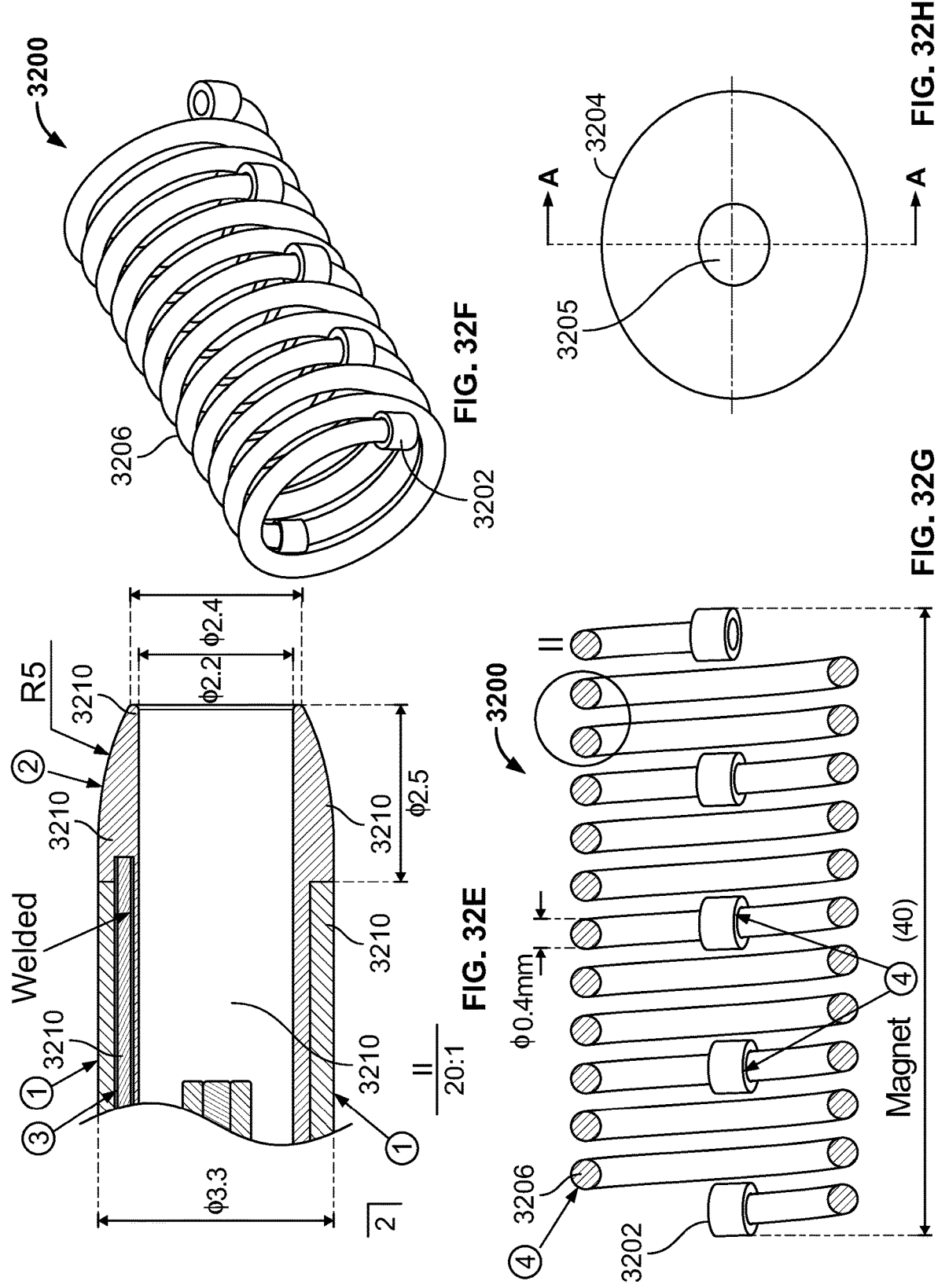

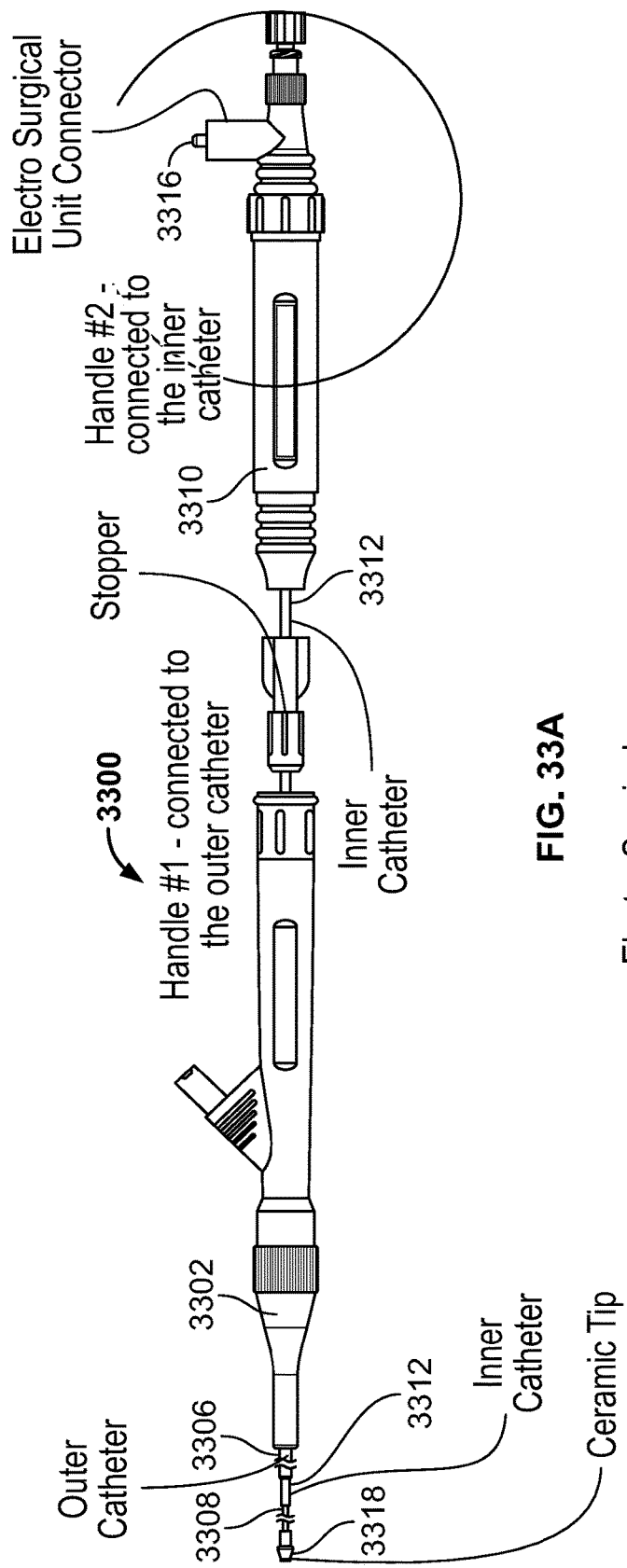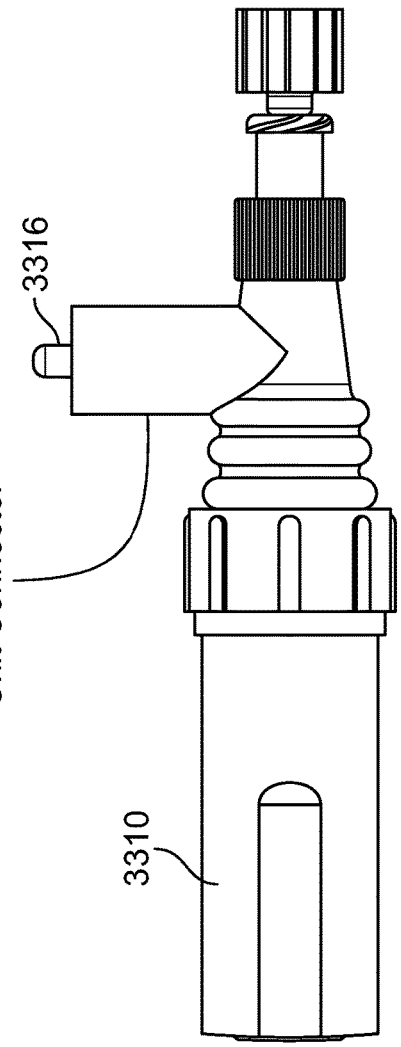
FIG. 33A
FIG. 33B

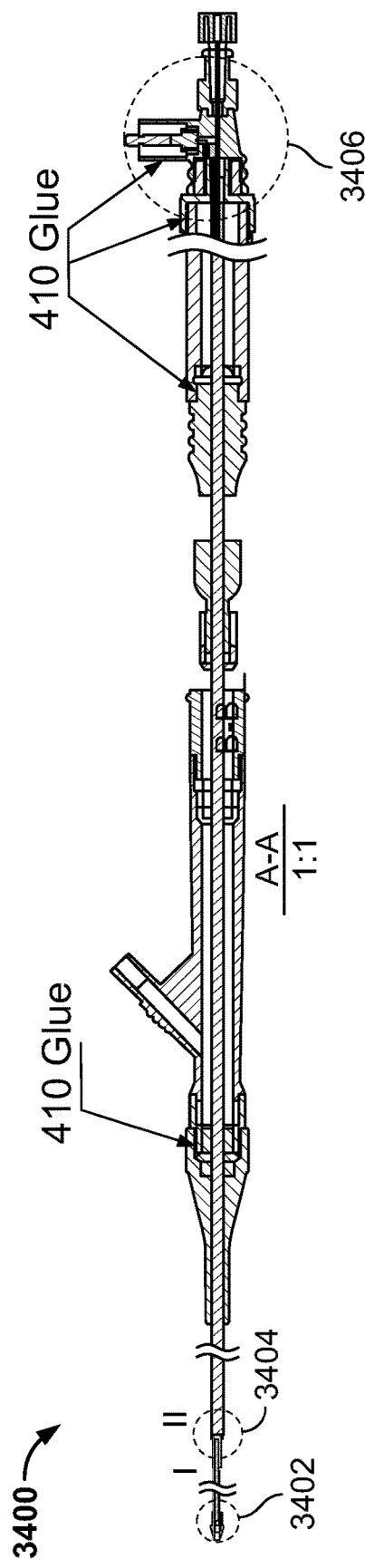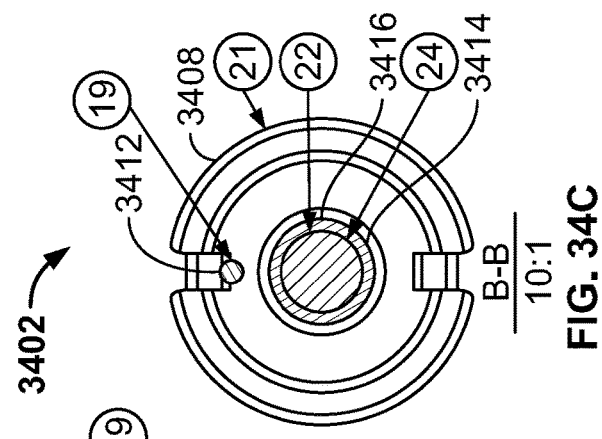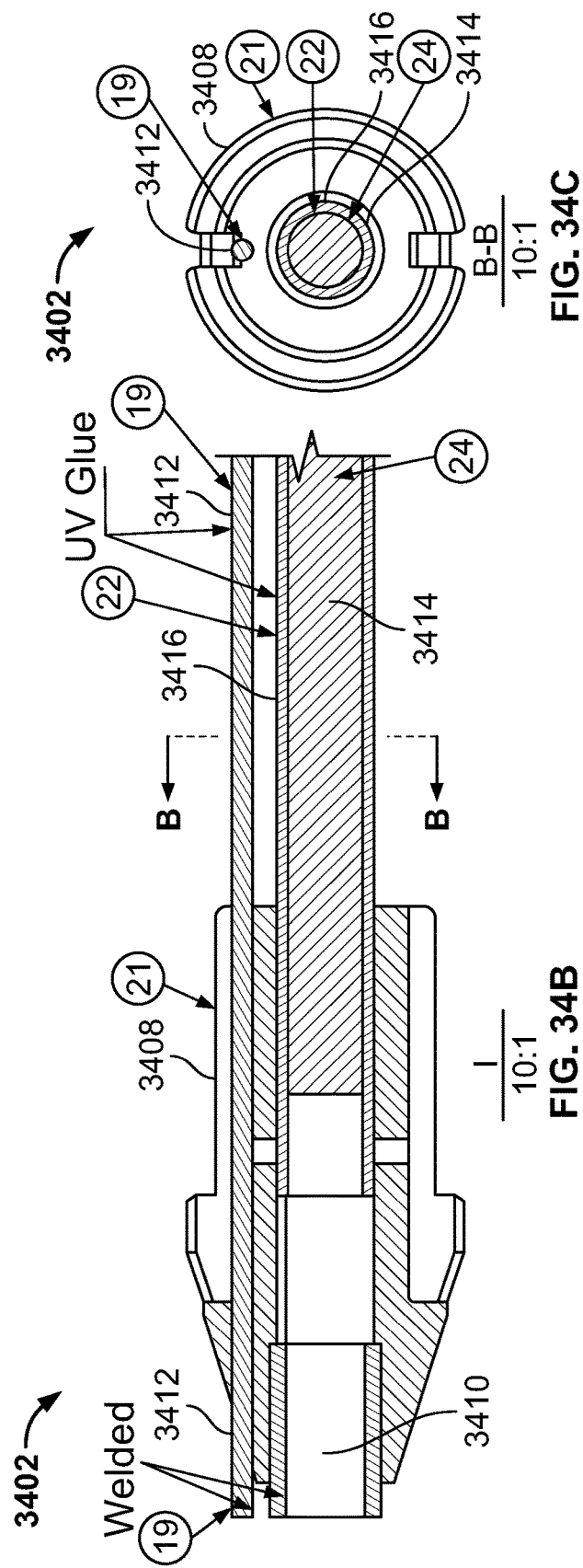

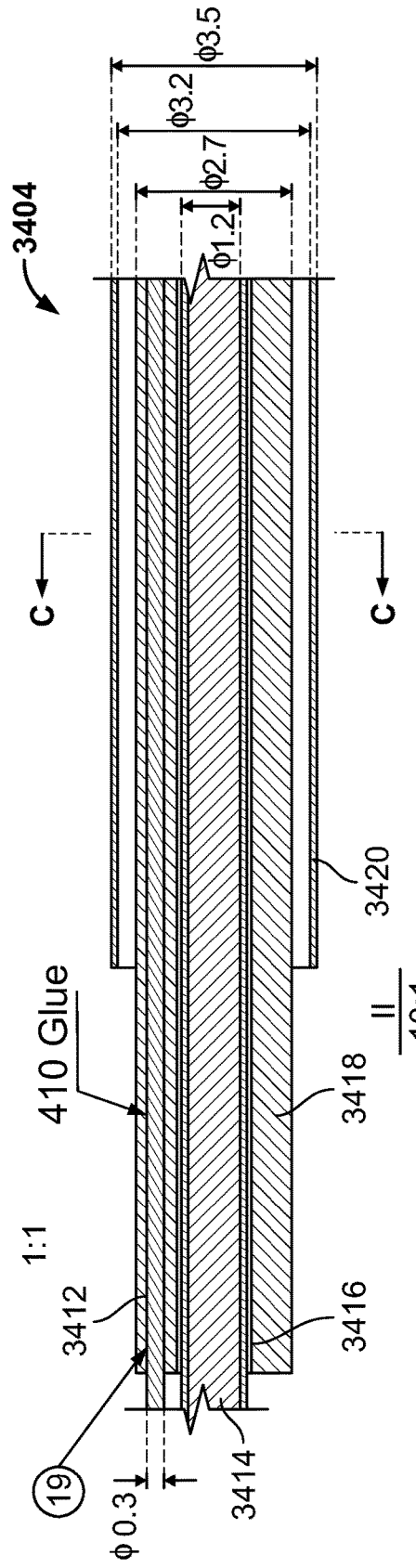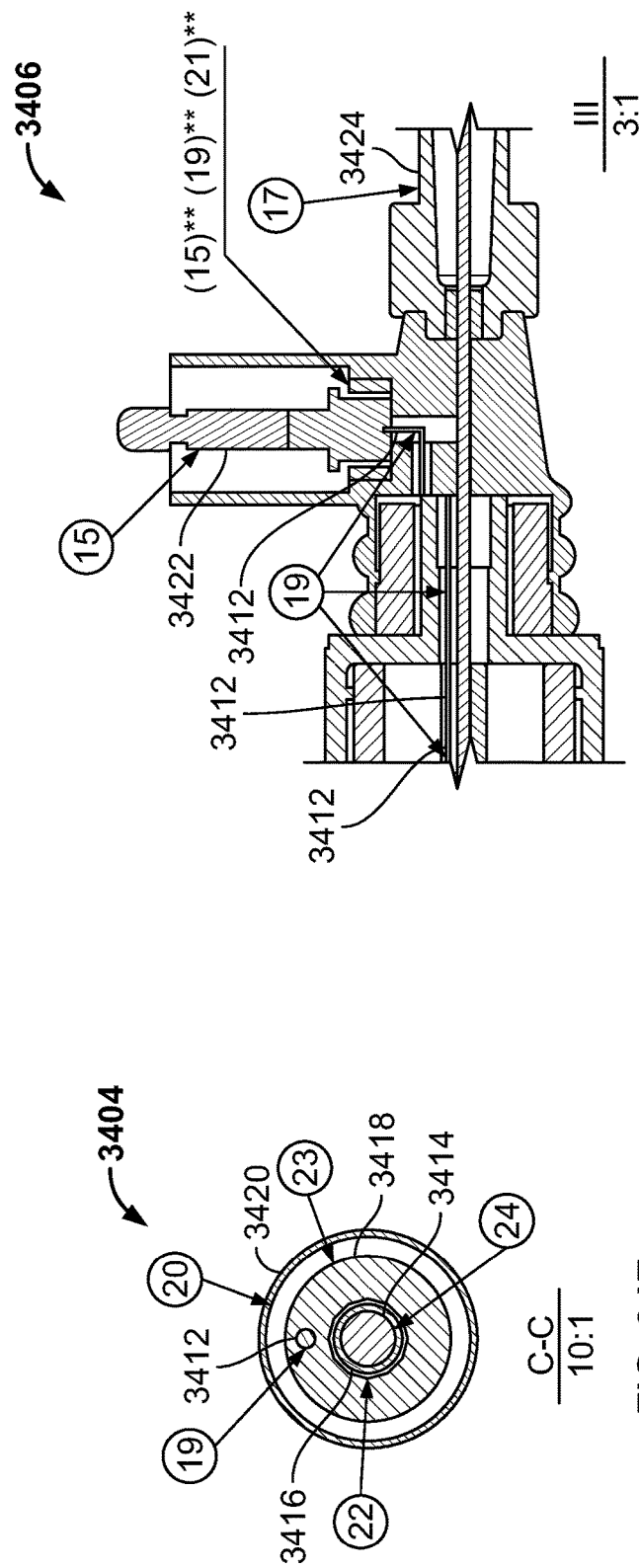
FIG. 34D
FIG. 34E
FIG. 34F

3502
In Order to Form an Anastomosis Between a First Organ and a Second Organ, Firstly, an Endoscope is Placed into the Lumen of a First Organ 3504
An Adjacent Second Organ is Identified Using Endoscopy or Ultrasound Imaging Techniques 3506
Walls of the First and the Second Organs are Punctured Through by Using a Catheter Passed Through or Alongside the Endoscope to Reach a Lumen of the Second Organ 3508
A Portion of the Shape Memory Wire Comprising Magnets is Deployed in the Lumen of the Second Organ and the Wire Transforms from a Straight to a Coiled Shape 3510
The Catheter is Pulled Back into the Lumen of the First Organ and the Remaining Portion of the Shape Memory Wire Comprising Magnets is Deployed in the Lumen of the First Organ and the Wire Transforms from a Straight to a Coiled Shape 3512
The Adjacent Walls of the First and the Second Organs are Compressed Due to the Compressive Force Created by the Coil, the Compressive Force Increases Over Time to Cause Compressive Anastomosis

FIG. 35

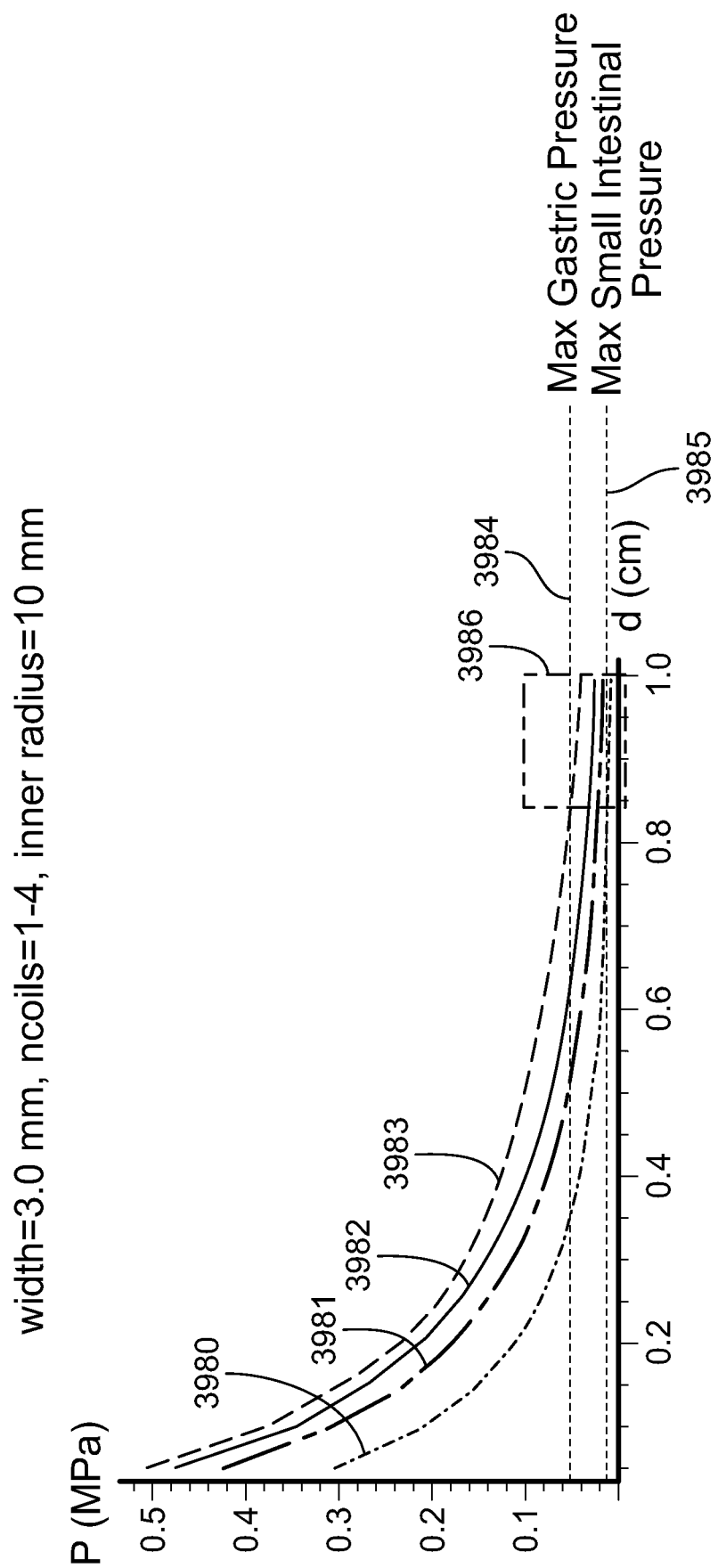

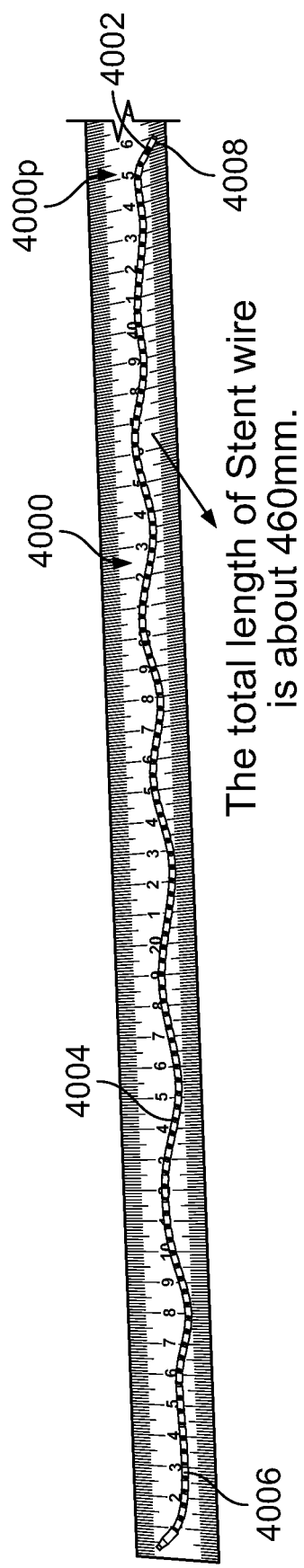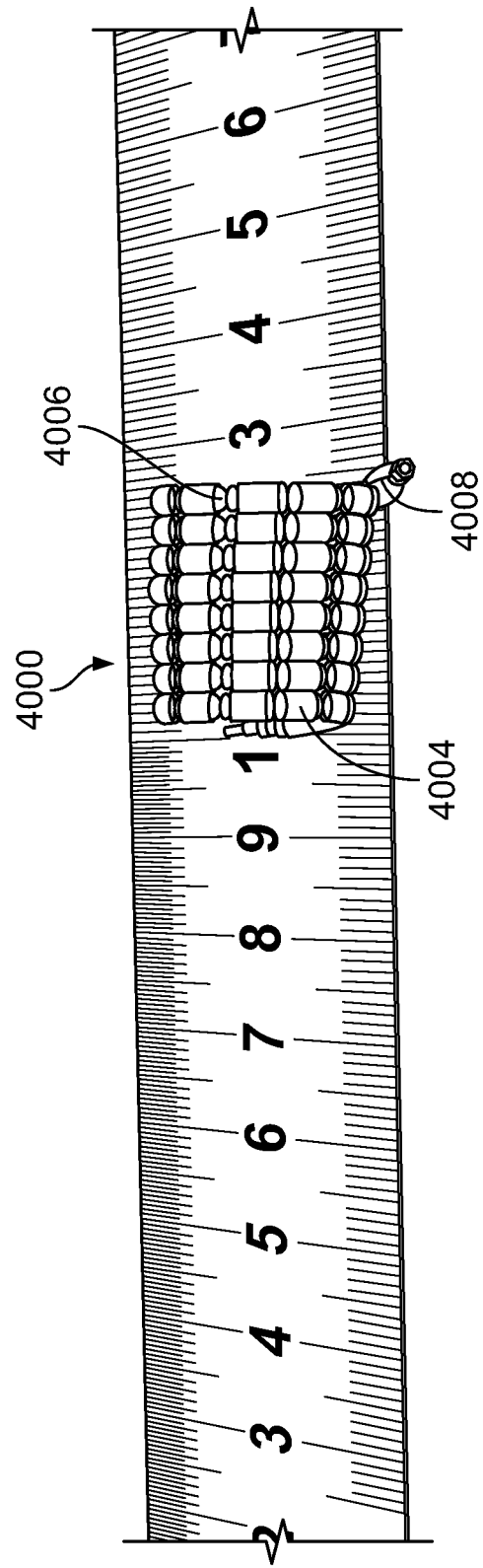
FIG. 40A
FIG. 40B

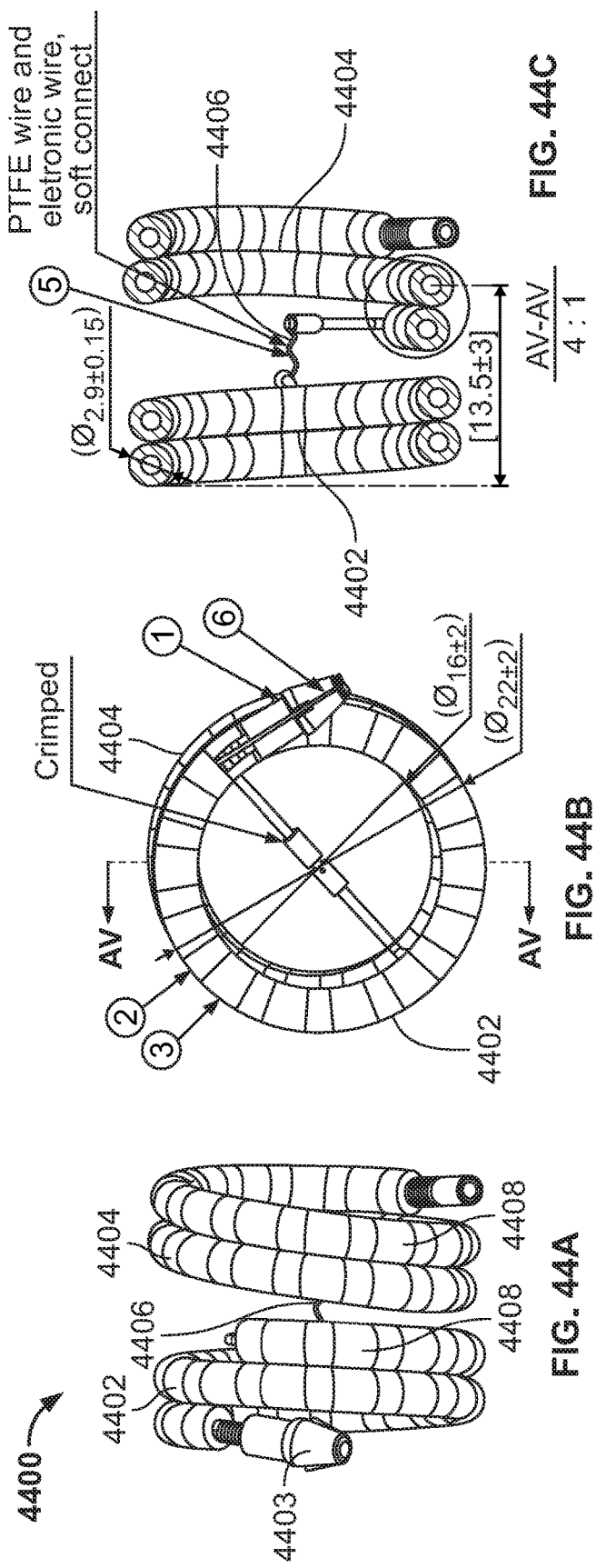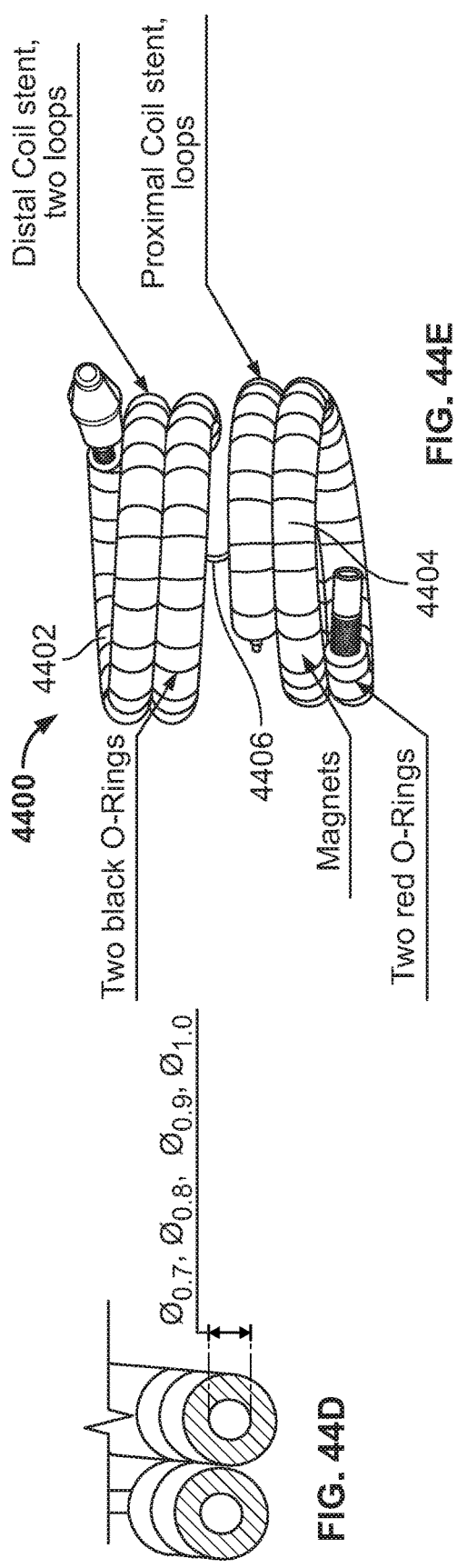

Scissor Cutting Action

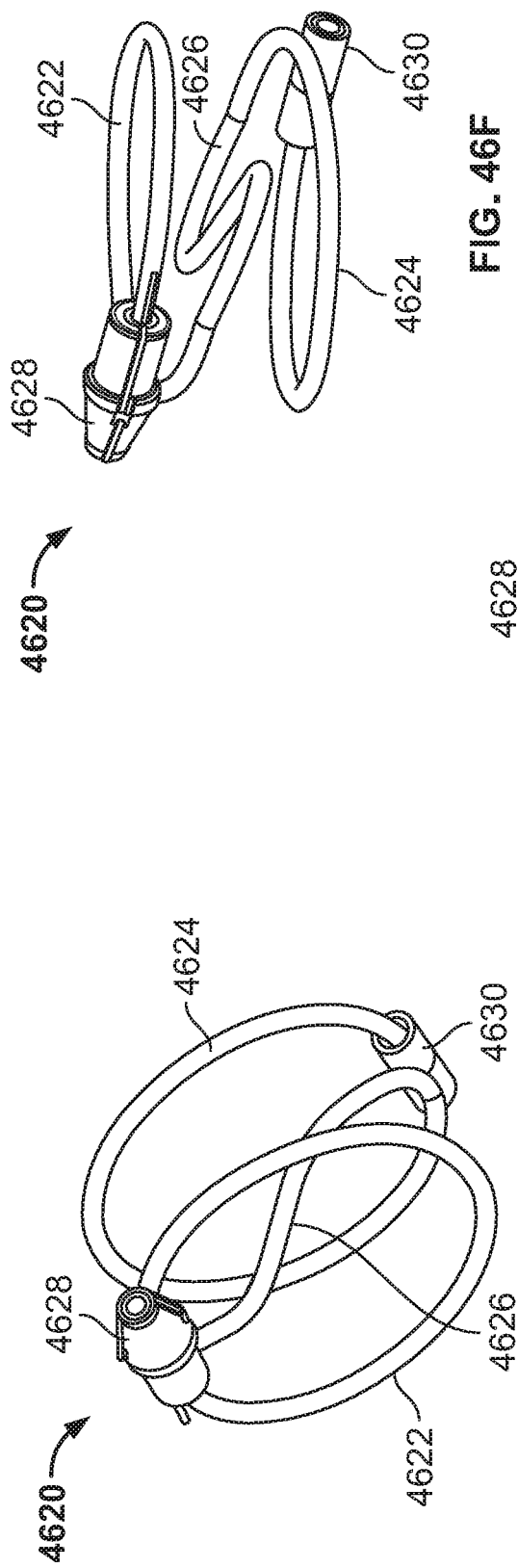
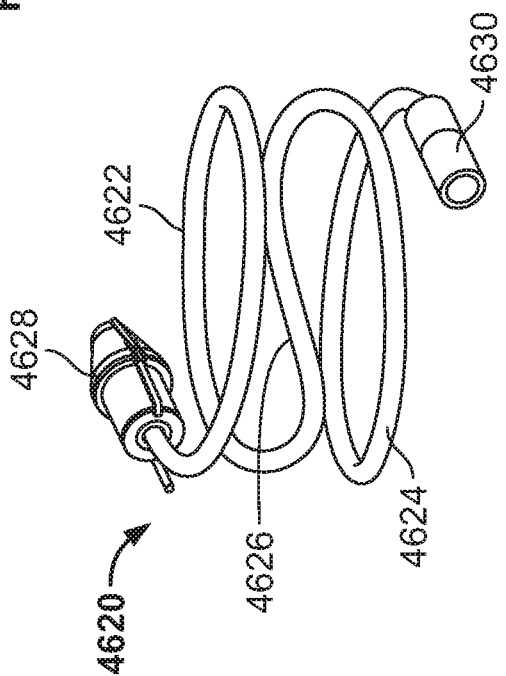
FIG. 46E
FIG. 46F
FIG. 46G

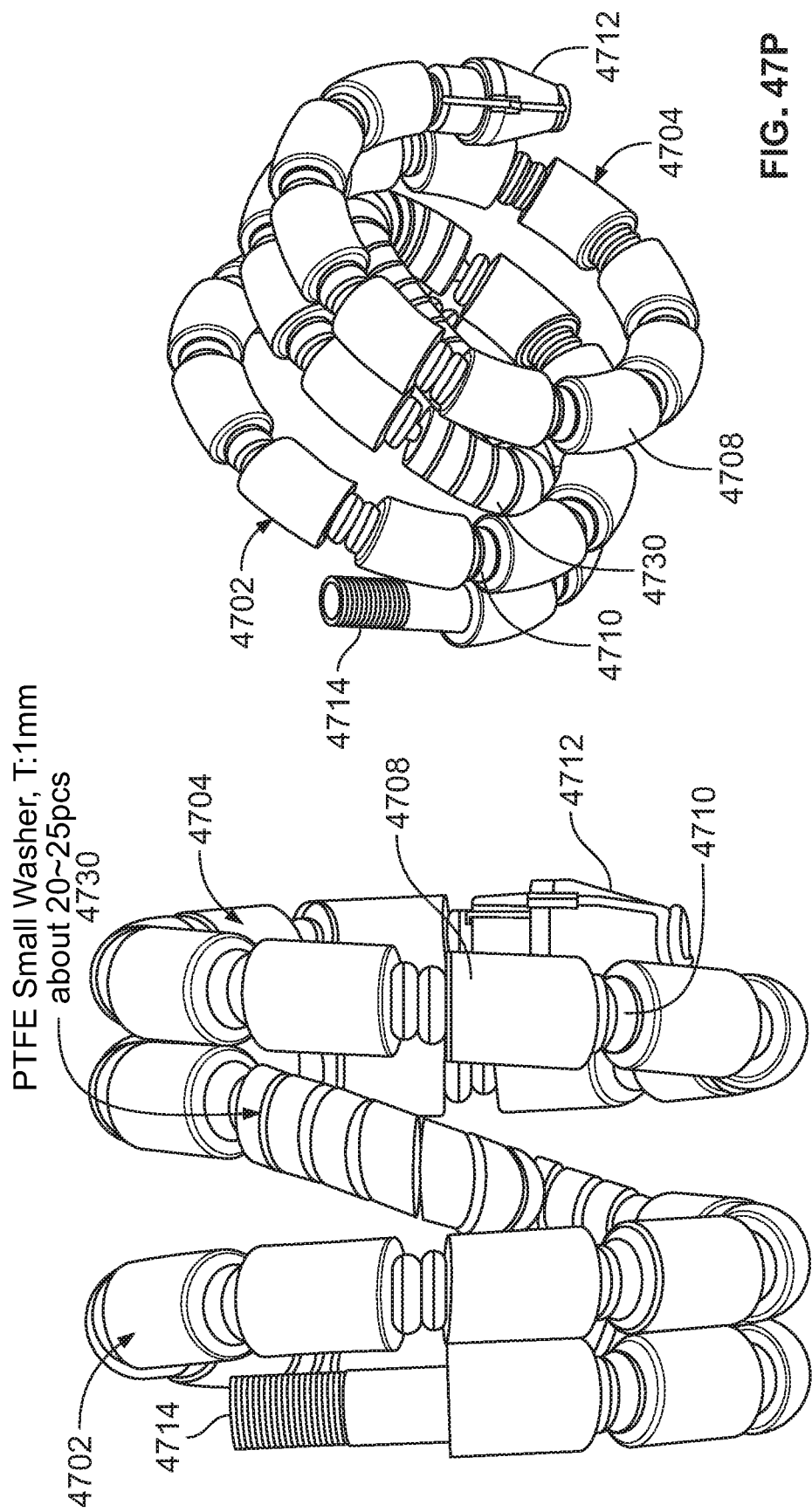

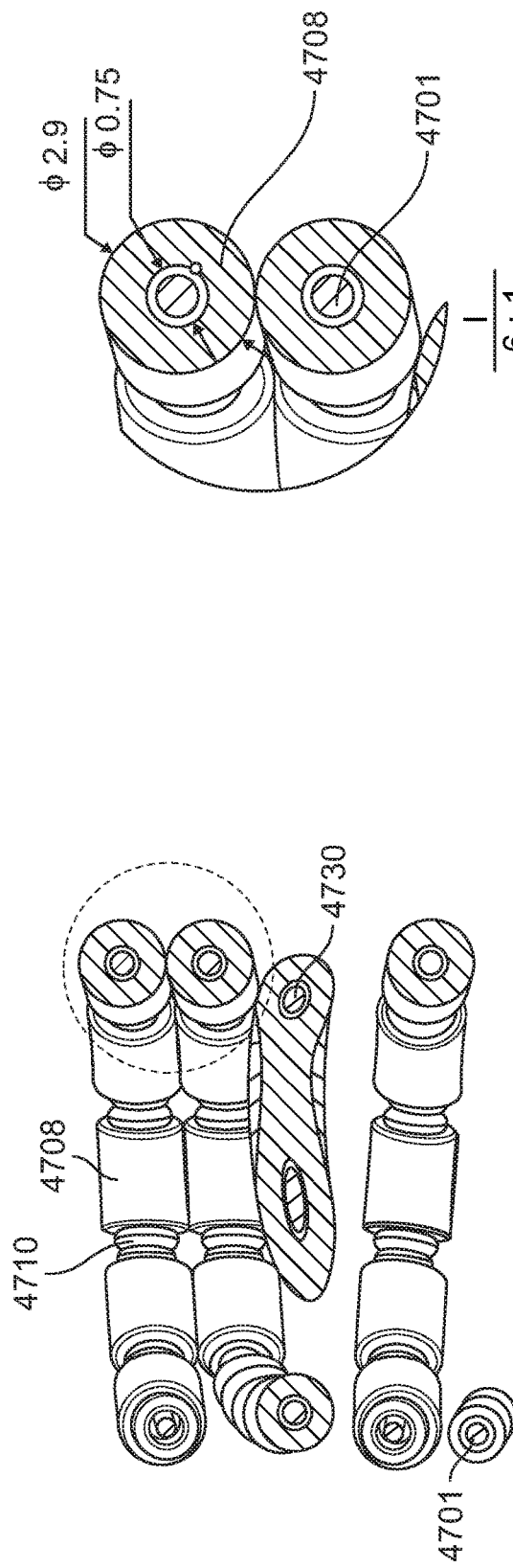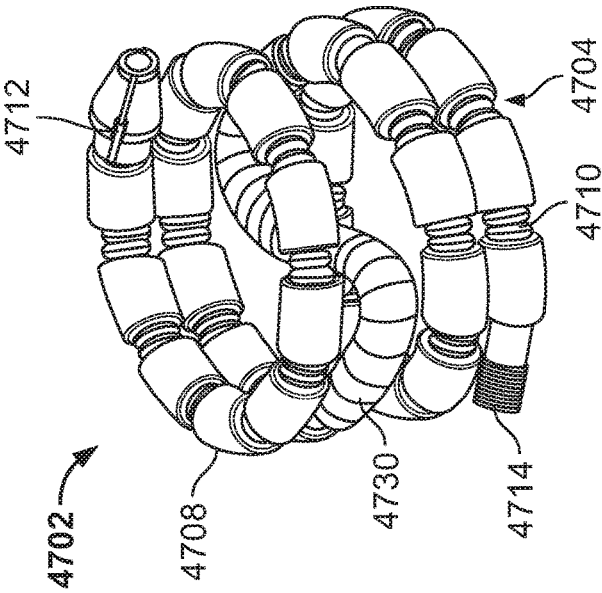
FIG. 47R
FIG. 47S
FIG. 47Q

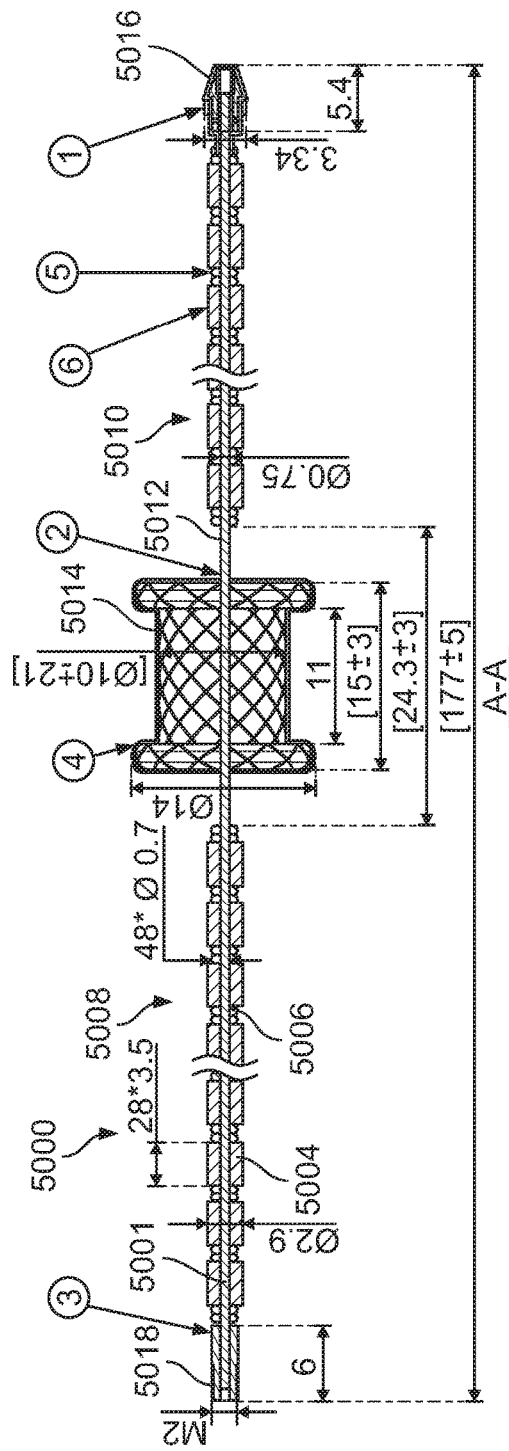
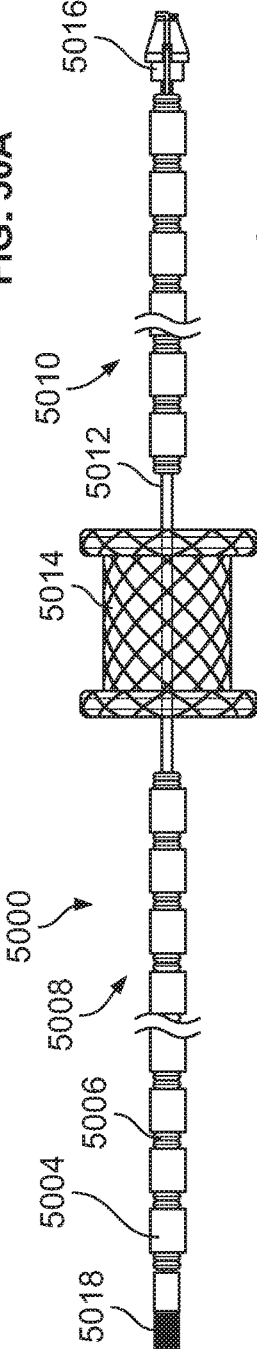
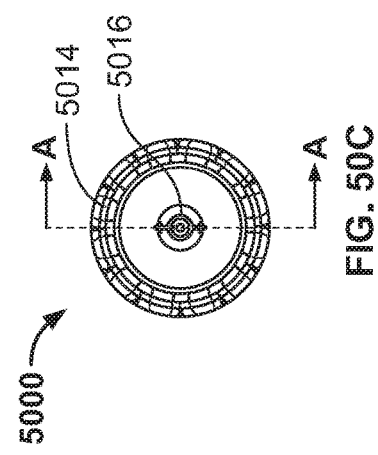
FIG. 50A
FIG. 50B
FIG. 50C

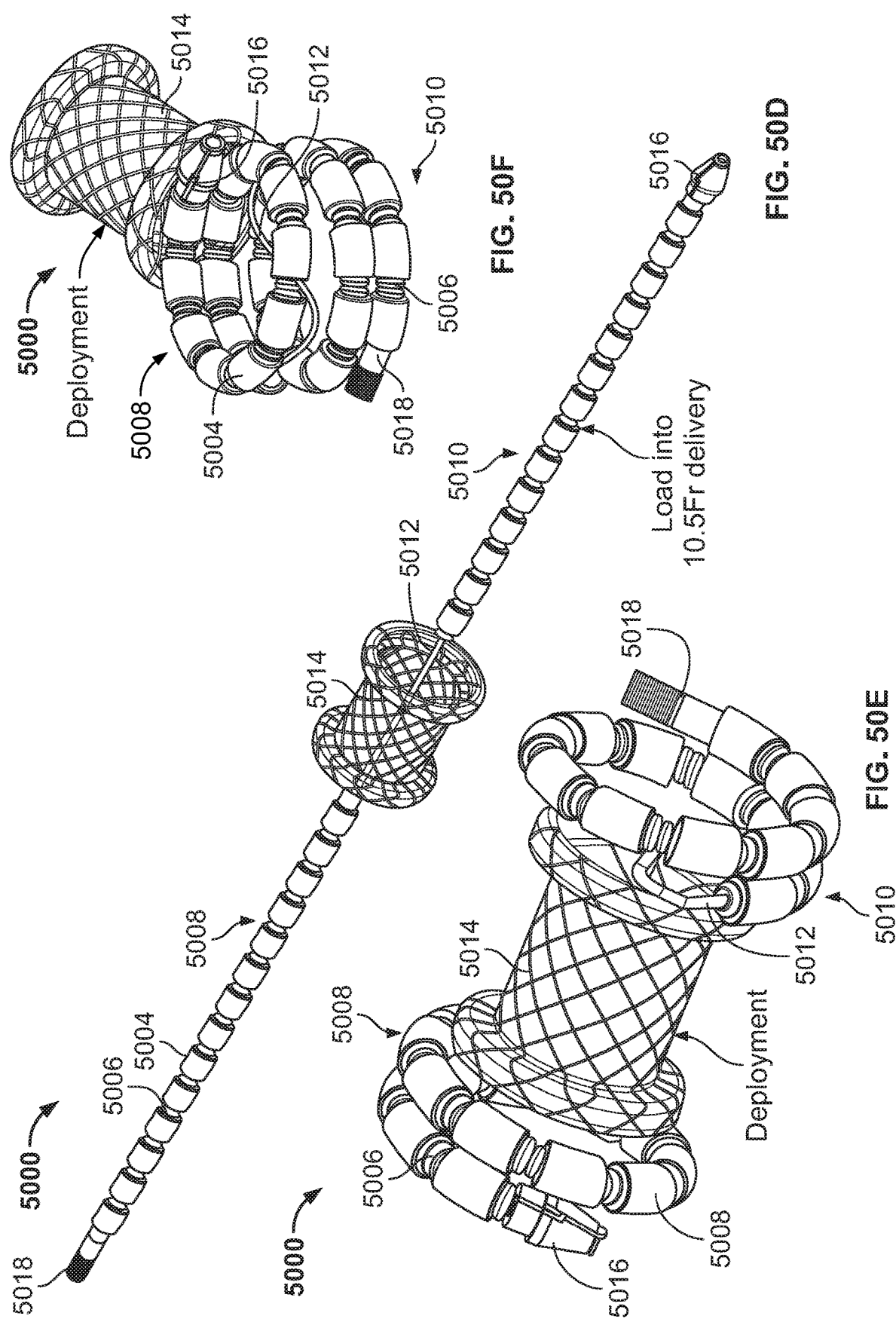

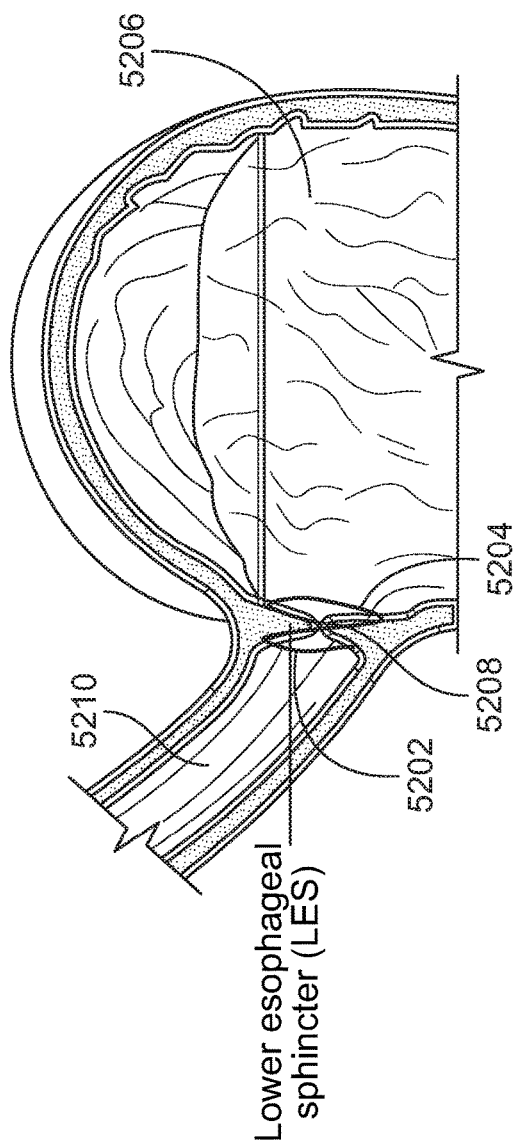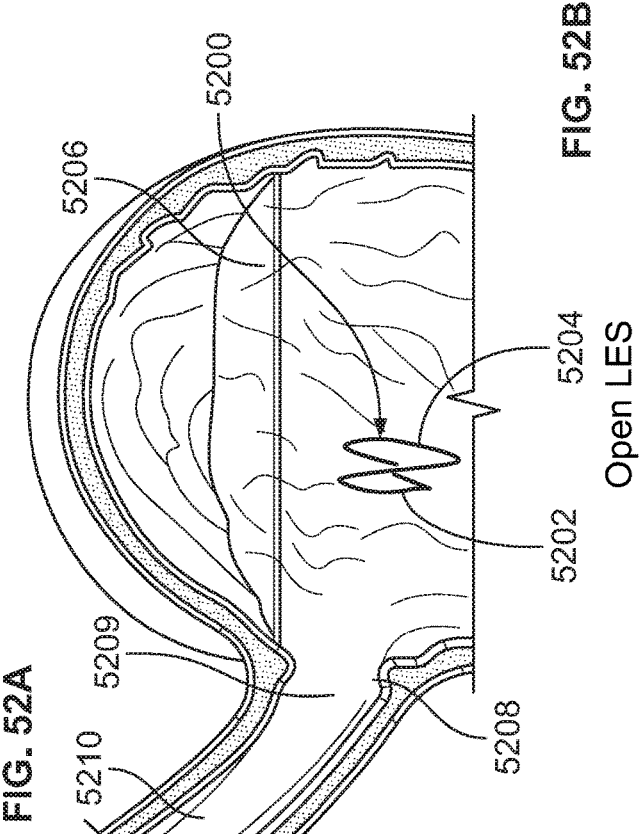

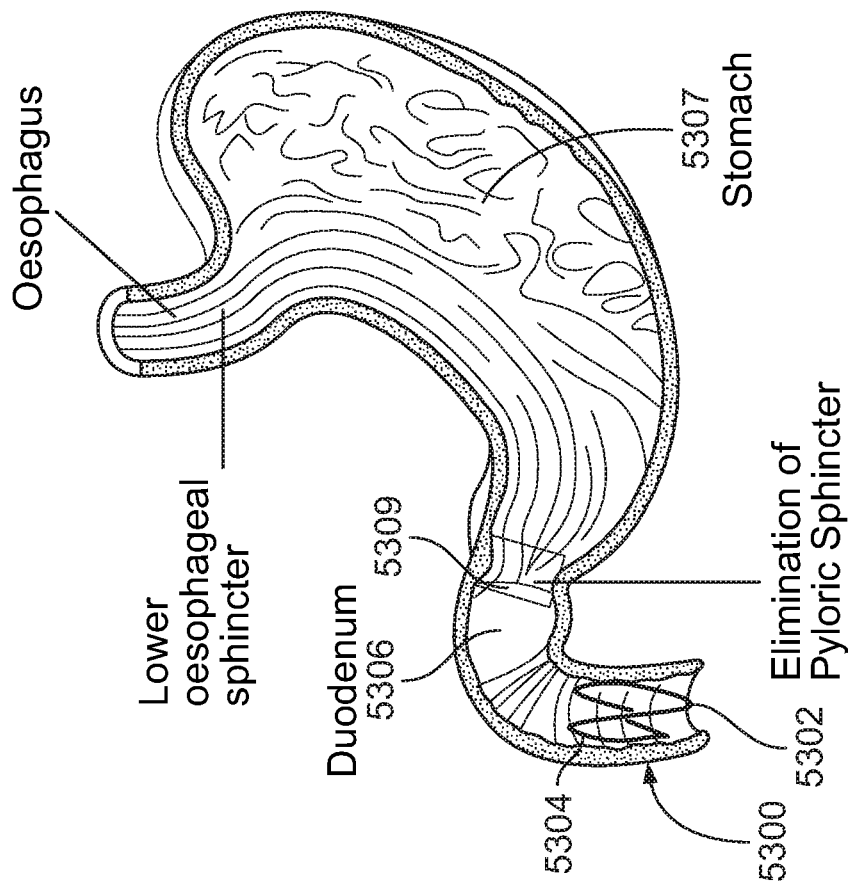
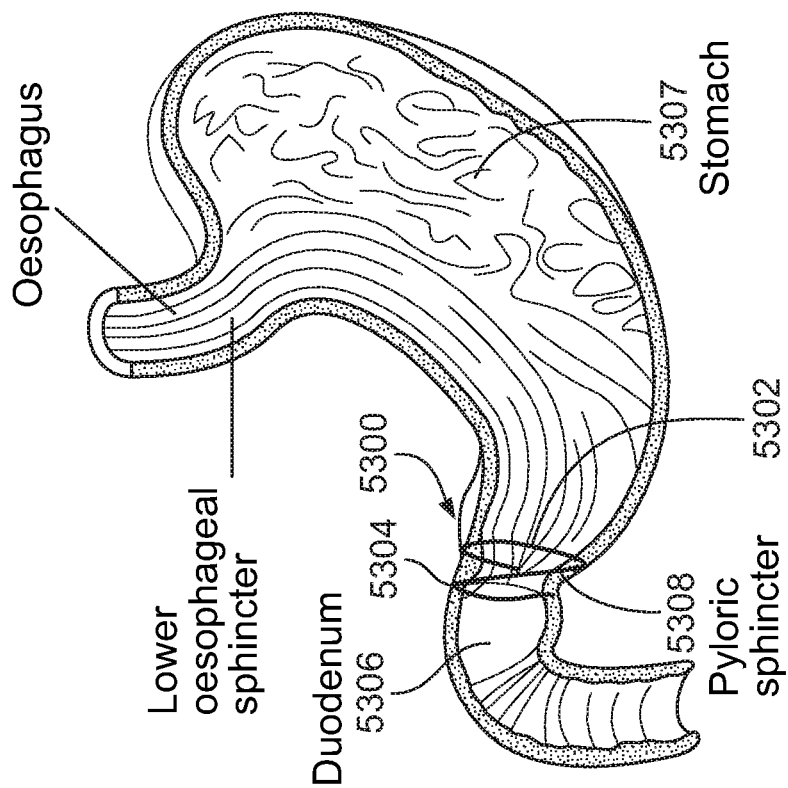
FIG. 53B
FIG. 53A

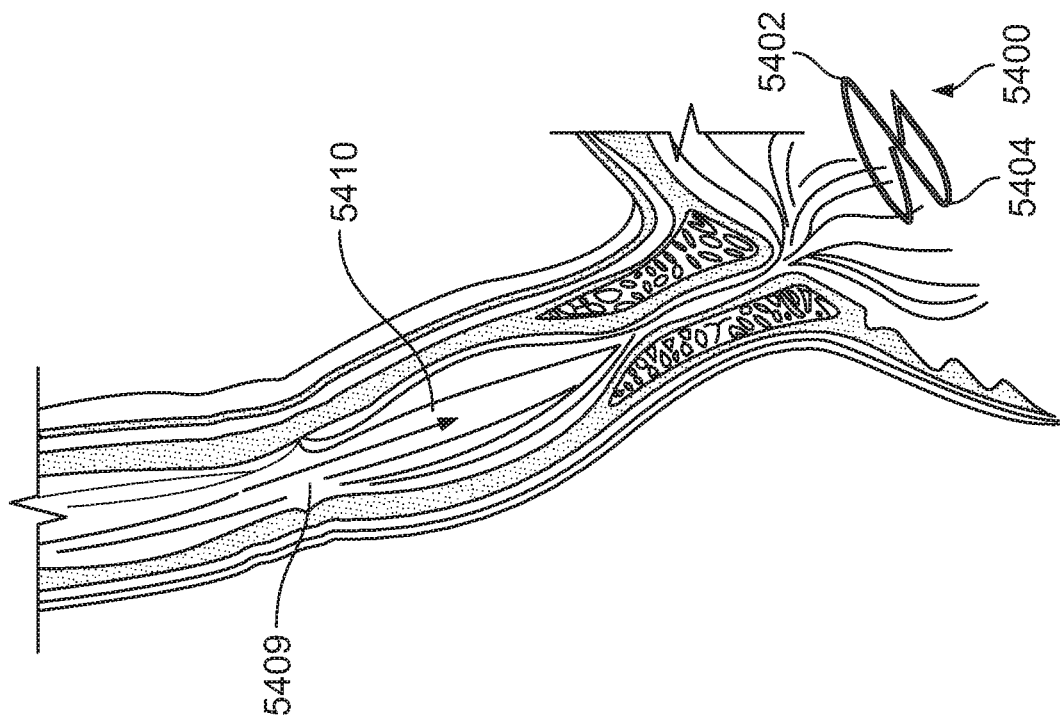
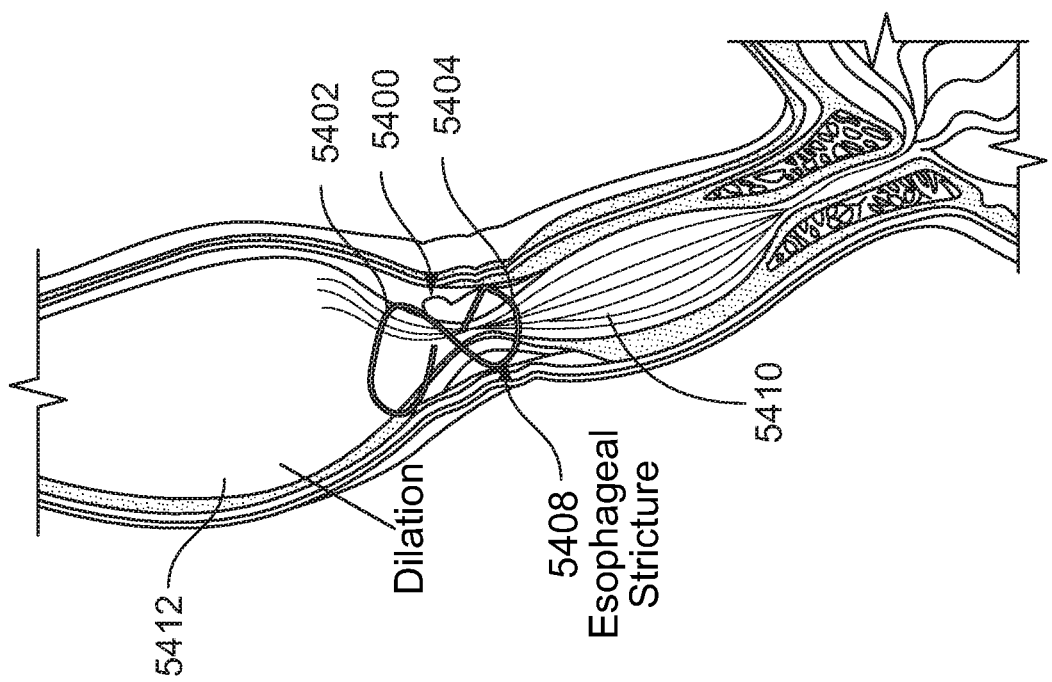

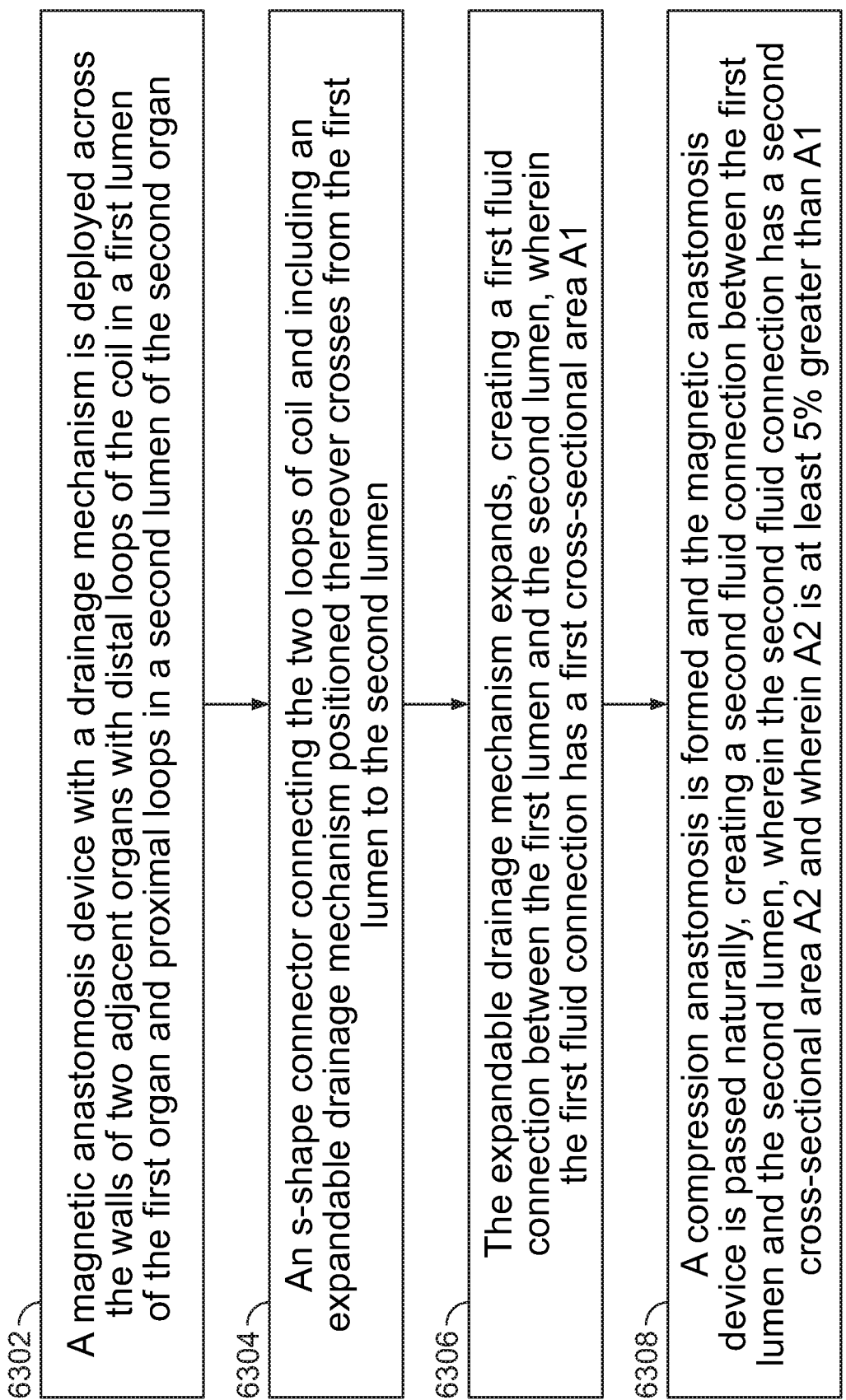

MAGNETIC ANASTOMOSIS DEVICE WITH OPPOSING COIL DIRECTIONALITY

CROSS-REFERENCE

The present application relies on U.S. Provisional patent application Ser. No. 62/832,154, entitled "Magnetic Anastomosis Device with an Embedded Stent" and filed on Apr. 10, 2019, for priority.

The present application is also a continuation-in-part application of U.S. patent application Ser. No. 16/171,779, entitled "Magnetic Anastomosis Device and Delivery System" and filed on Oct. 26, 2018, which is a continuation application of U.S. patent application Ser. No. 15/605,286, of the same title, filed on May 25, 2017, and issued on Dec. 18, 2018 as U.S. Pat. No. 10,154,844, which, in turn, relies on U.S. Patent Provisional Application No. 62/425,951, entitled "Anastomosis Device and Delivery System", filed on Nov. 23, 2016, U.S. Patent Provisional Application No. 62/408,795, entitled "Anastomosis Device and Delivery System", filed on Oct. 16, 2016, and U.S. Patent Provisional Application No. 62/366,185, entitled "Anastomosis Device and Delivery System", filed on Jul. 25, 2016.

All of the aforementioned applications are incorporated herein by reference in their entirety.

FIELD

The present specification is directed toward the placement of magnetic compression anastomosis devices in human bodies and, more specifically, to a magnetic compression anastomosis creation device which includes a mechanism to create immediate patency in the anastomosis at a desired location within the body.

BACKGROUND

Prior art devices for creating anastomoses often comprise a piercing tip which can be hazardous and cause injury to adjacent organs. The instruments often use a grasping mechanism which may be difficult to maneuver. Further, two punctures are required for the operation of some prior art instruments, which may increase the chance of leak from the puncture site from the grasper. Also, certain prior art devices are only able to oppose the adjacent walls without enough pressure to damage and necrose the intervening tissue to thereby create a large enough anastomosis that will remain open for long durations to provide adequate drainage. Additional interventions would be needed to create a large opening. While stents made of materials such as a shape memory alloy (SMA), which are endoscopically inserted into a human body for creating an anastomosis and draining a pancreatic pseudocyst, are known, using these devices requires multiple interventions for the placement and removal of the stent and dealing with several complications such as infection, bleeding, dislodgement, and frequent clogging from debris in the pancreatic fluid.

In addition, prior art magnetic anastomosis methods typically require the use of two separate mating devices deployed individually in two adjacent organs. A first device is delivered to the lumen of a first organ and a second device is delivered to a lumen of a second organ. Magnetic forces pull the two devices together, capturing and compressing portions of the walls of the two organs between the devices, eventually leading to tissue necrosis and anastomosis formation. The devices usually have a single loop polygon shape deployment configuration, with no out-of-plane bending. The devices often include additional features to assist in creating the desired deployment shape, such as an exoskeleton and guide and opening/closing elements.

Hence, what is needed is an efficient and small anastomosis device which may be easily delivered within a human body without the need for graspers. What is also needed is an anastomosis device which may be deployed by a single operator using single endoscopic procedure making a single puncture in an organ wall to deliver the entire device. It is desirable not to have a sharp piercing mechanism in the device that uses mechanical force for piercing. It is also desirable to have a piercing mechanism separate from the anastomosis device and which is not left in the body with the anastomosis device, decreasing the possibility of injury to internal organs. Further, there is need for an anastomosis device which exerts a sufficiently high enough compressive force on organ walls to create an anastomosis between the organs, yet remains a small enough profile to be delivered through an endoscope or laparoscopic or other minimally invasive tools. There is also a need for an anastomotic device that does not rely solely on the magnetic forces for correct orientation and positioning inside the human body and does not require the accurate manual positioning of two separate compressive elements. There is also a need for an anastomosis device that can connect two hollow organs via a stent without the need to advance an endoscope or laparoscope into both the organs and the device can be placed by endoscopically or laparoscopically accessing a first of the two organs while the second organ is accessed by the device delivery catheter. There is also need for a compression anastomosis device that provides for immediate fluid communication and drainage while minimizing anastomotic leaks. Finally, there is a need for a device that can efficiently deliver and embed a drainage element, such as a stent, at a location within a human body.

SUMMARY

The present specification discloses an anastomosis device comprising: a wire, wherein said wire has a first state and a second state, wherein, in said first state, the wire has a substantially linear form, wherein, in said second state, the wire forms a coil having at least a first loop and a second loop, and wherein said wire is adapted to transform from the first state to the second state when exposed to a temperature greater than a threshold value, and wherein the first loop is connected to the second loop by means of a bridging segment comprising a predefined length of the wire enabling the wire upon changing from the first state to the second state to coil into the first loop in a first direction and to coil into the second loop in a second opposing direction; a plurality of magnets positioned over the first loop and the second loop, wherein each of said plurality of magnets has a lumen through which said wire extends, wherein, in each of said first loop and second loop, a portion of adjacent magnets of said plurality of magnets are configured to not attach to each other, and wherein a portion of said plurality of magnets in the first loop are configured to attract a portion of said plurality of magnets in the second loop; and a stent positioned over the bridging segment, wherein the stent is expandable from a first collapsed state to a second expanded state, wherein the stent has a lumen through which the bridging segment extends.

Optionally, the bridging segment over which the stent is positioned is not coiled.

Optionally, a tip of the wire is coupled with a cautery tip made of a ceramic material for piercing body tissues.

Optionally, in said second state, the wire forms a coil having at least four coil loops.

Optionally, the anastomosis device is packaged in a shape setting mold prior to positioning said device, via a catheter, within a body cavity, the shape setting mold causing the device to remain in the second state wherein the wire forms a coil having a first proximal end comprising a threaded connector for coupling with the catheter and a second distal end having said tip for piercing the adjacent body tissues, and wherein the proximal and the distal ends are bent towards a center of the coil loops by an angle ranging from 15° to 20° for enabling said catheter to exit an endoscope elevator at an angle of at least 30° during positioning of said device within the body cavity.

Optionally, said wire is caused to transform from the first state to the second state by exposing said wire to a temperature greater than 37° Celsius.

Optionally, the anastomosis device is used to create an anastomosis between a gall bladder and a small bowel of a patient to treat one of diabetes, obesity and metabolic syndrome.

Optionally, the anastomosis device is used to create an anastomosis between a gall bladder and a small bowel of a patient to treat one of gallbladder motility disorder, gallbladder dyskinesia, biliary dyskinesia and biliary pancreatitis.

Optionally, the bridging segment coils into an 'S' shape when the wire changes from the first state to the second state.

Optionally, an end of the first loop not connected to the bridging segment is turned inwards towards a center of the first loop.

Optionally, an end of the second loop not connected to the bridging segment is turned inwards towards a center of the second loop.

Optionally, the anastomosis device further comprises non-ferromagnetic spacers positioned between adjacent magnets of said plurality of magnets.

Optionally, said wire comprises a shape memory alloy.

The present specification also discloses an anastomosis device comprising: a wire comprising a first section and a second section and a connecting section between the first section and the second section; a first plurality of magnets positioned coaxially about the first section of the wire; a second plurality of magnets positioned coaxially about the second section of the wire; and a stent covering the connecting section of the wire.

Optionally, anastomosis device further comprises non-ferromagnetic spacers positioned between adjacent magnets of said first plurality of magnets and said second plurality of magnets.

Optionally, said wire comprises a shape memory alloy.

Optionally, said first section, second section, and connecting section of the wire have a first state and a second state, wherein, in said first state, the first section, second section, and connecting section of the wire have a substantially linear form, and wherein, in said second state, the said first section and said second section of the wire form a coiled shape and said connecting section of said wire forms an 'S' shape, and wherein said first section, second section, and connecting section of the wire are adapted to transform from the first state to the second state when exposed to a temperature greater than a threshold value. Optionally, said first section, second section, and connecting section of the wire are caused to transform from the first state to the second state by exposing said wires to a temperature greater than 37° Celsius.

Optionally, said stent is expandable from a first collapsed state to a second expanded state.

Optionally, the stent has a lumen through which the connecting member extends.

Optionally, the first plurality of magnets and the second plurality of magnets are covered with a PTFE material.

Optionally, a tip of the wire is coupled with a cautery tip made of a ceramic material for piercing body tissues.

The present specification also discloses a delivery device for deploying an anastomosis device in a desired location within an organ, the delivery device comprising: a handle comprising an inner shaft coaxially surrounded by an outer tube; and a body comprising a tubular sheath positioned coaxially about the inner shaft, the inner shaft comprising a plurality of grooves for guiding the anastomosis device; wherein the inner shaft rotates relative to the outer tube during deployment of the anastomosis device through the tubular sheath at the desired location, and wherein the grooves enable the inner shaft to rotate inside the outer tube during at least a portion of the deployment.

The present specification also discloses a method of creating an anastomosis and embedding a stent between two adjacent body tissues comprising: positioning an anastomosis device, via a catheter, within a body cavity proximate at least one of said adjacent body tissues, wherein the anastomosis device comprises: a wire, wherein said wire has a first state and a second state, wherein, in said first state, the wire has a substantially linear form, wherein, in said second state, the wire forms a coil having at least a first loop and a second loop, and wherein said wire is adapted to transform from the first state to the second state when exposed to a temperature greater than a threshold value; a plurality of magnets positioned over a first portion of the wire, wherein each of said plurality of magnets has a lumen through which said wire extends, wherein, in each of said first loop and second loop, a portion of adjacent magnets of said plurality of magnets are configured to not attach to each other, and wherein a portion of said plurality of magnets in the first loop are configured to attract a portion of said plurality of magnets in the second loop; and a stent positioned over a second portion of the wire, wherein the stent is expandable from a first collapsed state to a second expanded state, wherein the stent has a lumen through which the wire extends, and wherein the second portion of the wire does not comprise any of the plurality of magnets; and piercing the adjacent body tissues and positioning the anastomosis device through a hole created by said piercing; releasing the anastomosis device such that, when it transforms from the first state to the second state, tissue between the two adjacent body tissues is caught between the first loop and the second loop, thereby being compressed and resulting in the anastomosis and the stent is positioned between the adjacent body tissues.

Optionally, the anastomosis device further comprises non-ferromagnetic spacers positioned between adjacent magnets of said plurality of magnets. Optionally, each of said non-ferromagnetic spacers has a length sufficient to keep a force of attraction between opposite poles of the adjacent magnets below a bending force of the coil.

Optionally, when in the second state, a maximum cross sectional diameter of the first loop and the second loop ranges from 5 mm to 50 mm.

Optionally, each of the plurality of magnets has a maximum cross sectional length or diameter ranging from 0.2 mm to 7 mm and a pull force ranging from 0.01 lb. to 4 lb.

Optionally, in the first loop and in the second loop, at least 50% of the adjacent magnets of said plurality of magnets are arranged with like poles facing each other, thereby creating a repulsive force between said adjacent magnets in the first loop and a repulsive force between said adjacent magnets in the second loop of the coil.

Optionally, at least one end of the wire is connected to a delivery device.

Optionally, said wire comprises a shape memory alloy.

Optionally, said threshold value is 20 degrees Celsius.

Optionally, said coil has at least one loop proximate to the first loop and at least one loop distal to the second loop.

Optionally, each of said plurality of magnets is cylindrically shaped and is a rare earth magnet covered with at least one of gold, nickel, Teflon, parylene, copper, zinc, silicone, epoxy and titanium.

Optionally, the method of claim 1 further comprises, before releasing the anastomosis device, exposing the anastomosis device to heat by passing electrical current through the anastomotic device to assist said transformation from the first state to the second state.

Optionally, a diameter of the wire ranges between 0.1 mm to 10 mm and a length of the wire ranges from 1 cm to 250 cm.

Optionally, a diameter of the wire ranges between 0.1 mm and 6 mm and has a maximum strain of less than 10% in the first state and wherein a maximum cross sectional dimension of the first loop and second loop ranges from 5 mm to 60 mm in the second state.

Optionally, the adjacent body tissues comprise a gall bladder and a duodenum and a maximum diameter of the first loop and the second loop is less than or equal to 30 mm.

Optionally, the adjacent body tissues comprise pancreatic tissue and a maximum diameter of the first loop and the second loop is greater than or equal to 5 mm.

Optionally, the adjacent body tissues comprise biliary tissue and a maximum diameter of the first loop and the second loop is greater than or equal to 5 mm.

Optionally, a diameter of the wire is less than 0.5 mm and wherein a maximum cross sectional dimension of the first loop and second loop is less than or equal to 15 mm.

Optionally, a diameter of the wire ranges from 0.5 mm to 1.0 mm and wherein a maximum cross sectional dimension of the first loop and second loop ranges from 10 mm to 45 mm.

Optionally, a diameter of the wire is greater than 1 mm and wherein a maximum cross sectional dimension of the first loop and second loop is greater than 20 mm.

Optionally, the first loop and the second loop have at least one of a circular shape, polygonal shape, and a star shape with four or more points.

Optionally, a portion of the adjacent magnets of said plurality of magnets on the same loop are configured to repel each other.

Optionally, the stent comprises a middle portion defined by a first radius and end portions defined by a second radius and wherein the second radius is greater than the first radius.

Optionally, the stent comprises a wire mesh covered by a biocompatible material.

Optionally, the stent is secured to the wire via a suture, a crimp, glue, or a weld.

Optionally, the stent is a cylinder defined by a length and a radius wherein the radius is constant over a portion of the length.

Optionally, the stent is a cylinder defined by a length and a radius wherein the radius is not constant over a portion of the length.

The aforementioned and other embodiments of the present shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 7J illustrates exemplary dimensions of a dodecagonal SMA coil in accordance with an embodiment of the present specification;

FIG. 14A illustrates an exemplary SMA wire coupled with magnets prior to deployment in a body for creating an anastomosis, in accordance with an embodiment of the present specification;

FIG. 14B illustrates the exemplary SMA wire coupled with magnets shown in FIG. 14A in a mid-deployment stage, in accordance with an embodiment of the present specification;

FIG. 15A illustrates an exemplary SMA wire coupled with magnets prior to deployment in a body for creating an anastomosis, in accordance with another embodiment of the present specification;

FIG. 15B illustrates the exemplary SMA wire coupled with magnets shown in FIG. 15A in a mid-deployment stage, in accordance with an embodiment of the present specification;

FIG. 17A illustrates an exemplary device comprising round shaped magnets coupled with a SMA coil used for creating an anastomosis, in accordance with an embodiment of the present specification;

FIG. 17B illustrates an exemplary device comprising round shaped magnets coupled with a SMA coil used for creating an anastomosis, wherein at least one magnet comprises a cutting edge, in accordance with an embodiment of the present specification;

FIG. 17C illustrates an exemplary device comprising square shaped magnets coupled with a SMA coil with serrated edges, used for creating an anastomosis, in accordance with an embodiment of the present specification;

FIG. 17D illustrates an exemplary device comprising square shaped magnets coupled with a SMA coil used for creating an anastomosis, in accordance with another embodiment of the present specification;

FIG. 17E illustrates an exemplary device comprising square shaped magnets coupled with a SMA coil used for creating an anastomosis, wherein at least one magnet comprises a cutting edge, in accordance with an embodiment of the present specification;

FIG. 18A illustrates a first configuration of a plurality of magnets arranged around a loop of a SMA wire coil for creating an anastomosis, in accordance with an embodiment of the present specification;

FIG. 18B illustrates a second configuration of a plurality of magnets arranged around a loop of a SMA wire coil for creating anastomosis, in accordance with another embodiment of the present specification;

FIG. 18E illustrates a fifth configuration of magnets around a loop of a SMA coil for creating an anastomosis, in accordance with an embodiment of the present specification;

FIG. 18F illustrates a sixth configuration of magnets around a loop of a SMA coil for creating an anastomosis, in accordance with an embodiment of the present specification;

FIG. 19A illustrates a first step of forming an anastomosis between two organs in a human body, in accordance with an embodiment of the present specification;

FIG. 19B illustrates a second step of forming an anastomosis between two organs in a human body, in accordance with an embodiment of the present specification;

FIG. 19C illustrates a third step of forming an anastomosis between two organs in a human body, in accordance with an embodiment of the present specification;

FIG. 26A illustrates a first view of an exemplary device for creating an anastomosis in a pre-coiled configuration, in accordance with an embodiment of the present specification;

FIG. 26B illustrates a second view of the device for creating an anastomosis of FIG. 26A in a pre-coiled configuration;

FIG. 26C illustrates a third view of the device for creating an anastomosis of FIG. 26A in a pre-coiled configuration;

FIG. 32A illustrates a cross sectional view of an anastomosis coil device in a pre-deployment configuration disposed in a delivery catheter, in accordance with another embodiment of the present specification;

FIG. 32B illustrates a cross sectional view along the BB axis shown in FIG. 32A;

FIG. 32C illustrates a cross sectional view along the CC axis shown in FIG. 32A;

FIG. 32D illustrates a cross sectional view along the DD axis shown in FIG. 32A;

FIG. 32E illustrates a blown up view of the conductor head shown in FIG. 32A;

FIG. 32F illustrates the anastomosis coil device shown in FIG. 32A in a post-deployment configuration after being delivered within a body;

FIG. 32G illustrates a cross sectional view of the anastomosis coil device shown in FIG. 32F;

FIG. 32H illustrates an O-ring being used as a spacer as shown in FIG. 32B;

FIG. 33A illustrates a dual handle delivery device for delivering an anastomosis coil device provided with a cauterizing tip, in accordance with an embodiment of the present specification;

FIG. 33B illustrates a blown up view of the second handle shown in FIG. 33A;

FIG. 34A illustrates a sectional view of a dual handle delivery device for delivering an anastomosis coil device provided with a cauterizing tip, in accordance with an embodiment of the present specification;

FIG. 34B illustrates a blown up sectional view of the tip portion shown in FIG. 34A;

FIG. 34C illustrates a cross sectional view of the tip portion shown in FIG. 34B;

FIG. 34D illustrates a blown up sectional view of the guidewire portion shown in FIG. 34A;

FIG. 34E illustrates a cross sectional view of the guidewire portion shown in FIG. 34D;

FIG. 34F illustrates a blown up sectional view of the handle portion shown in FIG. 34A;

FIG. 35 is a flowchart illustrating the steps of creating an anastomosis by using a shape memory wire and magnetic compression forces between adjacent organs or structures, in accordance with an embodiment of the present specification;

Figure 36:
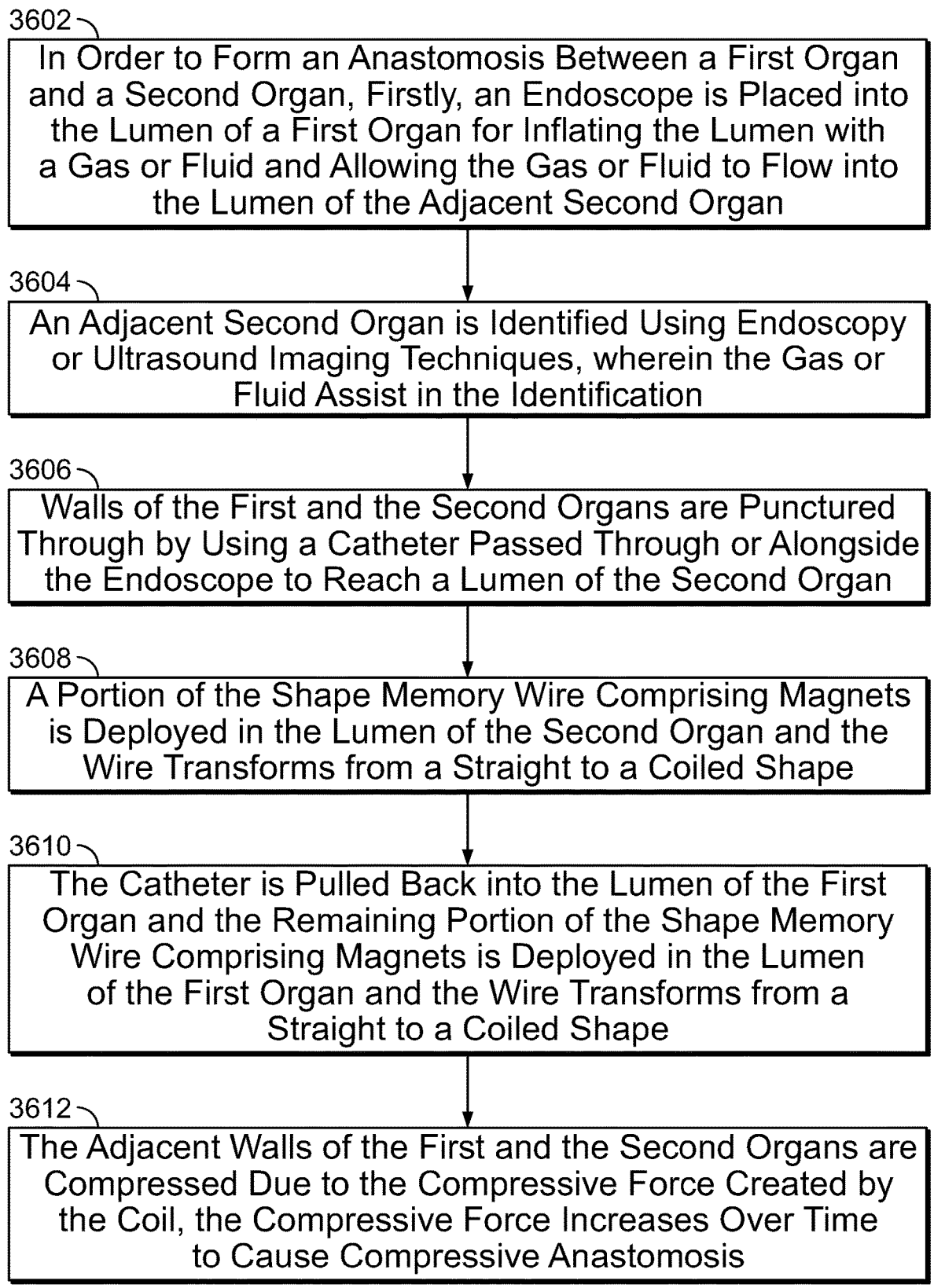
Figure 37:
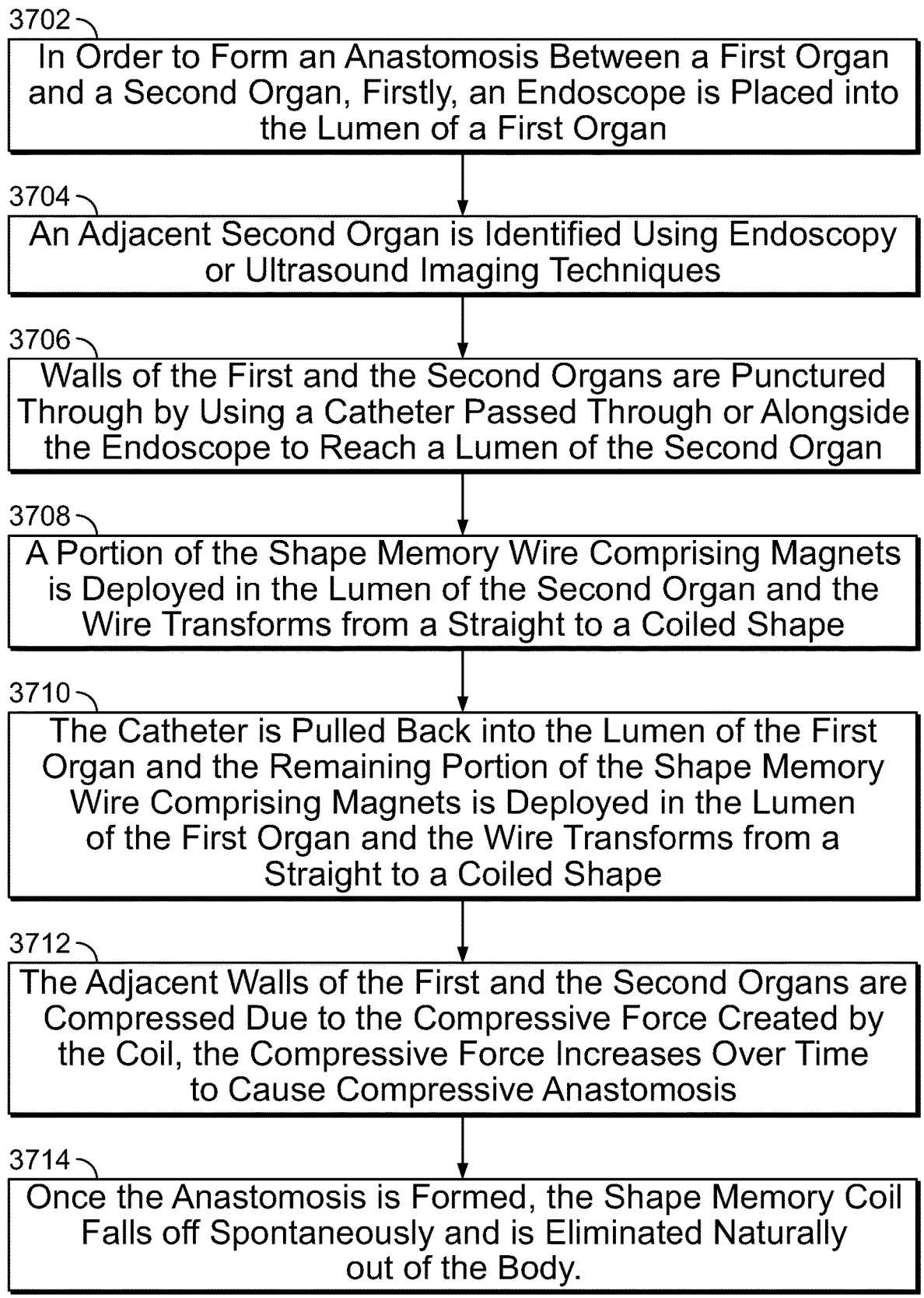
Figure 38:
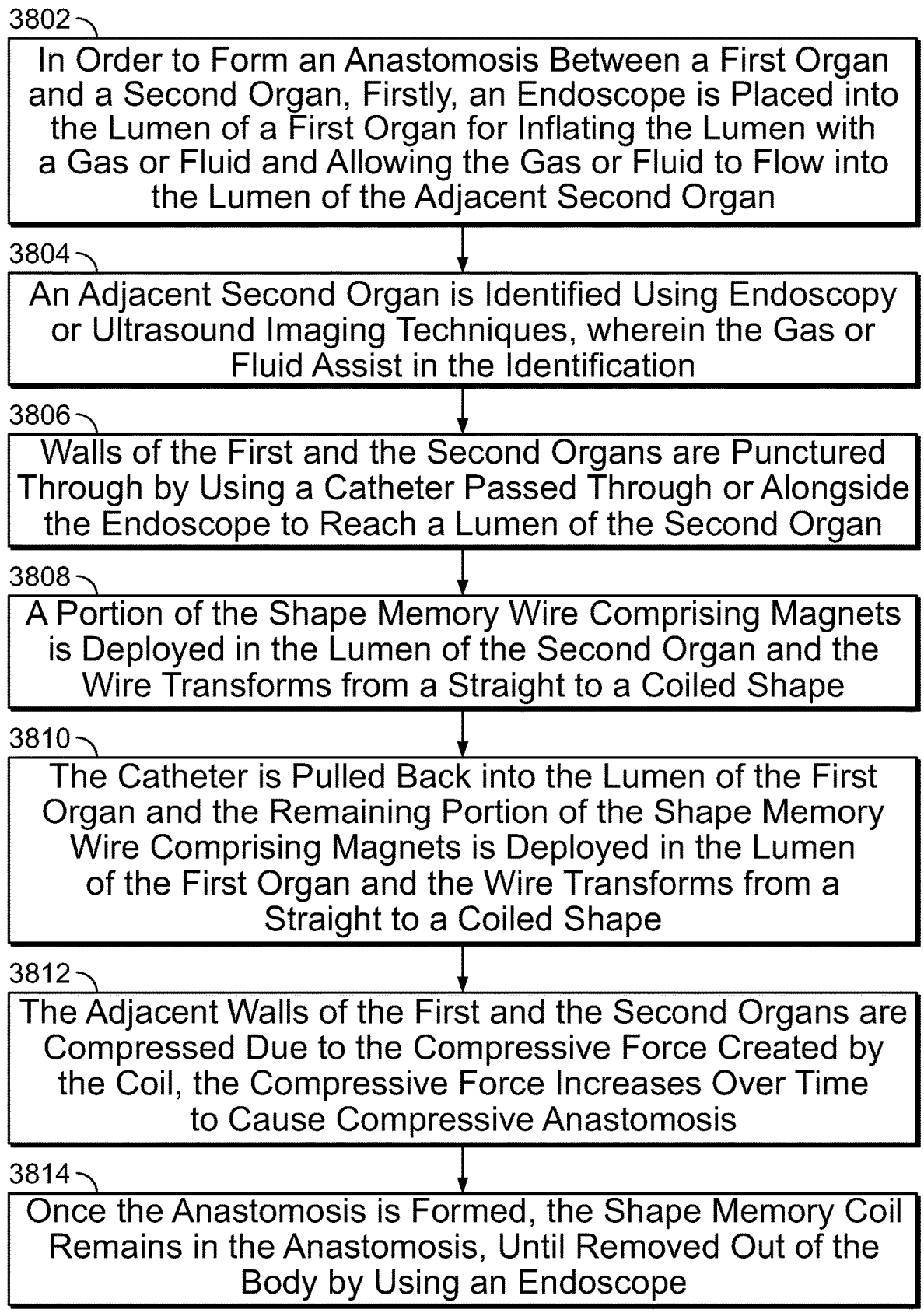
Figure 39A:
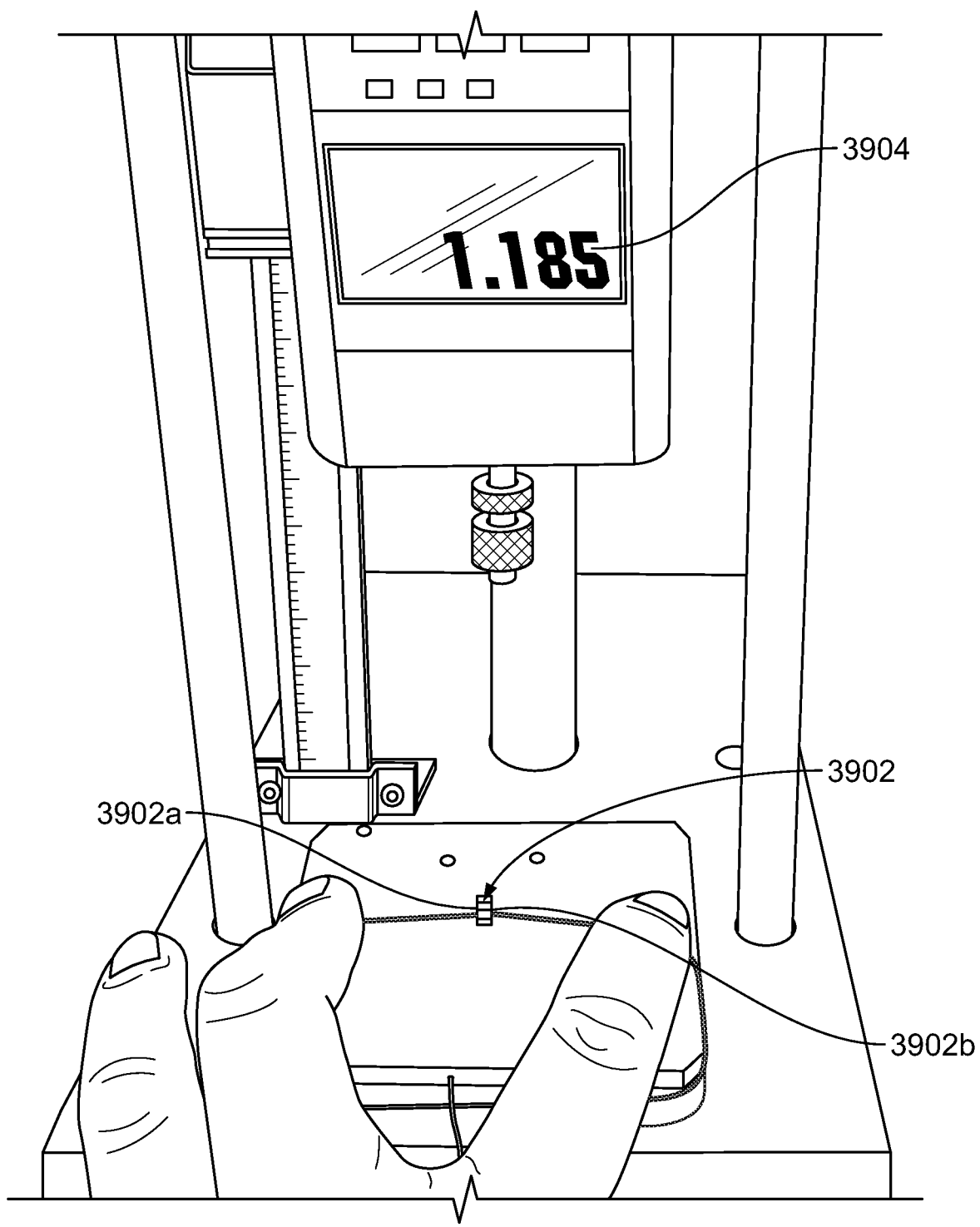
Figure 39B:
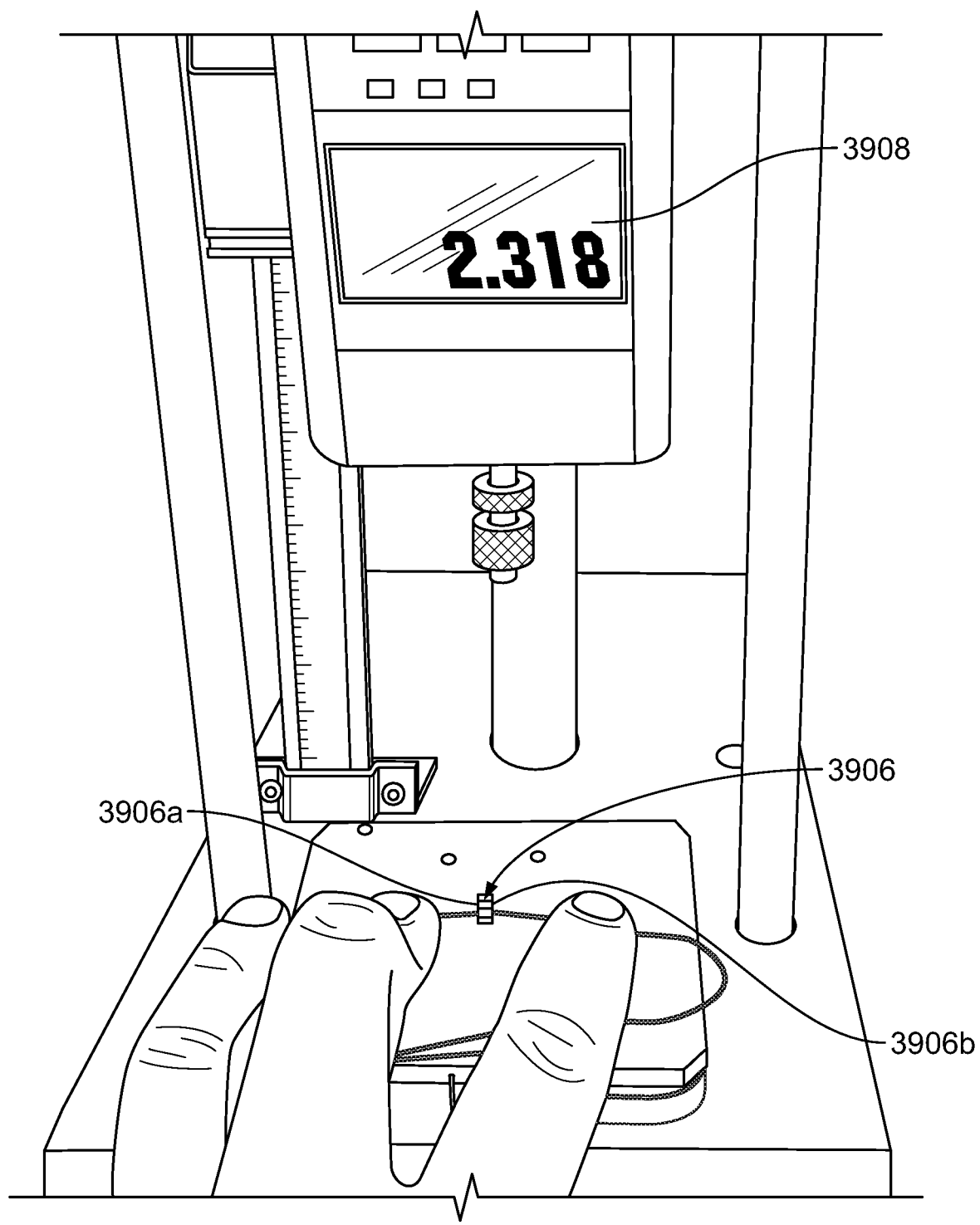
Figure 39C:
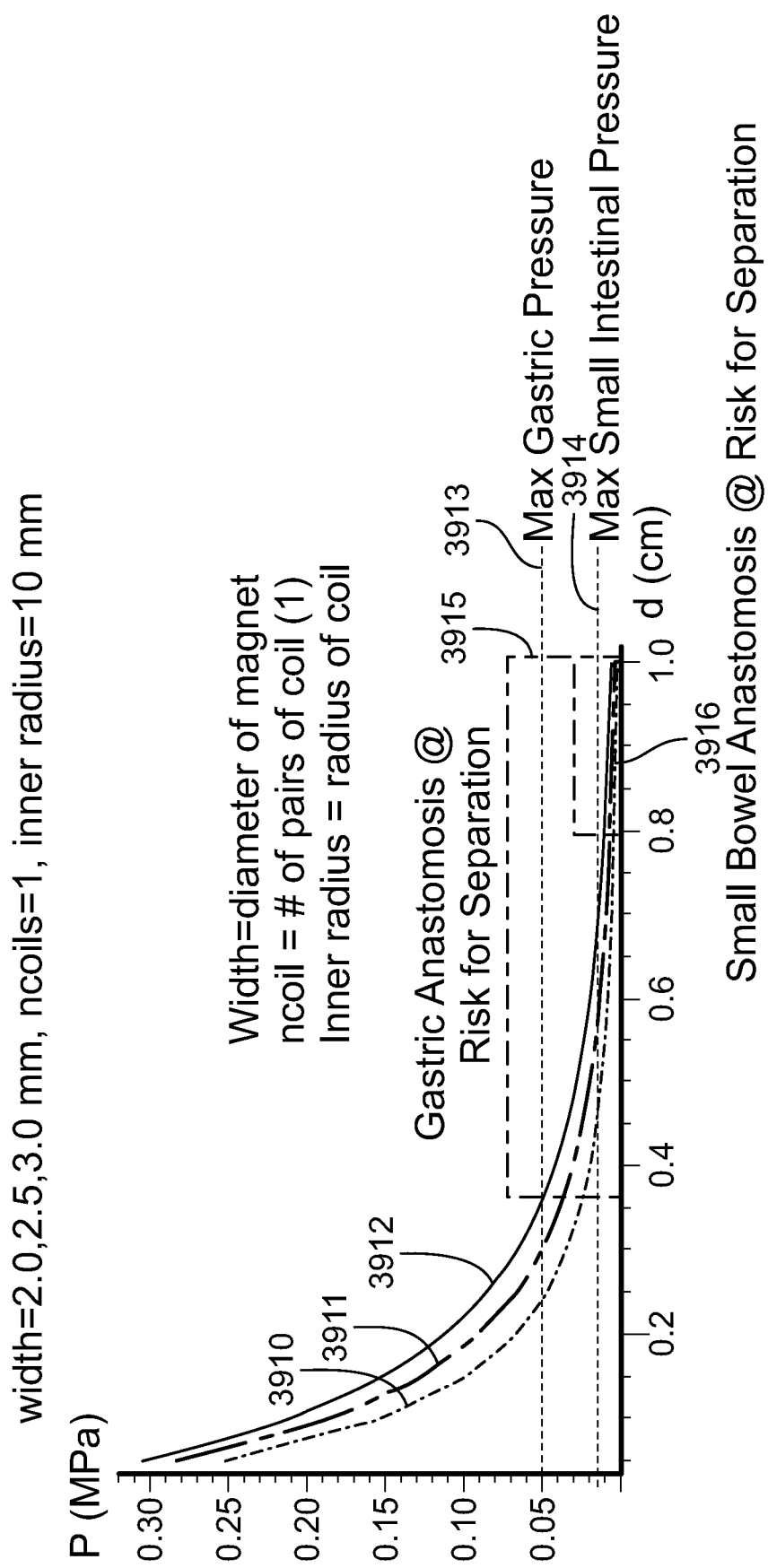
Figure 39D:
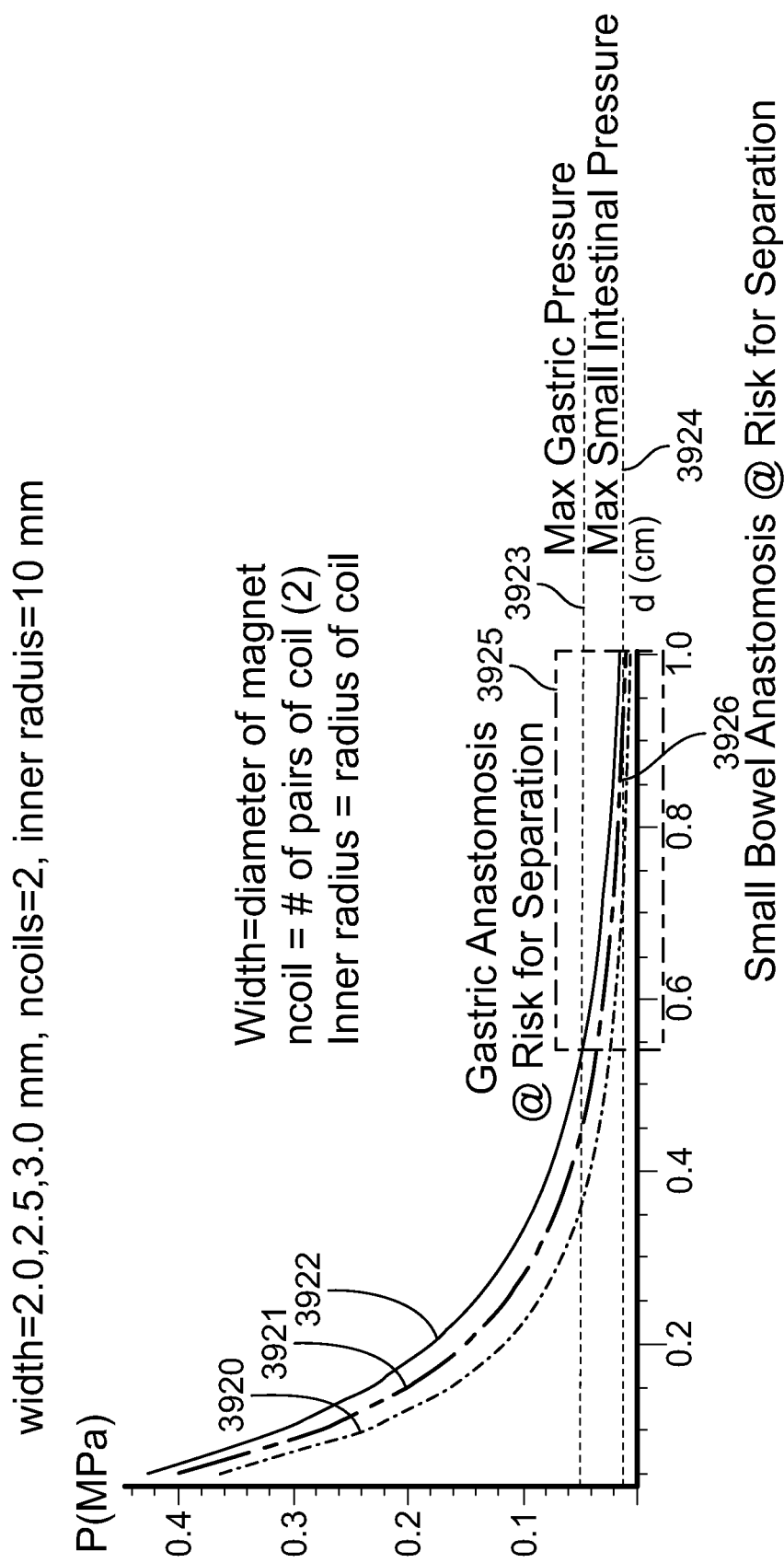
Figure 39E:
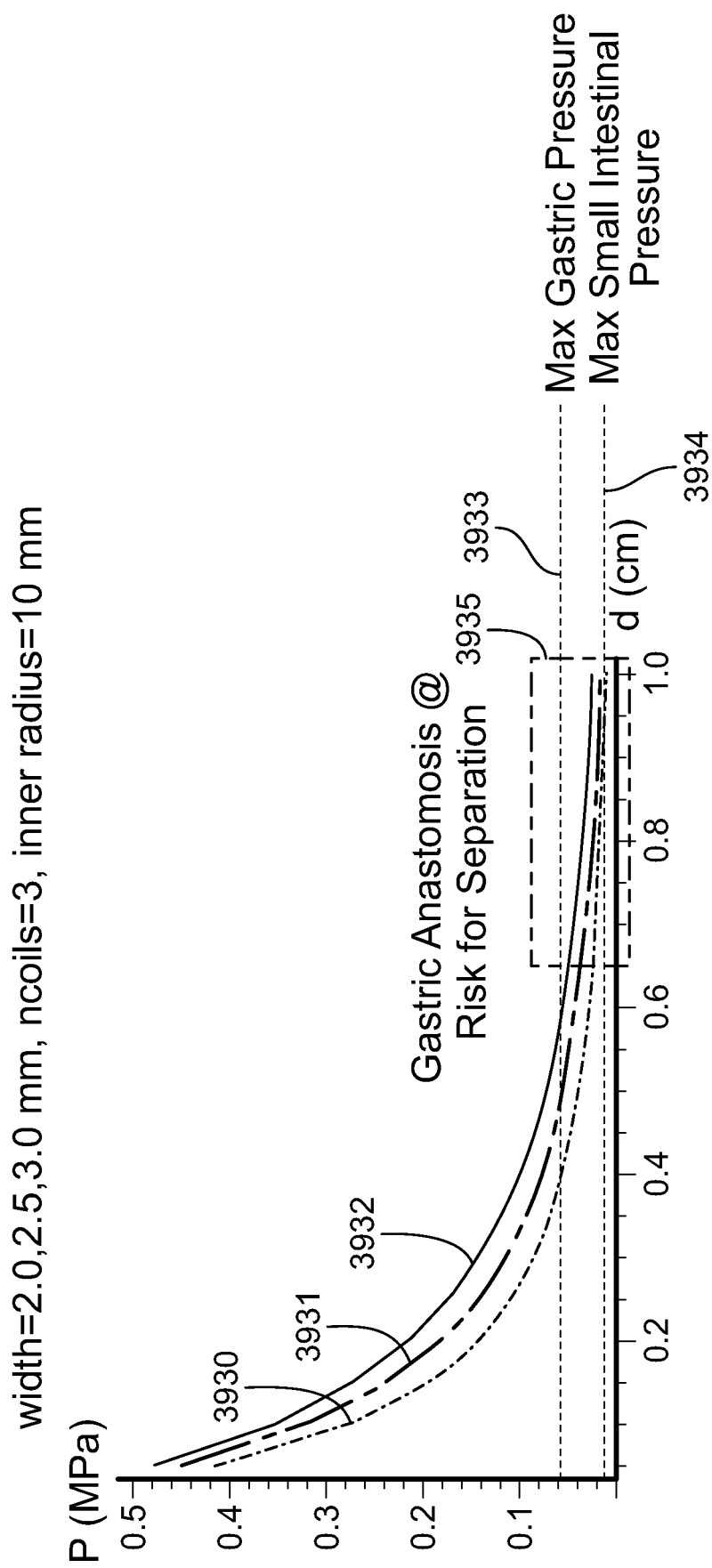
Figure 39F:
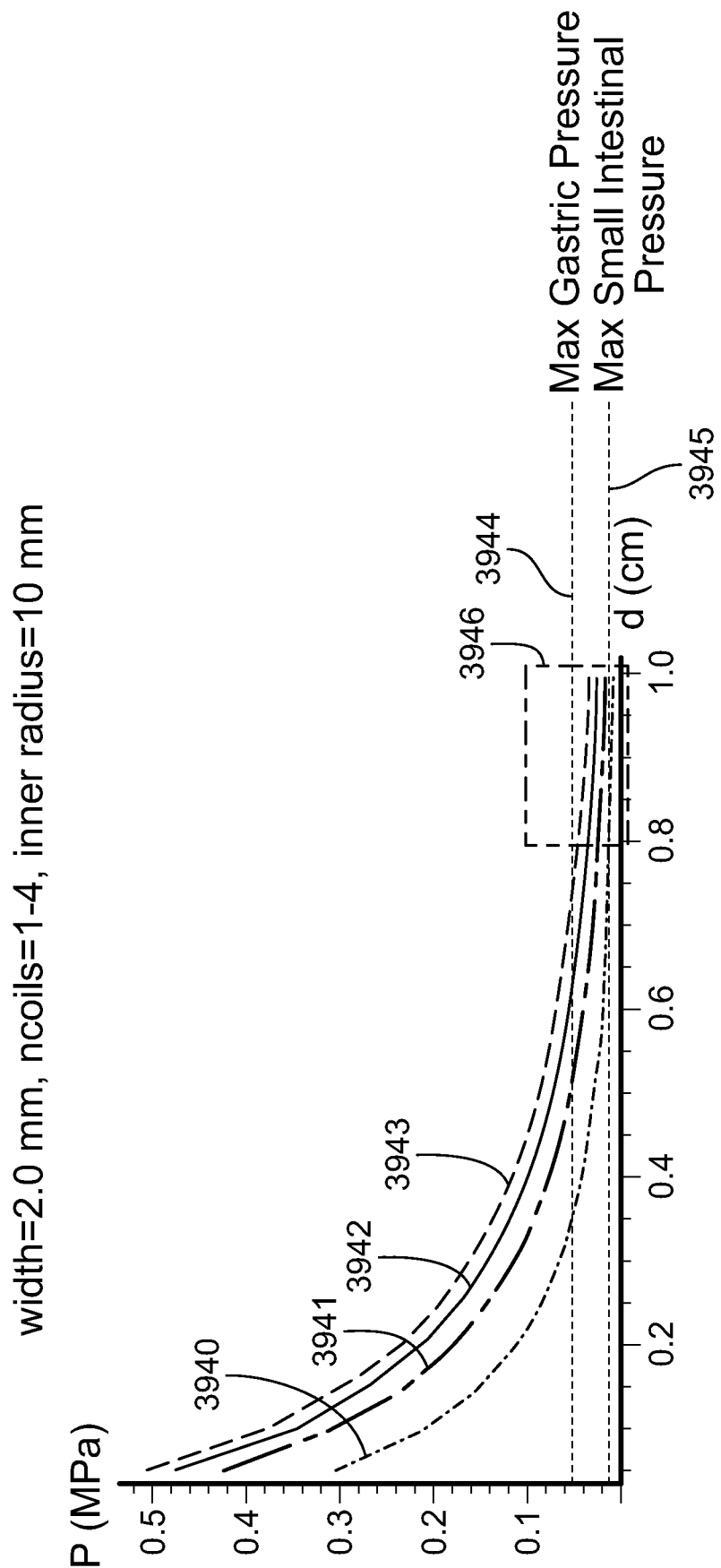
Figure 39G:
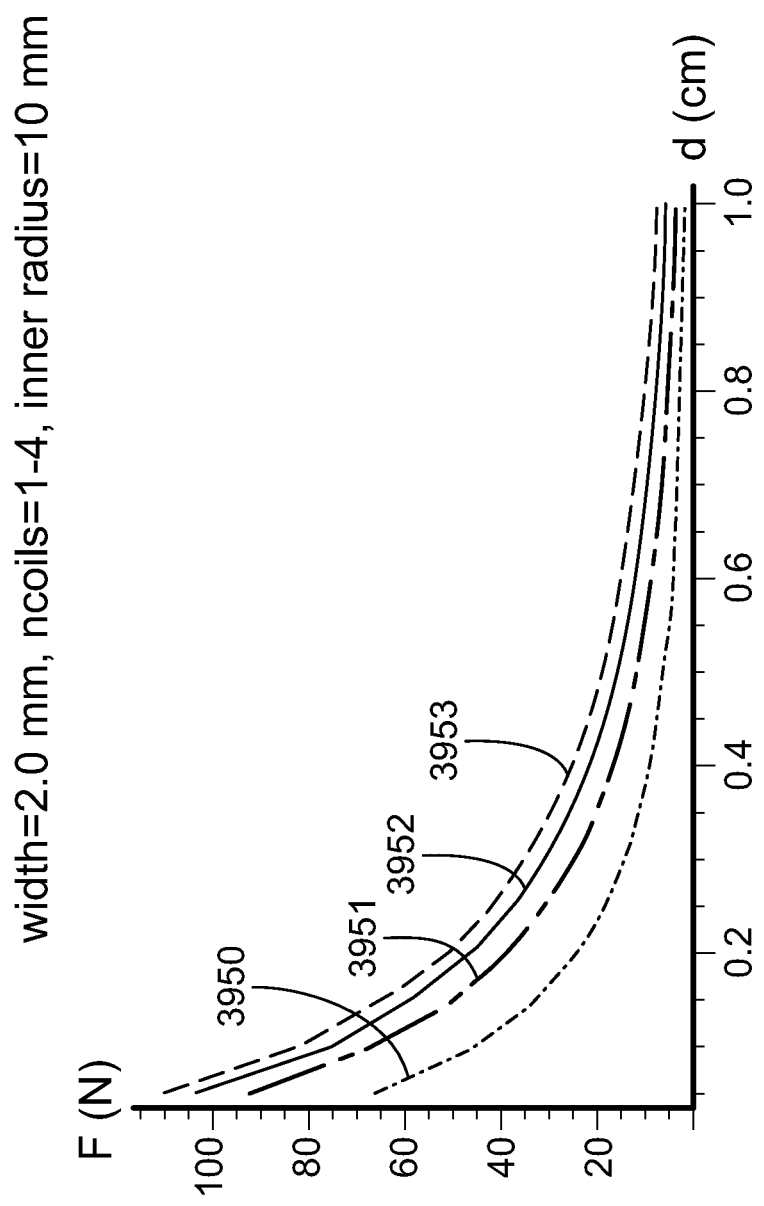
Figure 39H:
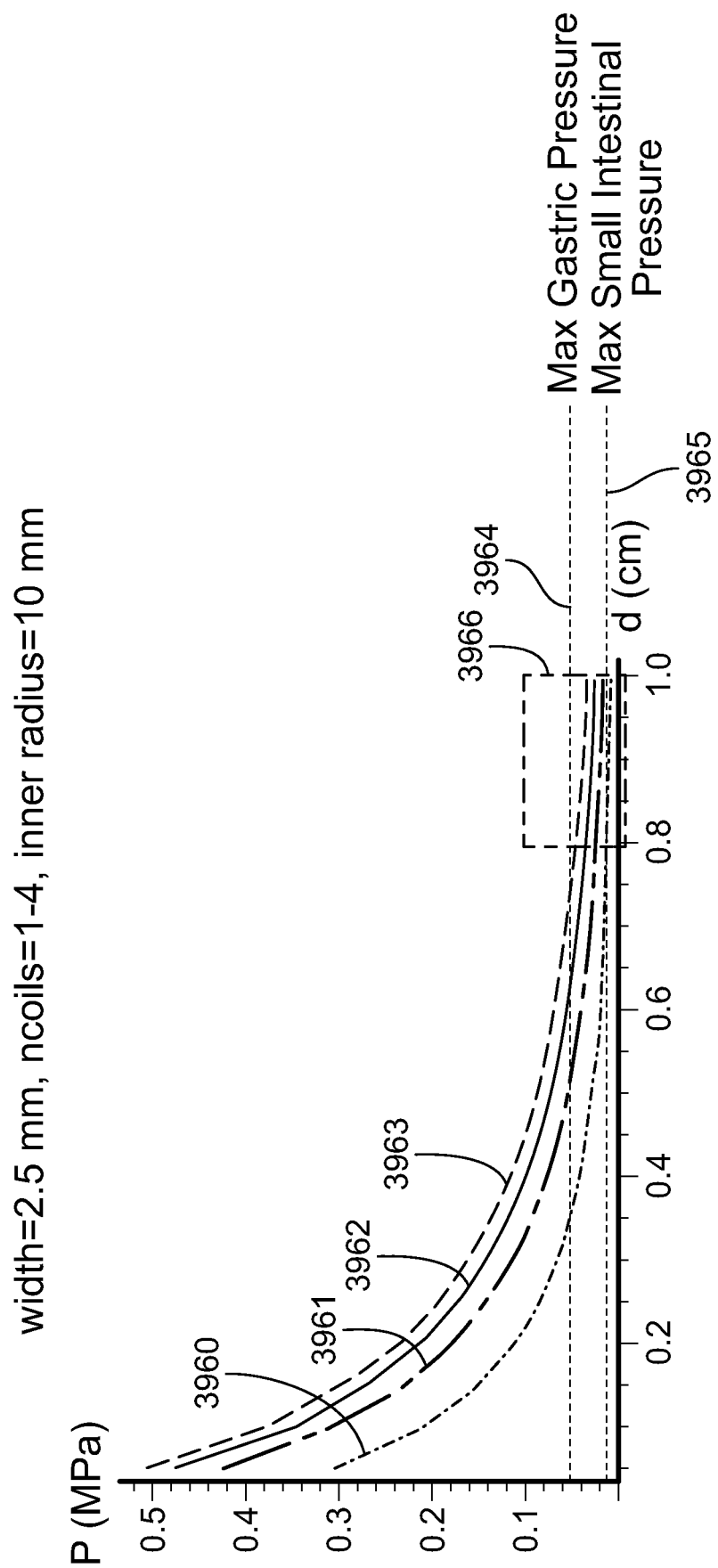
Figure 39I:
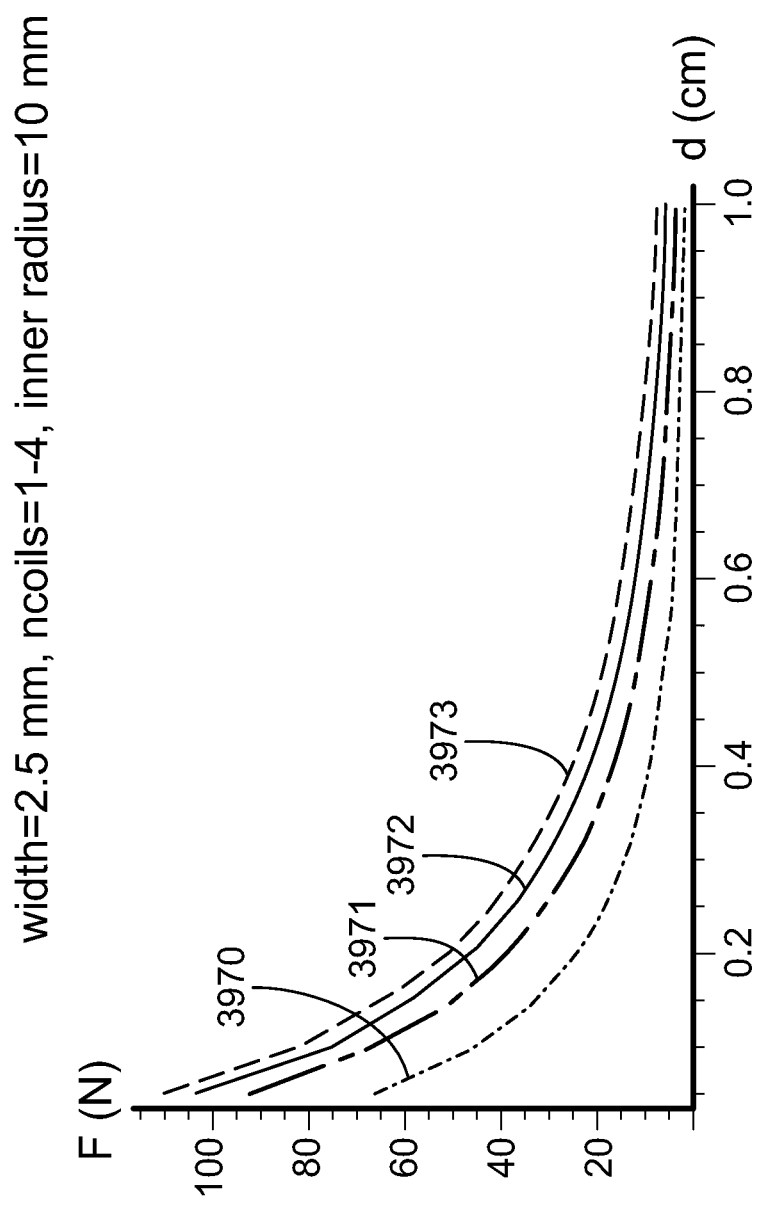
Figure 39K:
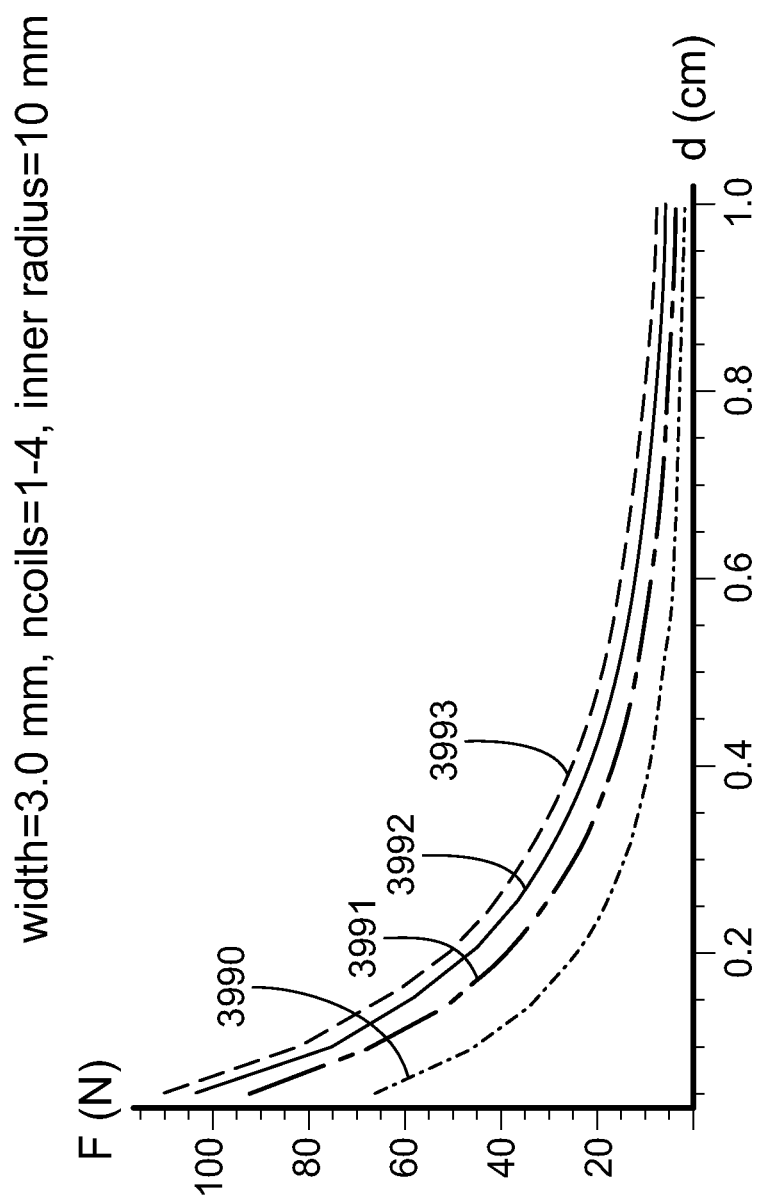
Figure 40C:
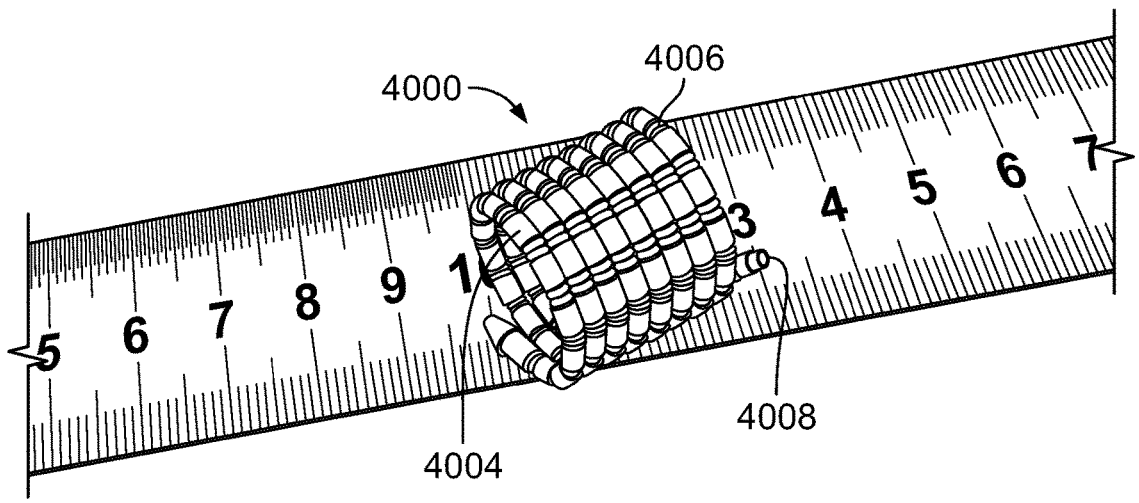
Figure 40D:
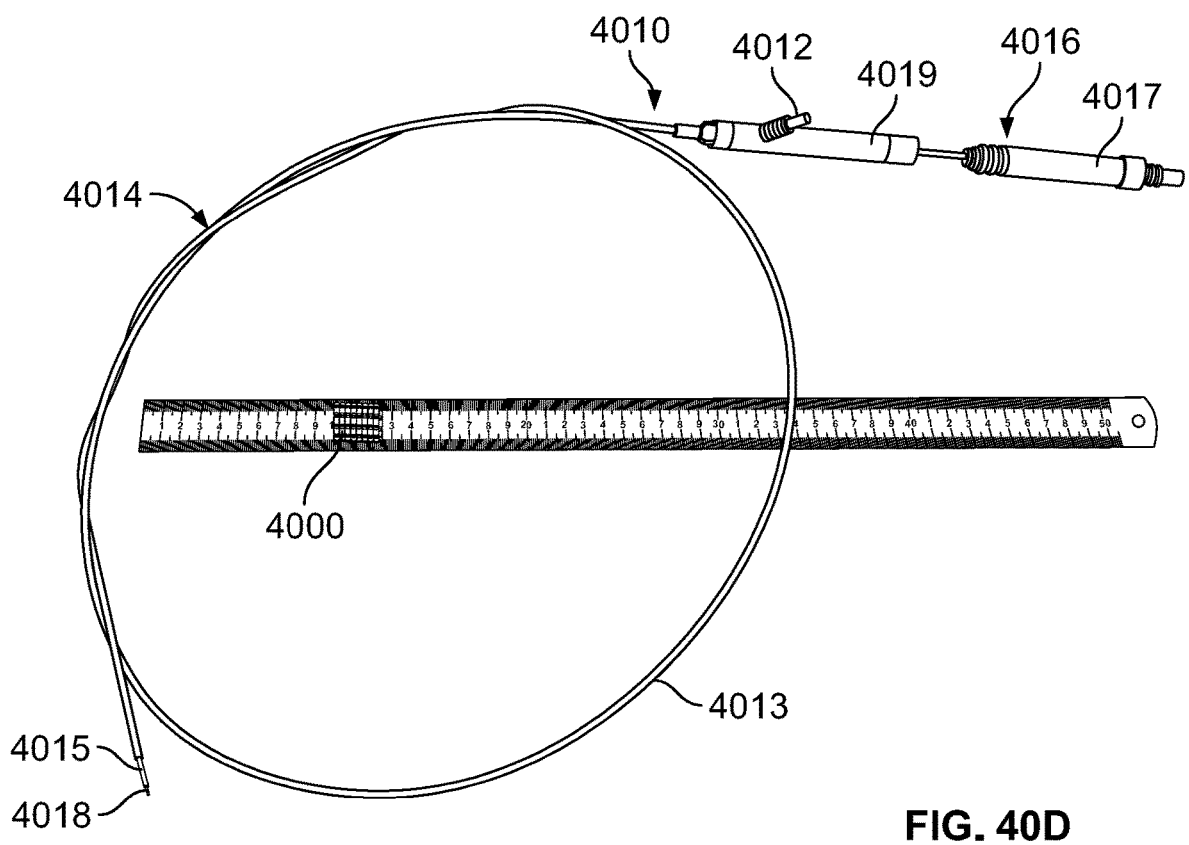
Figure 40E:
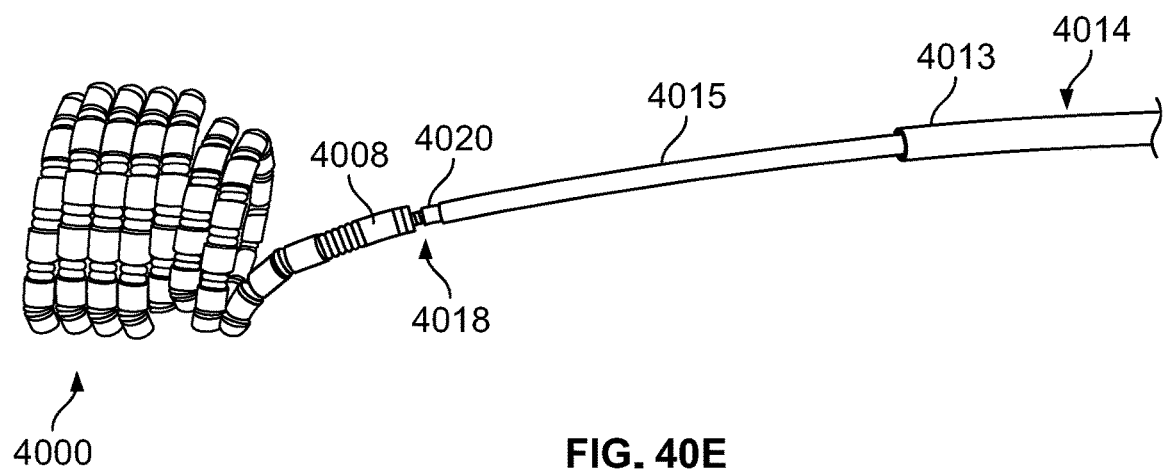
Figure 40F:
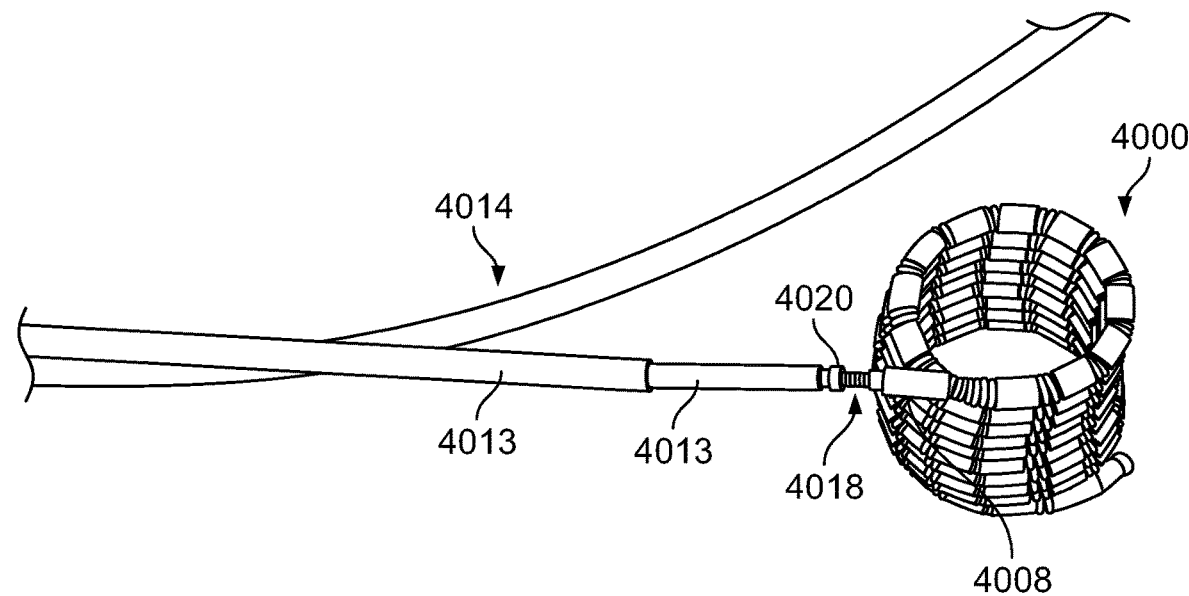
Figure 40G:
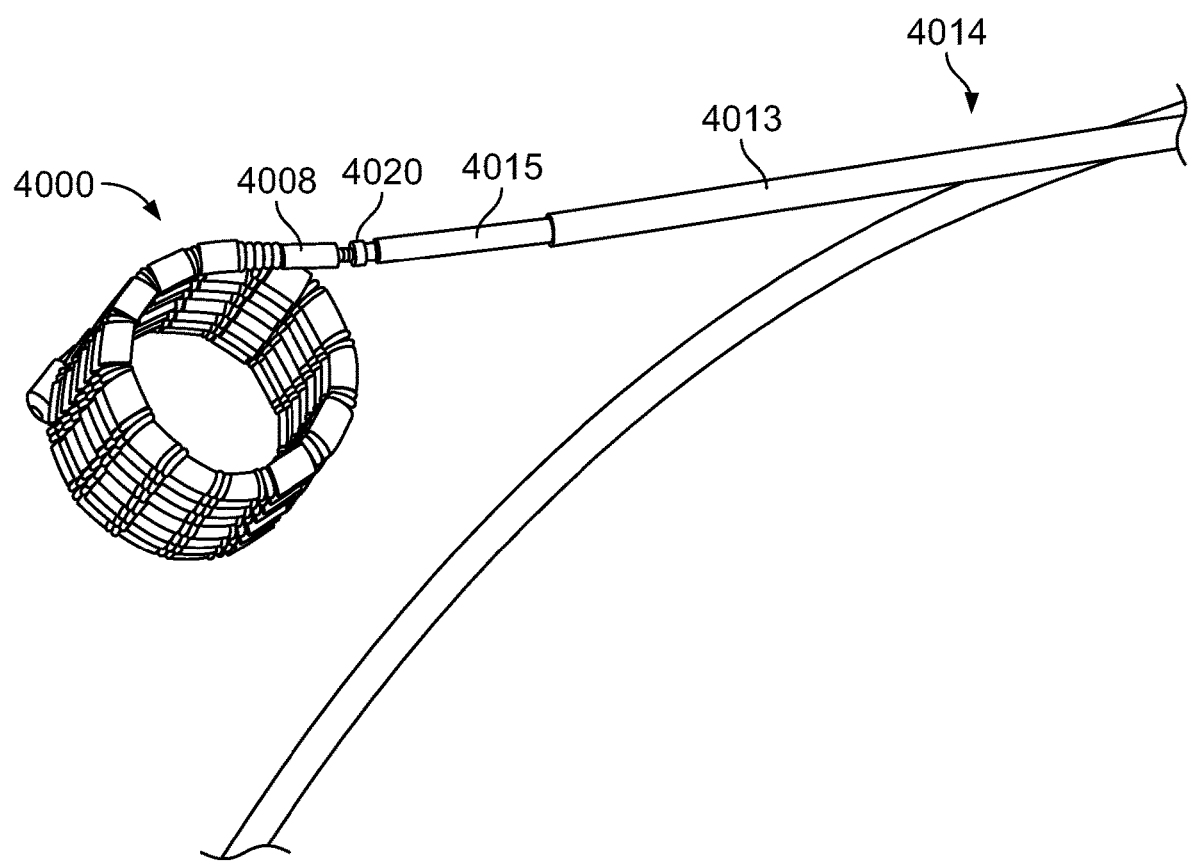
Figure 40H:
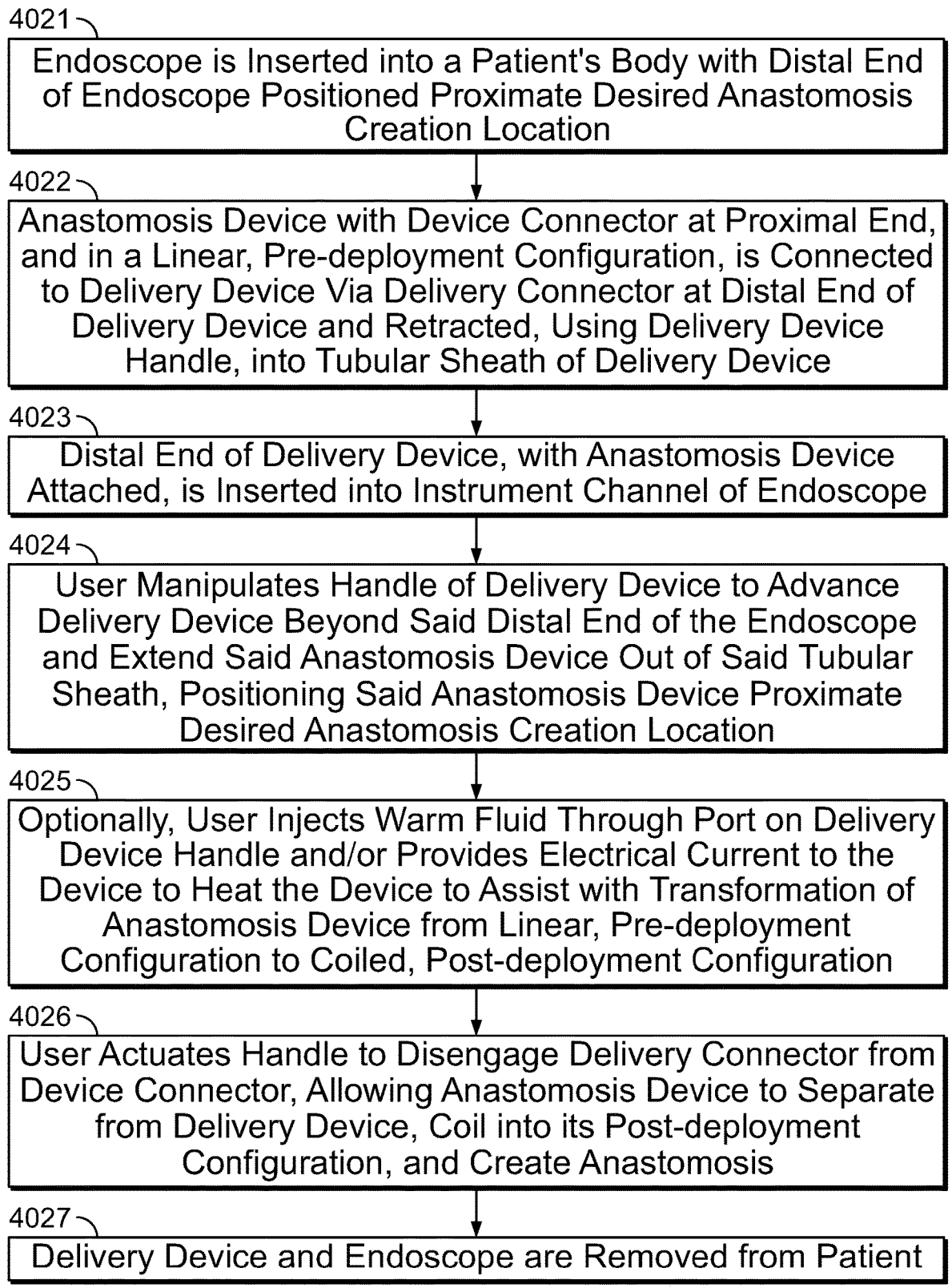

FIG. 36 is a flowchart illustrating the steps of creating an anastomosis by using a shape memory coil with magnets between adjacent organs, in accordance with an embodiment of the present specification; and FIG. 37 is a flowchart illustrating the steps of creating an anastomosis by using a shape memory wire and magnetic compression forces between adjacent organs or structures, in accordance with an embodiment of the present specification;

FIG. 38 is a flowchart illustrating the steps of creating an anastomosis by using a shape memory coil with magnets between adjacent organs, in accordance with an embodiment of the present specification;

FIG. 39A illustrates an exemplary magnet used with a device for creating an anastomosis, in accordance with an embodiment of the present specification;

FIG. 39B illustrates an exemplary magnet used with a device for creating an anastomosis, in accordance with another embodiment of the present specification;

FIG. 39C is a graph illustrating the relationship between compressive pressures and distances between coil loops provided by anastomosis devices having a single coil loop on each side of an anastomosis to be formed, in accordance with an embodiment of the present specification;

FIG. 39D is a graph illustrating the relationship between compressive pressures and distances between coil loops provided by anastomosis devices having two coil loops on each side of an anastomosis to be formed, in accordance with an embodiment of the present specification;

FIG. 39E is a graph illustrating the relationship between compressive pressures and distances between coil loops provided by anastomosis devices having three coil loops on each side of an anastomosis to be formed, in accordance with an embodiment of the present specification;

FIG. 39F is a graph illustrating the relationship between compressive pressures and distances between coil loops provided by anastomosis devices having 2.0 mm diameter magnets and varying numbers of coil loops on each side of an anastomosis to be formed, in accordance with an embodiment of the present specification;

FIG. 39G is a graph illustrating the relationship between force and distances between coil loops provided by anastomosis devices having 2.0 mm diameter magnets and varying numbers of coil loops on each side of an anastomosis to be formed, in accordance with an embodiment of the present specification;

FIG. 39H is a graph illustrating the relationship between compressive pressures and distances between coil loops provided by anastomosis devices having 2.5 mm diameter magnets and varying numbers of coil loops on each side of an anastomosis to be formed, in accordance with embodiments of the present specification;

FIG. 39I is a graph illustrating the relationship between force and distances between coil loops provided by anastomosis devices having 2.5 mm diameter magnets and varying numbers of coil loops on each side of an anastomosis to be formed, in accordance with embodiments of the present specification;

FIG. 39J is a graph illustrating the relationship between compressive pressures and distances between coil loops provided by anastomosis devices having 3.0 mm diameter magnets and varying numbers of coil loops on each side of an anastomosis to be formed, in accordance with embodiments of the present specification;

FIG. 39K is a graph illustrating the relationship between force and distances between coil loops provided by anastomosis devices having 3.0 mm diameter magnets and varying numbers of coil loops on each side of an anastomosis to be formed, in accordance with embodiments of the present specification;

FIG. 40A illustrates an exemplary device for creating an anastomosis in a pre-coiled configuration, in accordance with an embodiment of the present specification;

FIG. 40B illustrates the device for creating an anastomosis of FIG. 40A in a coiled configuration;

FIG. 40C illustrates another view of the device for creating an anastomosis of FIG. 40A in a coiled configuration;

FIG. 40D illustrates a delivery device for delivering the anastomosis device shown in FIGS. 40A, 40B, and 40C in a desired location within a body, in accordance with an embodiment of the present specification;

FIG. 40E illustrates the delivery device shown in FIG. 40D connected to the coiled anastomosis device shown in FIGS. 40B and 40C, in accordance with an embodiment of the present specification;

FIG. 40F illustrates another view of the delivery device shown in FIG. 40D connected to the coiled anastomosis device shown in FIGS. 40B and 40C, in accordance with an embodiment of the present specification;

FIG. 40G illustrates another view of the delivery device shown in FIG. 40D connected to the coiled anastomosis device shown in FIGS. 40B and 40C, in accordance with an embodiment of the present specification;

FIG. 40H is a flowchart listing the steps involved in a method of deploying an anastomosis device using a delivery device in accordance with one embodiment of the present specification.

Figure 41:
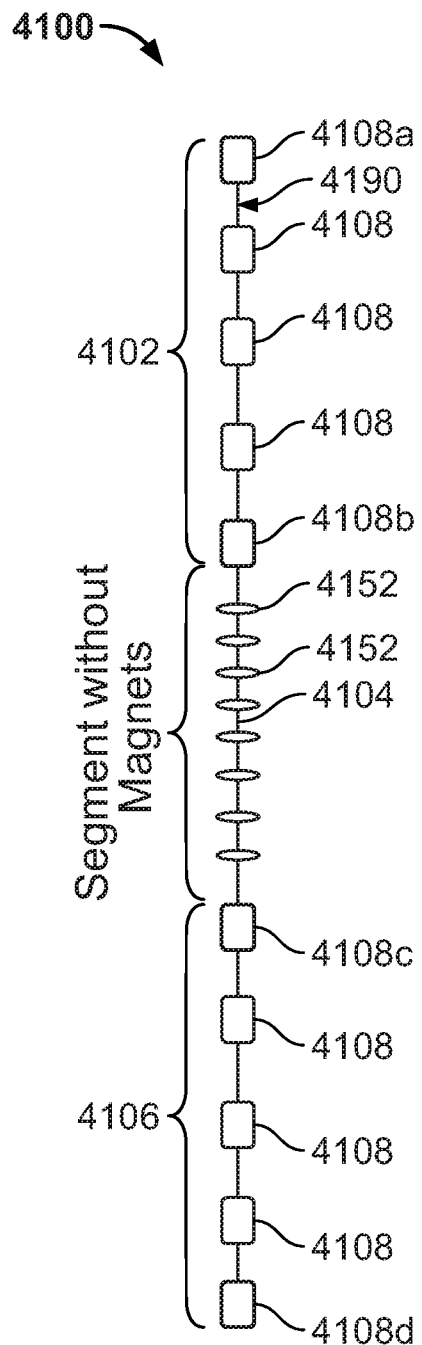
Figure 42:
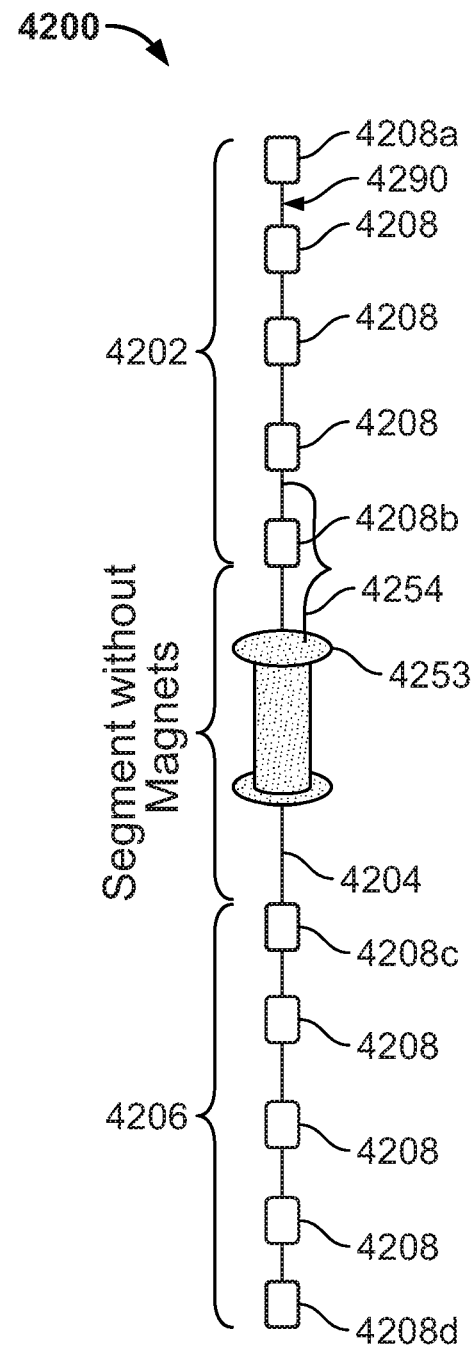
Figure 43A:
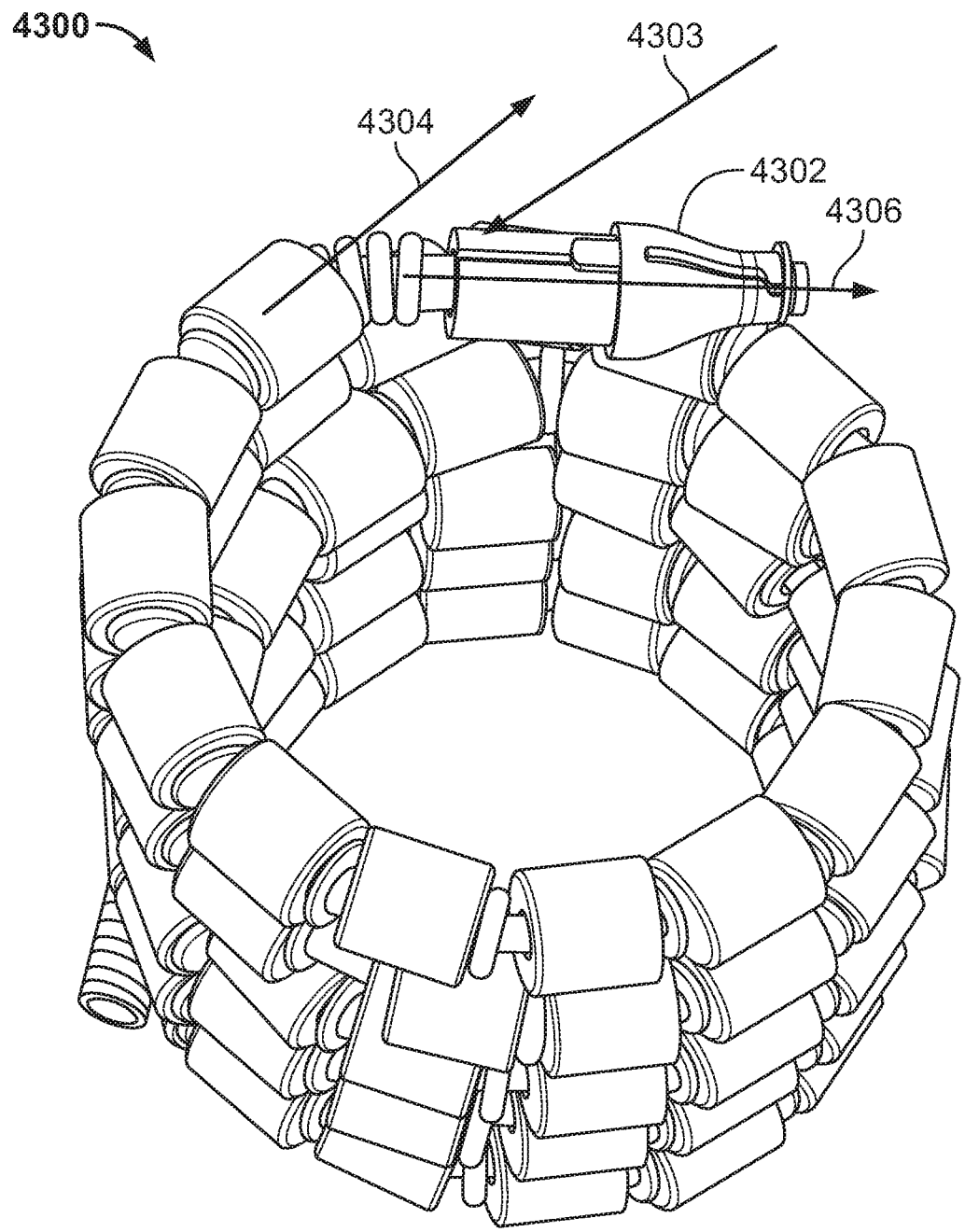
Figure 43C:
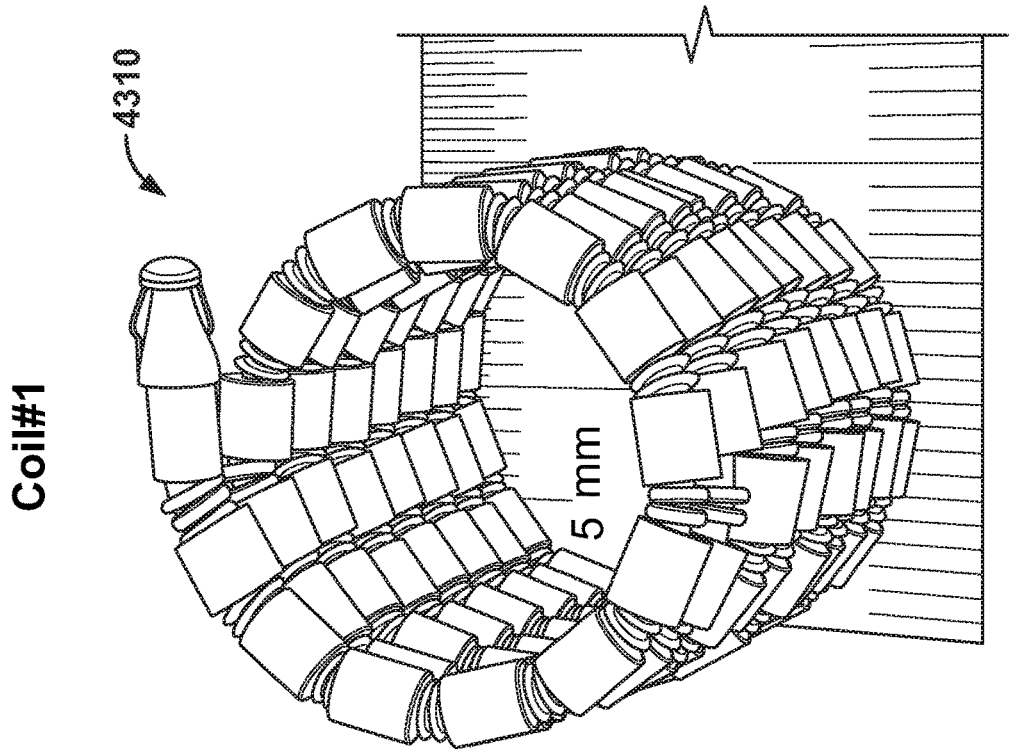
Figure 43B:
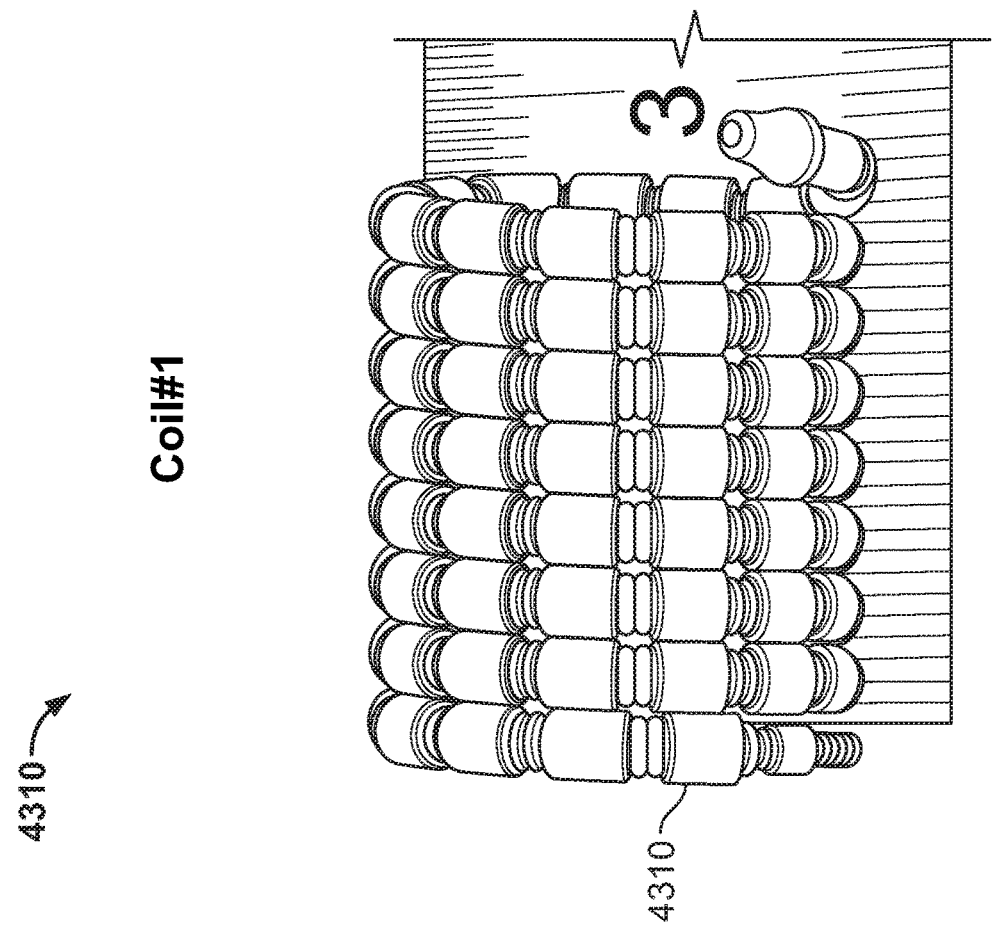
Figure 43D:
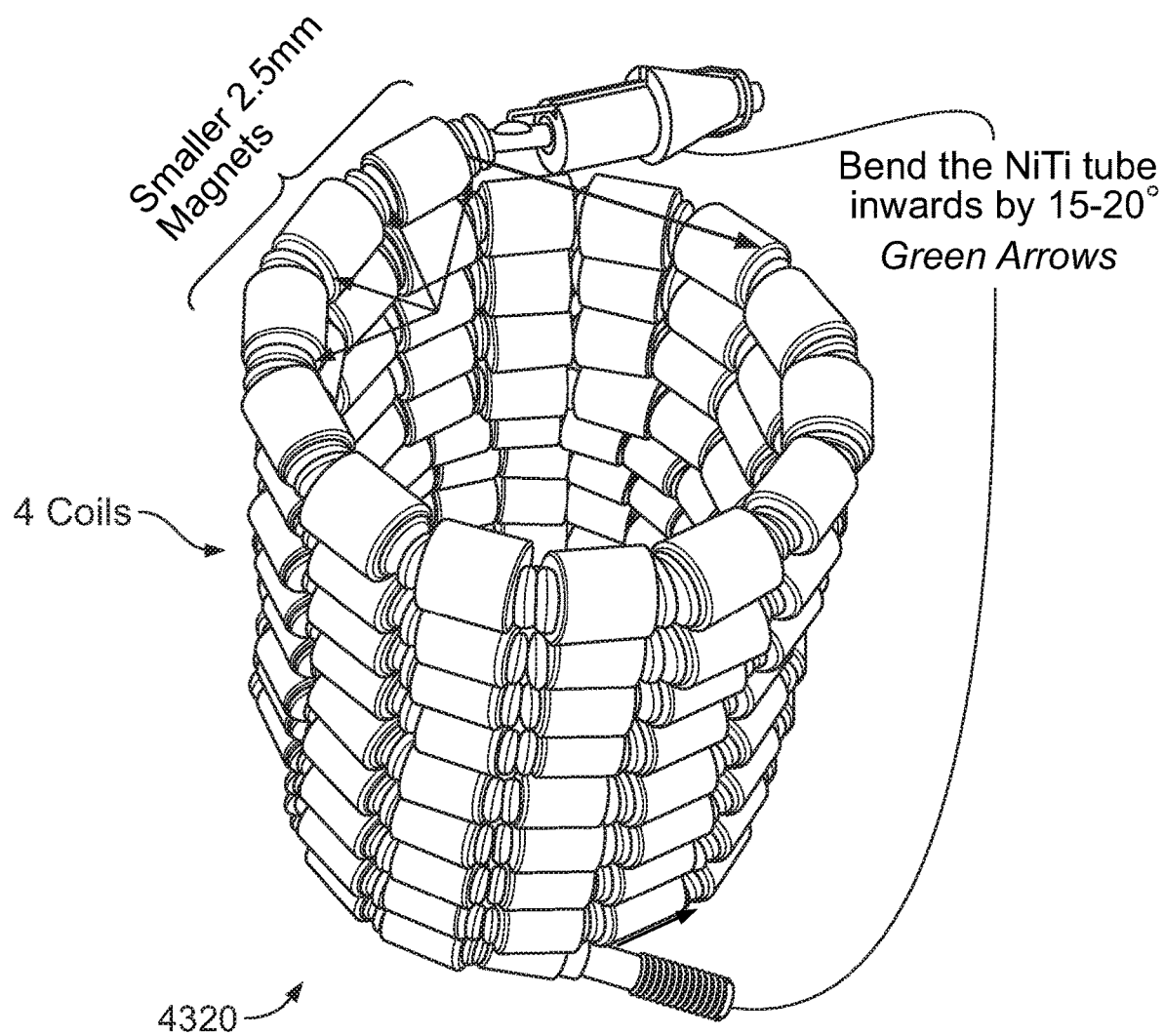
Figure 44F:
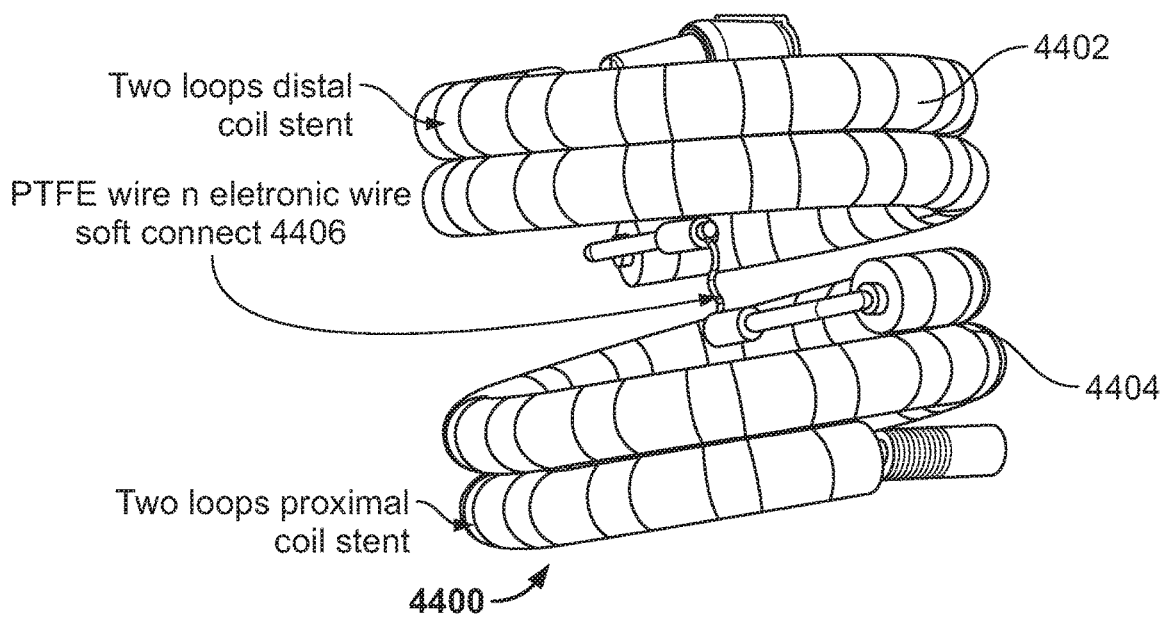
Figure 45:
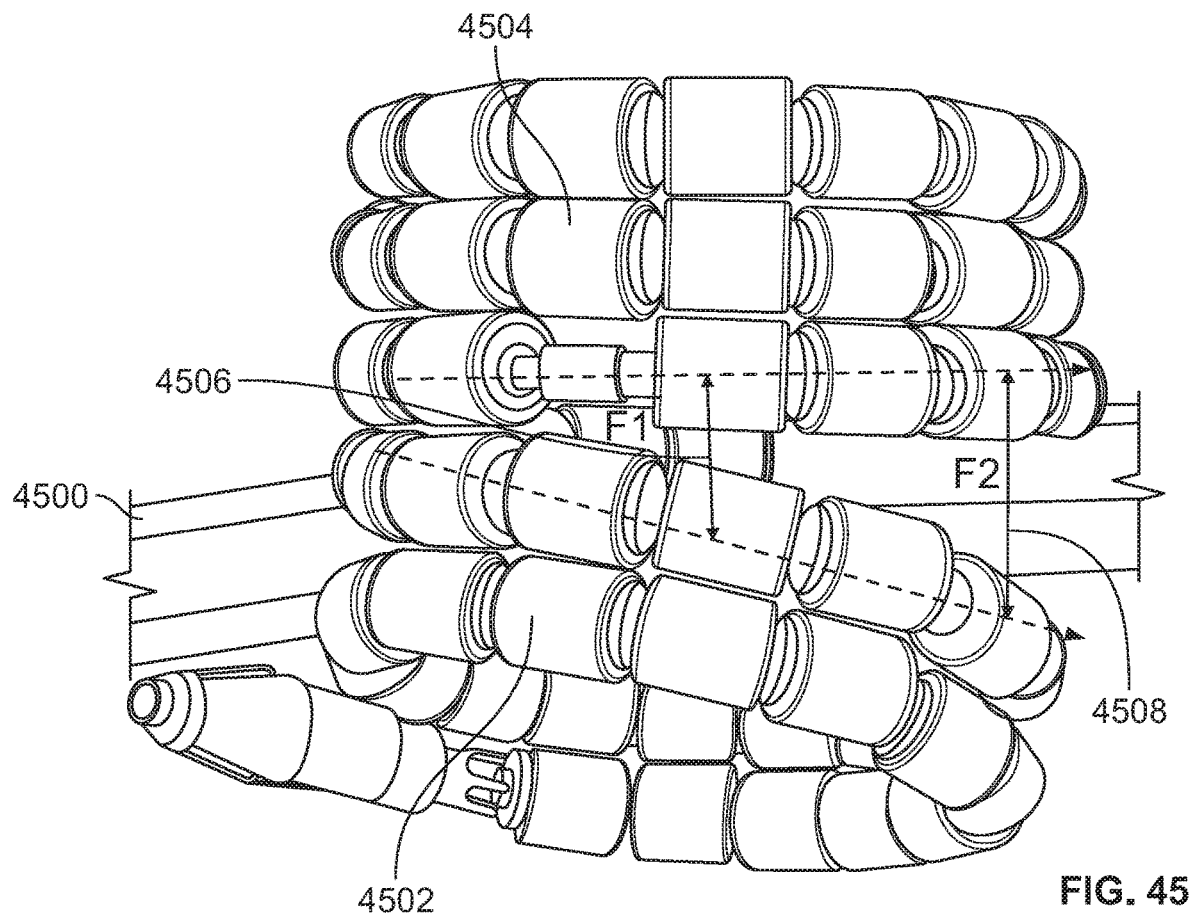
Figure 46A:
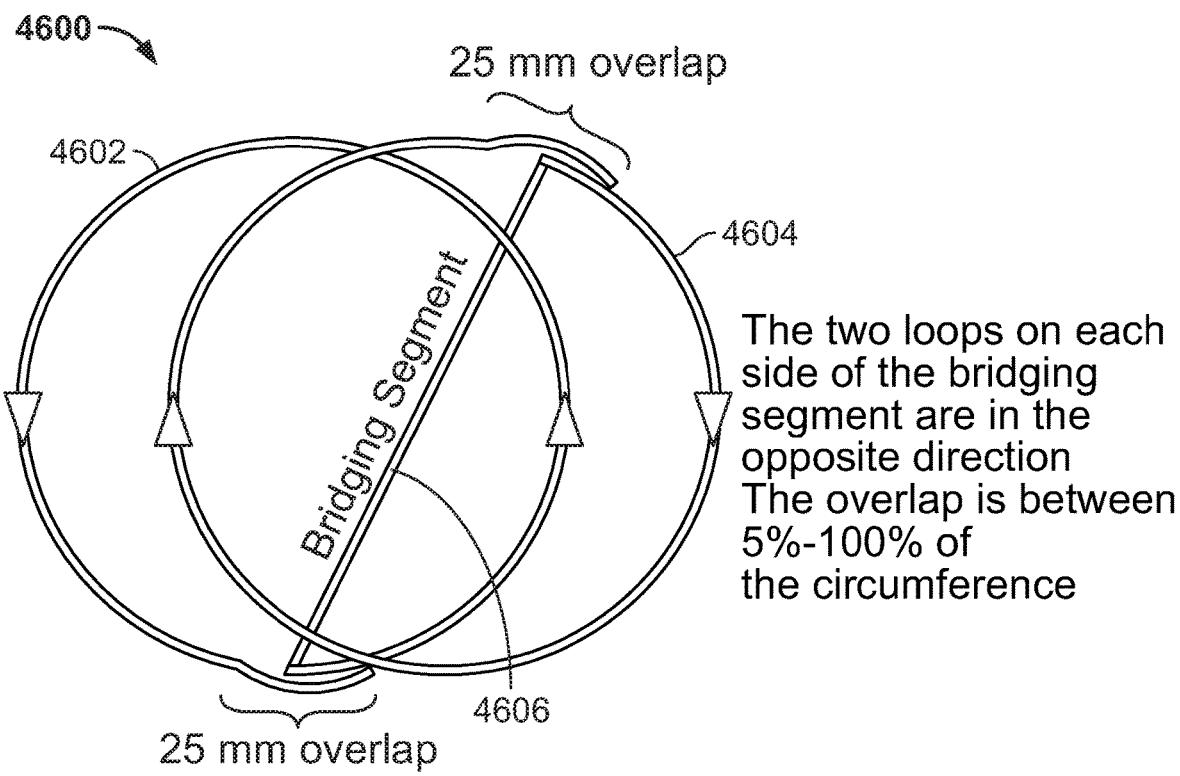
Figure 46B:
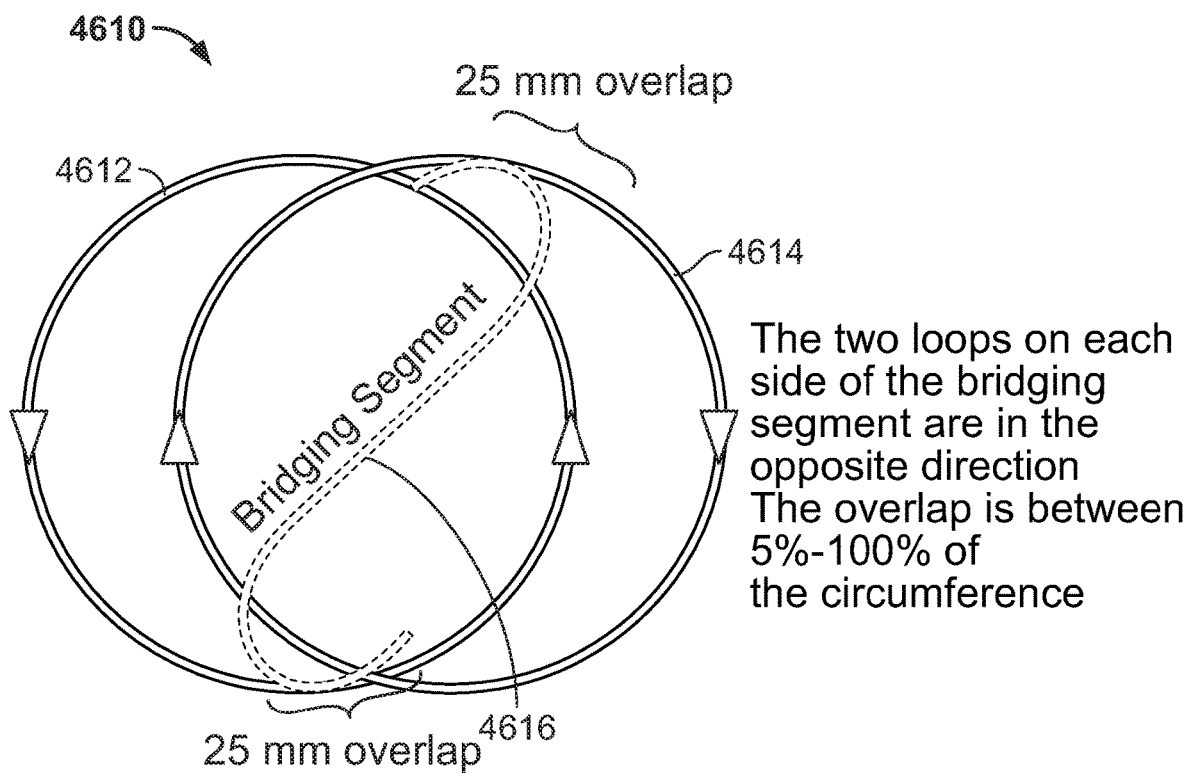
Figure 46D:
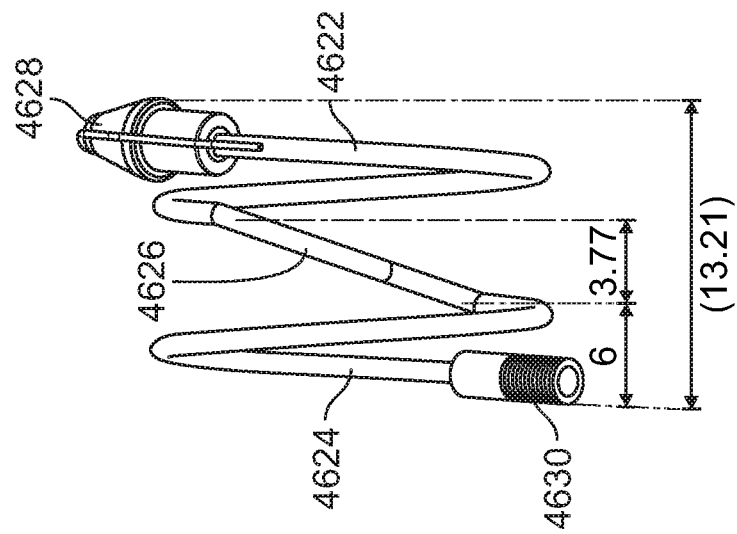
Figure 46C:
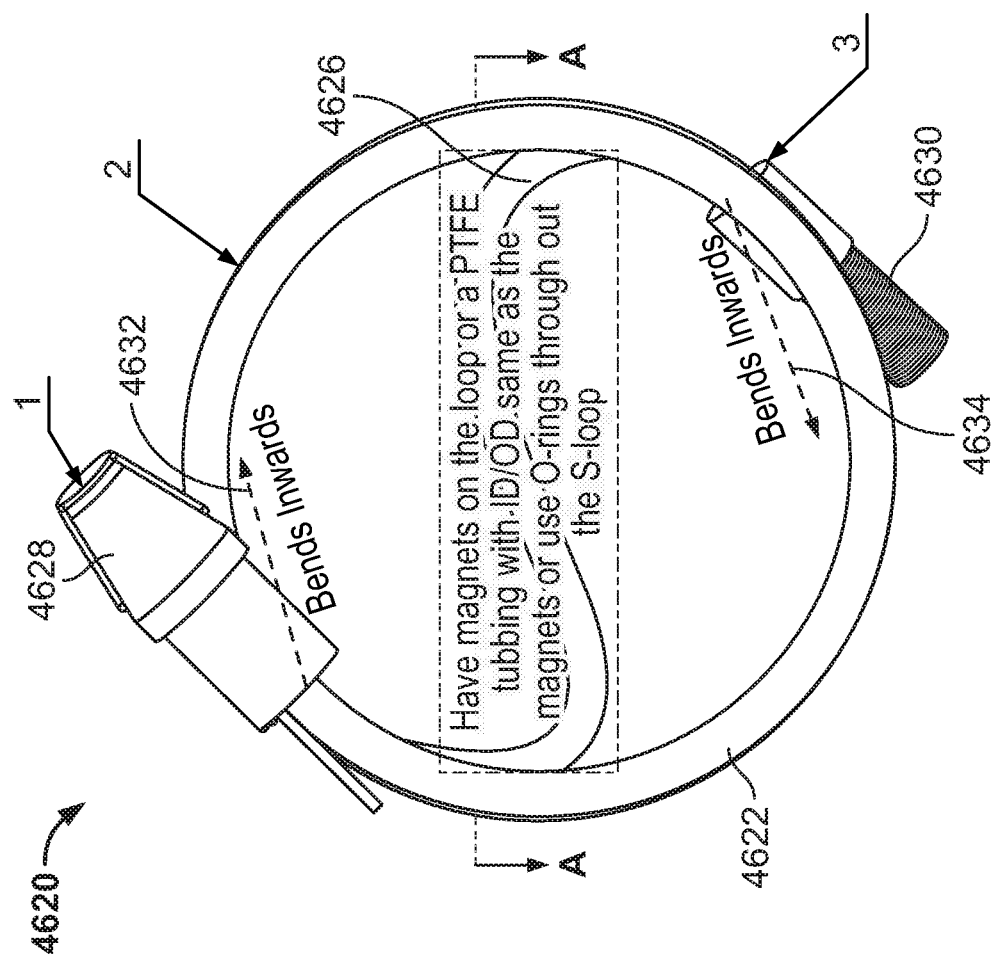
Figure 47C:
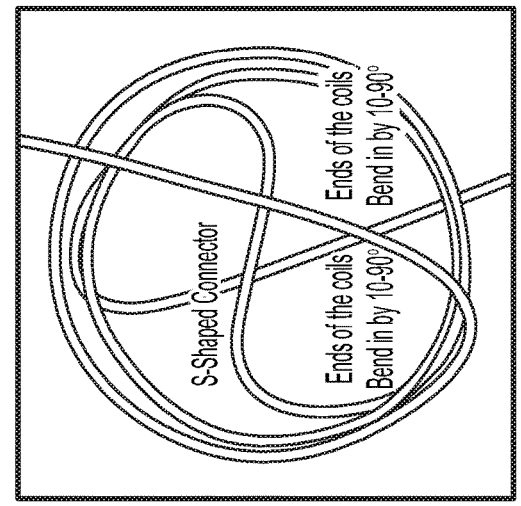
Figure 47B:
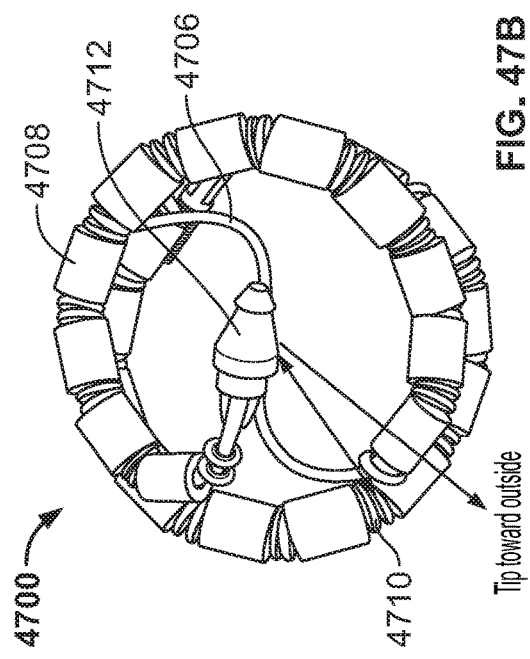
Figure 47A:
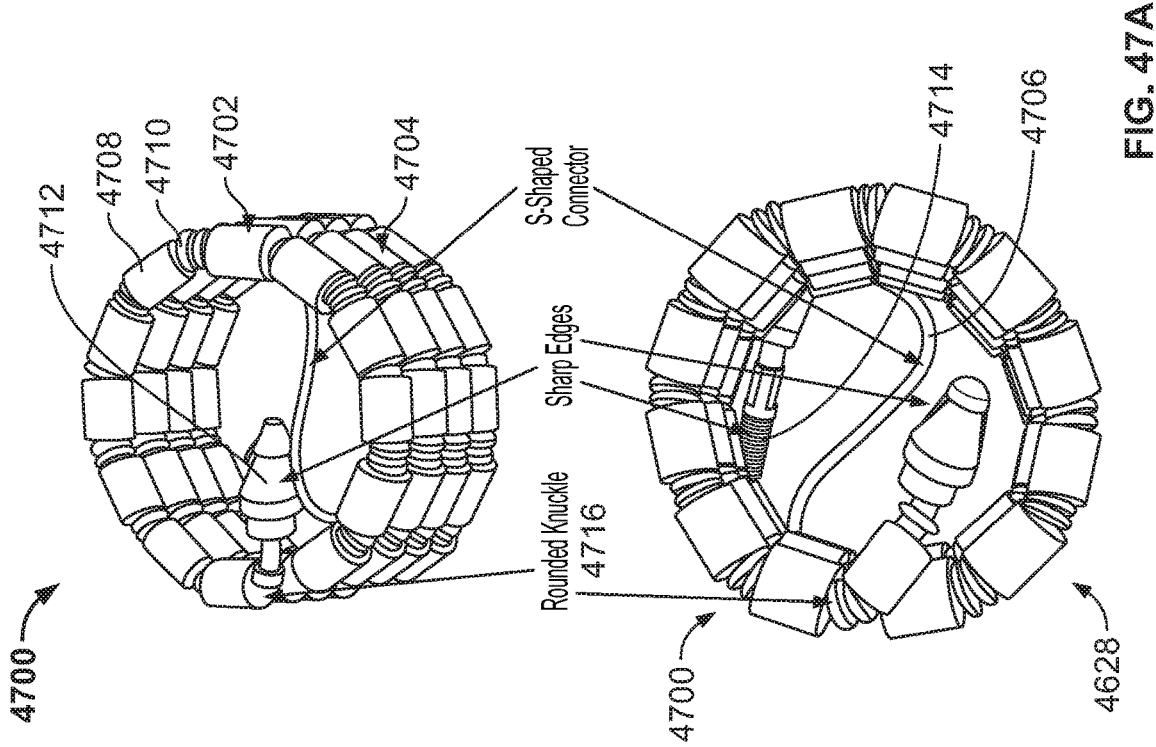
Figure 47E:
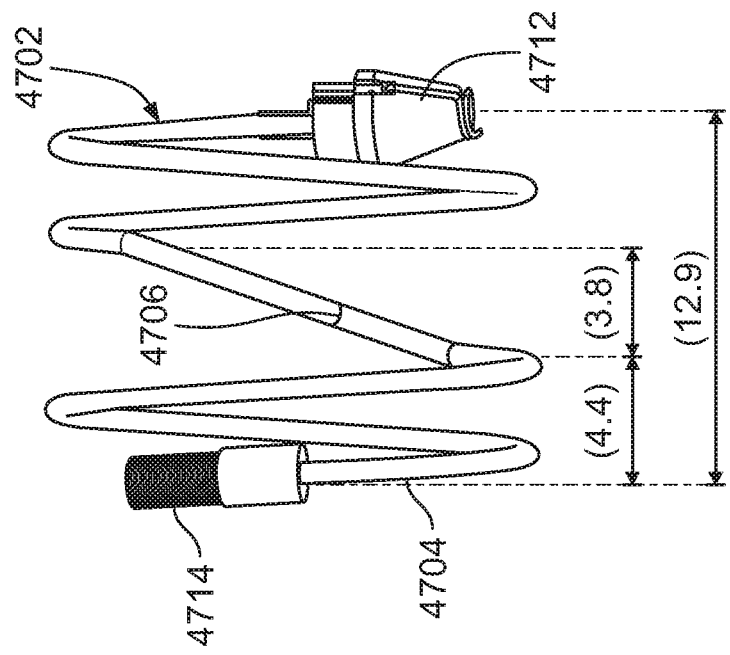
Figure 47D:
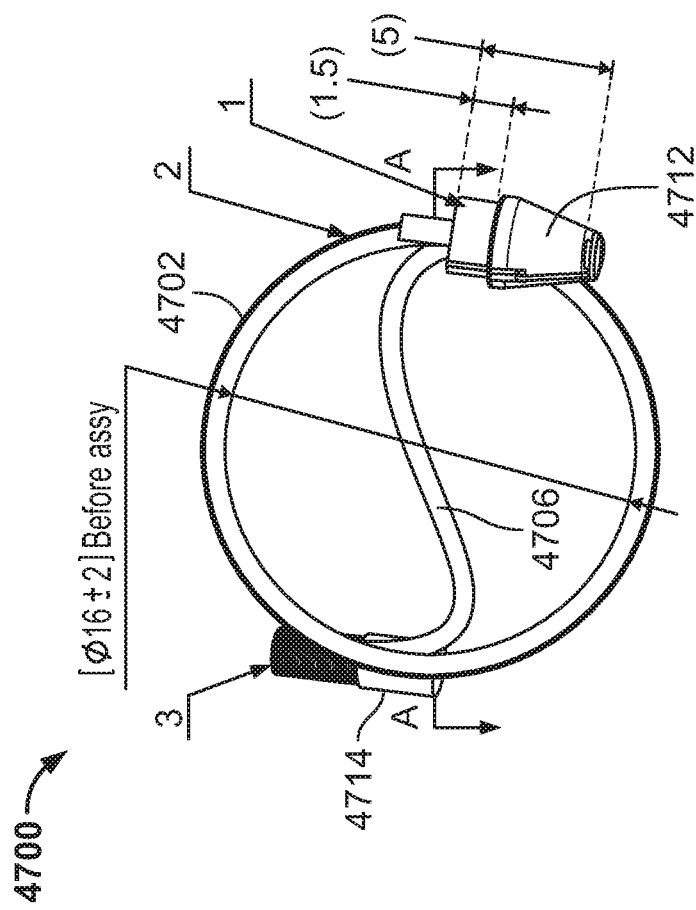
Figure 47G:
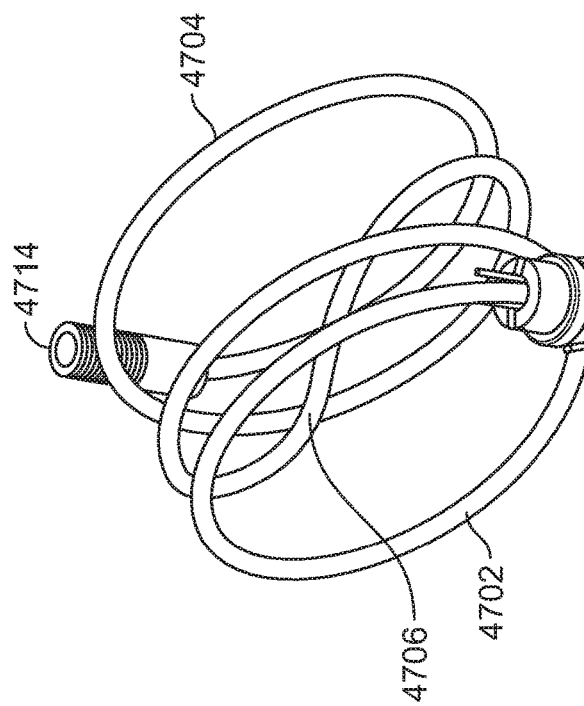
Figure 47H:
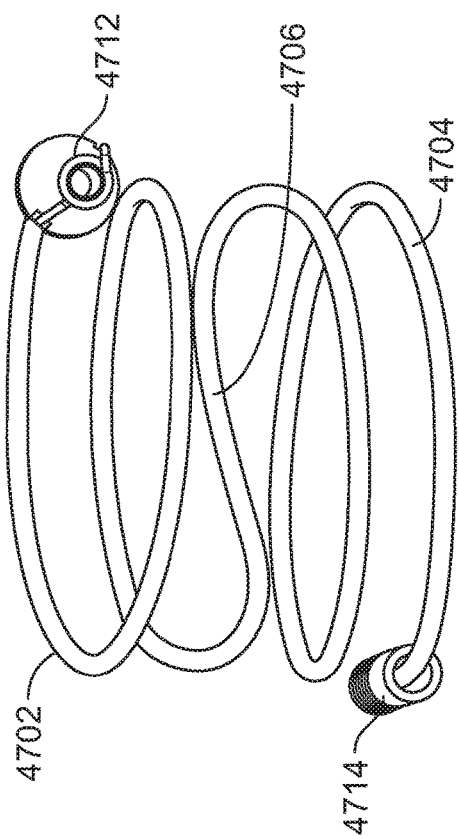
Figure 47F:
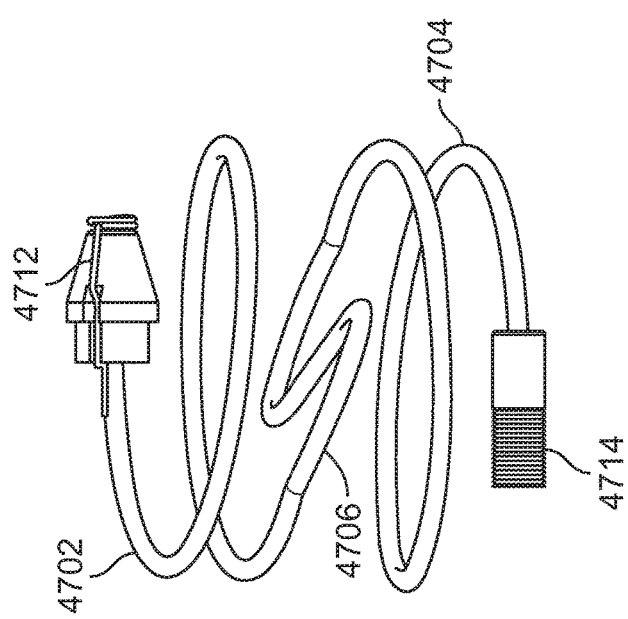
Figure 47J:
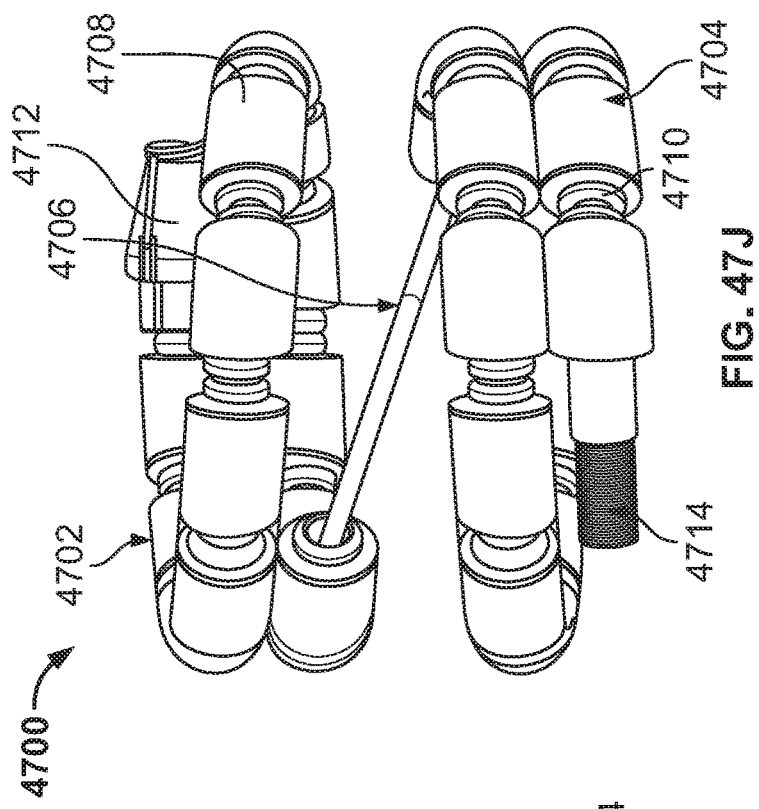
Figure 47I:
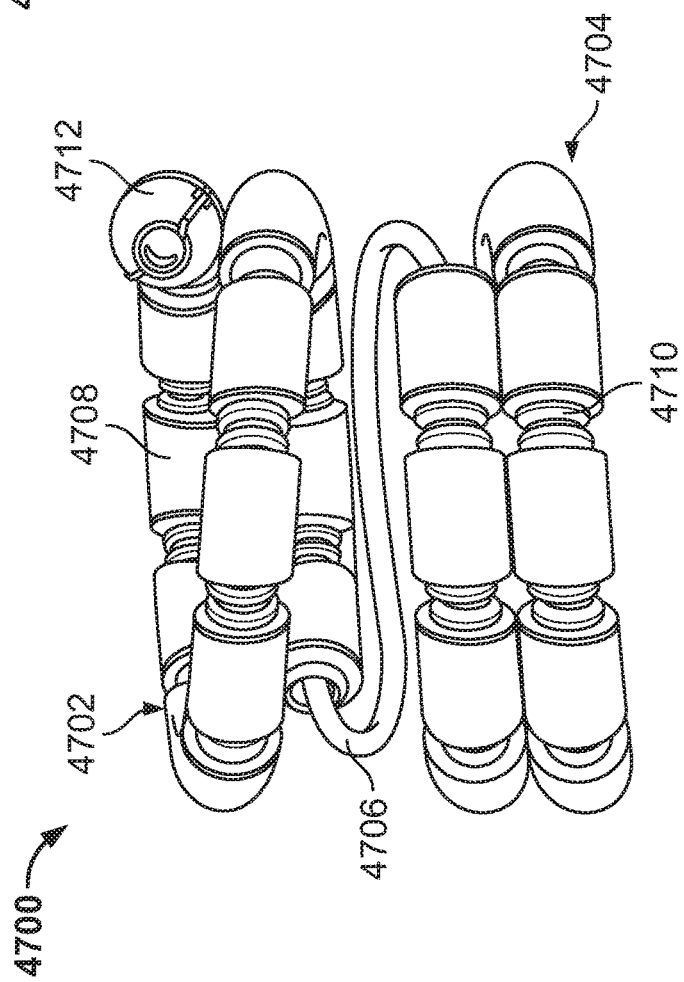
Figure 47L:
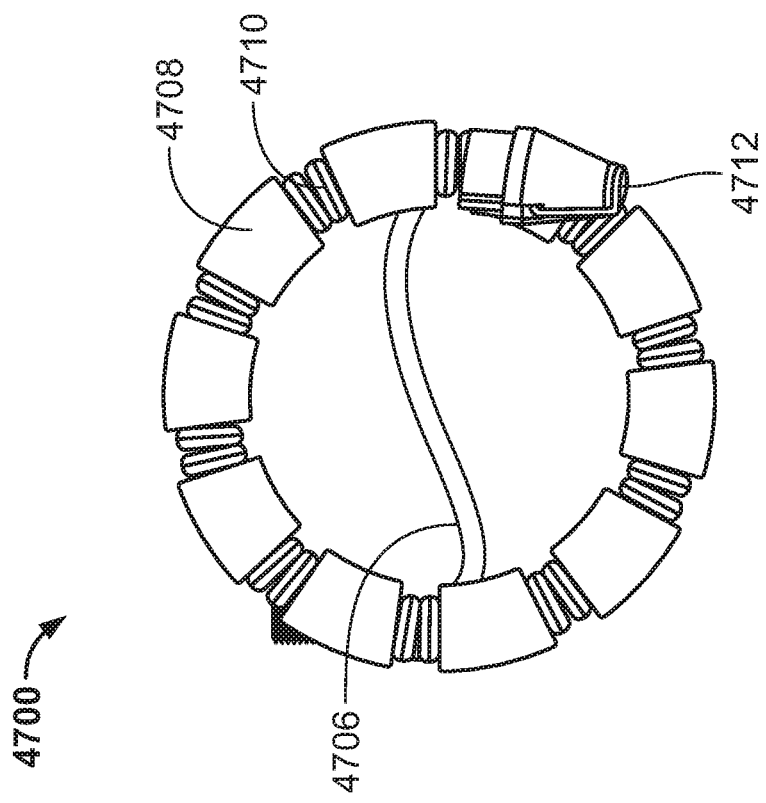
Figure 47K:
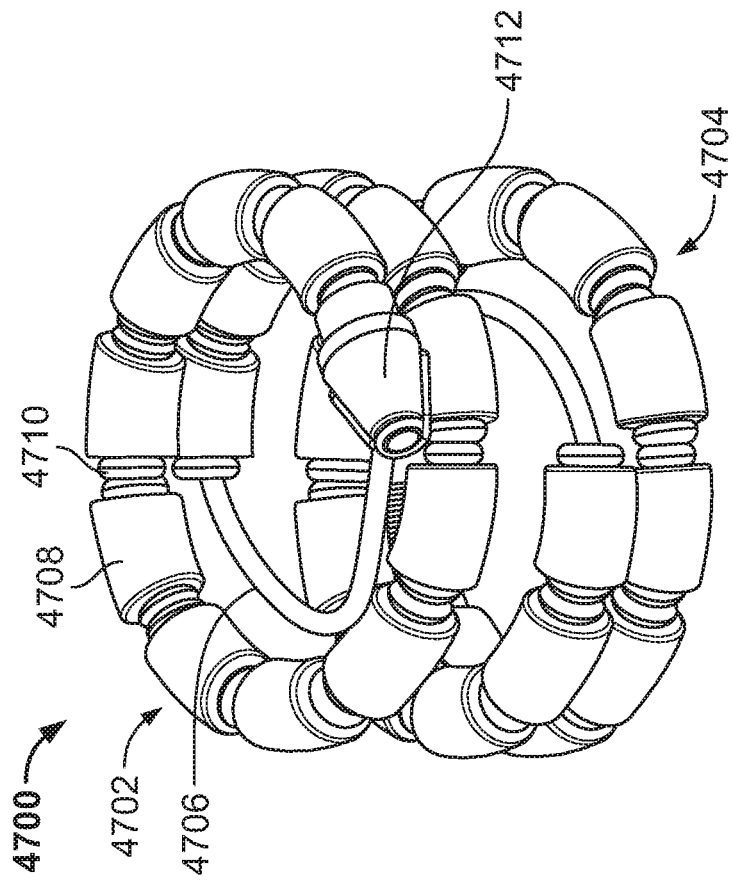
Figure 47N:
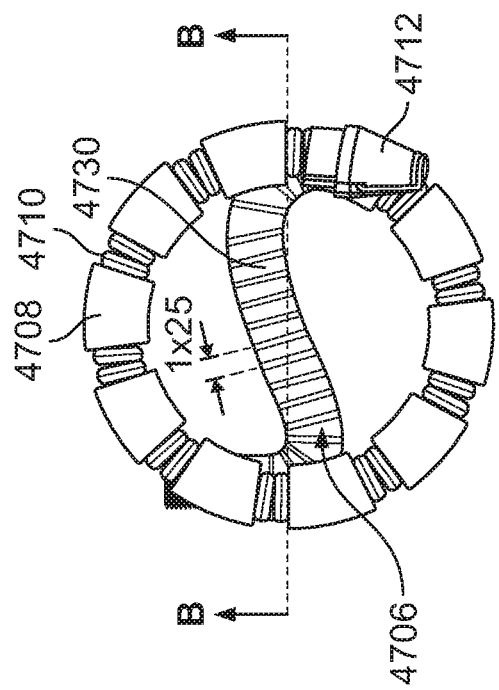
Figure 47M:
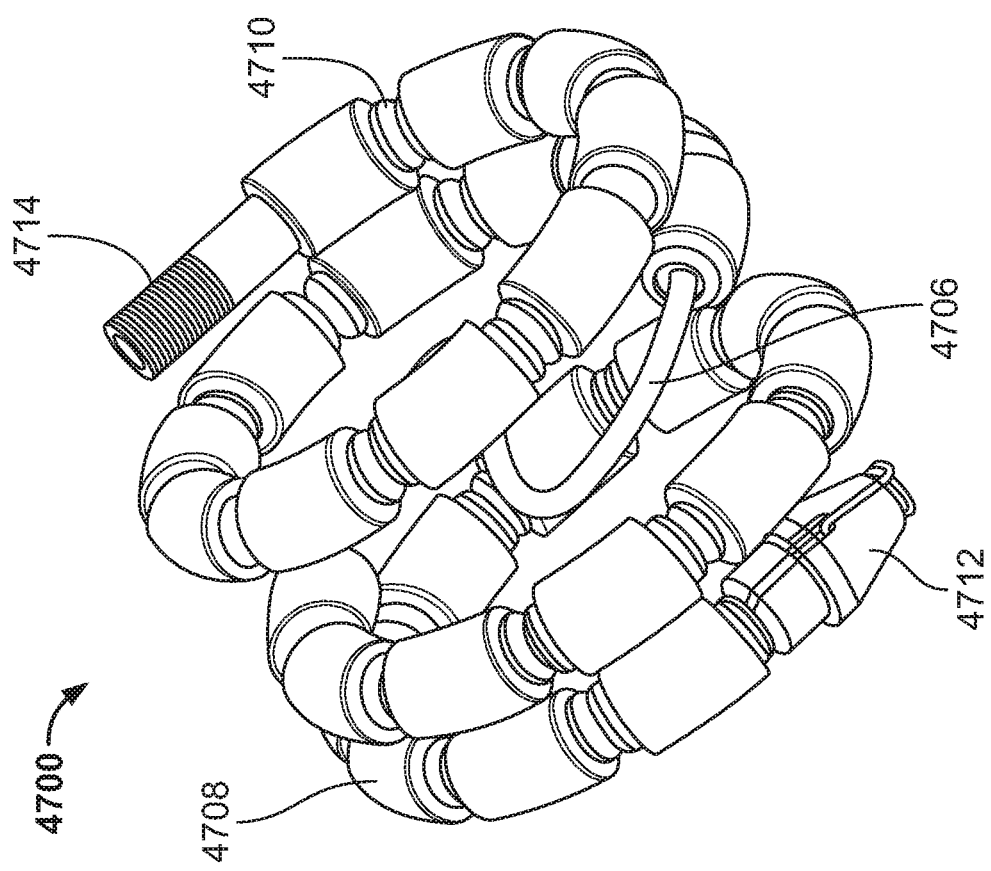
Figure 47T:
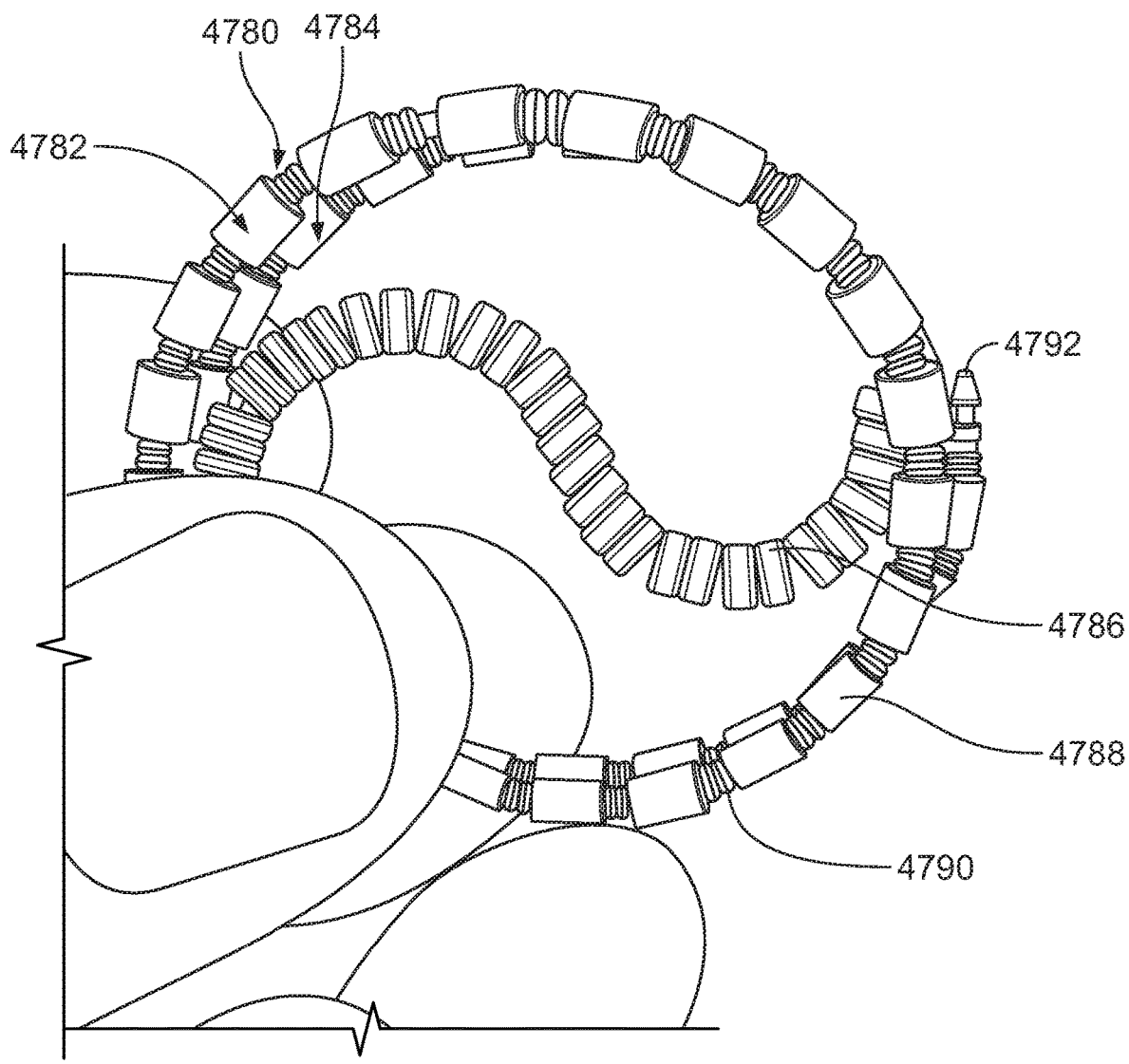
Figure 48B:
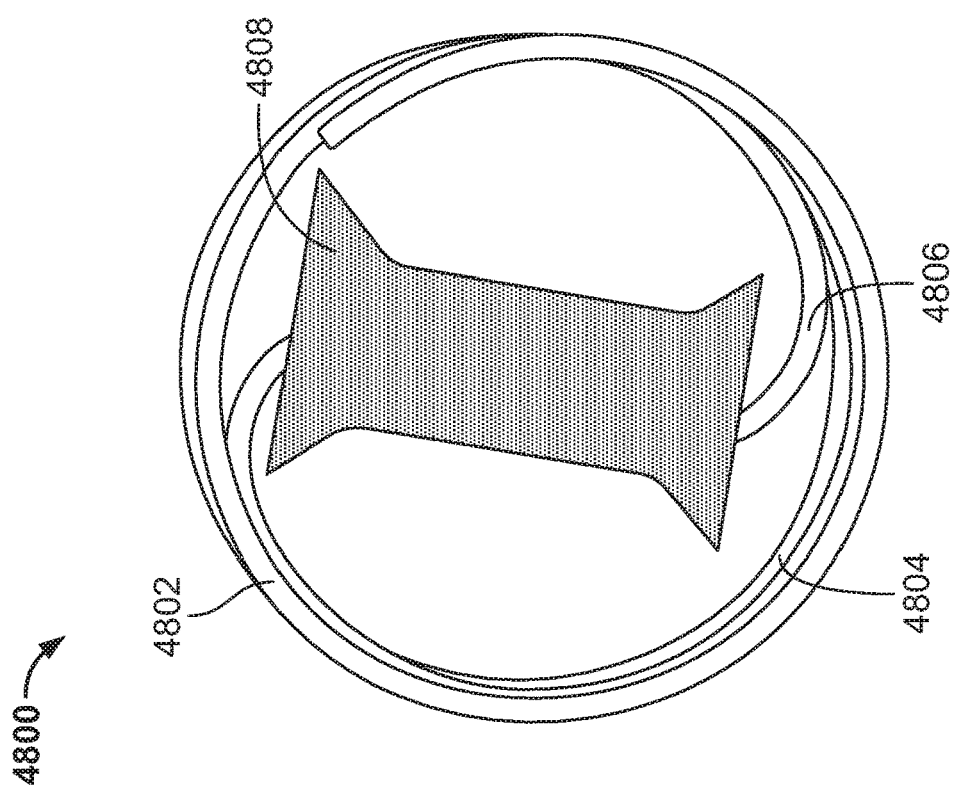
Figure 48A:
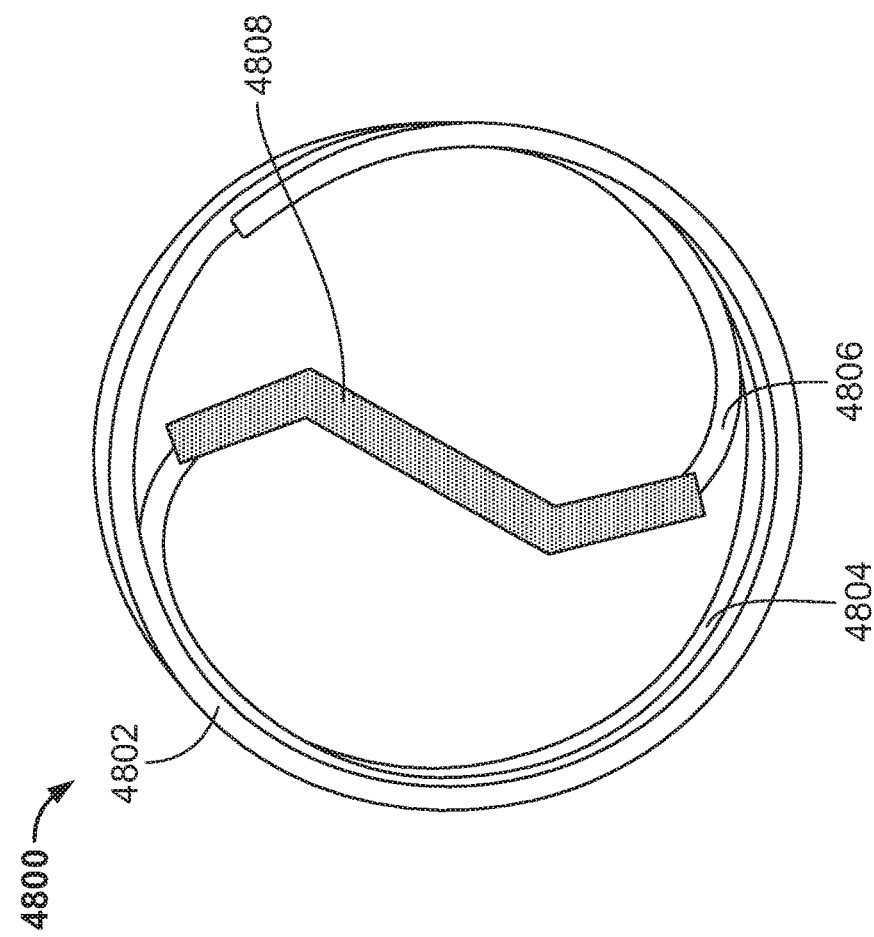
Figure 48C:
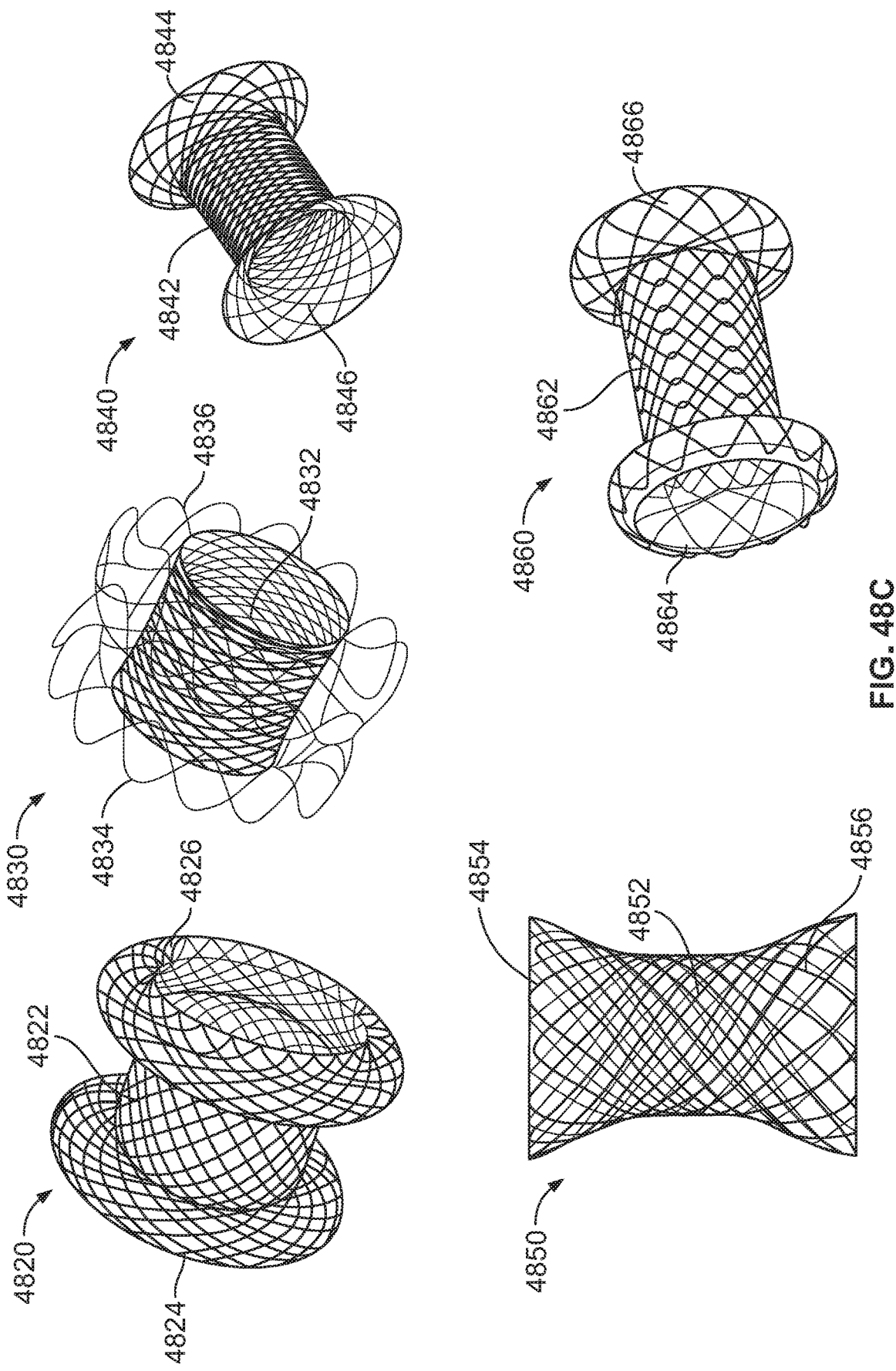
Figure 49B:
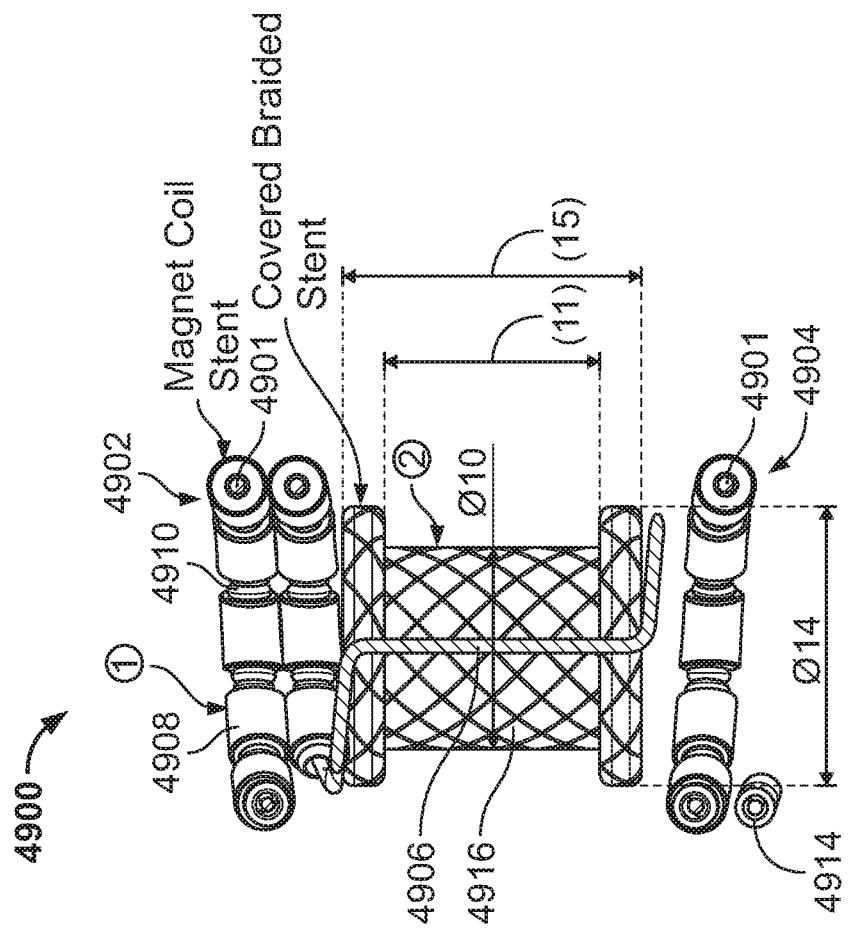
Figure 49A:
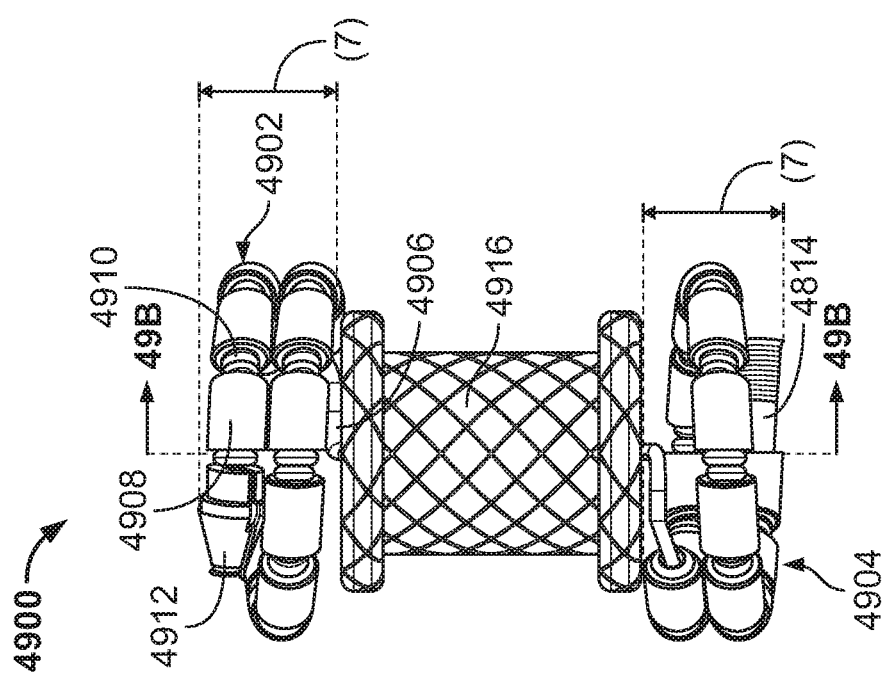
Figure 49D:
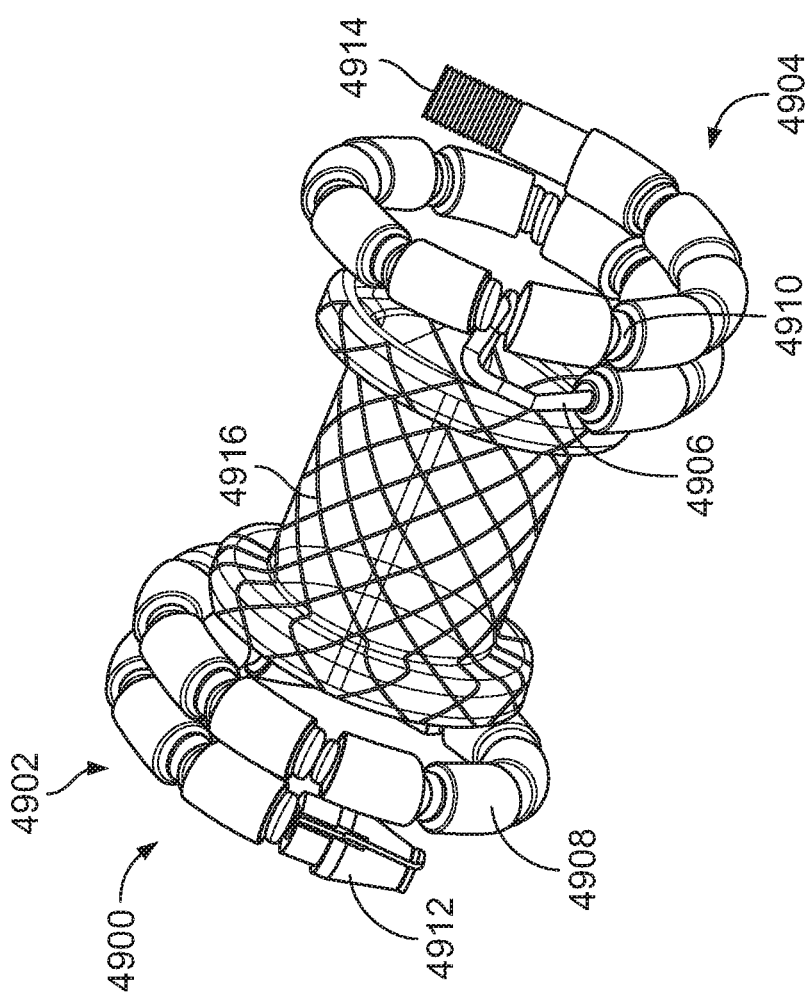
Figure 49C:
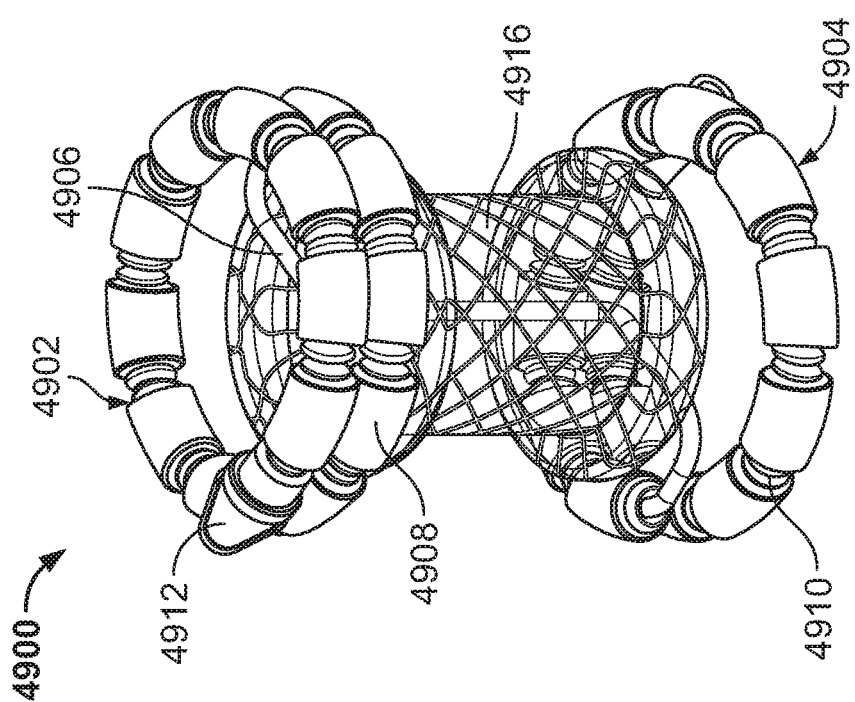
Figure 50G:
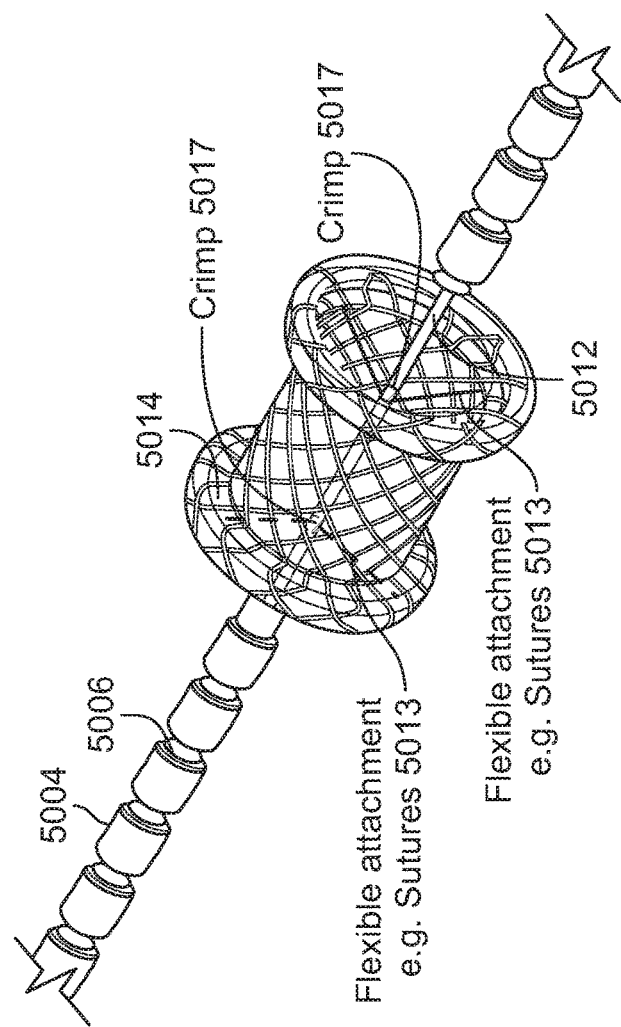
Figure 50H:
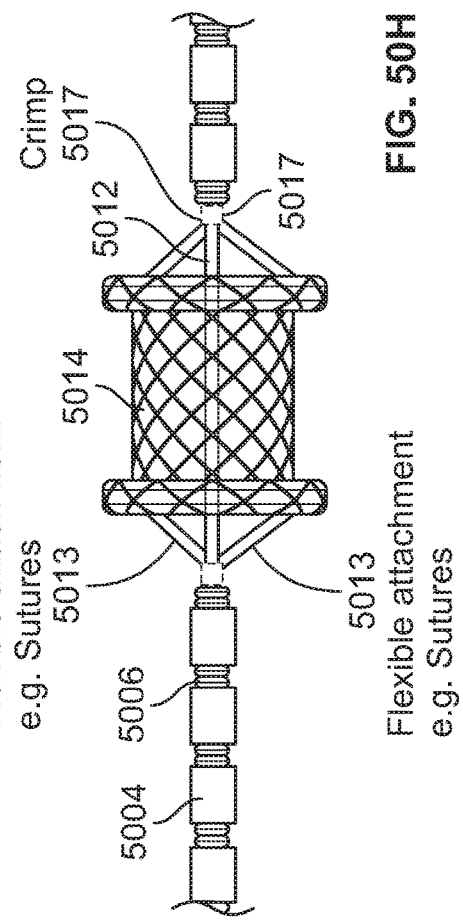
Figure 50J:
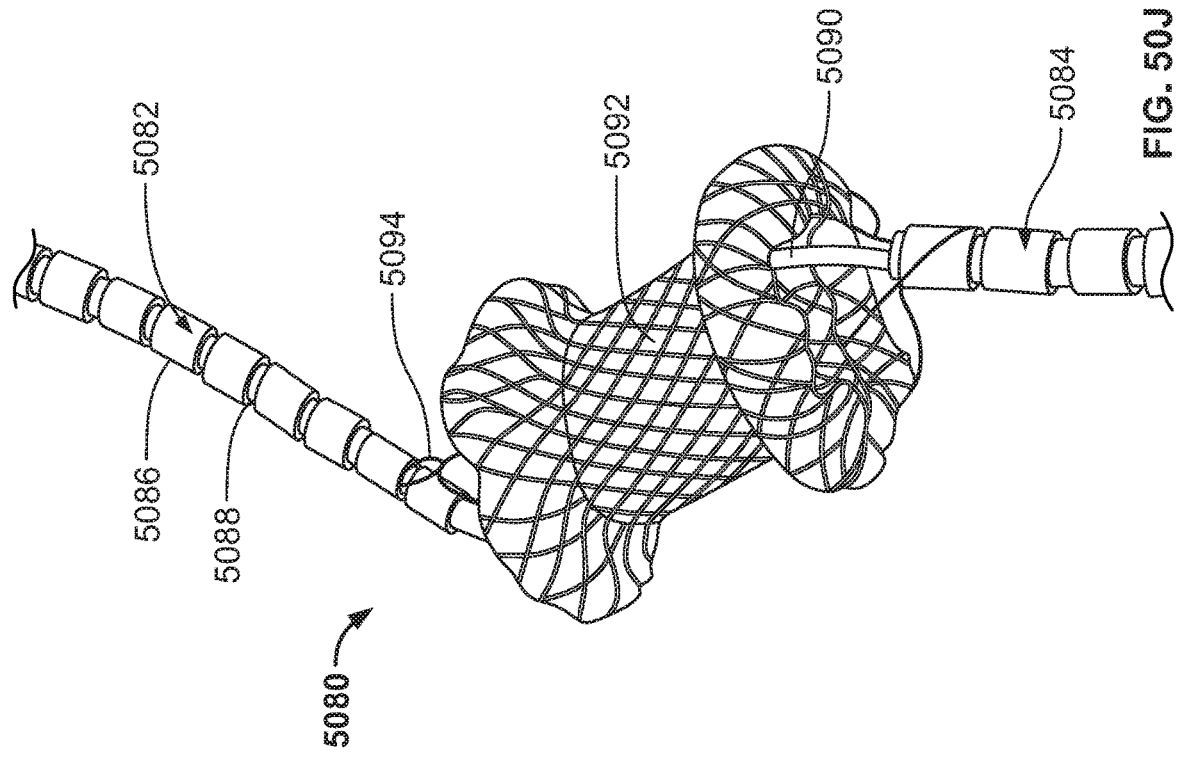
Figure 50I:
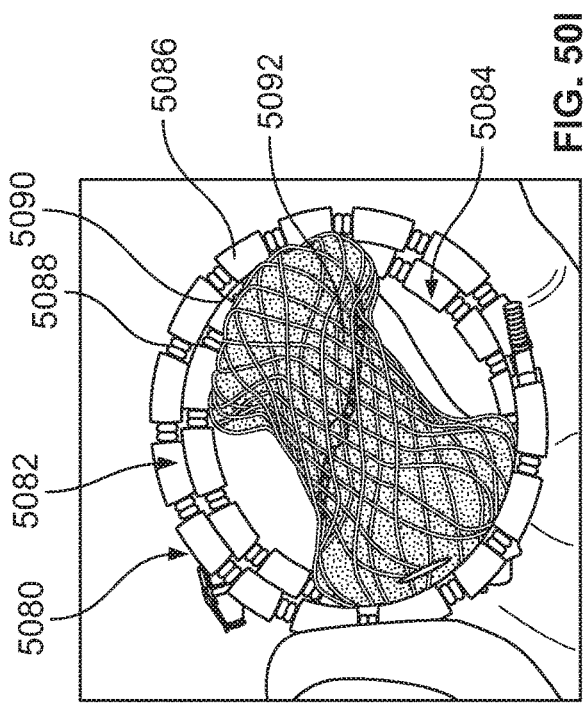
Figure 50K:
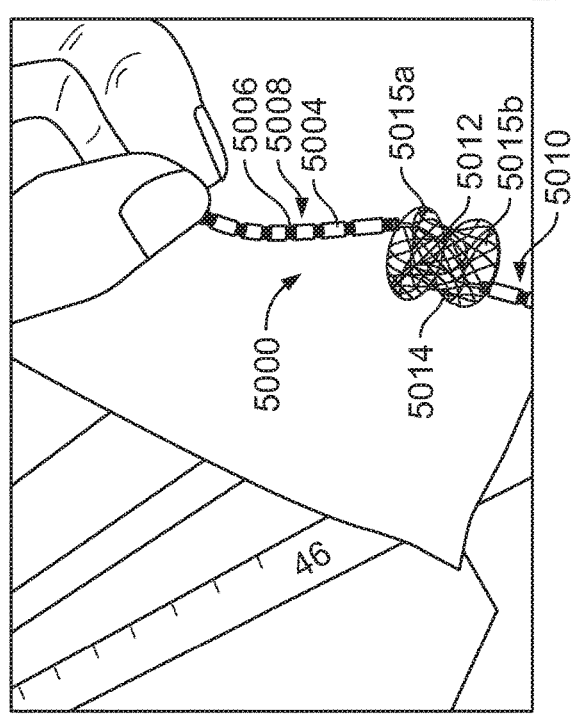
Figure 50L:
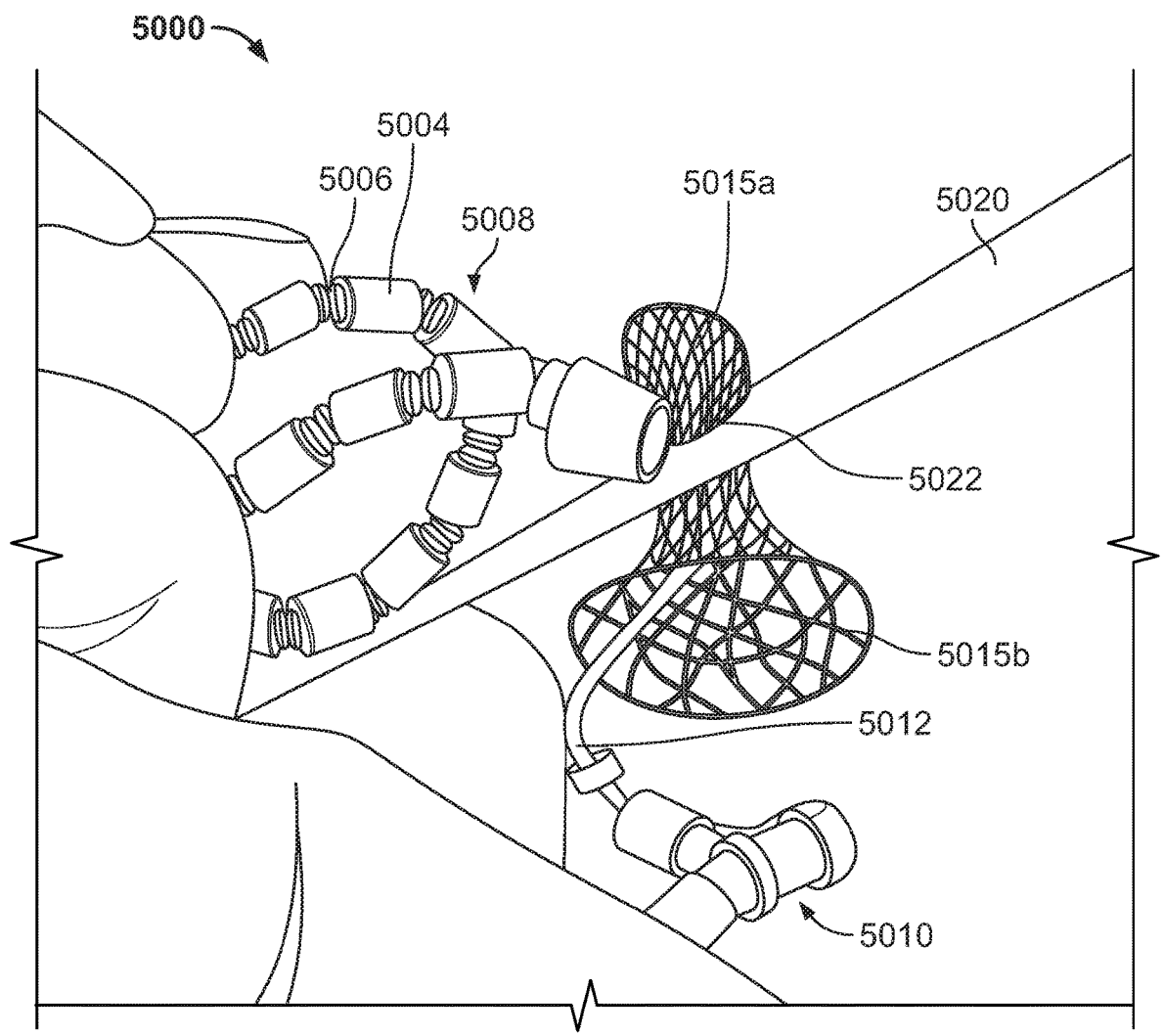
Figure 50M:
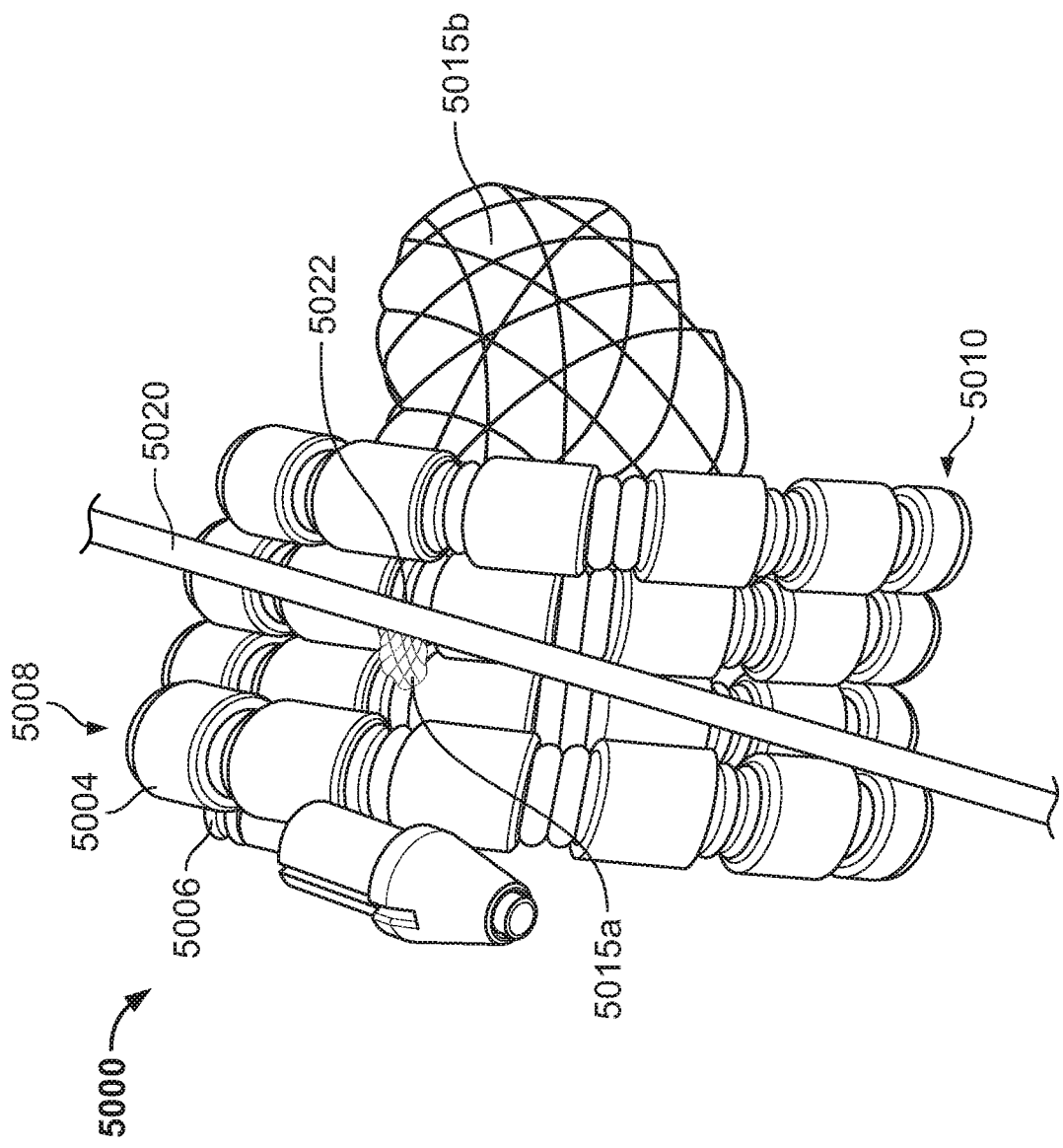
Figure 50N:
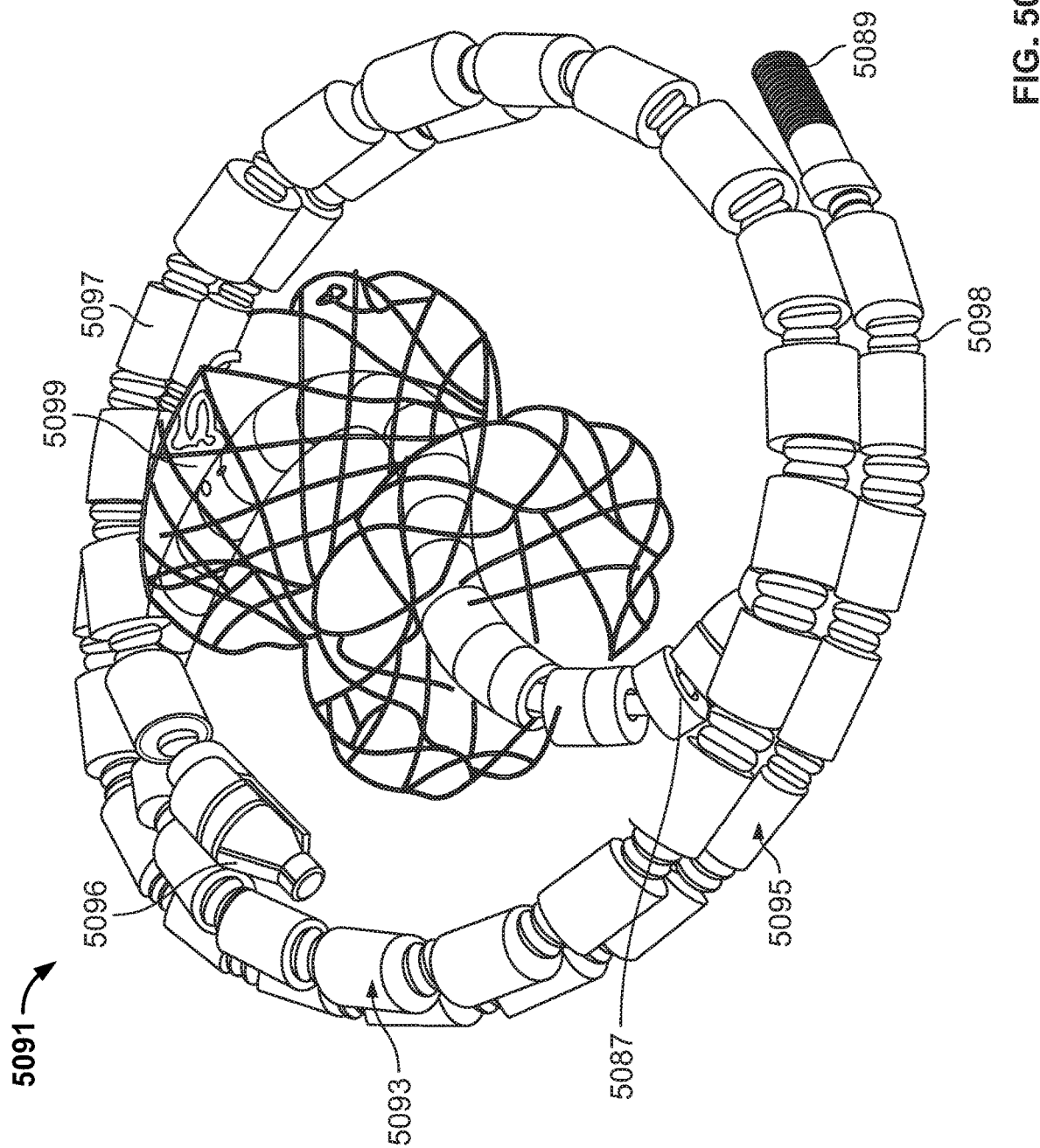
Figure 50O:
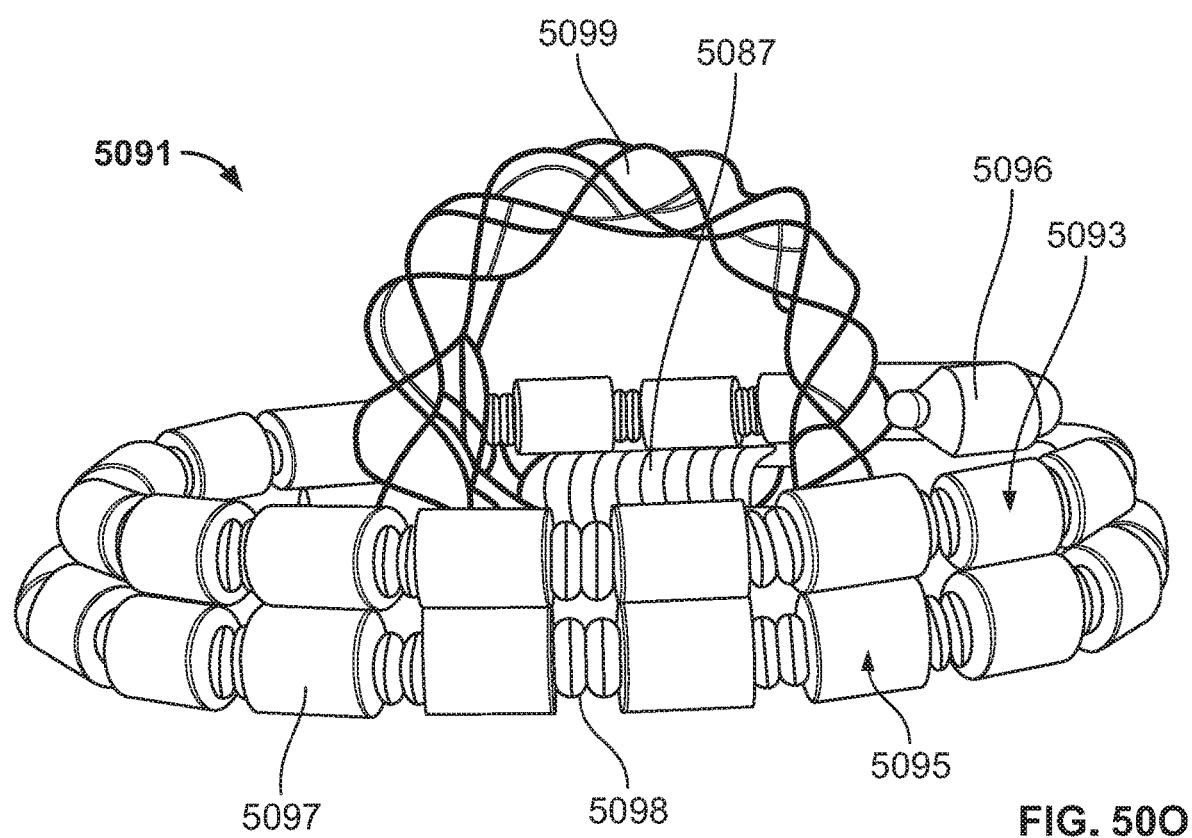
Figure 51A:
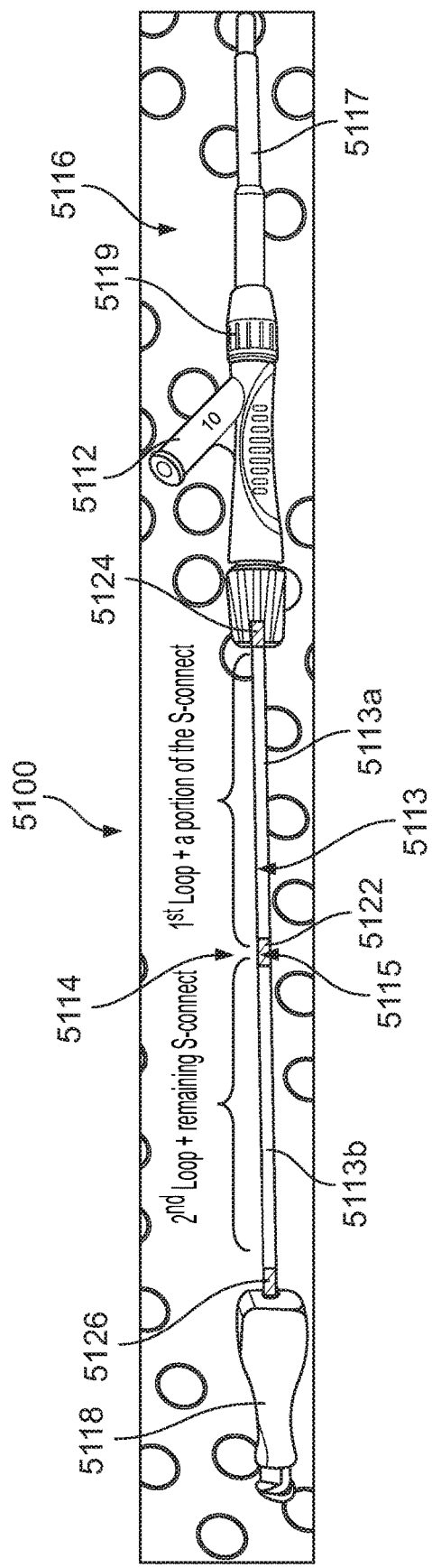
Figure 51B:
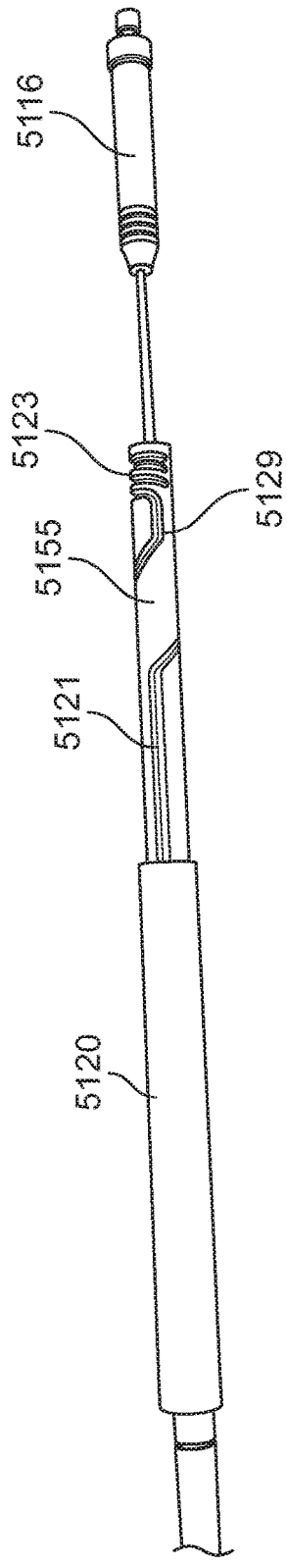
Figure 51C:
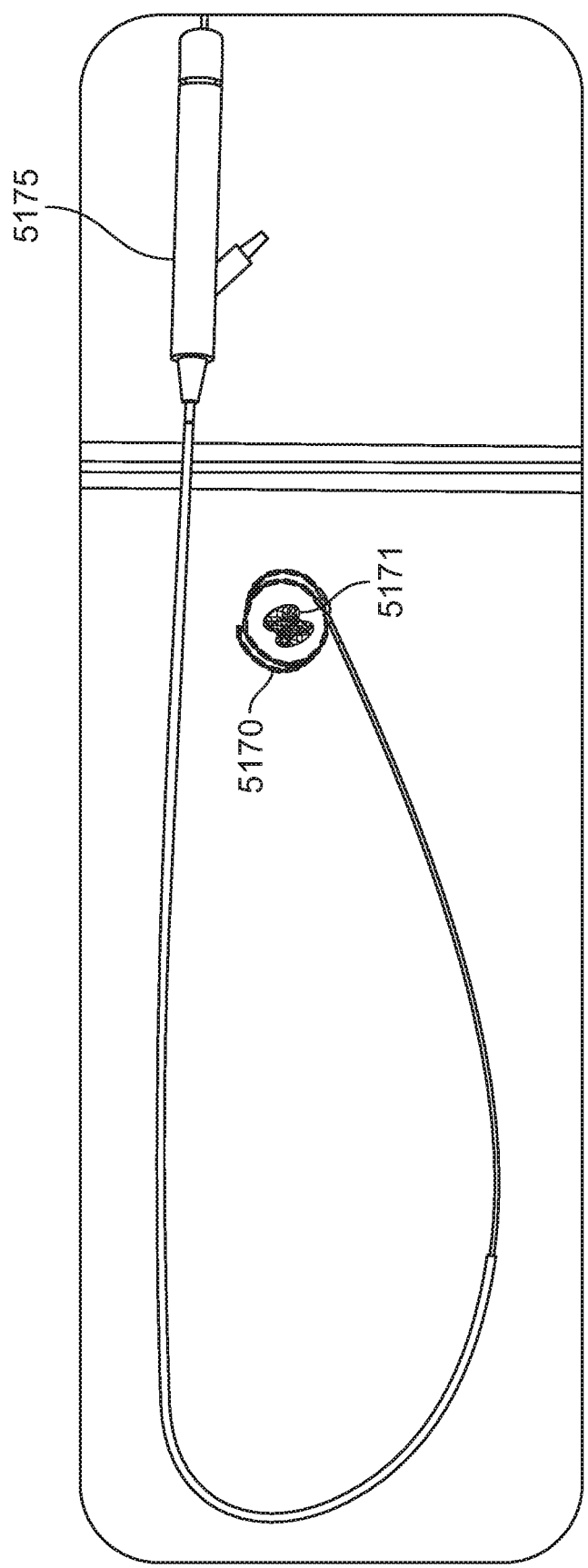
Figure 55:
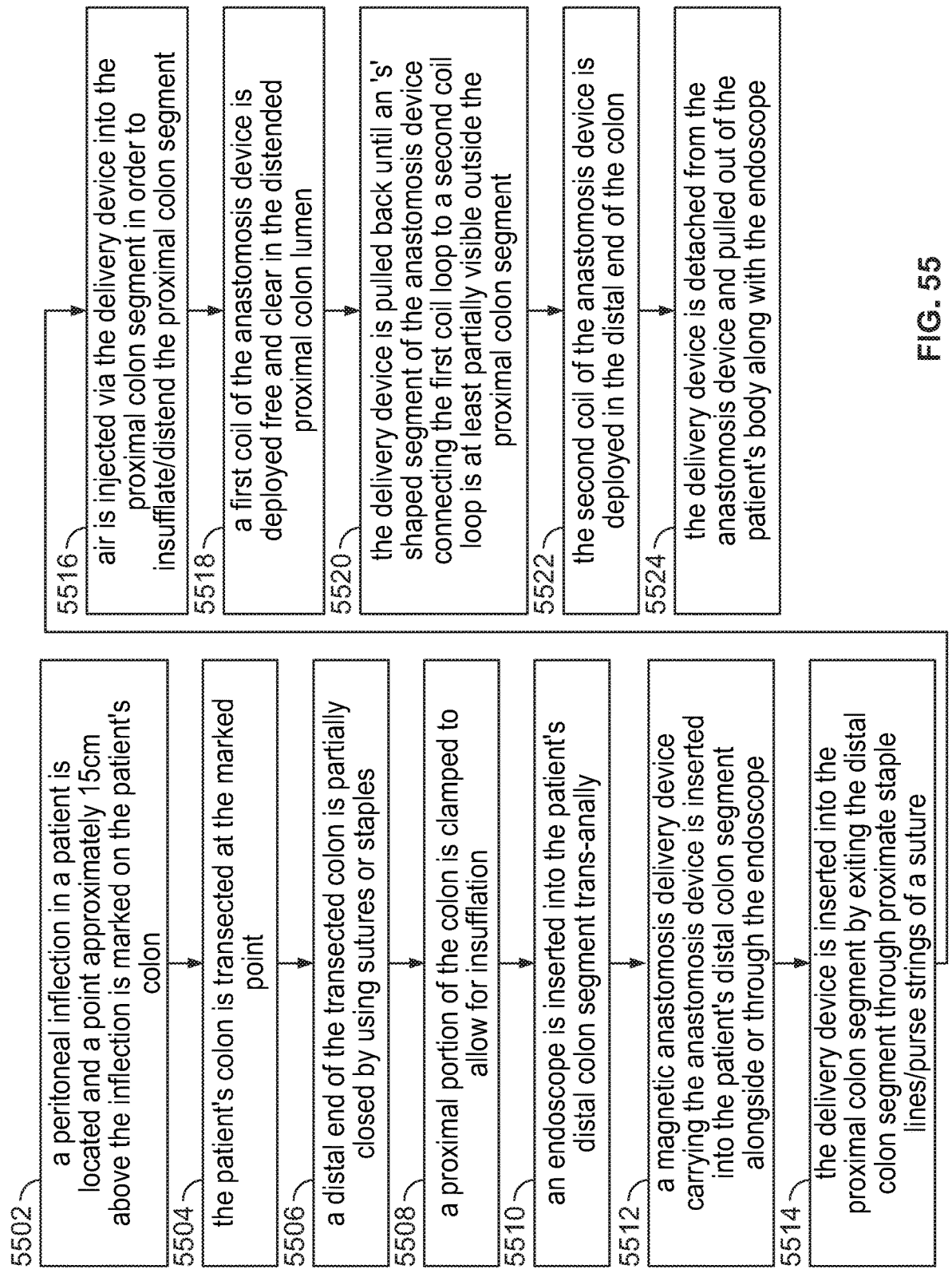
Figure 56:
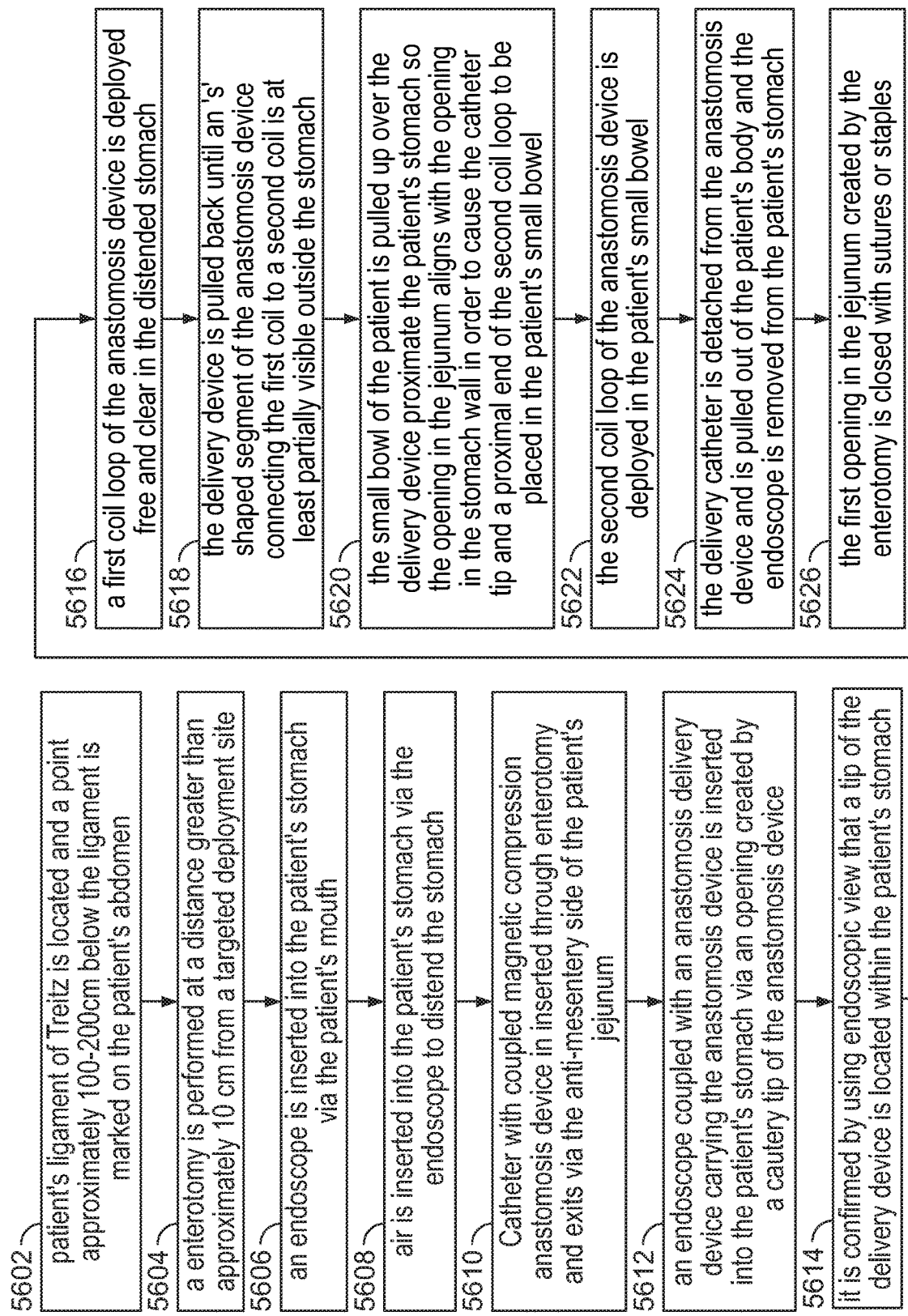
Figure 57A:
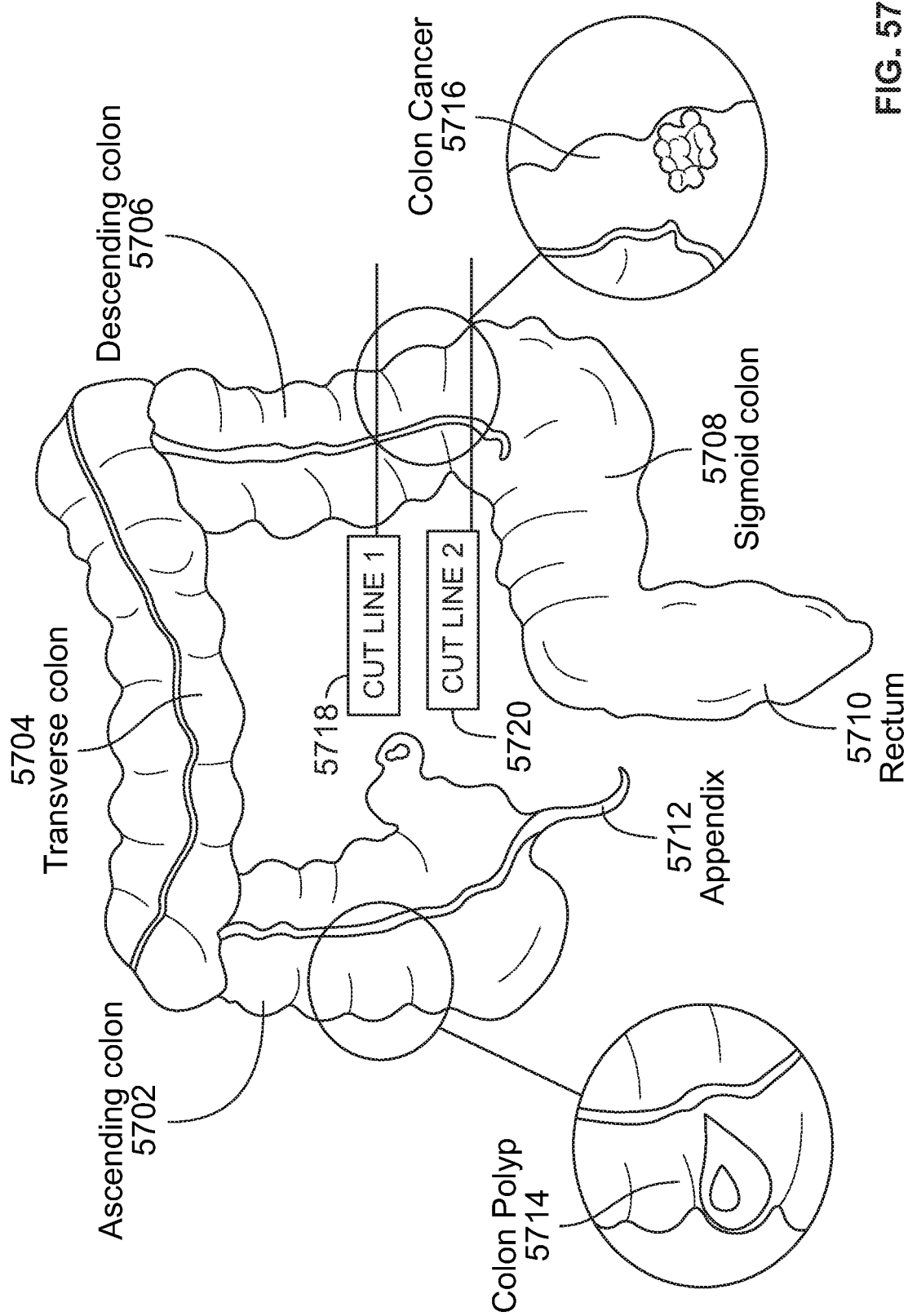
Figure 57B:
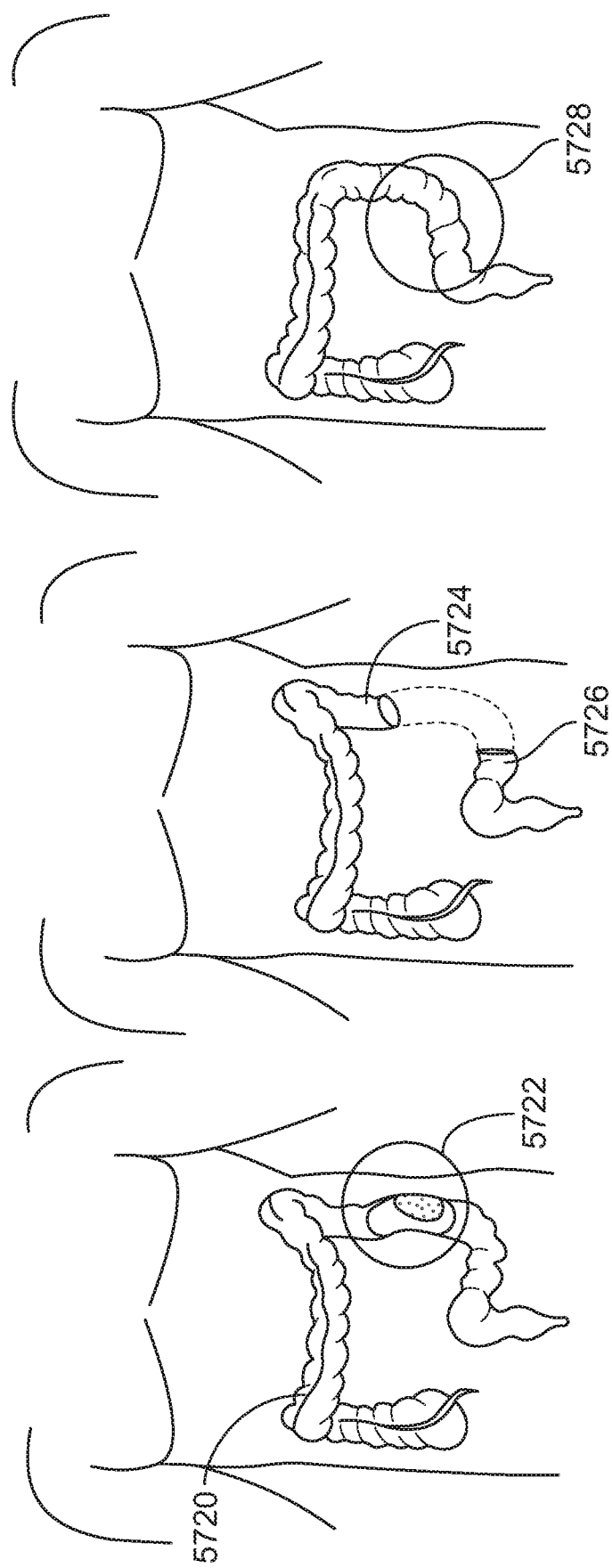
Figure 57C:
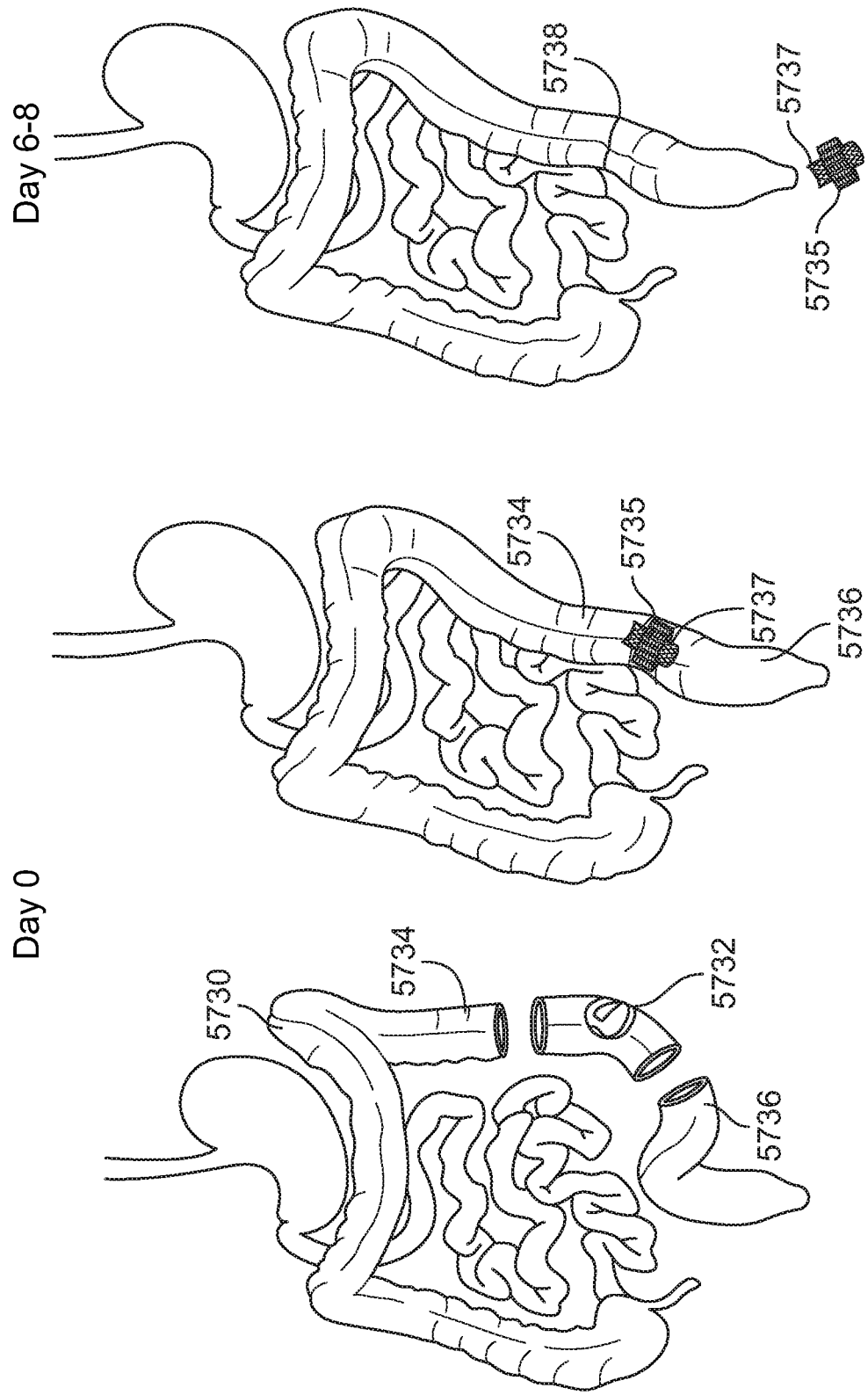
Figure 57D:
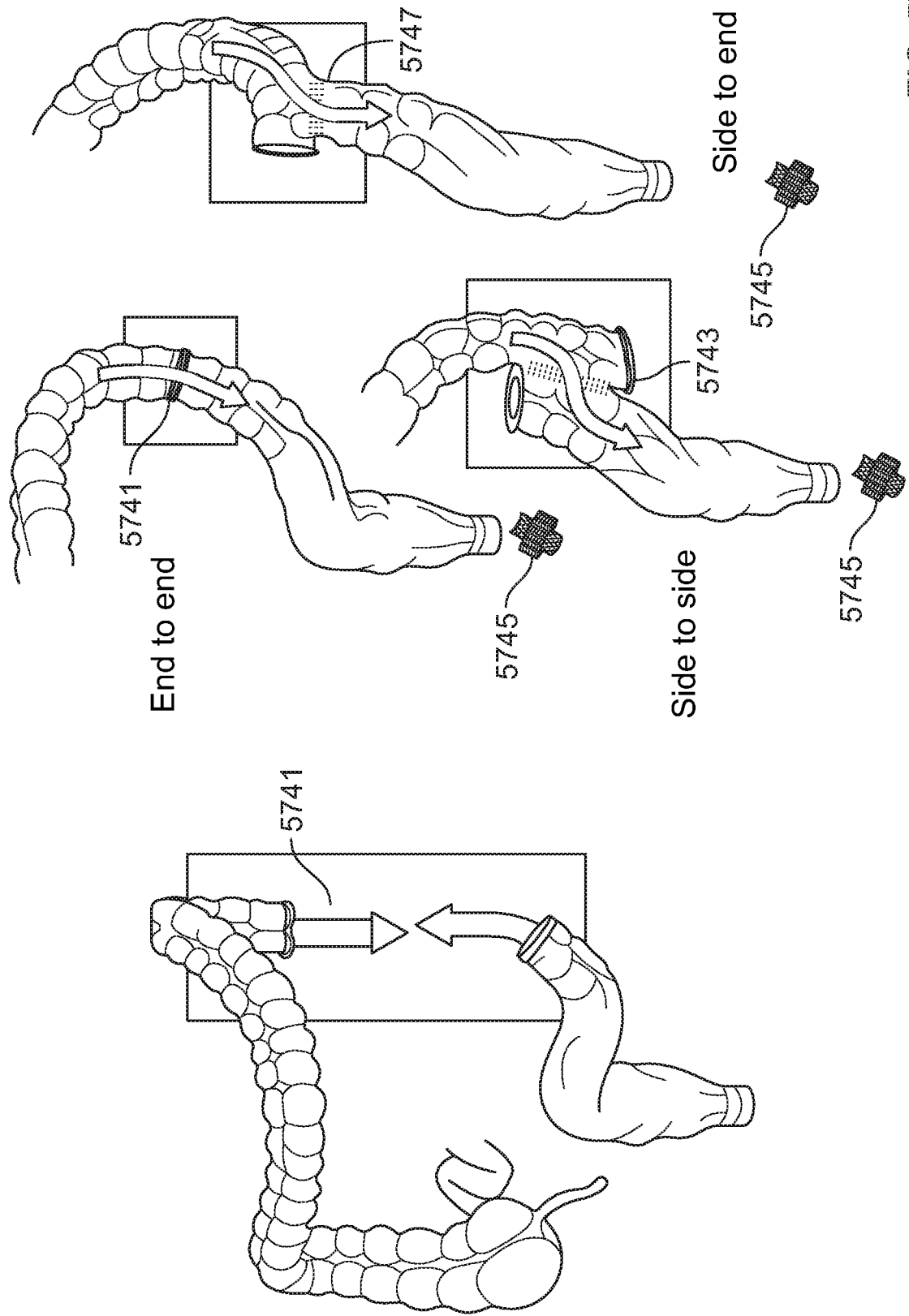
Figure 57E:
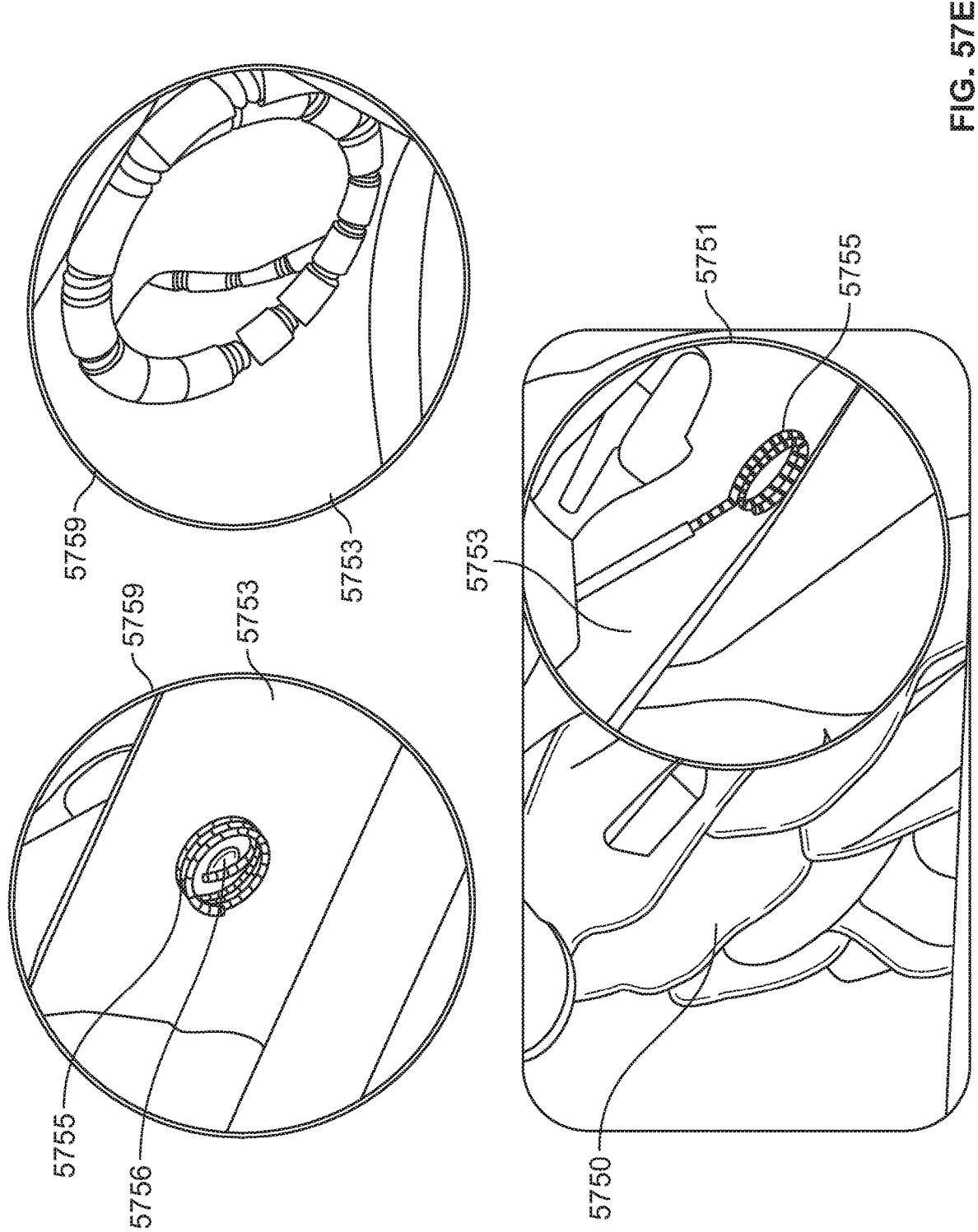
Figure 57F:
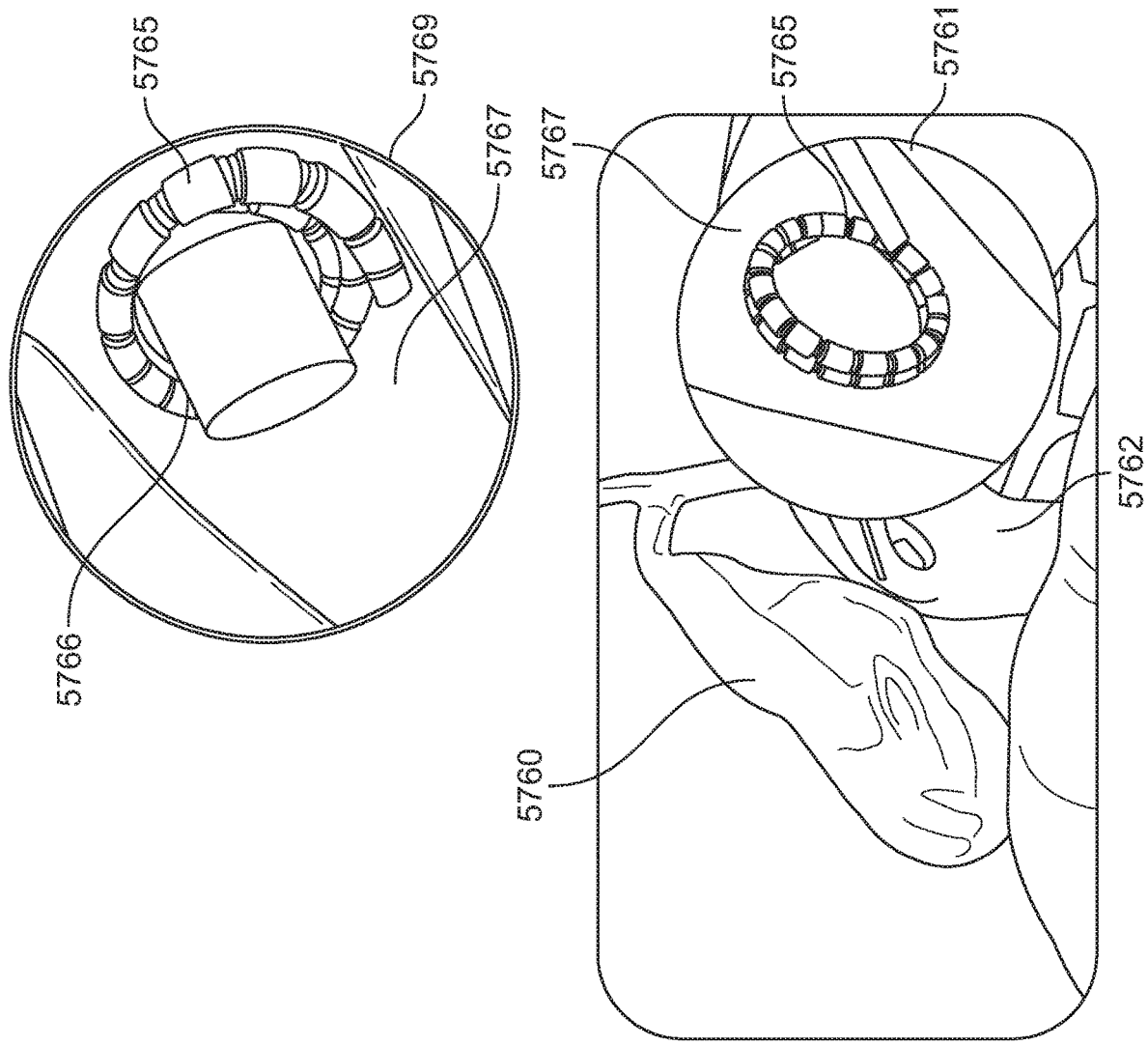
Figure 58:
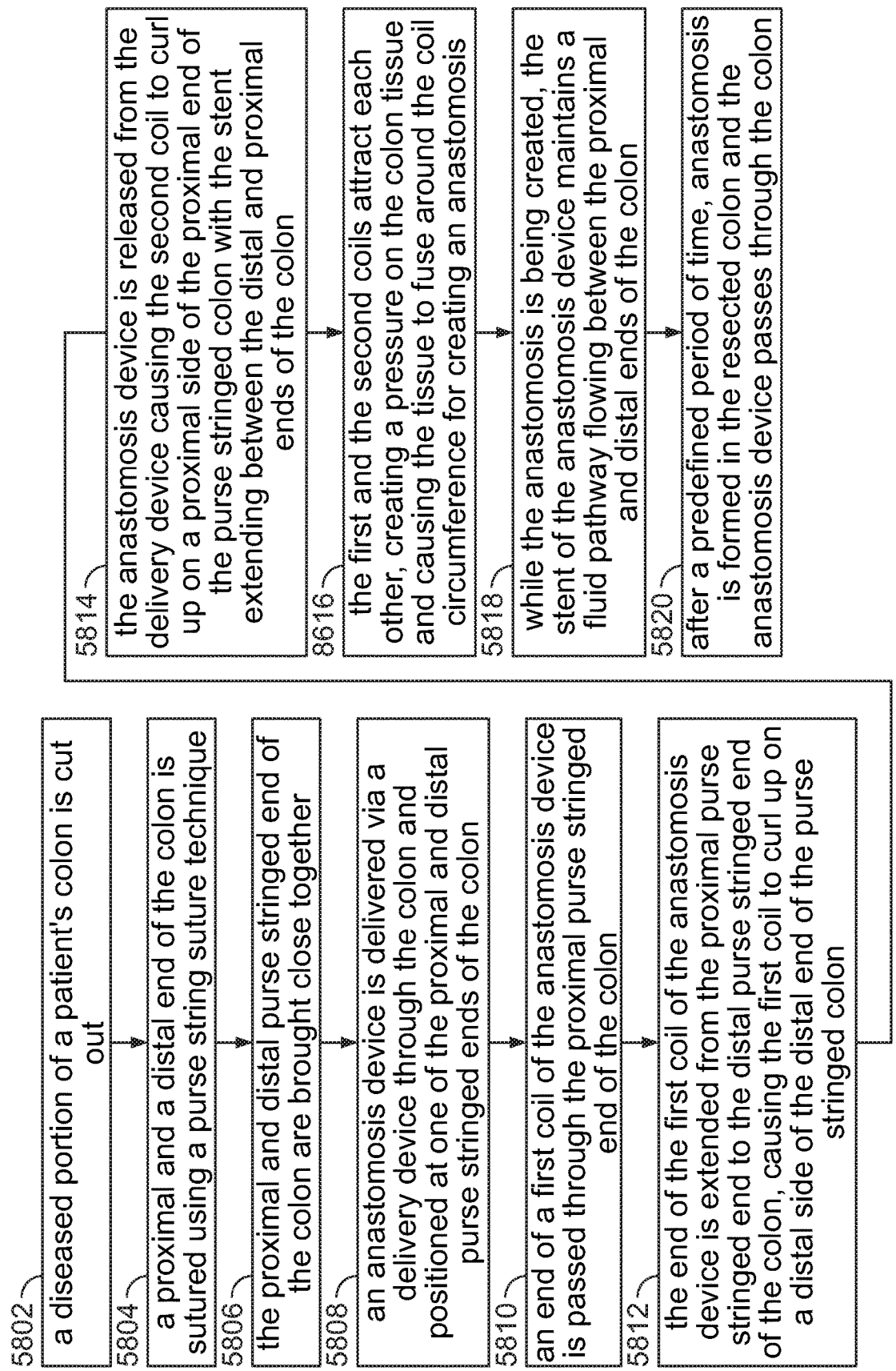
Figure 59:
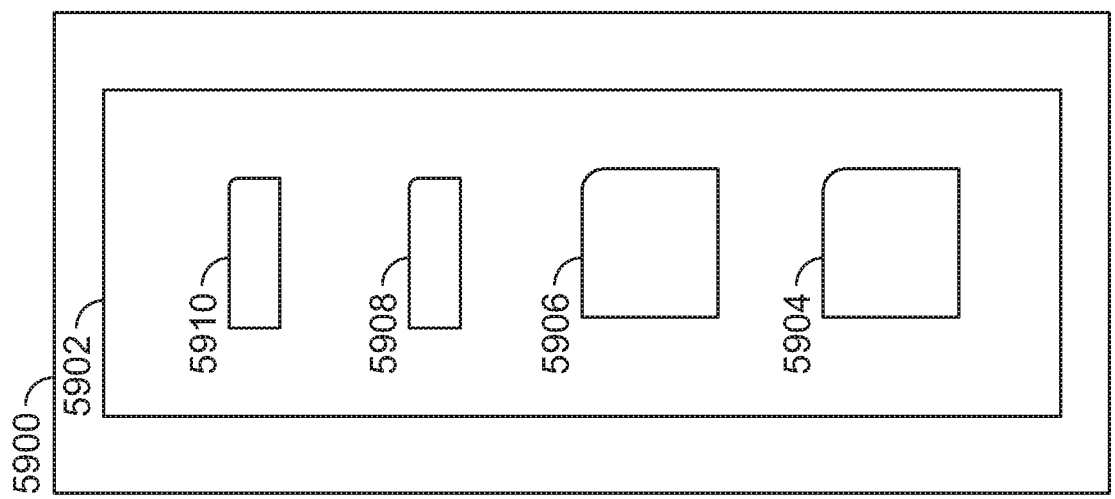
Figure 60:
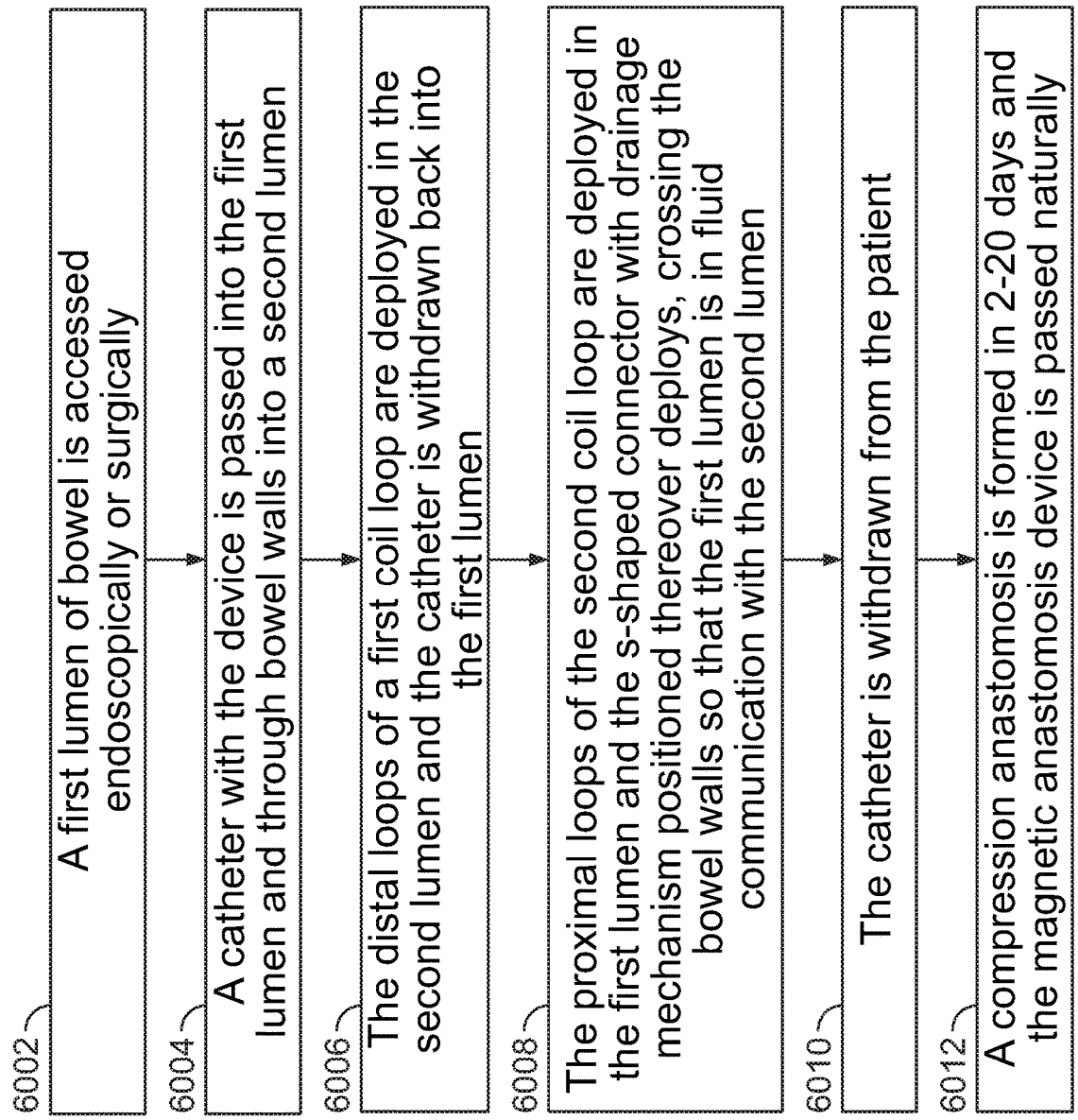
Figure 61:
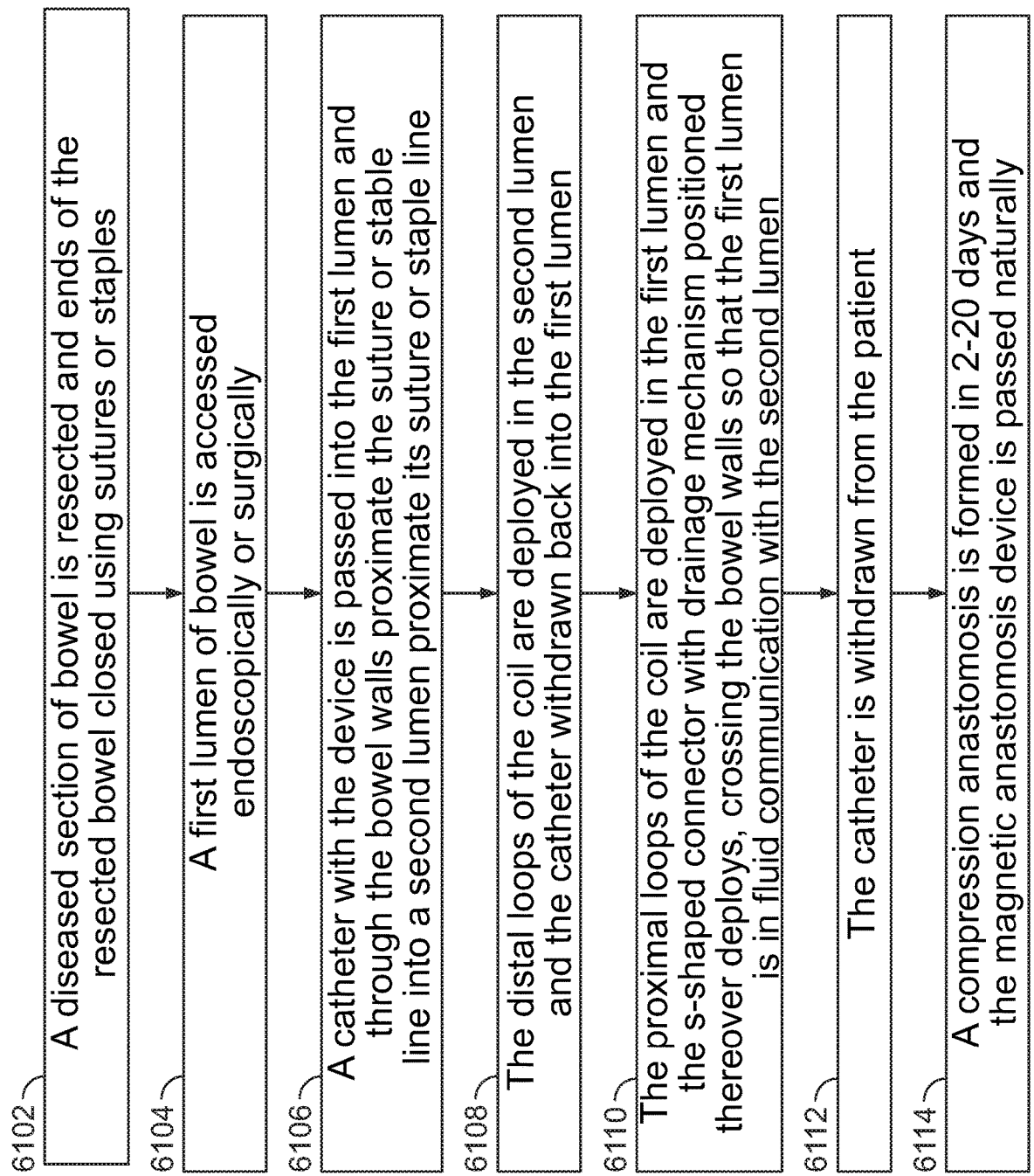
Figure 62:
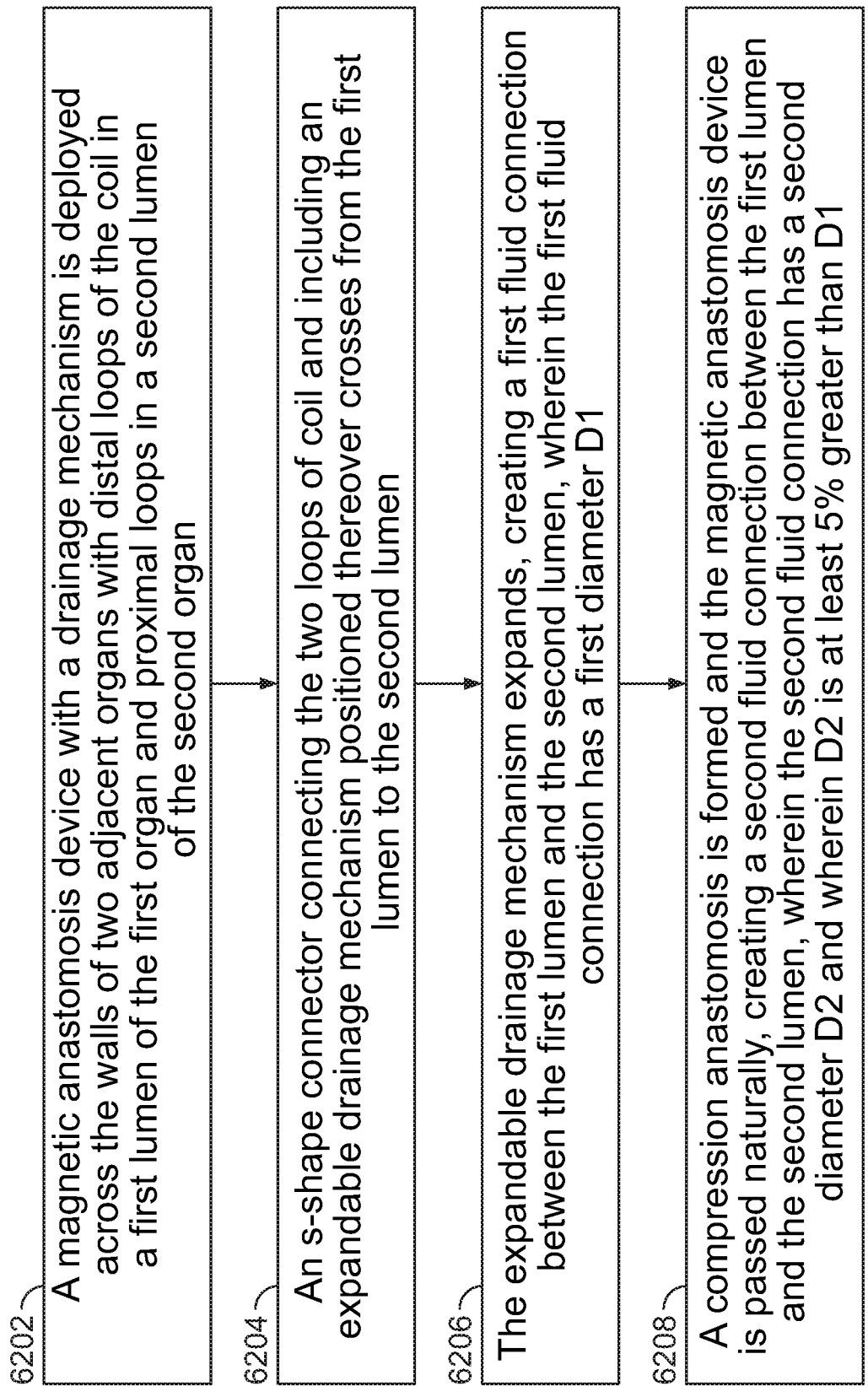

FIG. 41 illustrates a view of a device comprising a plurality of rings, in accordance with an embodiment of the present specification;

FIG. 42 illustrates a view of a device comprising an expandable stent as a drainage mechanism, in accordance with an embodiment of the present specification;

FIG. 43A illustrates an image of a coiled device with a distal end bent inward to prevent a sharp edge or end, in accordance with one embodiment of the present specification;

FIG. 43B illustrates a side view to scale of a coiled device with the distal end bent inward, in accordance with one embodiment of the present specification;

FIG. 43C illustrates a rear view to scale of the coiled device of FIG. 43B with the distal end bent inward, in accordance with one embodiment of the present specification;

FIG. 43D illustrates the coiled device of FIG. 43B, in accordance with an alternative embodiment of the present specification;

FIG. 44A illustrates a side horizontal view of a double coil design with PTFE wire and electrical wire connecting the two coils, maintaining both physical and electrical connectivity, in accordance with an embodiment of the present specification;

FIG. 44B illustrates a front view of the double coil design with PTFE wire and electrical wire connecting the two coils, in accordance with an embodiment of the present specification;

FIG. 44C illustrates a cross-sectional view of the double coil design with PTFE wire and electrical wire connecting the two coils, in accordance with an embodiment of the present specification;

FIG. 44D illustrates a close-up view of the cross-section of a proximal coil of the double coil design with PTFE wire and electrical wire connecting the two coils, in accordance with an embodiment of the present specification;

FIG. 44E illustrates a side vertical view of the double coil design with PTFE wire and electrical wire connecting the two coils, in accordance with an embodiment of the present specification;

FIG. 44F illustrates a perspective view of FIG. 44E, in accordance with an embodiment of the present specification;

FIG. 45 illustrates a scissor cutting action of a deployed coil, in accordance with an embodiment of the present specification;

FIG. 46A is a diagrammatic representation of a device for creating anastomosis comprising a bridging element and loops with opposite directionality, in accordance with an embodiment of the present specification;

FIG. 46B is a diagrammatic representation of another device for creating anastomosis comprising another bridging element and loops with opposite directionality, in accordance with another embodiment of the present specification;

FIG. 46C illustrates a front view of the coiled anastomosis device shown in FIG. 46B comprising a tip covering, in accordance with an embodiment of the present specification;

FIG. 46D illustrates a side view of the coiled anastomosis device shown in FIG. 46C comprising a tip covering, in accordance with an embodiment of the present specification;

FIG. 46E illustrates a perspective view of the coiled anastomosis device shown in FIG. 46C comprising a tip covering, in accordance with an embodiment of the present specification;

FIG. 46F illustrates another perspective view of the coiled anastomosis device shown in FIG. 46C comprising a tip covering, in accordance with an embodiment of the present specification;

FIG. 46G illustrates yet another perspective view of the coiled anastomosis device shown in FIG. 46C comprising a tip covering, in accordance with an embodiment of the present specification;

FIG. 47A illustrates a coiled anastomosis device comprising a bridging segment and inward bent proximal and distal ends in accordance with an embodiment of the present specification;

FIG. 47B illustrates another view of the device shown in FIG. 47A;

FIG. 47C illustrates a coiled anastomosis device made of an SMA wire and comprising a bridging segment and inward bent proximal and distal segment, in accordance with an embodiment of the present specification;

FIG. 47D illustrates the device shown in FIG. 47A without the magnets and spacers placed around the SMA wire in accordance with an embodiment of the present specification;

FIG. 47E illustrates a side view of the device shown in FIG. 47D;

FIG. 47F illustrates a perspective view of the device shown in FIG. 47D;

FIG. 47G illustrates another perspective view of the device shown in FIG. 47D;

FIG. 47H illustrates yet another perspective view of the device shown in FIG. 47D;

FIG. 47I illustrates a side view the device shown in FIG. 47A wherein the magnets are plated with a metallic material, and wherein the spacers are O-rings, in accordance with an embodiment of the present specification;

FIG. 47J illustrates another side view of the device shown in FIG. 47I;

FIG. 47K illustrates a perspective view of the device shown in FIG. 47I;

FIG. 47L illustrates a front view of the device shown in FIG. 47I;

FIG. 47M illustrates another perspective view of the device shown in FIG. 47I;

FIG. 47N illustrates a front view of the device shown in FIG. 47I with PTFE washers provided around the 'S' shaped bridging element, in accordance with an embodiment of the present specification;

FIG. 47O illustrates a side view of the device shown in FIG. 47N;

FIG. 47P illustrates a perspective view of the device shown in FIG. 47N;

FIG. 47Q illustrates a cross-sectional view of the device shown in FIG. 47N, depicting the elements of the device shown in FIG. 47N separately;

FIG. 47R illustrates close-up cross-sections of the SMA wire surrounded with magnet of the device shown in FIG. 47N;

FIG. 47S illustrates another perspective view of the device shown in FIG. 47N;

FIG. 47T illustrates another view of a coiled anastomosis device comprising a bridging segment, in accordance with an embodiment of the present specification;

FIG. 48A illustrates an anastomosis device comprising a bridging segment at least partially covered by a collapsed drainage element, in accordance with an embodiment of the present specification;

FIG. 48B illustrates an anastomosis device comprising a bridging segment at least partially covered by an expanded drainage element, in accordance with another embodiment of the present specification;

FIG. 48C illustrates a plurality of drainage elements that can be employed with the anastomosis devices of FIGS. 48A and 48B, in accordance with some embodiments of the present specification;

FIG. 49A illustrates a front view of an anastomosis device comprising magnets and a wire mesh drainage element covering an 'S' shaped bridging element, in accordance with an embodiment of the present specification;

FIG. 49B illustrates a cross-sectional view of the device shown in FIG. 49A;

FIG. 49C illustrates a perspective view of the device shown in FIG. 49A;

FIG. 49D illustrates another perspective view of the device shown in FIG. 49A;

FIG. 50A illustrates a side cross-sectional view of an anastomosis device comprising magnets and a wire mesh drainage element covering a bridging element, in a pre-deployment state, in accordance with an embodiment of the present specification;

FIG. 50B illustrates a side view of the device shown in FIG. 50A;

FIG. 50C illustrates a front view of the device shown in FIG. 50A;

FIG. 50D illustrates a perspective view of the device shown in FIG. 50A;

FIG. 50E illustrates the device of FIGS. 50A-50D after deployment, in accordance with an embodiment of the present specification;

FIG. 50F illustrates the device of FIG. 50E with the wire mesh drainage element separate from the bridging segment, in accordance with an embodiment of the present specification;

FIG. 50G illustrates a perspective view of the device shown in FIGS. 50A-50D along with means for attaching the wire mesh drainage element to the bridging element, in accordance with an embodiment of the present specification;

FIG. 50H illustrates a side view of the device shown in FIG. 50G;

FIG. 50I illustrates a front view of an anastomosis device comprising a wire mesh drainage element covered with a membrane and covering a bridging element of the coil, in a post-deployment state, in accordance with an embodiment of the present specification;

FIG. 50J illustrates a perspective view of the anastomosis device of FIG. 50I in a pre-deployment state, in accordance with an embodiment of the present specification;

FIG. 50K illustrates the anastomosis device comprising a wire mesh drainage element provided over the bridging element in a pre-deployment state, in accordance with an embodiment of the present specification;

FIG. 50L illustrates a view of the wire mesh drainage element shown in FIG. 50K in a post deployment state across a desired segment allowing for immediate drainage, in accordance with an embodiment of the present specification;

FIG. 50M illustrates another view of the device with wire mesh drainage element shown in FIG. 50L compressing two adjacent structures and providing immediate drainage between the two adjacent structures;

FIG. 50N illustrates a perspective view of an anastomosis device including a wire mesh drainage element, in accordance with some embodiments of the present specification;

FIG. 50O illustrates a side view of the an anastomosis device including a wire mesh drainage element of FIG. 50N;

FIG. 51A illustrates a handle of a delivery device for delivering the anastomosis device in a desired location within a body, in accordance with an embodiment of the present specification;

FIG. 51B illustrates another handle of an anastomosis device connected to a delivery device for delivering the anastomosis device in a desired location within a body, in accordance with an embodiment of the present specification;

FIG. 51C illustrates an anastomosis device including a wire mesh drainage element attached to a delivery device, in accordance with some embodiments of the present specification;

FIG. 52A illustrates a magnetic compression device being deployed to treat an achalasia dysfunction in a lower esophageal sphincter (LES) of a patient, in accordance with an embodiment of the present specification;

FIG. 52B illustrates an enlarged lumen created by a magnetic compression device to treat achalasia in a patient, in accordance with an embodiment of the present specification;

FIG. 53A illustrates a magnetic compression device being used to treat a gastroparesis dysfunction by creating an enlarged opening in a pylorus of a patient, in accordance with an embodiment of the present specification;

FIG. 53B illustrates an enlarged opening created by a magnetic compression device to treat gastroparesis in a patient, in accordance with an embodiment of the present specification;

FIG. 54A illustrates a magnetic compression device being used to treat a gastrointestinal stricture in the esophagus of a patient, in accordance with an embodiment of the present specification; and FIG. 54B illustrates an enlarged opening created by a magnetic compression device to treat a stricture in the esophagus of a patient, in accordance with an embodiment of the present specification;

FIG. 55 is a flowchart illustrating a method of performing a colorectal surgery for deploying an anastomosis device, in accordance with an embodiment of the present specification;

FIG. 56 is a flowchart illustrating a method of performing a gastrojejunostomy surgery for deploying an anastomosis device, in accordance with an embodiment of the present specification;

FIG. 57A illustrates a human colon, which may be resected to remove diseased portions, in accordance with an embodiment of the present specification;

FIG. 57B illustrates a human colon with a diseased portion being removed and the resultant ends of the colon anastomosed together;

FIG. 57C illustrates a human colon with a diseased portion being removed and the resultant ends of the colon anastomosed together using a magnetic compression anastomosis device in accordance with embodiments of the present specification;

FIG. 57D illustrates different types of anastomoses using a magnetic compression anastomosis device in accordance with embodiments of the present specification;

FIG. 57E illustrates a side-to-side colo-colic anastomosis created using a magnetic compression anastomosis device in accordance with embodiments of the present specification;

FIG. 57F illustrates an anastomosis created between a gall bladder and a duodenum using a magnetic compression anastomosis device in accordance with embodiments of the present specification;

FIG. 58 is a flowchart illustrating a method of using an anastomosis device to fuse two ends of a resected colon, in accordance with an embodiment of the present specification;

FIG. 59 is a block diagram of a handle of an anastomosis delivery device comprising a control mechanism, in accordance with an embodiment of the present specification;

FIG. 60 is a flowchart listing the steps in a method of creating a side-to-side anastomosis using a magnetic compression anastomosis device, in accordance with embodiments of the present specification;

FIG. 61 is a flowchart listing the steps in a method of creating a side-to-side anastomosis using a magnetic compression anastomosis device, in accordance with embodiments of the present specification;

FIG. 62 is a flowchart listing the steps in a method of creating an anastomosis with immediate fluid patency and delayed fluid patency, using a magnetic compression anastomosis device, in accordance with embodiments of the present specification; and FIG. 63 is a flowchart listing the steps in a method of creating an anastomosis with immediate fluid patency and delayed fluid patency, using a magnetic compression anastomosis device, in accordance with other embodiments of the present specification.

DETAILED DESCRIPTION

In various embodiments, a shape memory alloy (SMA) or smart alloy wire is used to create an anastomosis by creating the desired shape and size of the anastomosis and cutting through tissue layers in a human body to create an opening or anastomosis. In an embodiment, a straight piece of a SMA wire or a longitudinally stretched coil, or any other substantially planar structure, is delivered at a location requiring an anastomosis within a body. In an embodiment, the SMA wire is either superelastic or heat sensitive and curls up into a spring like coil in response to body heat within the body. In various embodiments, the wire has a straight or a longitudinally stretched coil or an elongate shape at room temperature and a compressed coil shape at the human body temperature, which is in the preferred range of 97.7 degrees Fahrenheit (F) to 99.5 degrees F. The coil may take a compressed shape at any temperature greater than 96 degrees F.

The compressed coil defines the desired shape and dimensions of the desired anastomosis. The compressing coil produces a compression force on tissue caught between loops of the coil. The coiling action also causes the wire to create ischemia, pressure necrosis and cut through the desired tissue layers, creating an anastomosis between two adjacent body tissues. In an embodiment, a plurality of magnets are provided on each concentric ring of the coiled wire. Magnets provided on adjacent rings attract each other, thereby enhancing the cutting action of the coil. In some embodiments, compression force is provided by the combination of the coiling wire and attraction force between the magnets. In some embodiments, the shape of the resultant anastomosis is predominantly determined by the shape of the coil and not by the forces between the magnets. In various embodiments, the number of magnets used and the length of the magnets are determined by the shape, dimensions or time needed to form an anastomosis. In various embodiments, the time period required to create the anastomosis ranges between one day and fourteen days. In various embodiments, the anastomosis is formed between two segments of the SMA wire, between two or more magnets, or between a segment of SMA wire and one or more magnets.

In various embodiments, an anastomosis device comprises a wire having a plurality of magnets provided on the wire. In various embodiments, only one anastomosis device is required to create the desired anastomosis. The device is delivered, using a delivery device, to a first lumen of a first organ, passed through a first wall of said first organ and through a second wall of a second organ and into a second lumen of said second organ, all while still at least partially maintained in a delivery configuration on said delivery device. The anastomosis device is then deployed such that a distal portion is disposed in said second lumen and a proximal portion of the device is disposed in said first lumen. Once deployed, the device curls into a coil shape having one or more coils such that a distal portion of the coil remains in said second lumen and a proximal portion of the coil remains in said first lumen. In other words, only a single anastomosis device as described in embodiments of the present specification is required to create the desired anastomosis, rather than two separate mating devices as encountered in the prior art, where a first device is deployed in a first lumen of a first organ and a second device is deployed in a second lumen of a second organ.

In various embodiments, the anastomosis devices of the present specification form a coil shape in a deployed configuration, having at least one coil with a proximal end and a distal end wherein said proximal end and said distal end are in different horizontal planes.

In various embodiments, the deployed coil shape of the anastomosis device is formed only through the actions of the shape memory wire and/or magnetic forces of the magnetic members and without the use of any additional guide element, manipulator, radial members, hinges, or opening members.

It should be appreciated that the presently disclosed embodiments have several advantages over the prior art. First, the wire, in a non-deployed state, transitioning to a coil structure, in a deployed state, enables an automatic compressive action without requiring the manual positioning of separate magnetic elements, which are not tethered to each other or positioned relative to each other in a fixed pre-deployment or post-deployment configuration. More specifically, the alignment of magnetic elements is achieved by their fixed position on a wire and it is the wire's natural transition from a straight, elongated member to a coil shape that achieves the requisite automatic alignment of the magnetic elements and compression of tissue. This is achieved because the embodiments disclosed herein provide magnetic elements which are tethered to each other or physically coupled such that the magnetic elements have a fixed, predefined position relative to each other in both the pre-deployment and post-deployment configurations. The coupling is preferably through a wire, although a suture, a tube, or other member, can be used to create the fixed relationship.

Therefore, the magnets used in the device have a fixed relation to each other both before and after deployment. The relative three dimensional position of a first magnet is known, and fixed, relative to the three dimensional position of a second magnet both in an undeployed configuration (along the length of a straight wire) and in a deployed configuration (in the shape of a coil). This fixed relation enables an automatic alignment because a user need not manually place the magnets into a particular position, relative to each other, before deployment, so that they will properly connect post deployment. Stated differently, when the device is in a deployed configuration, a first magnet in a first coil is in a predefined, fixed position relative to a second magnet in a second coil, where the coils are separated by the tissue subject to anastomosis. Note that the predefined fixed position may be one of several, but each of the positions are pre-defined and fixed. When the same device is in a non-deployed (straight wire, non-coil) configuration, the same first magnet (now along the length of the wire) is in a different (but still predefined and fixed) position relative to the second magnet (also along the length of the wire). These two relative positions, in the deployed and non-deployed configurations, are fixed and defined, regardless of human intervention. Therefore, the first magnet and second magnet transition from the first non-deployed relative fixed position to the second non-deployed relative fixed position automatically and, while a human deploying the device affects the transition from a non-deployed to deployed state, human intervention does not affect the predefined fixed position of the first magnet relative to the second magnet in the non-deployed state and the predefined fixed position of the first magnet relative to the second magnet in the deployed state.

In contrast, the prior art teaches separate magnetic assemblies (because they are not physically coupled to each other in a fixed configured in at least one of, or both, a pre-deployment or post-deployment shape) that must be manually aligned relative to each other in order to achieve the right compressive force. That means there is no predefined fixed position of the first magnet assembly relative to the second magnet assembly in the non-deployed state, since it is different every time and dependent on how the assembly is used. It also means that there is no predefined fixed position of the first magnet relative to the second magnet in the deployed state.

Operationally, this self-alignment feature improves the safety profile of the device. Various portions of the body are subject to tissue motion, such as peristalsis in the gastrointestinal (GI) tract, which can dislodge or separate the two opposing magnetic bodies that are compressing tissue. Because prior art devices comprise two independently moving magnetic structures, they always carry a high risk of detaching and re-attaching in a different configuration or location, thereby potentially creating an anastomosis in the wrong tissue, such as the wrong section of the patient's GI tract. In the presently disclosed embodiments, if, after the first magnetic element on a first coil attaches to a second magnetic element on a second coil, the two magnetic elements thereafter detach, the detachment will only be temporary and the two magnetic elements will automatically reattach over the target tissue region without requiring human intervention. First, the two magnetic elements are in a fixed relation, as described above. Second, they are in a fixed position relative to the target tissue because they have been inserted into place by puncturing through the target tissue. Accordingly, if they temporarily detach, the magnets will not travel (since the underlying wire has punctured through the target tissue) and they will coil back into their deployed configuration once the disruptive motion subsides. As a result, the two magnetic elements on opposing coils separated by target tissue automatically reattach to each other, after being momentarily separated by anatomical motion, at least 70% of the time, most likely at least 90%, 95%, and 99% of the time.

The aforementioned coupled structure also allows for an easier deployment procedure. Rather than having to individually deploy two separate assemblies on two opposing sides of the tissue subject to anastomosis, a physician deploys a single device, which is used to make an initial puncture through the tissue subject to anastomosis and then automatically coils, providing the requisite compressive force.

Second, the embodiments disclosed herein preferably use a solid wire, such as a Nitinol wire, to integrally couple the magnetic elements to each other. This has several benefits, including 1) being able to provide a conductive wire mechanism that integrates electrical cautery puncturing functionality into the anastomosis device itself, 2) avoiding the use of a tube, or a structure with any hollow lumen passing therethrough, which is more complicated to manufacture, is more challenging to deploy reliably, and results in a device that is either excessively thick or has magnets with too small a profile, thereby decreasing the amount of available compressive force, and 3) allowing physicians to place the device in locations that a thicker device or a catheter cannot reach, such as with pseudocysts. While a solid wire is a preferred embodiment, all of the presently disclosed embodiments can work with a hollow tube, such as a hollow Nitinol wire, through which a guide wire may be passed and used to position the device.

Third, the embodiments disclosed herein teach a wire with a plurality of magnetic elements that are preferably not fixedly attached to the wire but, rather, tightly positioned over the wire and separated from adjacent magnetic elements using a non-ferromagnetic spacer. This has several benefits. The disclosed devices are simpler to manufacture because each of the magnetic elements need not be individually fixed to the wire using solder, detents, tabs, glue, welding, or friction fits. Rather, magnetic elements may be individually manufactured with a lumen, allowing for greater tolerances, strung over the wire via their lumens, and separated from adjacent magnetic elements using non-ferromagnetic spacers, obviating any additional fixation step to attach the magnetic elements to the wire. This enables each magnetic element to have a fixed position relative to other magnetic elements on the same wire without actually having to attach each magnetic element to the wire. Furthermore, the fixed position of magnetic elements with non-ferromagnetic spacers in between each of the magnetic elements (thereby creating an alternating sequence of magnetic elements and non-ferromagnetic spacers) prevents the unwanted clumping or migration of magnets. While the prior art discloses the use of jackets or protrusions from the magnetic element, such structures fail to prevent clumping or the general migration of magnetics out of a preferred configuration or alignment. In fact, it is preferred for the magnetic elements to have smooth surfaces (no raised portions) to enable a more flexible degree of alignment and without having to align non-raised portions with raised portions. It should be appreciated, however, that in a less preferred embodiment, each magnetic element may be attached to the wire and separated from adjacent magnetic elements by a space (not a physical, non-ferromagnetic spacer made, for example, from plastic or other medically acceptable materials).

Fourth, the disclosed coil structure allows for the application of multiple magnetic layers, thereby increasing compressive force on a tissue surface, without increasing the complexity of a medical procedure. If prior art devices are used, one would have to manually mate multiple individual, physically separate magnetic assemblies, on both sides of the tissue surface, to achieve what the presently disclosed coil structures can achieve automatically: compression of tissue with multiple magnetic layers on both sides of the tissue that are automatically aligned with each other and in a fixed relative position in both the pre-deployment and post-deployment configurations. Specifically, the devices and methods of the present specification require only a single device and a single pathway to create an anastomosis. Prior art approaches require two separate access pathways to the area of the anastomosis. In addition, prior art devices require two separate implants, such that a physician would be required to endoscopically or laparoscopically access two different paths. The need for two separate and different paths is not only more invasive but also requires an extra step. The devices and methods of the present specification do not require the extra step necessary with prior art approaches. With the devices and methods of the present specification, one path leads to the positioning of both sides of the anastomosis device. Therefore, the devices and methods of the present specification have the advantages over the prior art of being directed toward the positioning of two sides of the anastomosis device using a single implant procedure and without requiring a second step.

The term "and/or" means one or all of the listed elements or a combination of any two or more of the listed elements.

In the description and claims of the application, each of the words "comprise" "include" and "have", and forms thereof, are not necessarily limited to members in a list with which the words may be associated.

Unless otherwise specified, "a," "an," "the," "one or more," and "at least one" are used interchangeably and mean one or more than one.

The term "pre-deployment" or "delivery" configuration refers to the configuration where the solid wire, over which the magnetic elements or members are placed, is substantially straight or linear.

The term "post-deployment" or "deployed" configuration refers to the configuration where the solid wire, over which the magnetic elements or members are placed, is substantially coiled or in a spiral shape.

The term "coil" refers to an entire magnetic anastomosis device and the term "loop" refers to an individual complete circle of wire, with or without magnets and spacers, of a "coil".

For any method disclosed herein that includes discrete steps, the steps may be conducted in any feasible order. And, as appropriate, any combination of two or more steps may be conducted simultaneously.

Also herein, the recitations of numerical ranges by endpoints include all whole or fractional numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements. That said, it should be appreciated that the dimensions provided herein are of critical importance because they enable a device that is small enough to be delivered to the required physical spaces in the body while still having enough compressive force to create an anastomosis.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

Figure 1:
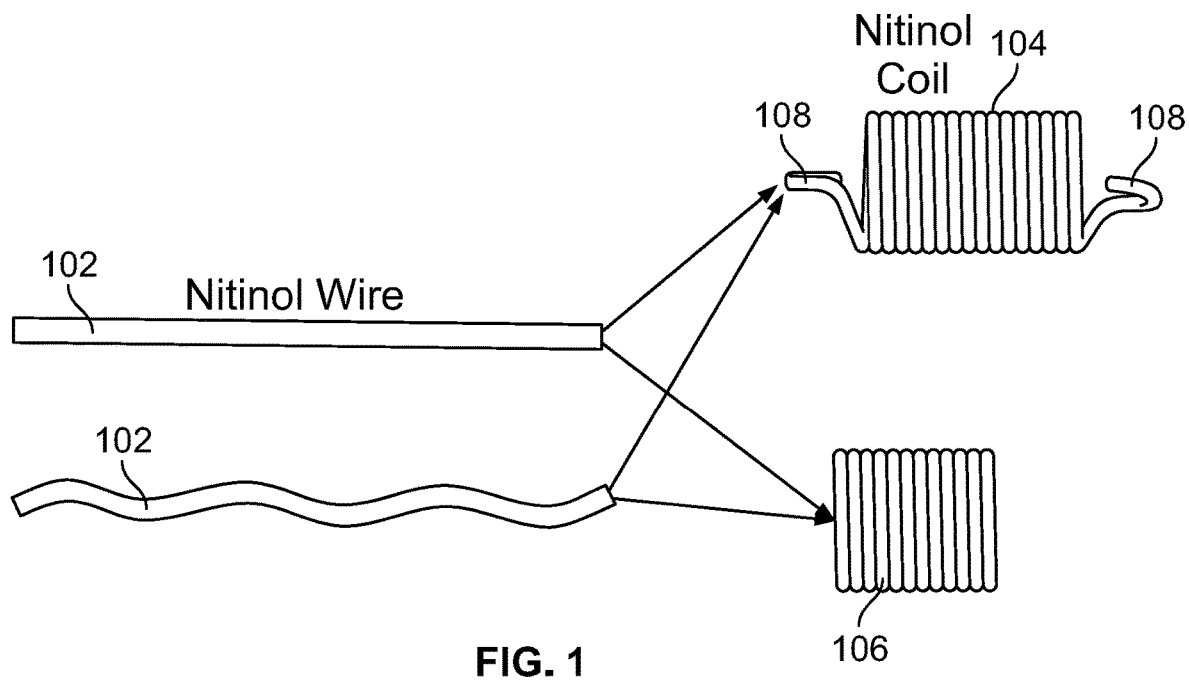
FIG. 1 illustrates a straight shape memory alloy (SMA) wire which coils within a human body, in accordance with an embodiment of the present specification.

FIG. 1 illustrates a straight SMA wire 102 which coils up within a human body, in accordance with an embodiment of the present specification. Wire 102 is made of a SMA material such as Nitinol. A shape-memory alloy, which shall be alternatively referred to as SMA, smart metal, memory metal, memory alloy, muscle wire, and/or smart alloy, is an alloy that "remembers" its original shape and that, when deformed, returns to its pre-deformed shape upon heating. NiTi alloys change from martensite to austenite upon heating. In an embodiment, the SMA wire 102 is made of a copper-aluminum-nickel alloy. In another embodiment the SMA wire 102 is made of a nickel-titanium alloy. In an embodiment, diameter of the wire 102 ranges between 0.1 to 6 mm, has a maximum strain of less than 10% in an uncoiled position and a maximum cross sectional dimension ranging from 5 mm to 60 mm in a coiled position. In an embodiment, for a 5% strain, and for wire diameters less than 0.75 mm, ranging between 0.75 mm and 1 mm, and greater than 1 mm, the diameters of the coiled up wires are less than 15 mm, between 15 mm and 20 mm, and greater than 20 mm respectively. In an embodiment, for a 10% strain, and for wire diameters of 1 mm, 1.25 mm, 1.5 mm, 1.7 mm, 2 mm and 2.5 mm the diameters of the coiled up wires are 10 mm, 12.5 mm, 15 mm, 17 mm, 20 mm, 25 mm and 45 mm respectively. In an embodiment, for a 6% strain, and for wire diameters of 0.6 mm, 0.75 mm, 0.9 mm, 1.02 mm, 1.2 mm and 1.5 mm the diameters of the coiled up wires are 10 mm, 12.5 mm, 15 mm, 17 mm, 20 mm, 25 mm and 45 mm respectively. Further, in various embodiments, the wire 102 coils up into at least 2 loops upon delivery into a body.

$A_s$ and $A_f$ are the temperatures at which the transformation from martensite to austenite starts and finishes. Upon insertion into a human body and placement in an anastomosis site, wire 102 changes shape and coils up as 104 or 106 in response to the higher temperature of the human body relative to the room temperature. In various embodiments, the diameter of the wire 102 ranges between 0.1 mm to 10 mm and the length of the wire 102 ranges from 1 cm to 250 cm. In some embodiments, loops 108 are provided at one or more ends of the wire for attachment with a delivery catheter as explained with reference to FIGS. 23A and B. In various embodiments, the $A_f$ temperature of the wire is less than or equal to 40° C. and $A_s$ temperature of the wire is less than or equal to 37° C. In various embodiments the strain on the Nitinol wire in its martensite shape is less than or equal to 10%. In one embodiment, the coil has a circular cross-section with a radius r where the circumference of the coil is $2\pi r$ and the area of the coils is $\pi r^2$ wherein the coil creates an anastomotic opining of a radius approximately r and area $\pi r^2$. In some embodiments, the Af temperature (transition temperature) of the wire is greater than or equal to 37° C. and a mechanism for heating the wire is provided to assist in heating the wire to transform the wire from its martensite to austenite shape. In one embodiment, the mechanism for heating the wire comprises passing an electrical current through the wire. In some embodiments, the Af temperature (transition temperature) of the wire is greater than or equal to 20° C.

Figure 2:
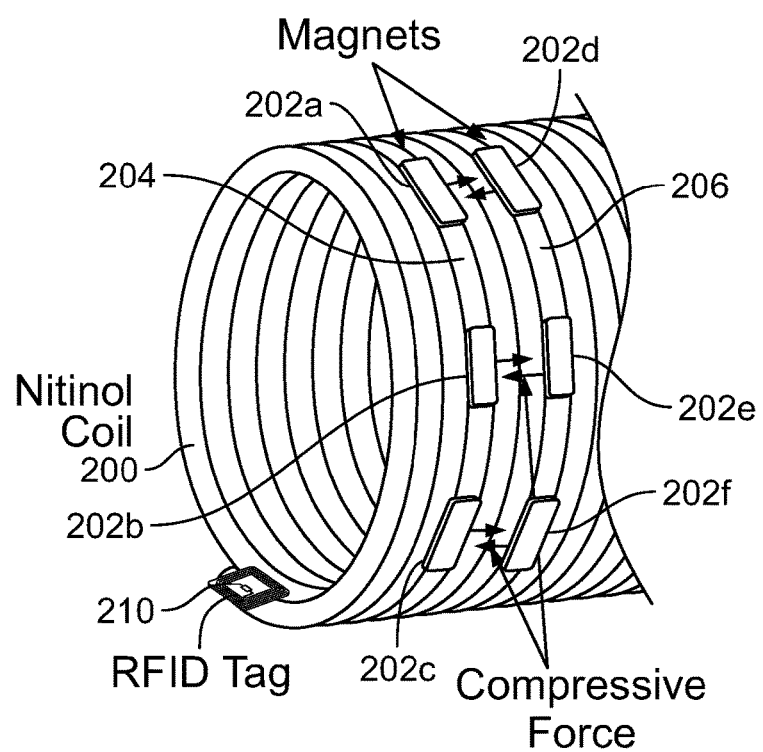
FIG. 2 illustrates a plurality of magnets threaded over loops of a SMA wire, in accordance with an embodiment of the present specification.

FIG. 2 illustrates a plurality of magnets 202a, 202b, 202c, 202d, 202e, 202f threaded through loops 204, 206 of a SMA wire, in accordance with an embodiment of the present specification. Magnets 202a, 202b, 202c, 202d, 202e, 202f are threaded through loops 204 and 206 of coil 200. In an embodiment, coil 200 is a Nitinol wire that coils up in response to temperature change. A repulsive force acts between adjacent magnets 202a, 202b and 202c which are threaded on the same loop 204, thereby maintaining a desired distance between said magnets. Similarly, a repulsive force acts between adjacent magnets 202d, 202e and 202f which are threaded on the same loop 206, thereby maintaining a desired distance between these magnets. An attractive force acts between the magnets threaded on loop 204 and the magnets on coil 206. Hence, there is attraction between the magnets 202a and 202d, between magnets 202b and 202e, and between magnets 202c and 202f. The attraction between the magnets on adjacent loops creates a compressive force 207 between loops of the coil, drawing the loops together to cut tissue between the loops and allow for anastomosis formation. In various embodiments, the compressive force ranges from 0.1 to 0.5 N and an associated pressure applied to layers of tissue caught between the loops ranges between 0.15 psi-145 psi (0.001 and 1 MPa). In an embodiment, at least two magnets are coupled with two adjacent loops of the coil 200 and the wire coils up into at least two loops. In an embodiment, the magnets are rare earth magnets covered with a biocompatible material such as gold, nickel, Teflon, parylene, copper, zinc, silicone, epoxy or titanium. In an embodiment, the coil 200 includes an RFID tag 210 to assist in the localization of the coil 200 after deployment and during anastomosis formation. Using an RFID scanner, the position of the coil can be identified, through communications with the embedded RFID tag, to determine the precise location of the coil in the patient without the need for radiation for visualization. In some embodiments, the grade of the magnet is N35 or greater.

In one embodiment, the Nitinol coil applies an amount of pressure less than or equal to 50 mm Hg (0.97 psi) on the tissue and the combined coil and magnets apply an amount of pressure greater than 50 mm Hg (0.97 psi) on the tissue. In another embodiment, the Nitinol coil applies an amount of pressure less than or equal to 80 mm Hg (1.57 psi) on the tissue and the combined coil and magnets apply an amount of pressure greater than 80 mm Hg (1.57 psi) on the tissue. In yet another embodiment, the Nitinol coil applies an amount of pressure less than or equal to 120 mm Hg (2.32 psi) on the tissue and the combined coil and magnets apply an amount of pressure greater than 120 mm Hg (2.32 psi) on the tissue. In yet another embodiment, the Nitinol coil applies an amount of pressure less than or equal to 150 mm Hg (2.90 psi) on the tissue and the combined coil and magnets apply an amount of pressure greater than 150 mm (2.90 psi) Hg on the tissue. In another embodiment, the Nitinol coil applies an amount of pressure less than or equal to 200 mm Hg (3.86) on the tissue and the combined coil and magnets apply an amount of pressure greater than 200 mm Hg (3.86) on the tissue. In an embodiment, the coil pressure at each coil tissue interface is sufficient to impede the capillary flow in the tissue by greater than 50%. In an embodiment, the coil creates a pressure of more than or equal to 20 mm Hg (0.39 psi) at more than one fourth of the circumference of coil and the pressure is relatively equally distributed among the two semicircles of each coil loop. In an embodiment, the pressure is more than or equal to 20 mm Hg (0.39 psi) at two or more points that are on the opposite sides on each coil loop.

In one of the embodiments, the majority of the compressive force, as described above, is initially provided by the SMA coil. However, as the magnets physically converge closer together, the magnetic compressive force overtakes the compressive force provided by the Nitinol coil and drives the anastomosis formation. In some embodiments, the process of anastomosis formation is accelerated by heating the coil via the passage of electrical current through the coil prior to deployment, thus damaging/coagulating or ablating the intervening tissue.

Figure 3A:
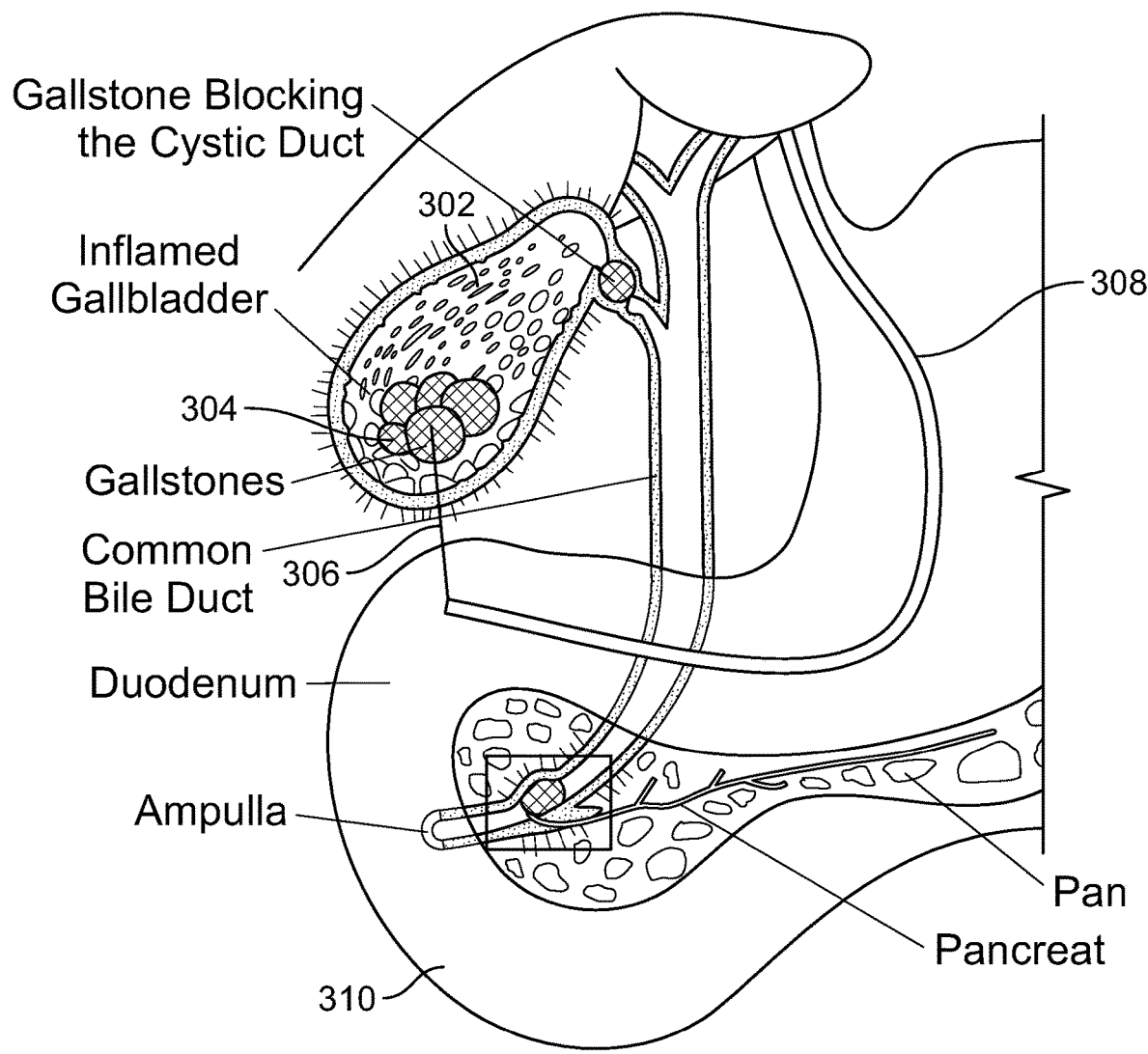
FIG. 3A illustrates a gall bladder with gallstones being punctured by using an endoscope for the placement of a SMA wire to create an anastomosis, in accordance with an embodiment of the present specification.

FIG. 3A illustrates a gall bladder 302 with cholecystitis and gallstones 304 being punctured by using a delivery catheter or needle and with an endoscope for the placement of a SMA anastomosis device to create an anastomosis, in accordance with an embodiment of the present specification. Gall bladder 302, having gall stones 304, is punctured by a delivery catheter or a needle 306 being delivered by means of an endoscope 308 inserted into a patient's duodenum 310. The catheter or needle 306 punctures a wall of the duodenum 310 and a gall bladder 302 in order to connect the gall bladder 302 with the duodenum 310 to form an anastomosis, using the devices of the present specification, for providing drainage to the gallbladder 302 and removal of the gall stones 304. The endoscope 308 in one embodiment is an echoendoscope and the puncture is made under ultrasonic visualization. The endoscope 308, in another embodiment, is a duodenoscope and the puncture is made under fluoroscopic visualization.

Figure 3B:
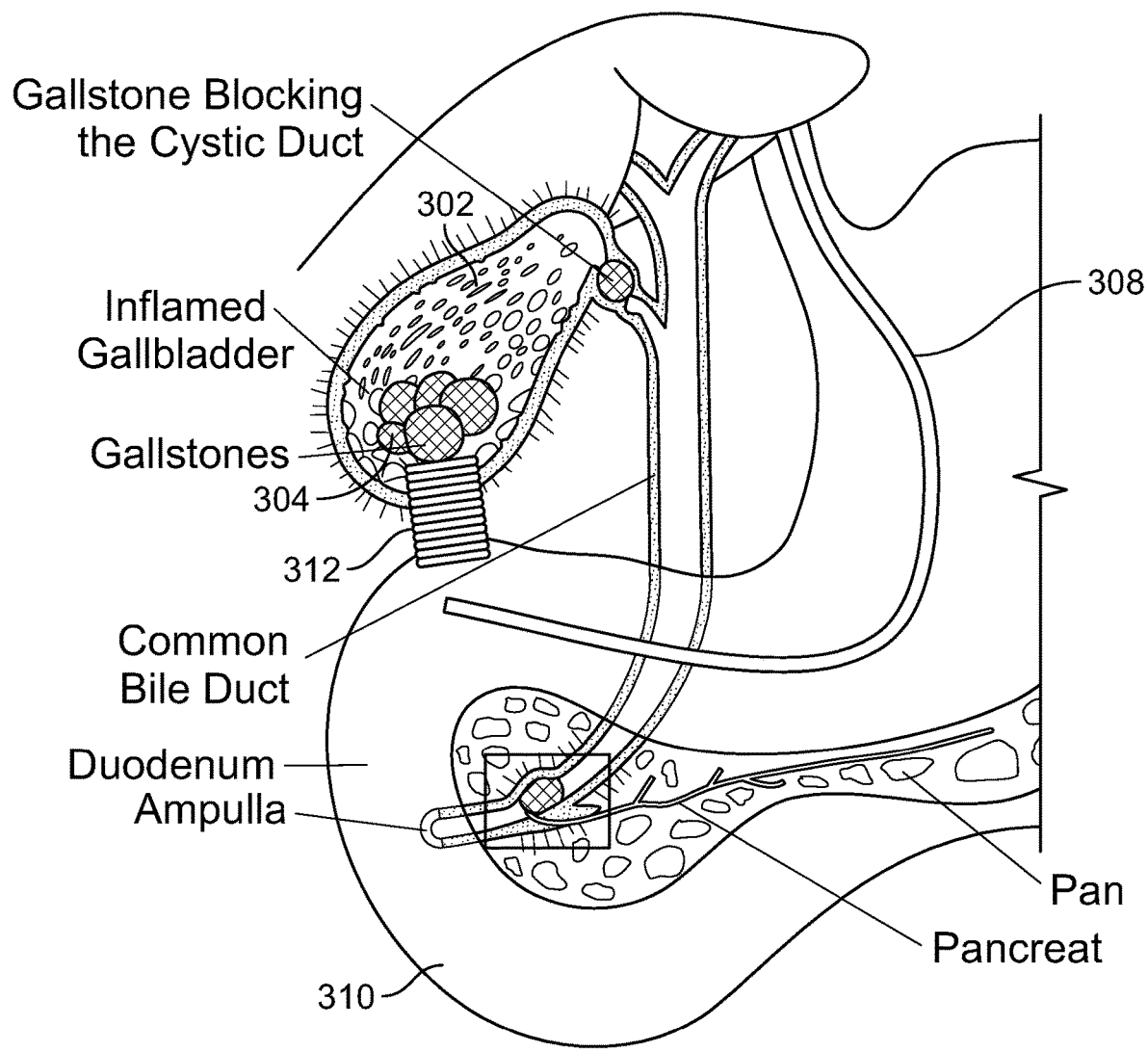
FIG. 3B illustrates a SMA coil forming an anastomosis between the gall bladder and duodenum shown in FIG. 3A, in accordance with an embodiment of the present specification.
Figure 3C:
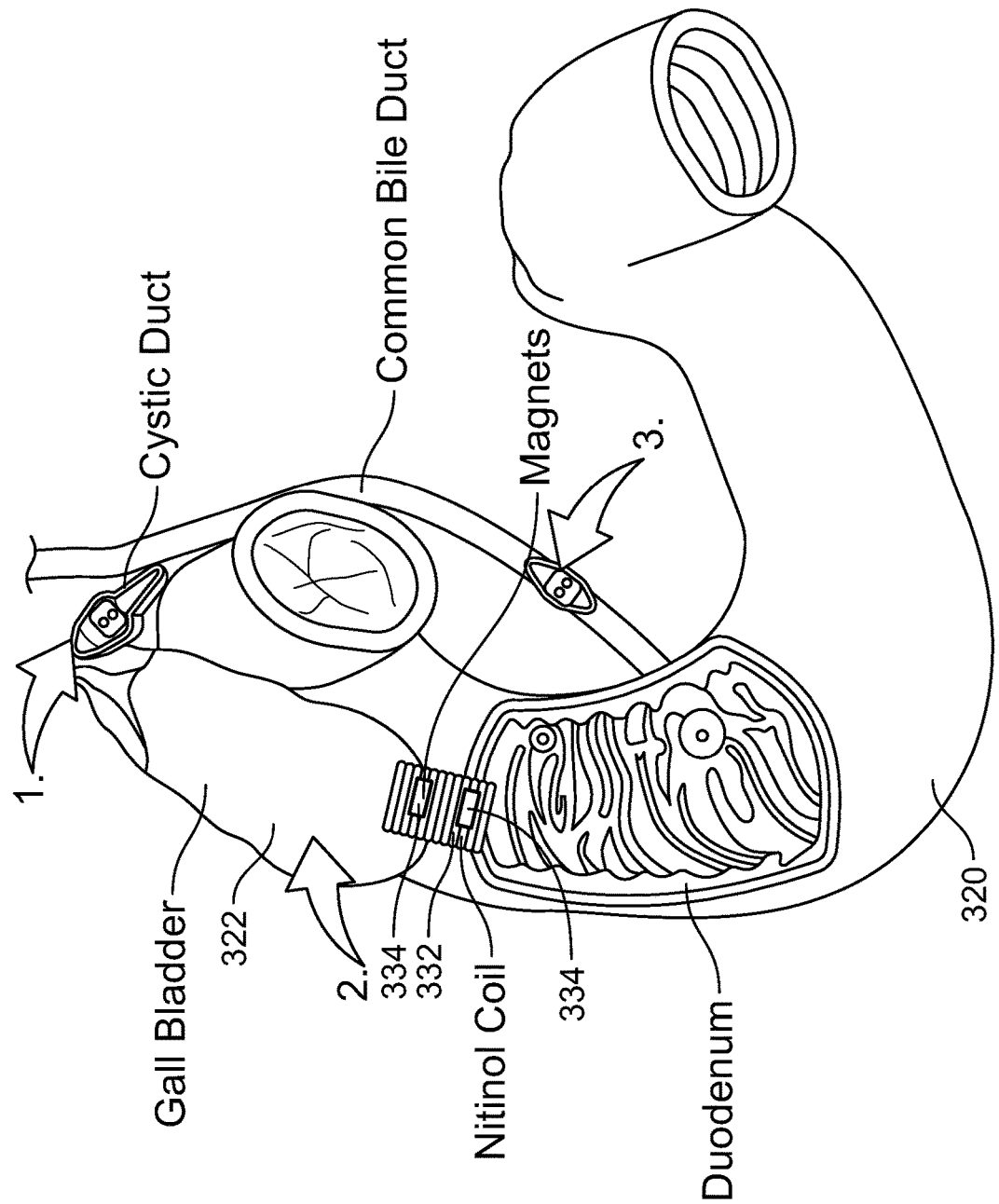
FIG. 3C illustrates a SMA coil threaded with magnets forming an anastomosis between a gall bladder and a duodenum, in accordance with another embodiment of the present specification.

FIG. 3B illustrates a SMA coil 312 deployed and forming an anastomosis between the gall bladder 302 and duodenum 310 shown in FIG. 3A, in accordance with an embodiment of the present specification. The SMA coil 312, which, in an embodiment, comprises a Nitinol wire, is delivered through the hole punctured by a catheter or needle in the gall bladder 302 wall via the endoscope 308. In response to exposure to body heat, the Nitinol wire changes shape and coils up, holding the tissue of the gall bladder 302 wall and the duodenum 310 wall in between the turns of coil 312 as shown in FIG. 3B, thereby forming an anastomosis between the gallbladder 302 and the duodenum 310. The coiling up of wire 312 causes a compressive force to act on the tissue caught between the coils, thereby cutting through the tissue to form the anastomosis. In an embodiment, magnets may be threaded in the coil 312 to further increase the compressive force, as shown in FIG. 2 and FIG. 3C. In various embodiments the anastomosis is formed over some time allowing time for neovascularization of the anastomosis resulting in a robust and stable anastomosis without significant leaks.

FIG. 3C illustrates a SMA coil 332 threaded with magnets 334 forming an anastomosis between a gall bladder 322 and a duodenum 320, in accordance with another embodiment of the present specification. The SMA coil 332, which in an embodiment comprises Nitinol, is threaded with magnets 334 placed in different/adjacent coil loops. The magnets 334 placed in different coil loops attract each other, thereby further increasing the compressive force in the coil 332 and accelerating or improving the cutting of the walls of gall bladder and duodenum to form an anastomotic opening. In an embodiment, one or more otomies or one or more stoma are created in the walls of gall bladder and/or duodenum to place the SMA coil 332 threaded with magnets 334 for forming the anastomosis.

Figure 3D:
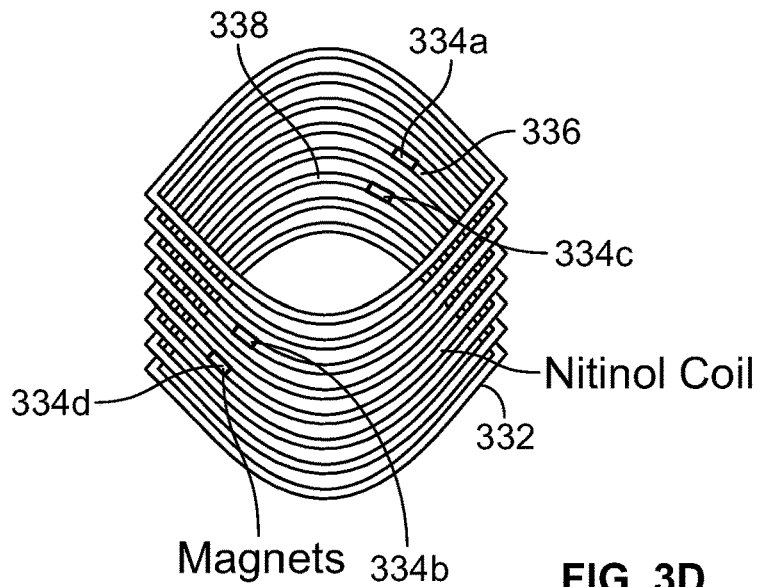
FIG. 3D is a close-up illustration of the SMA coil threaded with magnets shown in FIG. 3C, in accordance with an embodiment of the present specification.

FIG. 3D is a close-up illustration of the SMA coil 332 threaded with magnets shown in FIG. 3C, in accordance with an embodiment of the present specification. Coil 332 is threaded with magnet 334a and 334b in loop 336 and magnets 334c and 334d in loop 338. The poles of magnets 334a and 334b are arranged such that the magnets repel each other, thereby maintaining a constant pre-defined distance between each other on the loop 336. Similarly, the poles of the magnets 334c and 334d are arranged such that the magnets repel each other, thereby maintaining a constant pre-defined distance between each other on the loop 338. The poles of magnets 334a and 334c are arranged such that the magnets attract each other, thereby pulling the loops 336 and 338 of the coil 332 closer towards each other and increasing the compressive force exerted by the coil 332 on the tissue layers caught between the coil 332 loops. Similarly, a compressive force is caused by the attraction between magnets 334b and 334d. The compressive force gradually increases over time as the magnets cut through the tissue and get closer, slowly accelerating the cutting action and anastomosis formation once the two walls have had time to fuse together. This approach decreases the chances of a leak in situations where the anastomosis was performed too fast, not allowing for enough time for apposition and fusion of the two adjacent walls.

Figure 4A:
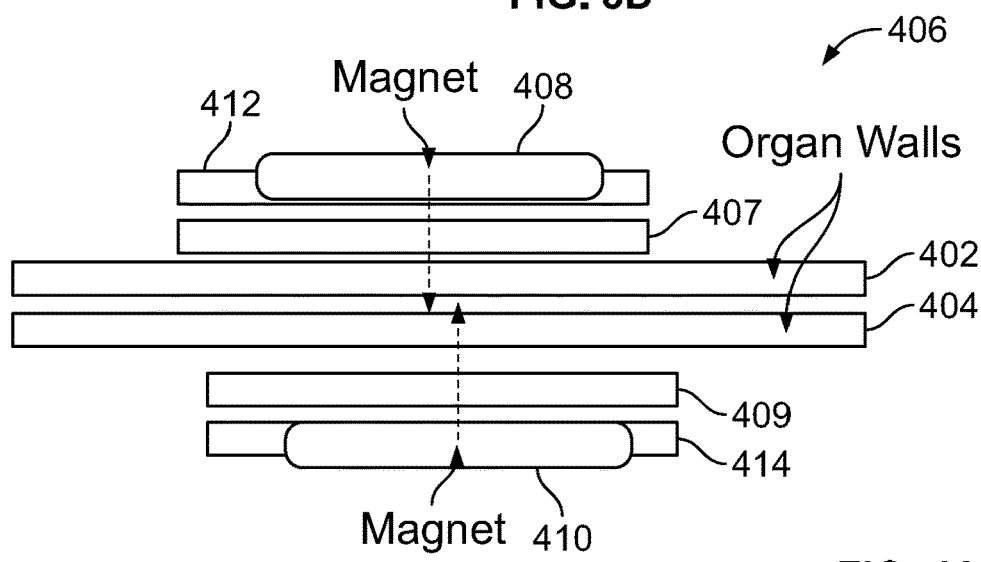
FIG. 4A illustrates a first stage of an anastomosis process, in accordance with an embodiment of the present specification.

FIG. 4A illustrates a first stage of an anastomosis process, in accordance with an embodiment of the present specification. As shown in the figure, organ walls 402 and 404 are caught between adjacent loops 407, 409 of coil 406. In an embodiment, the coil 406 is made of a SMA material, such as Nitinol, and is delivered into the organ as a straight piece of wire or an elongated relative straight coil, which, as a result of exposure to body heat, changes shape to form a coil of predetermined shape and dimension such that the adjacent organ walls are caught between the coil loops. With reference to FIG. 3A, in an embodiment, the organ wall 402 is the wall of the gall bladder 302 and the organ wall 404 is the adjoining wall of the duodenum 410. Referring to FIG. 4A, magnets 408 and 410 are coupled with loops 412 and 414 respectively of the coil 406. The poles of magnets 408 and 410 are arranged such that the magnets attract each other, thereby pulling the loops 407, 412 and 409, 414 closer towards each other and increasing the compressive force exerted by the coil 406 on the organ walls 402 and 404. The SMA wires exert relatively stable force over time while the magnets will exert a progressively increasing compressive force which accelerates as the anastomosis forms, thereby resulting in an initial fusion of the walls and later cutting through the walls once the two walls have fused. In some embodiments, the compressive surface is provided by two opposing magnets or a wire and a magnet.

Figure 4B:
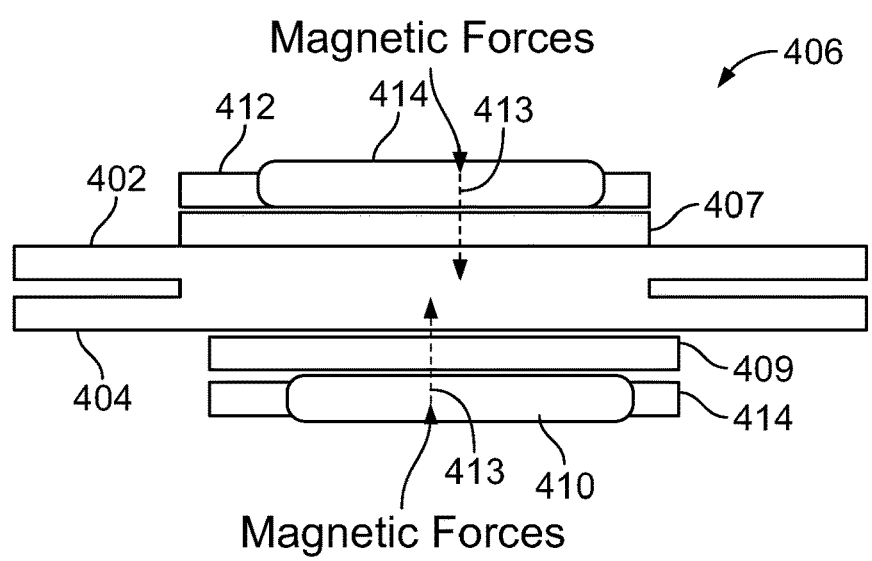
FIG. 4B illustrates a second stage of the anastomosis process shown in FIG. 4A, in accordance with an embodiment of the present specification.
Figure 4C:
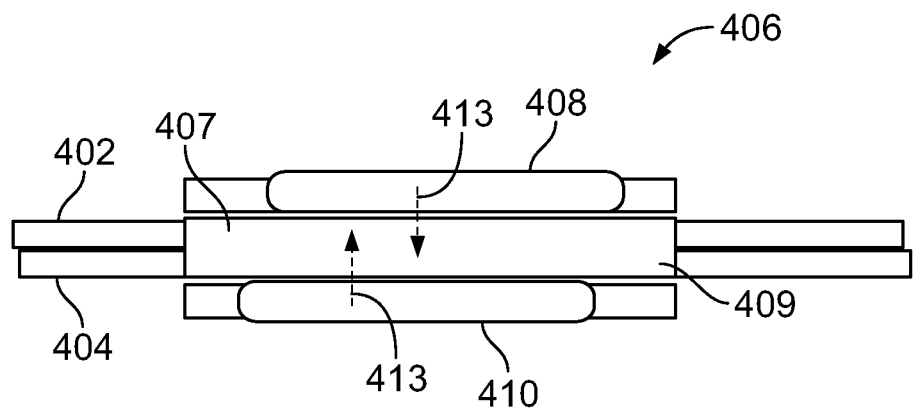
FIG. 4C illustrates a third stage of the anastomosis process shown in FIGS. 4A and 4B, in accordance with an embodiment of the present specification.
Figure 4D:
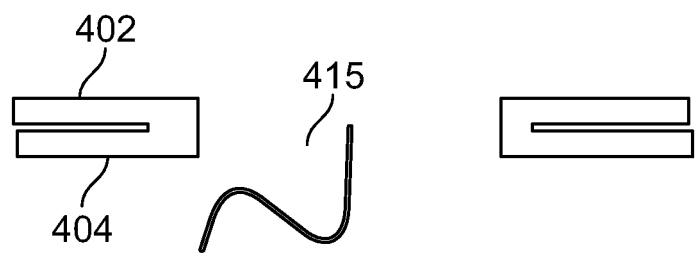
FIG. 4D illustrates formation of the anastomosis as a fourth and final stage of the anastomosis process shown in FIGS. 4A, 4B and 4C, in accordance with an embodiment of the present specification.

FIG. 4B illustrates the second stage of the anastomosis process shown in FIG. 4A, in accordance with an embodiment of the present specification. As shown in FIG. 4B, the loops 407, 412 and 409, 414 of coil 406 are pulled closer together by the magnetic forces 413 attracting magnets 408, 410 together, thereby compressing the organ walls 402 and 404 between loops 407 and 409 causing ischemia, followed by neovascularization fusing the two organ walls. FIG. 4C illustrates a third stage of the anastomosis process shown in FIGS. 4A and 4B, in accordance with an embodiment of the present specification. As shown, the compressive force of the coil 406, further enhanced due to the attractive magnetic force 413 between the magnets 408, 410, causing complete ischemia, apoptosis and ischemic necrosis of the tissue caught in the center of the coil and causes loops 407, 409 and/or the magnets 408 of the coil 406 to cut through the organ walls 402, 404. FIG. 4D illustrates formation of the anastomosis as a fourth and final stage of the anastomosis process shown in FIGS. 4A, 4B and 4C, in accordance with an embodiment of the present specification. As shown, an opening/anastomosis 415 is formed due to cutting through of organ walls 402, 404 by the coil, which then drops off and is naturally passed through without the need for an endoscopy. In one embodiment, the coil is designed to facilitate passage after cutting through the wall in either an anterograde or retrograde direction. In another embodiment, the coil is configured to remain in the anastomosis for later removal with the use of an endoscope.

Figures 5, 6:
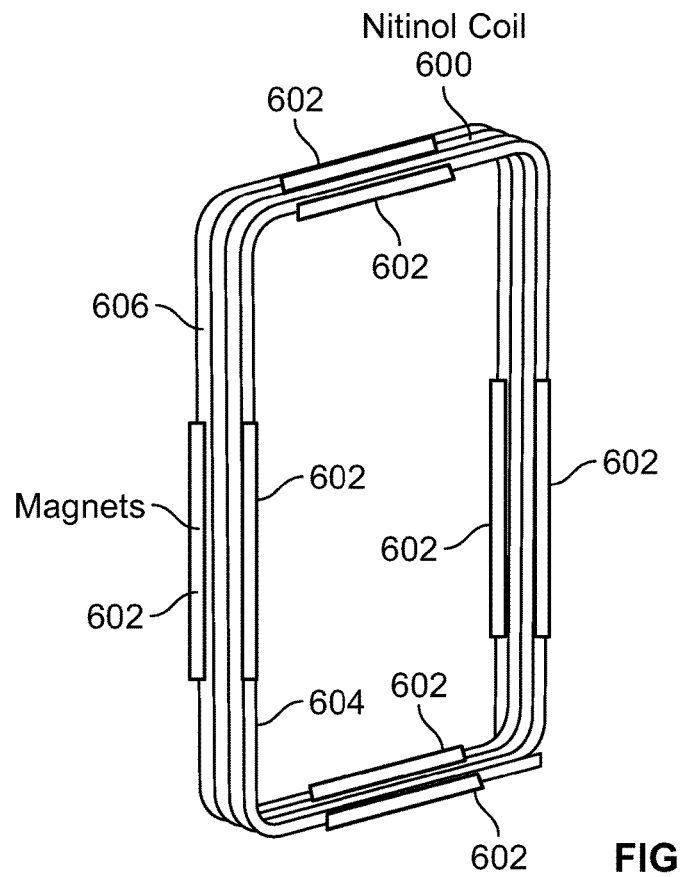
FIG. 5 illustrates a table showing exemplary dimensions of a SMA wire used for creating an anastomosis, in accordance with embodiments of the present specification.
FIG. 6 illustrates a square SMA coil coupled with magnets for creating an anastomosis, in accordance with an embodiment of the present specification.

FIG. 5 illustrates a table 500 showing exemplary dimensions of an anastomosis device used for creating an anastomosis, in accordance with embodiments of the present specification. Column 502 shows the exemplary diameters in mm of the coil, while columns 504, 506, 508, 510, and 512 show corresponding exemplary lengths in cm of a wire coiled up into 1, 2, 4, 8 and 16 loops respectively. The desired diameter of the anastomosis is between 0.5 cm and 5 cm and the desired length of the coil wire is from 3 cm to 250 cm. The preferred diameter of the anastomosis will depend on the specific organ and would be between 1-2 cm for a gall bladder, 0.5-1 cm for a bile duct, 1-2 cm for a cyst-gastrectomy or cystojejunostomy and 2-5 cm for a gastrojejunostomoy of entero-enterostomy. These are representative numbers, however, and, in practice, the diameter of the coil will be determined based on the diameter of the organ and the indication being treated. In various embodiments, the diameter of the coil is less than or equal to the diameter of the organ to be anastomosed. For example, in cases of biliary anastomosis, small bowel anastomosis, colonic anastomosis, gall bladder anastomosis, pseudocyst anastomosis, and vascular anastomosis, the diameters of the coil are less than or equal to 10 mm, less than or equal to 30 mm, less than or equal to 60 mm, less than or equal to 30 mm, less than or equal to 30 mm, and less than or equal to 25 mm respectively. The preferred number of loops will depend upon the total magnetic force needed to create the anastomosis, which in turn will depend upon the total thickness of the organ wall being anastomosed. In some embodiments, the SMA wire is delivered within a body by using an endoscope, hence, a length of the wire is required to be less than the length of the scope. In an embodiment, the length of the SMA wire is less than 250 cm, or more specifically less than 75 cm. In an embodiment where the length of the SMA wire is 75 cm, the number of coil loops that are obtained are 8. In an embodiment, where the length of the SMA wire is 100 cm, 16 coil loops having a diameter of 2 cm each or 8 coil loops having a diameter of 4 cm each are obtained. In an embodiment where the length of the SMA wire is 250 cm, 16 coil loops having a diameter of 5 cm each are obtained. Further, in various embodiments, a device having two coil loops, each comprising 8 magnets and another device having 8 coil loops, each comprising 2 magnets, each cause the same compression force on tissue caught between the respective coil loops. A size of the anastomosis required in a tissue governs the diameter of each coil loop, which in turn governs the number of magnets (and their lengths) being used in conjunction with the SMA wire causing the anastomosis. The compressive force required is a compressive pressure greater than the capillary blood flow in the tissue. In various embodiments, a predefined minimum pressure is required to be exerted by the SMA coil on the tissue being anastomosed, and said pressure is required to be distributed all along each coil loop. In an embodiment, said pressure is applied at least along four points on each coil loop. In other embodiments, pressure is applied along two or eight points along the circumference of each loop depending upon the dimensions of the loops.

In various embodiments, the diameter of a SMA wire being used for anastomosis ranges from 0.1 mm to 6 mm, while the pitch of the coil is less than 10 mm. In various embodiments, a maximum cross sectional diameter of a SMA coil ranges from 5 mm to 50 mm wherein the number of loops in the coil are at least two and maximum 100 and the total length of the coil wire is less than or equal to 250 cm.

The maximum strain in the wire in the straight position (martensite shape) is less than or equal to 10%. In various embodiments, the diameter of the coil will determine the diameter of the wire, with a coil less than or equal to 15 mm in diameter being best created with a wire diameter of less than or equal to 0.75 mm, a coil diameter of 15-25 mm being best created with a wire diameter of 0.75-1.0 mm and a coil diameter greater than or equal to 25 mm being best created with a wire diameter greater than or equal to 1 mm. In various embodiments, at the coil-tissue boundary interface, the magnets and SMA wire cause at least 0.15 psi, more preferably at least 1.0 psi pressure, and most preferably at least 2.50 psi pressure, to cut off blood supply in the tissue. In some embodiments, a pressure as high as 4.0 psi is applied. In various embodiments, at the coil-tissue boundary interface, the magnets and SMA wire cause pressure equal to or less than 145 psi.

In various embodiments, the magnets coupled with the SMA coil are rare-earth or permanent magnets, wherein each magnet has a maximum cross sectional length ranging from 0.2 mm to 7 mm, and a pull force ranging from 0.1 lb. to 4 lb (0.04-17.8 N). In some embodiments, a Neodymium magnet having a maximum energy product ranging from 35 to 55 is used. In some embodiments, the magnets are coated with materials such as Teflon, Parylene, silicone, epoxy, gold, titanium, nickel or copper. The ideal operating temperature of the magnet is less than 80° C. and the desired material grade for a Neodymium magnet is N30-N60. Ideally a neodymium magnet of N35-N110, N55, or a comparable rare earth magnet will be used.

In various embodiments, the shape of the anastomosis formed between two organs by using a SMA wire with or without magnets according to various embodiments of the present specification, such as those shown in FIGS. 4A-4D, is determined by the shape of the coiled SMA wire. For example, a square shaped coil would create a square shaped anastomosis. FIG. 6 illustrates a square SMA coil 600 coupled with magnets 602 for creating an anastomosis, in accordance with an embodiment of the present specification. The square shaped Nitinol coil 600 is coupled with eight magnets 602, four each on two separate loops 604 and 606 respectively. A repulsive force acts between the magnets coupled with the same loop, thereby keeping the magnets separated by a predefined distance. An attractive force acts between corresponding magnets placed on adjacent loops 604 and 606, thereby increasing the compressive force of the coil 600 and pulling loops 604 and 606 closer to each other for creating a square shaped cut in tissue.

Figure 7B:
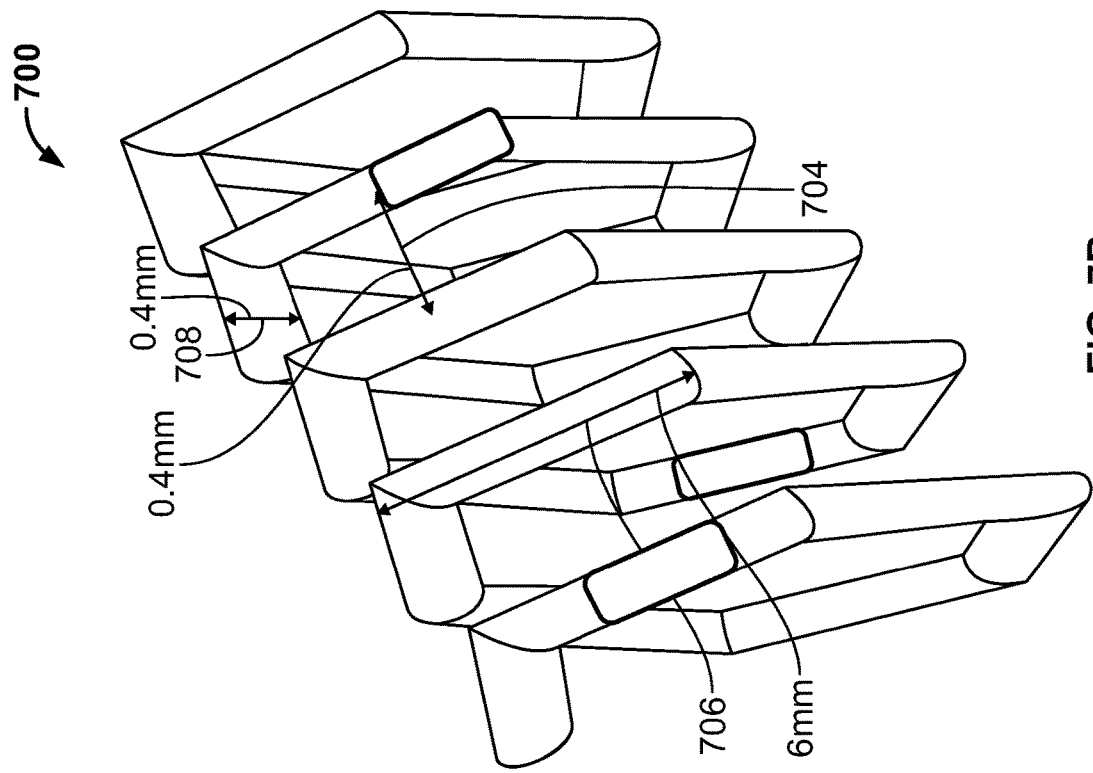
FIG. 7B illustrates exemplary dimensions of the hexagonal SMA coil shown in FIG. 7A, in accordance with an embodiment of the present specification.
Figure 7A:
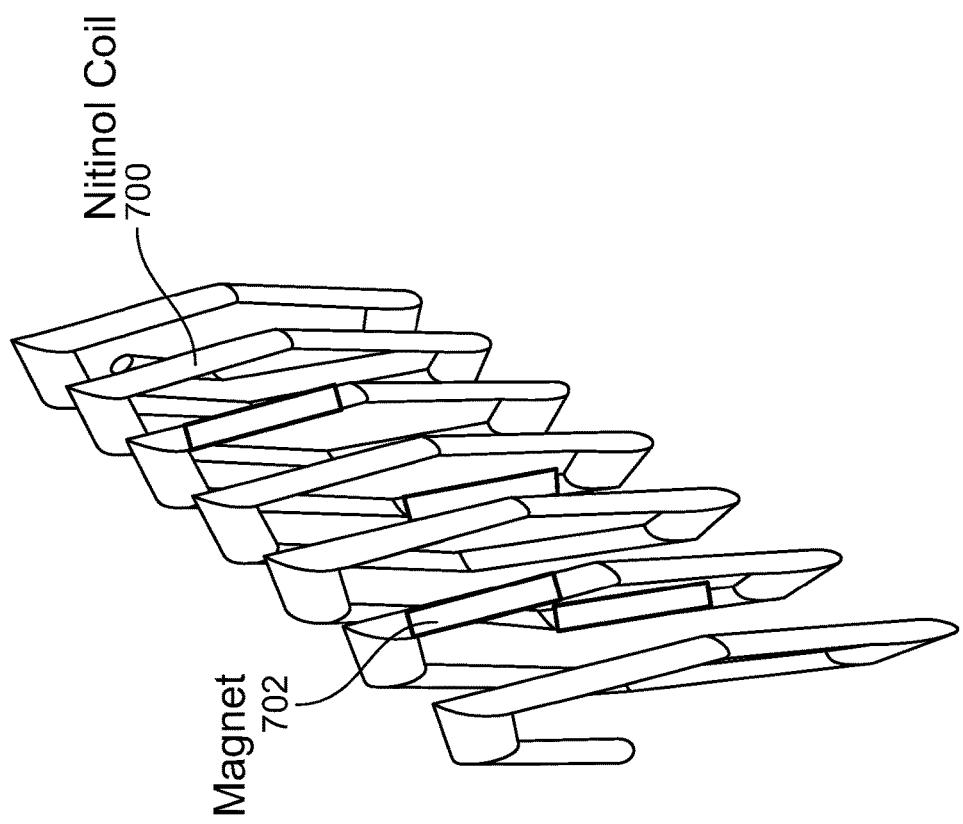
FIG. 7A illustrates a hexagonal SMA coil coupled with magnets for creating an anastomosis, in accordance with an embodiment of the present specification.

FIG. 7A illustrates a hexagonal SMA coil 700 coupled with magnets 702 for creating an anastomosis, in accordance with an embodiment of the present specification. Hexagonally coiled SMA wire 700 coupled with magnets 702 creates a hexagonal shaped anastomosis between two organs by cutting through the organ walls hexagonally. FIG. 7B illustrates exemplary dimensions of the hexagonal SMA coil 700 shown in FIG. 7A, in accordance with an embodiment of the present specification. In an embodiment, a distance or separation 704 between two loops of the coil 700 or the pitch measures approximately 0.4 mm, a length 706 of one side of a hexagonal loop is approximately 6 mm, and a circumference 708 of the wire forming the coil is approximately 0.4 mm. In various embodiment's the pitch of the coil in its post-deployment (austenite shape) could vary from the diameter of the SMA wire to 5 times the diameter of the wire used in the coil and is always less than the diameter of the coil.

Figure 7E:
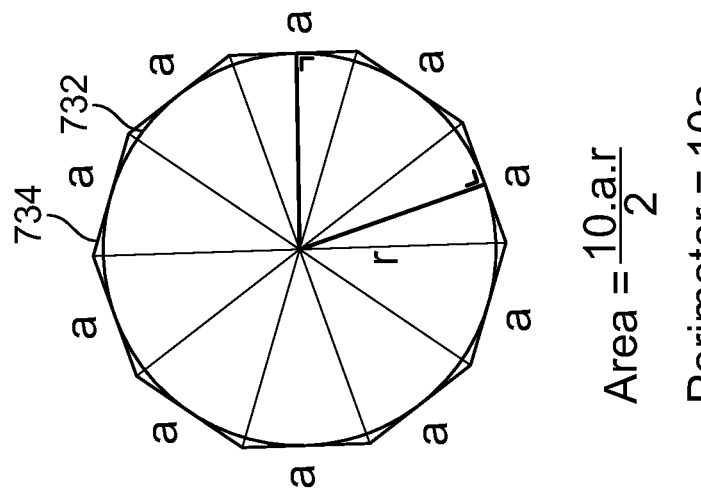
FIG. 7E illustrates exemplary dimensions of a decagonal SMA coil coupled with magnets for creating an anastomosis, in accordance with an embodiment of the present specification.
Figure 7D:
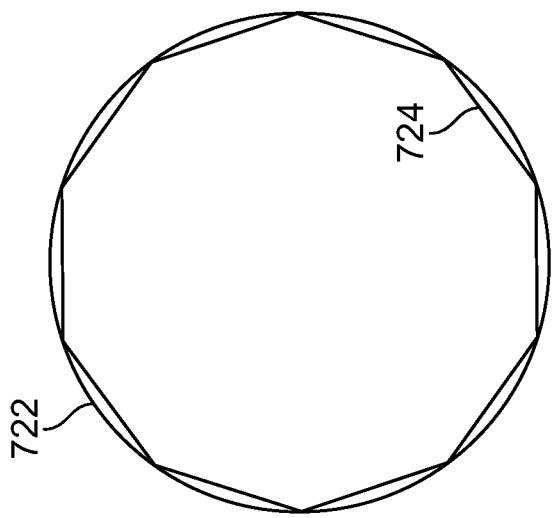
FIG. 7D illustrates a second decagonal SMA coil coupled with magnets for creating an anastomosis, in accordance with another embodiment of the present specification.
Figure 7C:
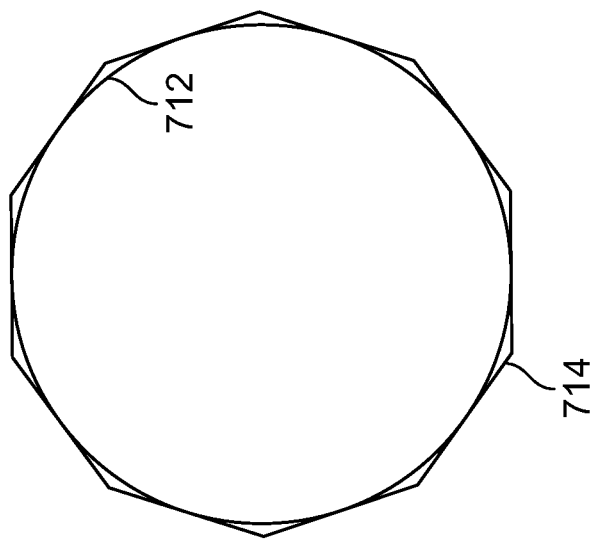
FIG. 7C illustrates a first decagonal SMA coil coupled with magnets for creating an anastomosis, in accordance with an embodiment of the present specification.

FIG. 7C illustrates a decagonal SMA coil 712 coupled with magnets 714 for creating an anastomosis, in accordance with an embodiment of the present specification. Referring to FIG. 7C, the magnets 714 are coupled to the coil 712 such that the magnets 714 are positioned predominantly on an outer surface of the coil 712. FIG. 7D illustrates a decagonal SMA coil 722 coupled with magnets 724 for creating an anastomosis, in accordance with another embodiment of the present specification. Referring to FIG. 7D, the magnets 724 are coupled to the coil 722 such that the magnets 724 are positioned predominantly on an inner surface of the coil 722. The coil in FIG. 7C is preferred in indications where it's desirable for the anastomotic device to spontaneously pass after the anastomosis is created while the coil in FIG. 7D is preferred in indications where it's desirable for the anastomotic device not to spontaneously pass after the anastomosis is created.

FIG. 7E illustrates exemplary dimensions of a decagonal SMA coil 732 coupled with magnets 734 for creating an anastomosis, in accordance with an embodiment of the present specification. The magnets 734 are coupled to the coil 732 such that the magnets 734 are positioned predominantly on an outer surface of the coil 732. In an embodiment, an area of the coil 732 with magnets 734, which would produce an anastomosis with a same area, is equal to 10*a*r/2, where a is a length of each magnet 734 and r is a radius of a circle formed by the coil 732. In an embodiment, a perimeter of the coil 732 with magnets 734, which would produce an anastomosis with a same perimeter, is equal to 10*a, where a is a length of each magnet 734.

Figure 7F:
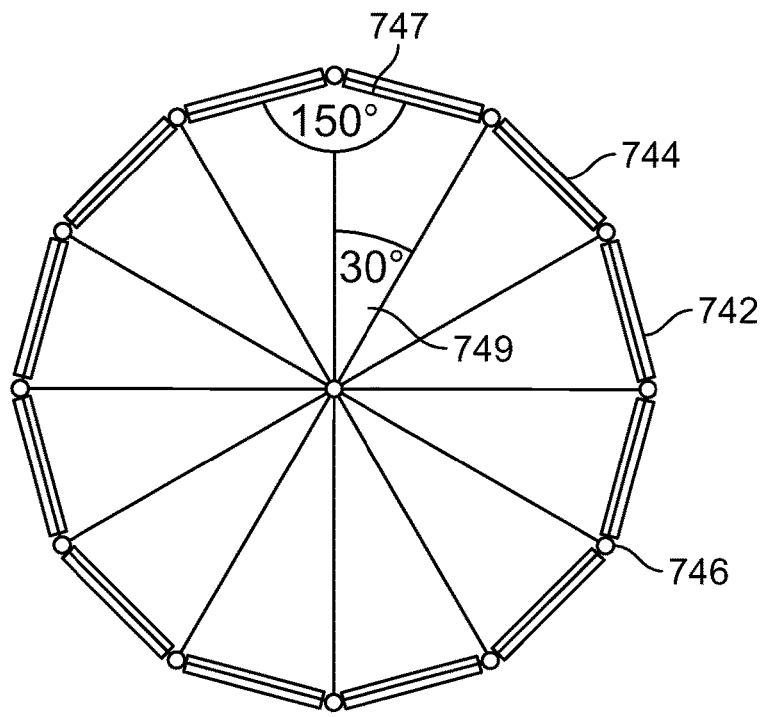
FIG. 7F illustrates a dodecagon SMA coil coupled with magnets for creating an anastomosis, in accordance with an embodiment of the present specification.

FIG. 7F illustrates a dodecagon SMA coil 742 coupled with magnets 744 for creating an anastomosis, in accordance with an embodiment of the present specification. Spacers 746 are included on the coil 742 between each pair of magnets 744. In an embodiment, spacers are included on the SMA coil for decreasing the number of magnets required for achieving a required compressive force. In an embodiment, the spacers 746 are composed of a non-ferromagnetic or biocompatible material. In various embodiments, the spacers 746 comprise silicone or Nitinol tubes or O-rings or circular balls. In an embodiment, an inner angle 747 formed between adjacent magnets 744 is equal to 150°. In an embodiment, an angle 749 formed at a center of a circle formed by the coil 742 and corresponding to each magnet 744 is equal to 30°. The non-ferromagnetic spacers prevents the magnets from sticking together while the coil is in its relatively straight, martensite pre-deployment shape and preventing it from assuming its coiled, austenite, post-deployment shape. The dimensions of the spacers are determined by the attractive forces between the two magnets and the bending force of the Nitinol coil such that the bending force of the coil is greater that than the attracting force between the ends of the magnet on the same coil allowing for the coil to achieve its pre-determined post-deployment shape. In an embodiment, an outer diameter of a spacer ring is between 25% and 300% of the outer diameter of the magnet and a length of a spacer ring is less than five times the length of the magnet.

Figure 7G:
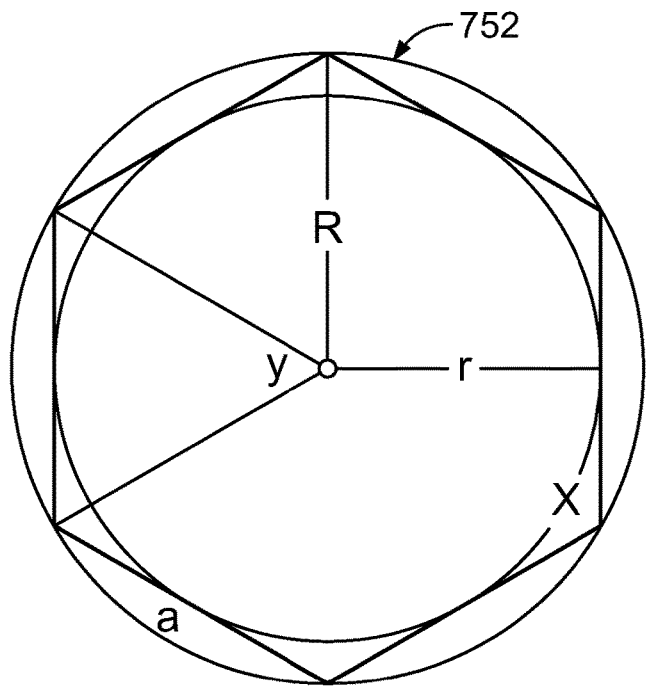
FIG. 7G illustrates exemplary dimensions of a hexagonal SMA coil in accordance with an embodiment of the present specification.
Figure 7H:
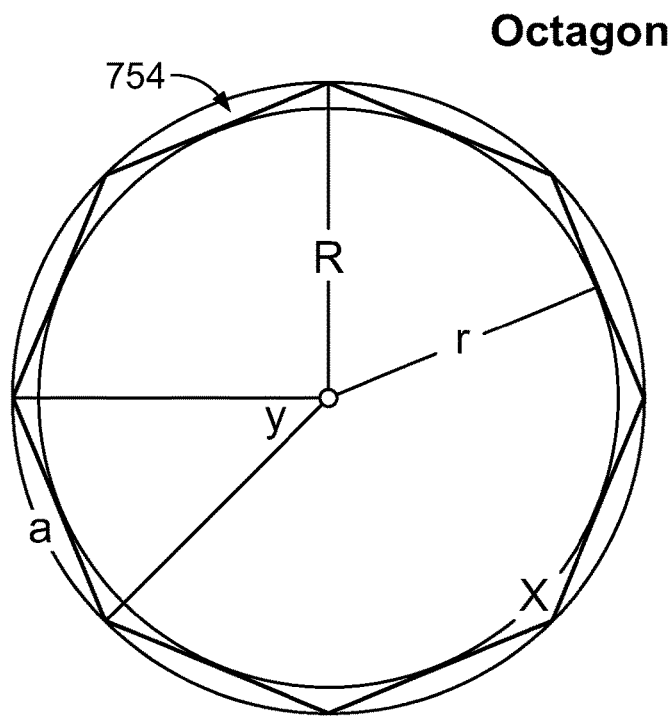
FIG. 7H illustrates exemplary dimensions of an octagonal SMA coil in accordance with an embodiment of the present specification.
Figure 7I:
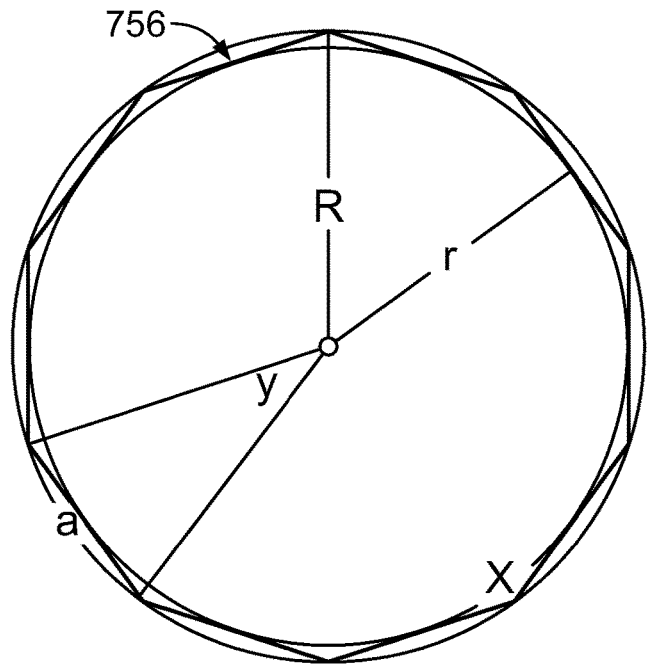
FIG. 7I illustrates exemplary dimensions of a decagonal SMA coil in accordance with an embodiment of the present specification.
Figure 7K:
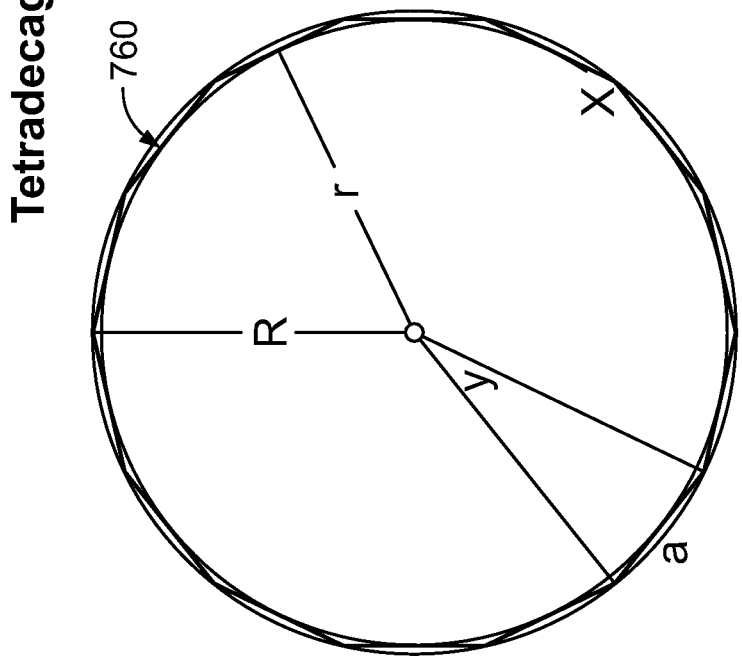
FIG. 7K illustrates exemplary dimensions of a tetradecagonal SMA coil in accordance with an embodiment of the present specification.

FIGS. 7G-7K illustrate various embodiments in which the coil has a regular polygonal cross-section that is both equiangular and equilateral where a=side length, r=in radius (apothem), R=circumradius, A=area, P=perimeter, x=interior angle, y=exterior angle and n=number of sides. The Side Length a is described by the formula a=2r tan($\pi$/n)=2R sin($\pi$/n); the Inradius r is described by the formula r=($\frac{1}{2}$)a cot($\pi$/n)=R cos($\pi$/n); the circumradius R is described by the formula R=($\frac{1}{2}$) a csc($\pi$/n)=r sec($\pi$/n); the Area A is described by the formula A=($\frac{1}{4}$)na$^2$ cot($\pi$/n)=nr$^2$ tan($\pi$/n); the Perimeter P is described by the formula P=na; the Interior Angle x is described by the formula x=((n−2)$\pi$/n) radians=(((n−2)/n)×180° degrees and the Exterior Angle y is described by the formula y=(2$\pi$/n) radians=(360°/n) degrees. The shape and dimensions of the polygon determines the shape and dimensions of the anastomosis. In accordance with various embodiments of the present specification, FIG. 7G illustrates a hexagonal shaped SMA coil 752, FIG. 7H illustrates an octagonal shaped SMA coil 754, FIG. 7I illustrates a decagonal shaped SMA coil 756, FIG. 7J illustrates a dodecagonal shaped SMA coil 758, and FIG. 7K illustrates a tetradecagonal SMA coil 760.

Figure 8:
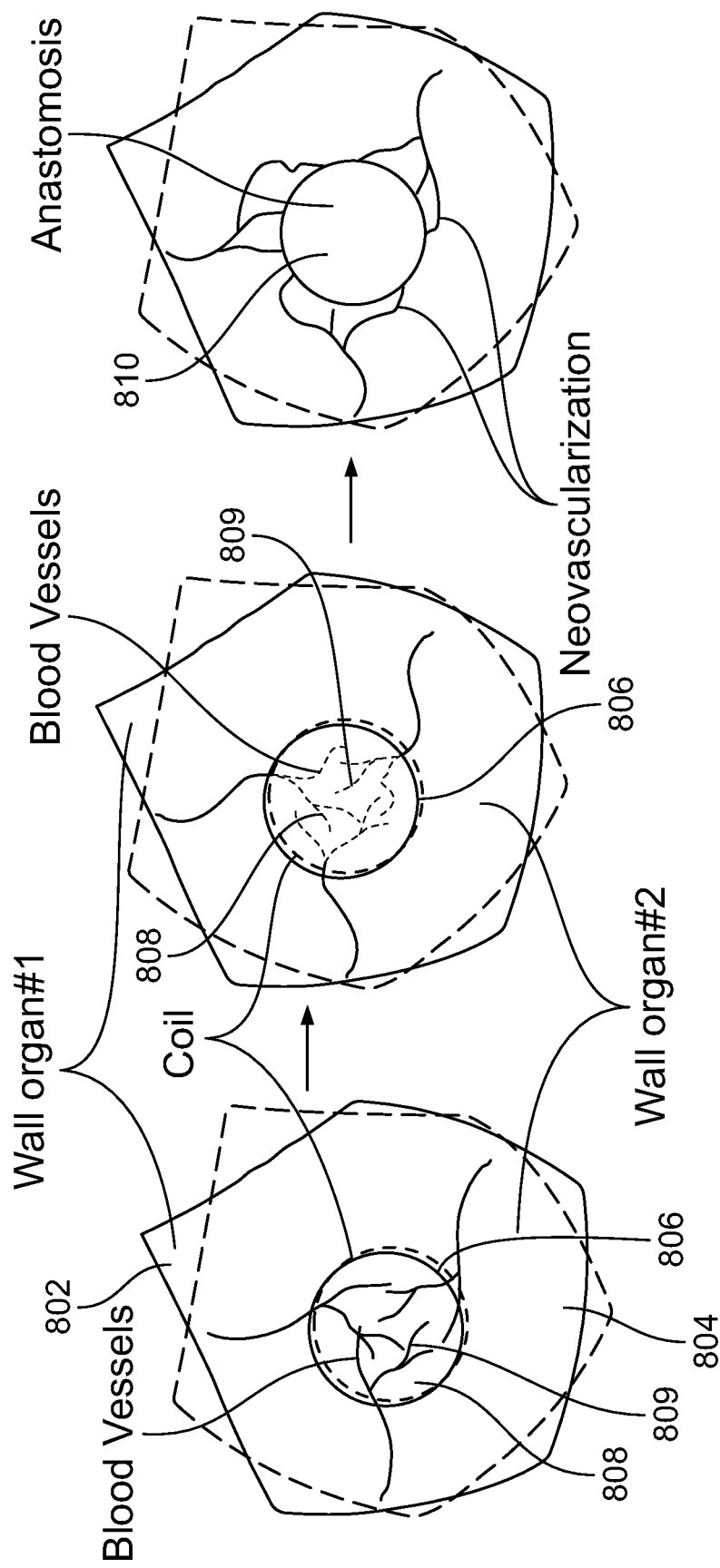
FIG. 8 illustrates a process of creating an anastomosis by using a SMA coil, in accordance with an embodiment of the present specification.

FIG. 8 illustrates a process of creating an anastomosis by using a SMA coil with or without magnets, in accordance with an embodiment of the present specification. As shown in the figure, first wall 802 of a first organ and second wall 804 of a second organ are compressed between the loops of a SMA wire 806 coiled up in a circular shape. A circular portion 808 of the tissue of both the first and the second organs is caught between the wire 806. Due to the pressure exerted by the wire 806, blood supply 809 to the portion 808 is slowly and incrementally reduced, resulting first in ischemia, inflammation, neovascularization and fusion of the adjacent walls and later as the pressure increase in ischemic damage and necrosis to the tissue 808, which eventually sloughs off, leaving a circular anastomosis 810 between the first and the second organ walls. In this embodiment, the slow and incremental increase in pressure allows for a neovascularization process occurs at the anastomosis site to ensure a healthy anastomosis.

Figure 9A:
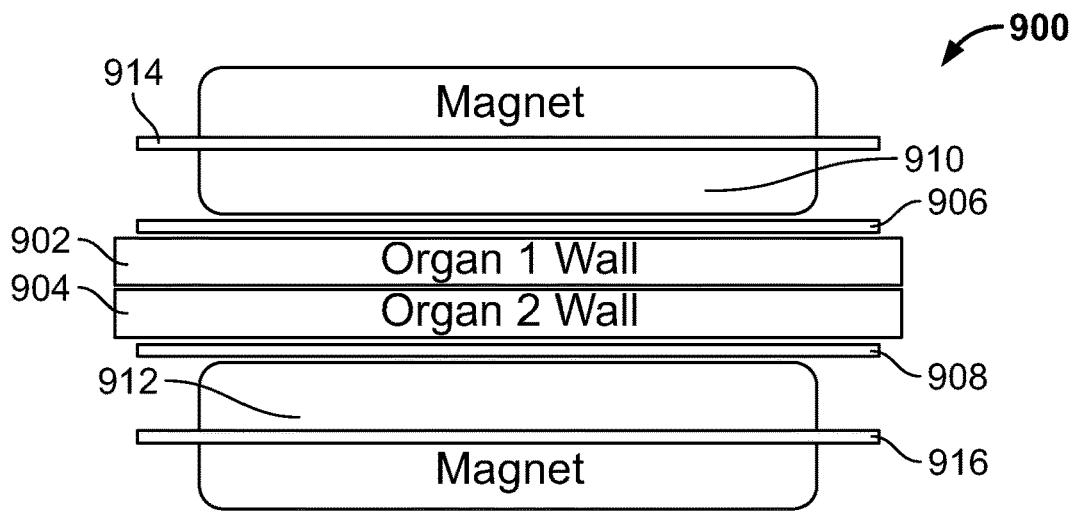
FIG. 9A illustrates walls of two organs compressed between loops of a SMA coil, in accordance with an embodiment of the present specification.
Figure 9B:
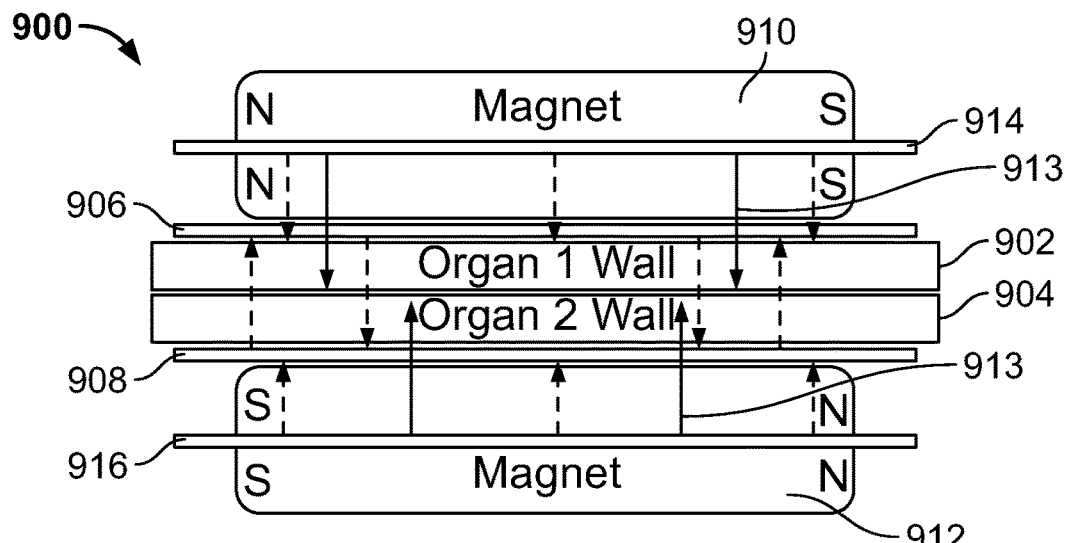
FIG. 9B illustrates walls of two organs compressed between loops of a SMA coil, the compressive force being enhanced with the use of magnets, in accordance with an embodiment of the present specification.

FIG. 9A illustrates walls 902, 904 of two organs compressed between loops 906, 908 of a SMA coil 900, in accordance with an embodiment of the present specification and the compressive force is provided by the combination of the Nitinol wires and the magnets and the cutting surface is created by the two SMA wires 906 and 908. FIG. 9B illustrates walls 902, 904 of two organs compressed between loops of a SMA coil 900, the compressive force being enhanced with the use of magnets, in accordance with an embodiment of the present specification. Referring to both FIGS. 9A and 9B, a wall 902 of a first organ and a wall 904 of a second organ are compressed between a first loop 906 and a second loop 908 of a SMA coil 900, which in an embodiment is a Nitinol wire coil. The pressure being exerted upon the organ walls 902, 904 is enhanced by the attractive force 913 between magnets 910 and 912 coupled with loops 914 and 916 respectively, of the SMA coil 900. In an embodiment, a first pressure greater than 0.19 psi (10 mmHg) is exerted by the combination of the coil and magnets upon the tissue caught in between the coil loops and the pressure incrementally increases to a pressure greater than or equal to 0.97 psi (50 mm Hg) and further may increase to a pressure of 145 psi (7499 mm Hg), depending on the dimensions of the magnets and number of coils.

Figure 10:
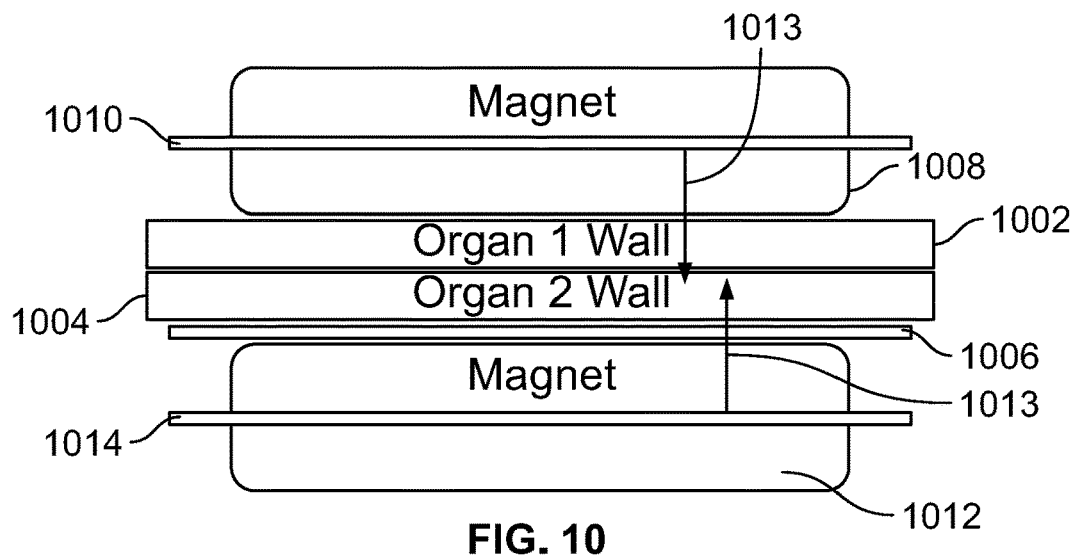
FIG. 10 illustrates walls of two organs compressed between a loop of a SMA coil and a magnet, in accordance with an embodiment of the present specification.

FIG. 10 illustrates walls 1002, 1004 of two organs compressed between a loop 1006 of a SMA coil 1000 and a magnet 1008, in accordance with an embodiment of the present specification. A wall 1002 of a first organ and a wall 1004 of a second organ are compressed between a first loop 1006 of a SMA coil 1000 and a magnet 1008 coupled with a second loop 1010 of a SMA coil. In an embodiment, the SMA coil 1000 is a Nitinol wire coil. The pressure being exerted upon the organ walls 1002, 1004 is enhanced by the attractive force 1013 between the magnet 1008 and another magnet 1012 coupled with another loop 1014 of the SMA coil 1000.

Figure 11:
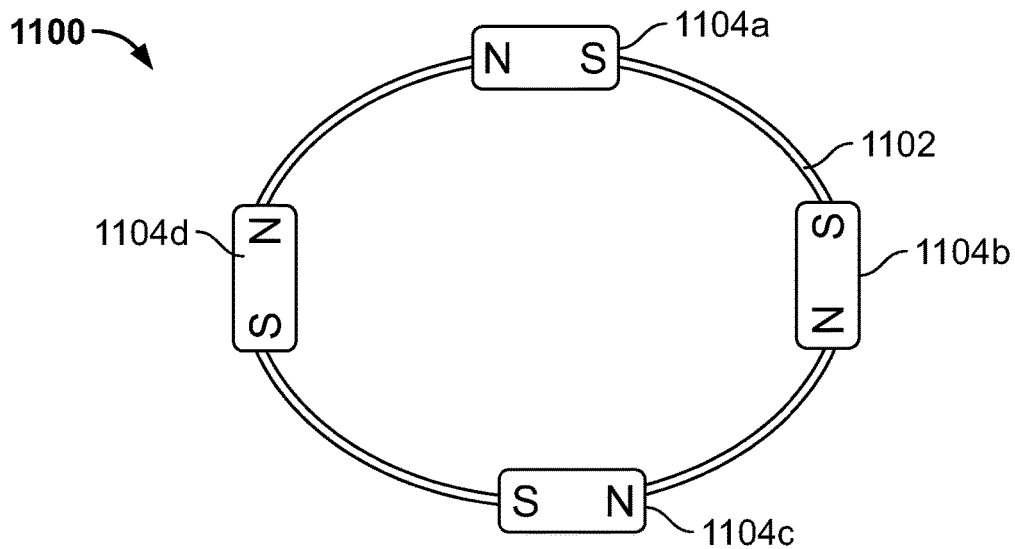
FIG. 11 illustrates a plurality of magnets coupled with a loop of a SMA coil for creating an anastomosis, in accordance with an embodiment of the present specification.
Figure 13:
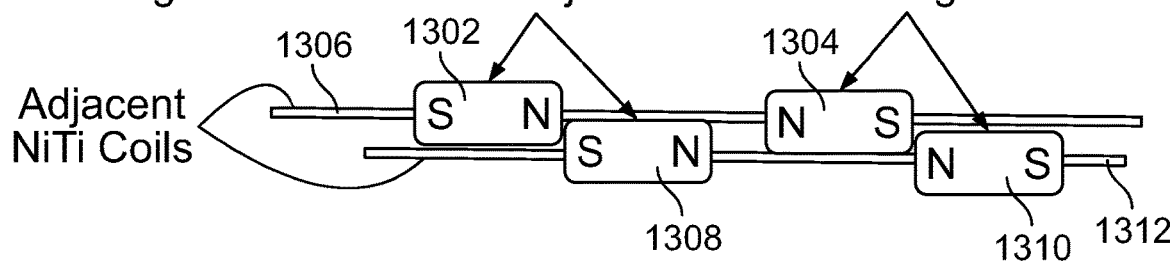
FIG. 13 illustrates placement of magnets coupled with adjacent loops of a SMA coil for creating an anastomosis, in accordance with an embodiment of the present specification.

It is important that the magnets do not attract and clump together in the pre-deployment shape interfering with the SMA coil to shape change to its pre-determined, post-deployment austenite shape. FIG. 11 illustrates a plurality of magnets 1104a, 1104b, 1104c, 1104d coupled with a loop 1102 of a SMA coil 1100 for creating an anastomosis, in accordance with an embodiment of the present specification. Magnets 1104a-1104d are arranged around a loop 1102 of a SMA coil 1100 being used for creating an anastomosis. In an embodiment, the SMA coil 1100 is made of Nitinol wire. In an embodiment, the combined length of all the magnets coupled with a SMA coil is less than half of the length of the SMA coil. In an embodiment, the magnets are coupled with the coil in a manner such that the magnets can slide over the coil (like beads in a necklace). In an embodiment, at least 50% of the adjacent magnets (such as magnets 1104a and 1104b) on each loop of the coil are arranged with like poles facing each other (as indicated by 'S' for south and 'N' for north on each magnet), creating a repulsive force between the two adjacent magnets in the same loop of the coil. This configuration is desired in situation where the anastomosis need to be created between a Nitinol wire and a magnet is as shown in FIGS. 10 and 13. In various embodiments, magnets on a single loop of coil are separated by a distance less than, equal to, or greater than a length of each of two adjacent magnets.

Figure 12:
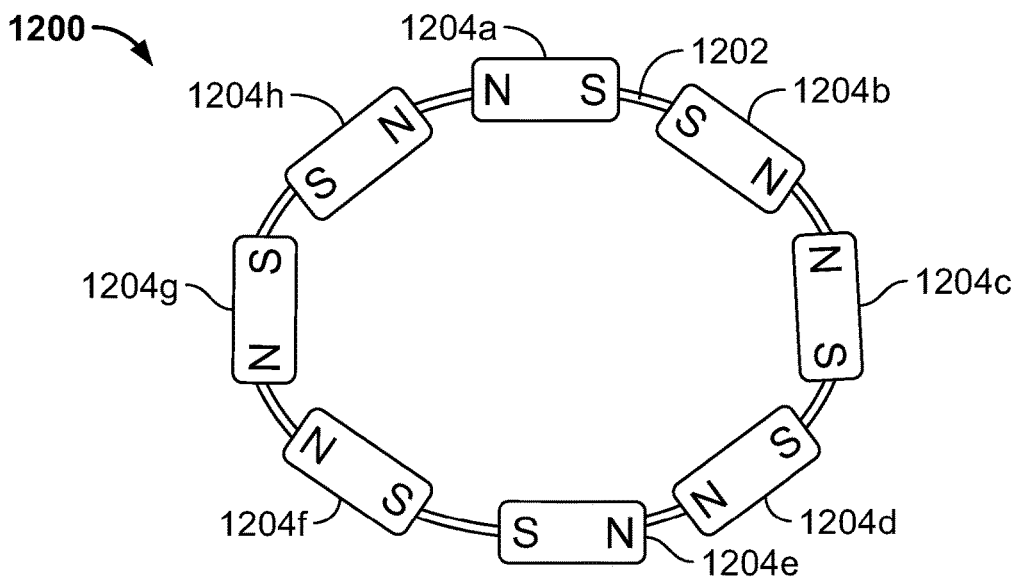
FIG. 12 illustrates a plurality of magnets coupled with a loop of a SMA coil for creating an anastomosis, in accordance with another embodiment of the present specification.

FIG. 12 illustrates a plurality of magnets 1204a, 1204b, 1204c, 1204d, 1204e, 1204f, 1204g, 1204h coupled with a loop 1202 of a SMA coil 1200 for creating an anastomosis, in accordance with another embodiment of the present specification. Magnets 1204a-1204h are arranged around a loop 1202 of a SMA coil 1200 being used for creating an anastomosis. In an embodiment, the SMA coil 1200 is made of Nitinol wire. In an embodiment, the combined length of all the magnets coupled with a SMA coil is greater than or equal to 50% but less than 99% of the length of the SMA coil. In an embodiment, the magnets 1204a-1204h are coupled with the coil loop 1202 in a manner such that the magnets can slide over the coil (like beads in a necklace). In an embodiment, at least 50% of the adjacent magnets (such as magnets 1204a and 1204b) on each loop of the coil are arranged with like poles facing each other (as indicated by 'S' for south and 'N' for north on each magnet), thereby creating a repulsive force between the two adjacent magnets in the same loop of the coil. It is important that the magnets do not clump together such that they would significantly interfere with the functionality of the Nitinol coil. It is also important that the repulsive forces between the magnets do not overpower the coil and significantly interfere with the functionality of the Nitinol coil. In some embodiments, an axis defining the direction of magnetic attraction between magnets on adjacent loops of the coil is perpendicular to a long axis of each magnet. In some embodiments, an axis defining the direction of magnetic attraction between magnets on adjacent loops of the coil is perpendicular to an axis extending through the center of the coil.

FIG. 13 illustrates placement of magnets 1302, 1304, 1308, 1310 coupled with adjacent loops 1306, 1312 of a SMA coil for creating an anastomosis, in accordance with an embodiment of the present specification. As shown, adjacent magnets 1302 and 1304 on wire loop 1306 are held at a distance greater than the length of each of the magnets. Similarly, adjacent magnets 1308 and 1310 on the adjacent wire loop 1312 are held at a distance greater than the length of each of the magnets, thereby allowing for a magnet 1308 to slide and occupy a position that is in between the magnets 1302 and 1304, such that opposite poles of the magnets 1308 and 1302 are aligned. This generates pressure between the magnets on the adjacent wire loops, which in turn assists the anastomosis process as explained earlier with respect to FIG. 10.

FIG. 14A illustrates an exemplary SMA wire 1400 coupled with magnets 1408, 1408a, 1408b, 1408c, 1408d prior to deployment in a body for creating an anastomosis, in accordance with an embodiment of the present specification. FIG. 14B illustrates the exemplary SMA wire 1400 coupled with magnets 1408 shown in FIG. 14A in a mid-deployment stage, in accordance with an embodiment of the present specification. FIG. 14C illustrates the exemplary SMA wire 1400 coupled with magnets 1408 shown in FIG. 14A after deployment in a body for creating an anastomosis, in accordance with an embodiment of the present specification. Referring to FIG. 14A, prior to deployment, SMA wire 1400 is straight and divided into at least three sections 1402, 1404 and 1406. Sections 1402 and 1406 are coupled with a plurality of magnets 1408, 1408a, 1408b, 1408c, 1408d such that positions of first magnets 1408a, 1408c and last magnets 1408b, 1408d of sections 1402 and 1404 respectively, are fixed and immovable. Remaining magnets 1408 of each section are movable/slidable in the space between the first and last magnets of each section. As shown, no magnets are provided on section 1404. Referring to FIG. 14B, SMA wire 1400 begins to coil up upon coming in contact with body heat. Referring to FIG. 14C, SMA wire 1400 forms a tight coil, cutting through tissue caught between the coil loops, with the cutting force being further strengthened due to attractive forces between magnets placed on adjacent loop sections 1402 and 1406. The mechanism of this anastomosis is shown in FIGS. 9A and 9B.

Figure 14D:
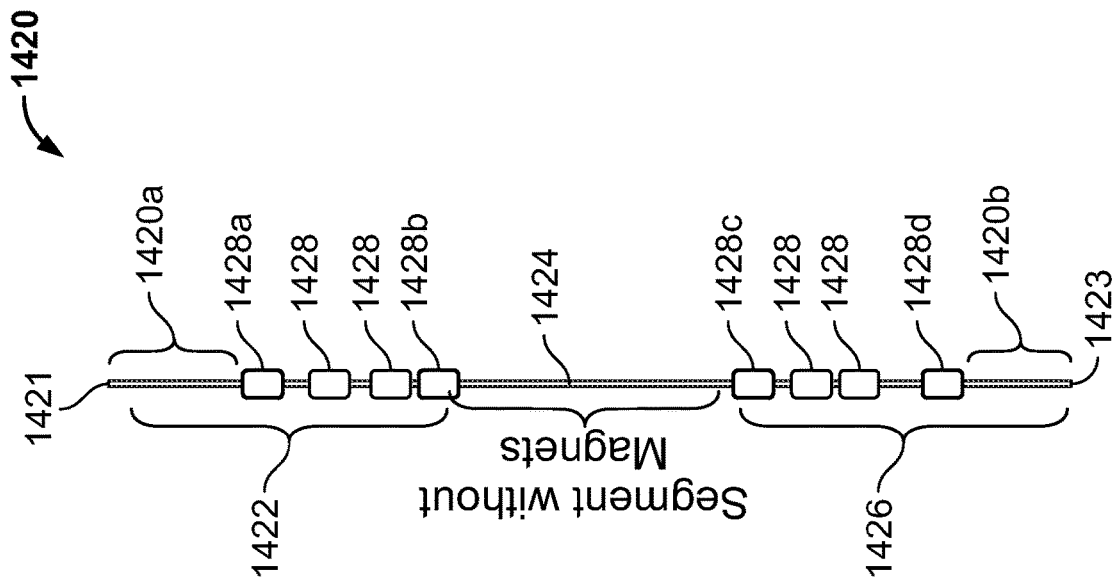
FIG. 14D illustrates an exemplary SMA wire coupled with magnets prior to deployment in a body for creating an anastomosis, in accordance with another embodiment of the present specification.
Figure 14C:
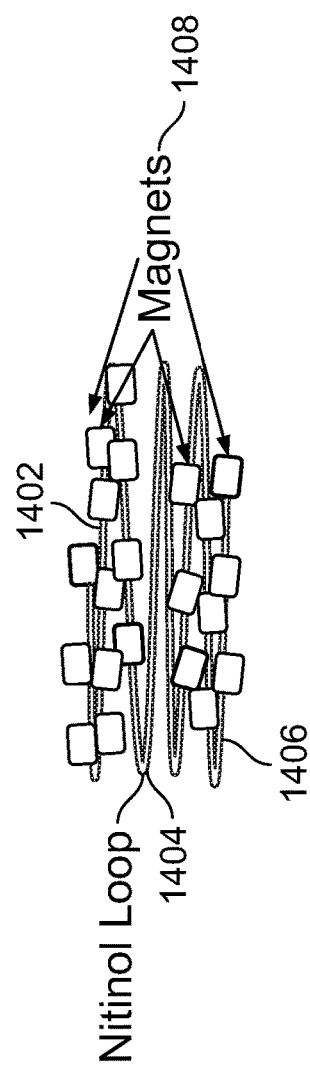
FIG. 14C illustrates the exemplary SMA wire coupled with magnets shown in FIG. 14A after deployment in a body for creating an anastomosis, in accordance with an embodiment of the present specification.

FIG. 14D illustrates an exemplary SMA wire 1420 coupled with magnets 1428, 1428a, 1428b, 1428c, 1428d prior to deployment in a body for creating an anastomosis, in accordance with another embodiment of the present specification. Prior to deployment, SMA wire 1420 is straight and divided into at least three sections 1422, 1424 and 1426. Sections 1422 and 1426 are coupled with a plurality of magnets 1428, 1428a, 1428b, 1428c, 1428d such that positions of first magnets 1428a, 1428c and last magnets 1428b, 1428d of sections 1422 and 1424 respectively, are fixed and immovable. Remaining magnets 1428 of each section are movable/slidable in the space between the first and last magnets of each section. As shown, no magnets are provided on section 1424. In addition, a first portion 1420a of the wire 1420, extending from a first end 1421 of the wire 1420 to magnet 1428a, and a second portion 1420b of the wire 1420, extending from a second end 1423 of the wire 1420 to magnet 1428d, include no magnets. In various embodiments, the portions 1420a, 1420b of bare wire are greater than or equal in length to one half of the circumference of one of the coil loops. The length of the bare segment in the middle of the device is also greater than or equal to one-half the circumference of the one of the coil loops of the coil depicted in FIG. 14F. The advantage of the bare portions at the end is that the SMA coil shapes better (more round) and consistently (under the influence of magnetic forces) if a loop has already formed which forces the following loops to shape. This is a result of the strain inherent in the wire.

Figure 14F:
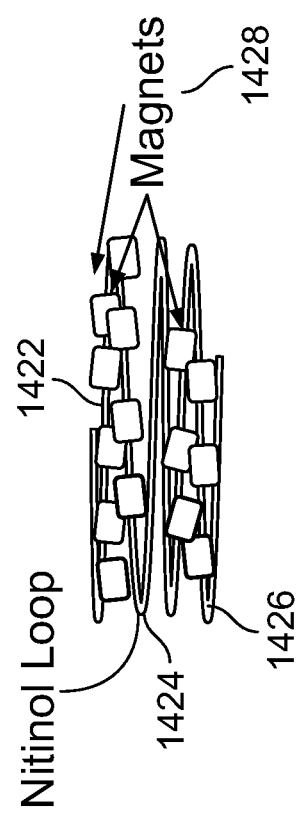
FIG. 14F illustrates the exemplary SMA wire coupled with magnets shown in FIG. 14D after deployment in a body for creating an anastomosis, in accordance with an embodiment of the present specification.
Figure 14E:
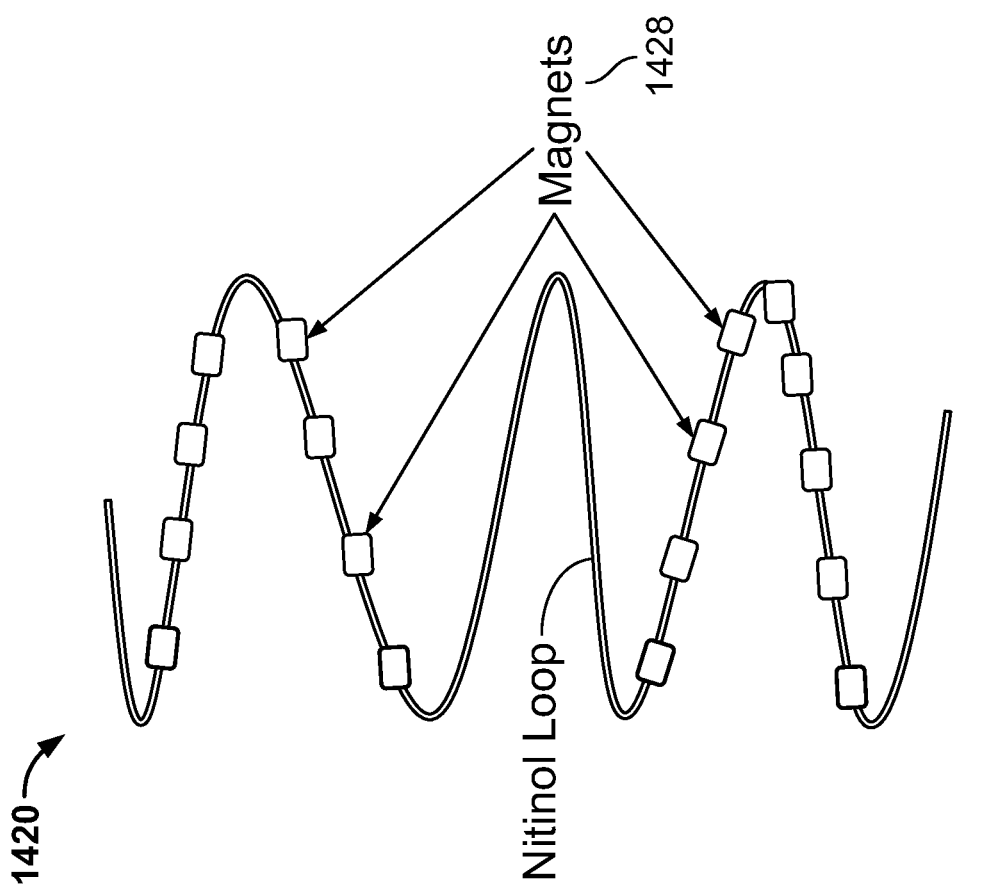
FIG. 14E illustrates the exemplary SMA wire coupled with magnets shown in FIG. 14D in a mid-deployment stage, in accordance with an embodiment of the present specification.

FIG. 14E illustrates the exemplary SMA wire 1420 coupled with magnets 1428 shown in FIG. 14D in a mid-deployment stage, in accordance with an embodiment of the present specification. FIG. 14F illustrates the exemplary SMA wire 1420 coupled with magnets 1428 shown in FIG. 14D after deployment in a body for creating an anastomosis, in accordance with an embodiment of the present specification. Referring to FIG. 14E, SMA wire 1420 begins to coil up upon coming in contact with body heat. Referring to FIG. 14F, SMA wire 1420 forms a tight coil, cutting through tissue caught between the coil loops, with the cutting force being further strengthened due to attractive forces between magnets placed on adjacent loop sections 1422 and 1426. The mechanism of this anastomosis is shown in FIGS. 9A and 9B.

FIG. 15A illustrates an exemplary SMA wire 1500 coupled with magnets 1502, 1502a, 1502b prior to deployment in a body for creating an anastomosis, in accordance with another embodiment of the present specification. FIG. 15B illustrates the exemplary SMA wire 1500 coupled with magnets 1502, 1502a, 1502b shown in FIG. 15A in a mid-deployment stage, in accordance with an embodiment of the present specification. FIG. 15C illustrates the exemplary SMA wire 1500 coupled with magnets 1502 shown in FIG. 15A after deployment in a body for creating an anastomosis, in accordance with an embodiment of the present specification. Referring to FIG. 15A, prior to deployment, SMA wire 1500 is straight and is coupled with a plurality of magnets 1502, 1502a, 1502b such that positions of a first magnet 1502a, and a last magnet 1502b in the series of magnets 1502 are fixed and immovable. Remaining magnets 1502 are movable/slidable in the space between the first and last magnets 1502a, 1502b. Referring to FIG. 15B, SMA wire 1500 begins to coil up upon coming in contact with body heat. Referring to FIG. 15C, SMA wire 1500 forms a tight coil, cutting through tissue caught between the coil loops, with the cutting force being further strengthened due to attractive forces between magnets 1502 placed on adjacent loops of coil 1500. The mechanism of the anastomosis is shown in FIG. 10. In certain embodiments the two cutting surfaces can be provided by two magnets as shown in FIG. 17. In some embodiments the movement of magnets 1502a and 1502b can be restricted by stoppers at the end, thereby preventing the end magnets from sliding off the SMA coil.

Figure 15D:
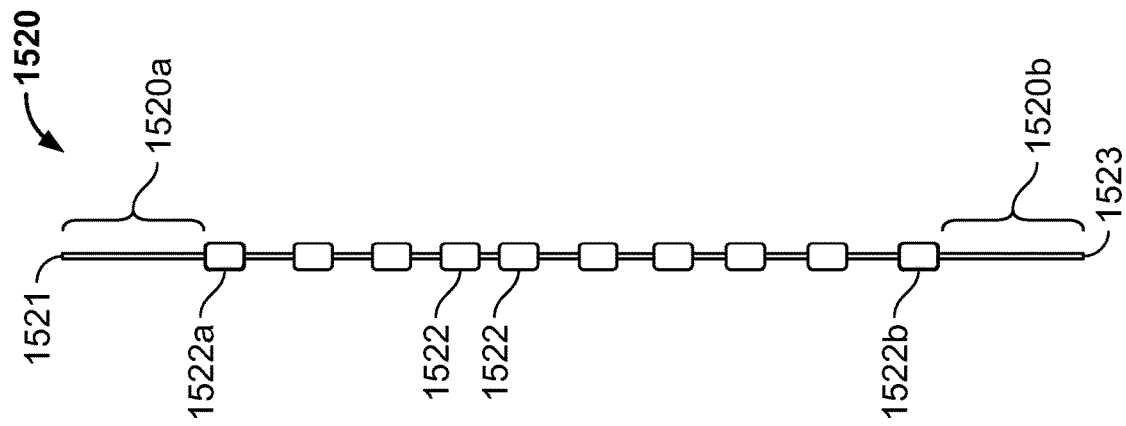
FIG. 15D illustrates an exemplary SMA wire coupled with magnets prior to deployment in a body for creating an anastomosis, in accordance with yet another embodiment of the present specification.
Figure 15C:
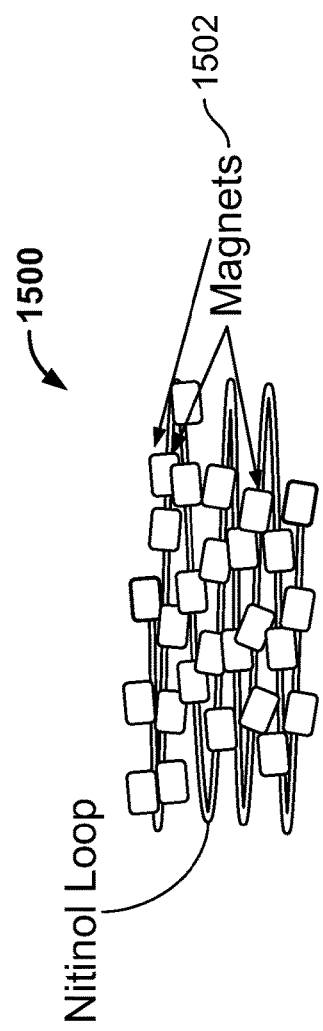
FIG. 15C illustrates the exemplary SMA wire coupled with magnets shown in FIG. 15A after deployment in a body for creating an anastomosis, in accordance with an embodiment of the present specification.

FIG. 15D illustrates an exemplary SMA wire 1520 coupled with magnets 1522, 1522a, 1522b prior to deployment in a body for creating an anastomosis, in accordance with yet another embodiment of the present specification. Prior to deployment, SMA wire 1520 is straight and is coupled with a plurality of magnets 1522, 1522a, 1522b such that positions of a first magnet 1522a, and a last magnet 1522b in the series of magnets 1502 are fixed and immovable. Remaining magnets 1522 are movable/slidable in the space between the first and last magnets 1522a, 1522b. A first portion 1520a of the wire 1520, extending from a first end 1521 of the wire 1520 to magnet 1522a, and a second portion 1520b of the wire 1520, extending from a second end 1523 of the wire 1520 to magnet 1522d, include no magnets. In various embodiments, the portions 1520a, 1520b of bare wire are greater than or equal in length to one half of the circumference of one of the coil loops. The length of the bare segment in the middle of the device is also greater than or equal to one-half the circumference of the one of the coil loops of the coil depicted in FIG. 15F. The advantage of the bare portions at the end is that the SMA coil shapes better (more round) and consistently (under the influence of magnetic forces) if a loop has already formed which forces the following loops to shape. This is a result of the strain inherent in the wire.

Figure 15F:
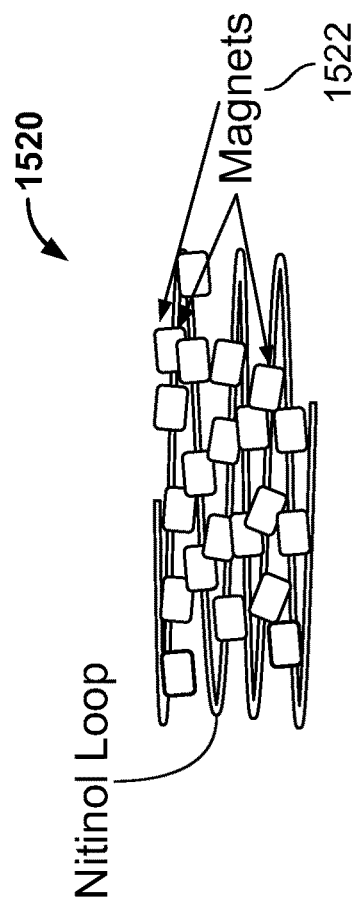
FIG. 15F illustrates the exemplary SMA wire coupled with magnets shown in FIG. 15D after deployment in a body for creating an anastomosis, in accordance with an embodiment of the present specification.
Figure 15E:
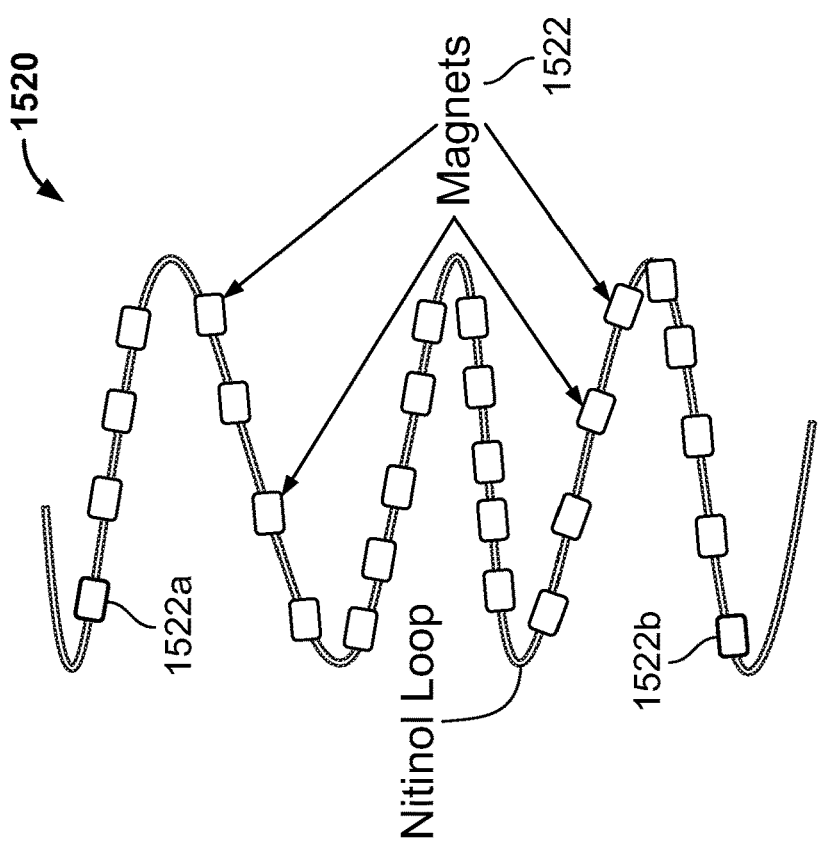
FIG. 15E illustrates the exemplary SMA wire coupled with magnets shown in FIG. 15D in a mid-deployment stage, in accordance with an embodiment of the present specification.

FIG. 15E illustrates the exemplary SMA wire 1520 coupled with magnets 1522, 1522a, 1522b shown in FIG. 15D in a mid-deployment stage, in accordance with an embodiment of the present specification. FIG. 15F illustrates the exemplary SMA wire 1520 coupled with magnets 1522 shown in FIG. 15D after deployment in a body for creating an anastomosis, in accordance with an embodiment of the present specification. Referring to FIG. 15E, SMA wire 1520 begins to coil up upon coming in contact with body heat. Referring to FIG. 15F, SMA wire 1520 forms a tight coil, cutting through tissue caught between the coil loops, with the cutting force being further strengthened due to attractive forces between magnets 1522 placed on adjacent loops of coil 1502. The mechanism of the anastomosis is shown in FIGS. 9A and 9B. In some embodiments, the two cutting surfaces can be provided by two magnets as shown in FIG. 17A. In some embodiments, the movement of magnets 1522a and 1522b is restricted by stoppers at the end, thereby preventing the end magnets from sliding off the SMA coil.

Figure 15G:
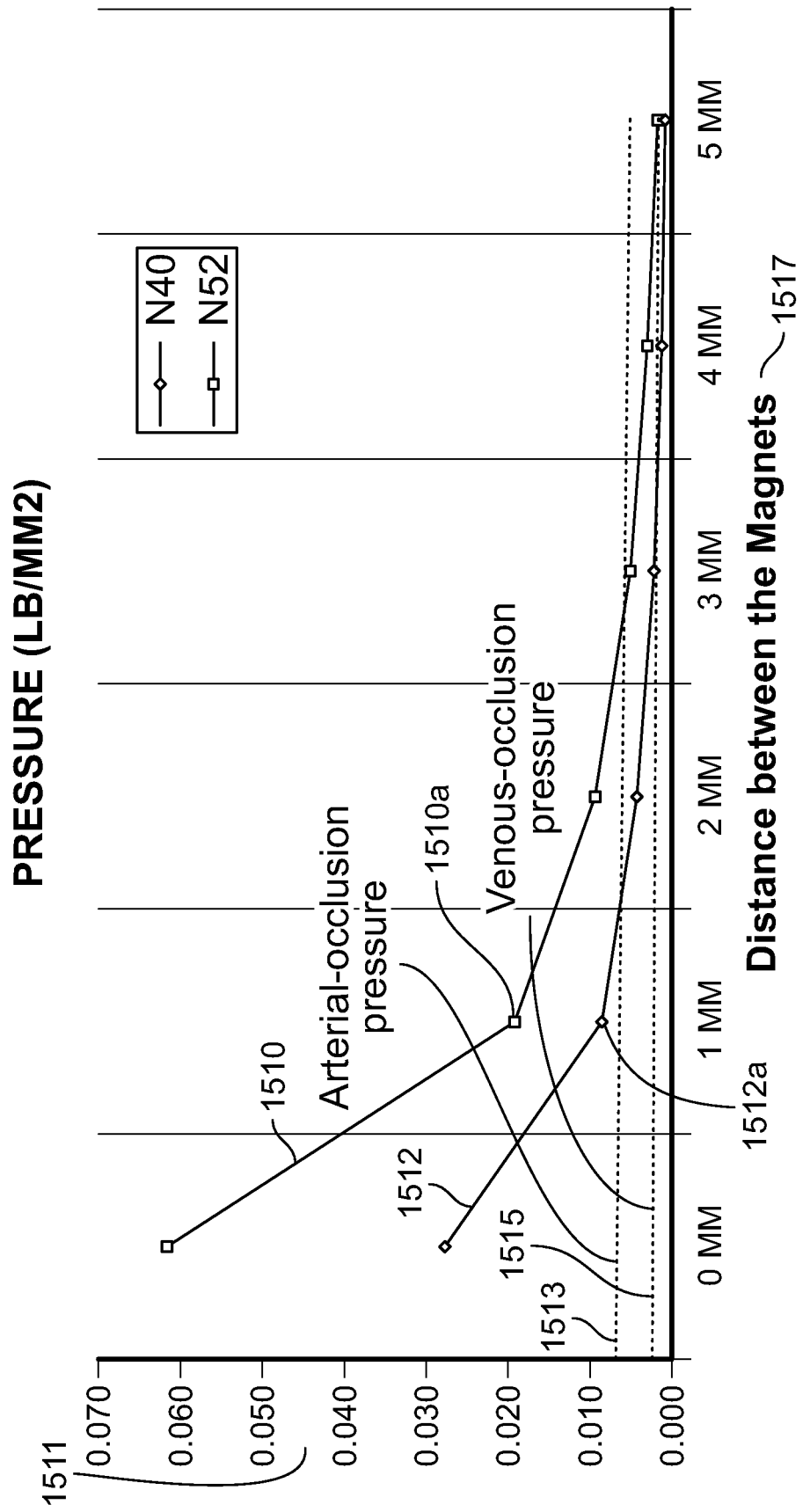
FIG. 15G is a graph illustrating the pressure exerted on body tissues by loops of a coil as the distance between magnets on the coil decreases, in accordance with an embodiment of the present specification.

FIG. 15G is a graph illustrating the pressure 1511 exerted on body tissues by loops of a coil as the distance 1517 between magnets on the coil decreases, in accordance with an embodiment of the present specification. A first curve 1510 represents the pressure exerted by a coil having N52 Neodymium magnets. A second curve 1512 represents the pressure exerted by a coil having N40 Neodymium magnets. The pressure 1511 exerted by the loops of coil represented by both curves 1510, 1512 increases as the distance 1517 between the magnets decreases, particularly at distances less than 2 mm. At a distance greater than or equal to 5 mm the anastomotic device causes occlusion of the capillary blood flow without occluding the arterial or venous blood flow, setting low level inflammation and fibrosis and causing fusion between the walls of two adjacent organs. Once the distance 1517 becomes 1 mm or less, the pressure exerted by both curves 1510, 1512 is greater than arterial-occlusion pressure 1513 and venous-occlusion pressure 1515, as depicted by points 1510a and 1512a on curves 1510 and 1512 respectively. Therefore, once the distance 1517 is 1 mm or less, the pressure 1511 exerted by the loops of the coil is great enough to cause occlusion of all blood vessels in the body tissue caught between said loops, thereby causing ischemic damage, necrosis of the tissue and leading to an anastomosis formation, the dimension of which approximates the dimensions of the Nitinol loop. This slow increase in pressure on the tissue allows for neovascularization, fusion of the adjacent tissue walls, and formation of a healthy anastomosis without the rate of anastomotic leaks typically seen with surgical anastomosis.

Figure 16C:
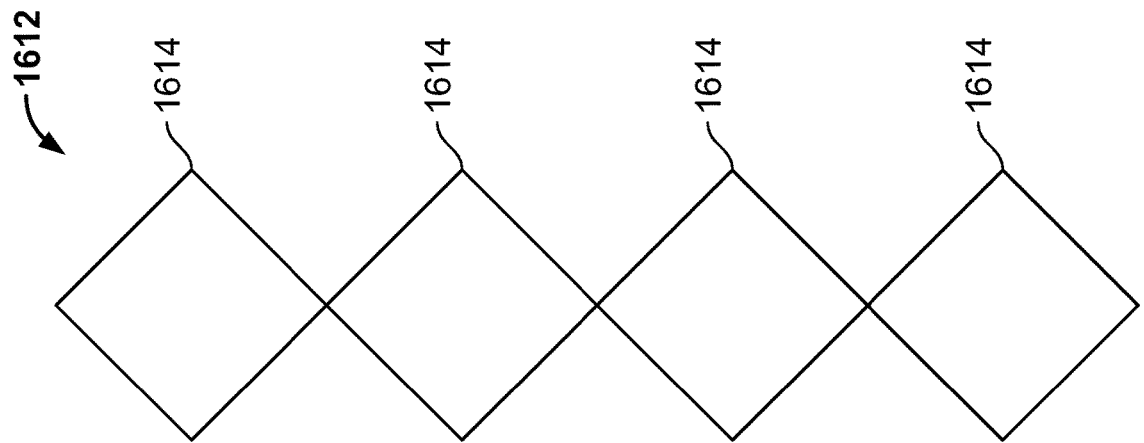
FIG. 16C illustrates an exemplary square shaped SMA coil used for creating an anastomosis, in accordance with an embodiment of the present specification.
Figure 16B:
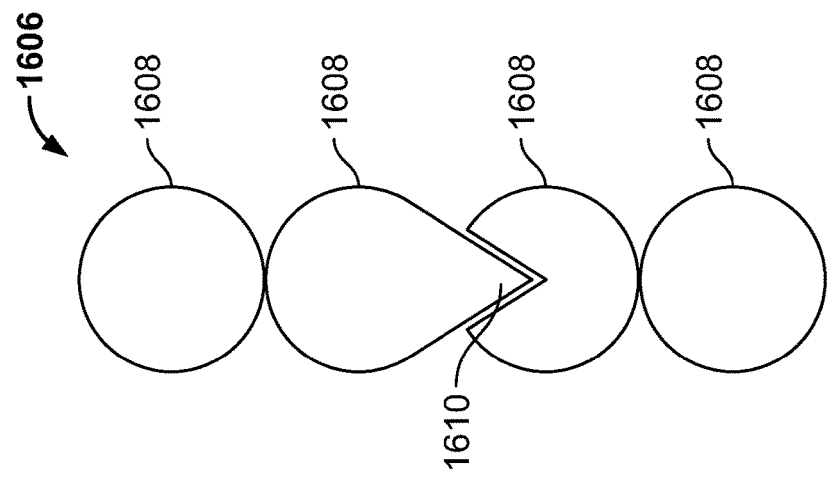
FIG. 16B illustrates an exemplary round shaped SMA coil having a cutting edge, used for creating an anastomosis, in accordance with an embodiment of the present specification.
Figure 16A:
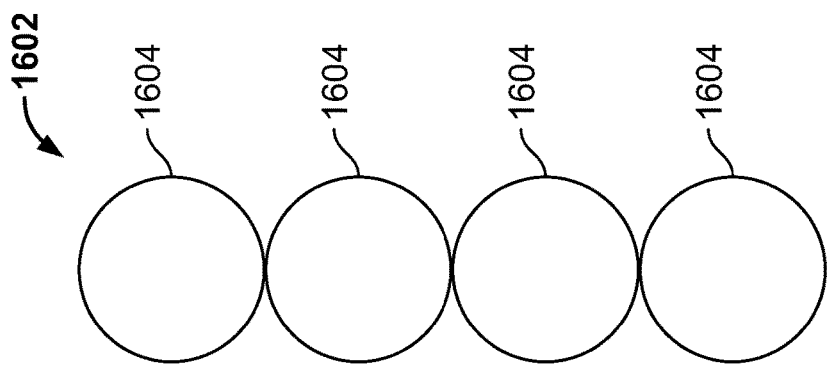
FIG. 16A illustrates an exemplary round shaped SMA coil used for creating an anastomosis, in accordance with an embodiment of the present specification.

FIG. 16A illustrates an exemplary round shaped SMA coil 1602 used for creating an anastomosis, in accordance with an embodiment of the present specification. Coil 1602 comprises a plurality of round shaped loops 1604. FIG. 16B illustrates an exemplary round shaped SMA coil 1606 having a cutting edge 1610, used for creating an anastomosis, in accordance with an embodiment of the present specification. Coil 1606 comprises a plurality of round shaped loops 1608. One of the loops 1608 is provided with a pointed/sharp cutting edge 1610 for cutting through tissue compressed between the loops of the coil. FIG. 16C illustrates an exemplary square shaped SMA coil 1612 used for creating an anastomosis, in accordance with an embodiment of the present specification. Coil 1612 comprises a plurality of square shaped loops 1614. The sharp edges of the square loop provide for the cutting surface.

FIG. 17A illustrates an exemplary device 1700 comprising round shaped magnets 1702 coupled with a SMA coil used for creating an anastomosis, in accordance with an embodiment of the present specification. Round shaped magnets 1702 are each coupled with coil loops 1704 for creating an anastomosis when deployed in a body. FIG. 17B illustrates an exemplary device 1705 comprising round shaped magnets 1706 coupled with a SMA coil used for anastomosis, wherein at least one magnet comprises a cutting edge 1710, in accordance with an embodiment of the present specification. As shown, round shaped magnets 1706 are each coupled with coil lops 1708 for creating an anastomosis when deployed in a body. At least one of the magnets 1706 is provided with a pointed/sharp protrusion 1710 designed to interlock with other magnets/coil loops and enhance the cutting through the tissue compressed between the loops of the coil and magnets.

FIG. 17C illustrates an exemplary device 1711 comprising square shaped magnets 1712 coupled with a SMA coil with serrated edges, used for creating an anastomosis, in accordance with an embodiment of the present specification. Square shaped magnets 1712 are arranged around coil loops 1714 having serrated edges to prevent spinning action of the magnets 1712. In an embodiment, the magnets 1712 are arranged as shown in FIG. 17C such that edges 1716 of the magnets slide over each other, as the SMA wire changes shape and coils up, and is further enhanced by the attractive forces between the magnetic surfaces thereby creating a cutting action/force.

FIG. 17D illustrates an exemplary device 1721 comprising square shaped magnets 1718 coupled with a SMA coil used for creating an anastomosis, in accordance with an embodiment of the present specification. Square shaped magnets 1718 are each coupled with coil loops 1720 for creating an anastomosis when deployed in a body. FIG. 17E illustrates an exemplary device 1725 comprising square shaped magnets 1722 coupled with a SMA coil used for creating an anastomosis, wherein at least one magnet comprises a cutting edge 1726, in accordance with an embodiment of the present specification. As shown, square shaped magnets 1722 are each coupled with coil loops 1724 for creating an anastomosis when deployed in a body. At least one of the magnets 1722 is provided with a pointed/sharp protrusion 1726 designed to interlock with other magnets/coil loops and enhance the cutting through the tissue compressed between the loops of the coil and magnets.

Figure 17G:
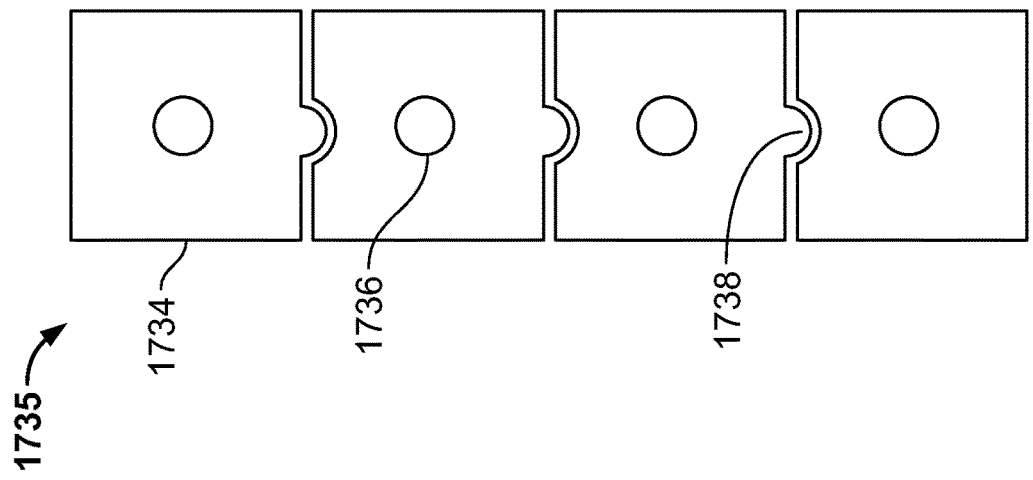
FIG. 17G illustrates a cross sectional view of an exemplary device comprising square shaped magnets coupled with a SMA coil used for creating an anastomosis, wherein the magnets comprise a protruding edge to assist with cutting, in accordance with an embodiment of the present specification.
Figure 17F:
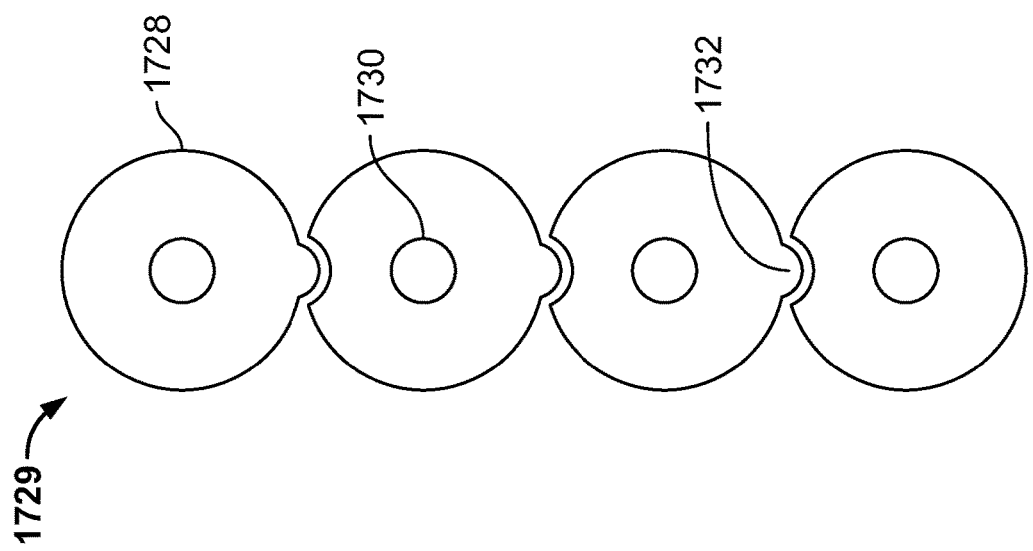
FIG. 17F illustrates a cross sectional view of an exemplary device comprising round shaped magnets coupled with a SMA coil used for creating an anastomosis, wherein the magnets comprise a protruding edge to assist with cutting, in accordance with an embodiment of the present specification.

FIG. 17F illustrates a cross sectional view of an exemplary device 1729 comprising round shaped magnets 1728 coupled with a SMA coil used for creating an anastomosis, wherein the magnets 1728 comprise a protruding edge 1732, in accordance with an embodiment of the present specification. Round shaped magnets 1728 are each coupled with coil loops 1730 for creating an anastomosis when deployed in a body. Magnets 1728 are provided with a protruding edge 1732 designed to interlock with other magnets/coil loops and enhance the cutting through the tissue compressed between the loops of the coil and magnets. FIG. 17G illustrates a cross sectional view of an exemplary device 1735 comprising square shaped magnets 1734 coupled with a SMA coil used for creating an anastomosis, wherein the magnets comprise a protruding edge 1738, in accordance with an embodiment of the present specification. Square shaped magnets 1734 are each coupled with coil loops 1736 for creating an anastomosis when deployed in a body. Magnets 1734 are provided with a protruding edge 1738 designed to interlock with other magnets/coil loops and enhance the cutting through the tissue compressed between the loops of the coil and magnets.

FIGS. 18A and 18B illustrate a plurality of magnets 1802, 1803 arranged around a loop 1804 of a SMA wire coil 1800, 1801 for creating an anastomosis, in accordance with embodiments of the present specification. Magnets 1802, 1803 are arranged equidistantly around a loop 1804 of a SMA wire coil in a manner such that opposite poles of adjacent magnets face each other, thereby creating a repulsive force which keeps the magnets 1802, 1803 fixed in a desired position on the loop 1804. Thus, the magnets 1802, 1803 do not clump together on the loop 1804. In an embodiment, as shown in FIG. 18A, magnets 1802 are provided with rings 1806 through which the loop 1804 is threaded for coupling the magnets 1802 with the loop 1804. In another embodiment, as shown in FIG. 18B, the magnets 1802 are coupled with the loop 1804 in wherein the magnets 1803 comprise a hollow conduit (not shown) through which the loop 1804 is threaded. In other embodiments, magnets are coupled to the loop in any suitable manner wherein the magnets may freely slide along the loop.

Figure 18D:
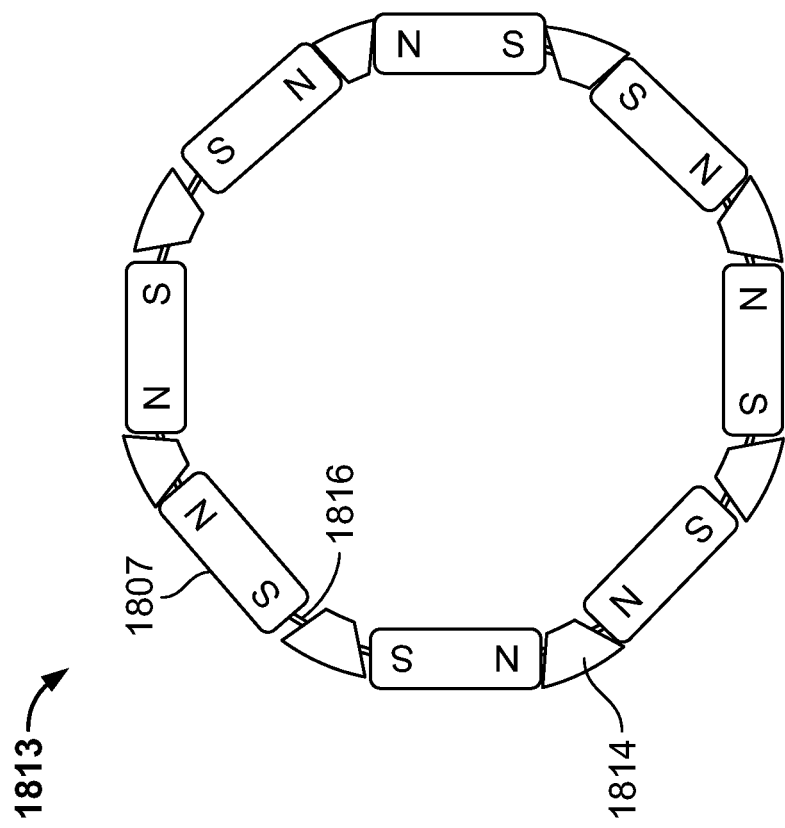
FIG. 18D illustrates a fourth configuration of a plurality of magnets arranged around a loop of a SMA wire coil separated by non-ferromagnetic spacers, for creating an anastomosis, in accordance with another embodiment of the present specification.
Figure 18C:
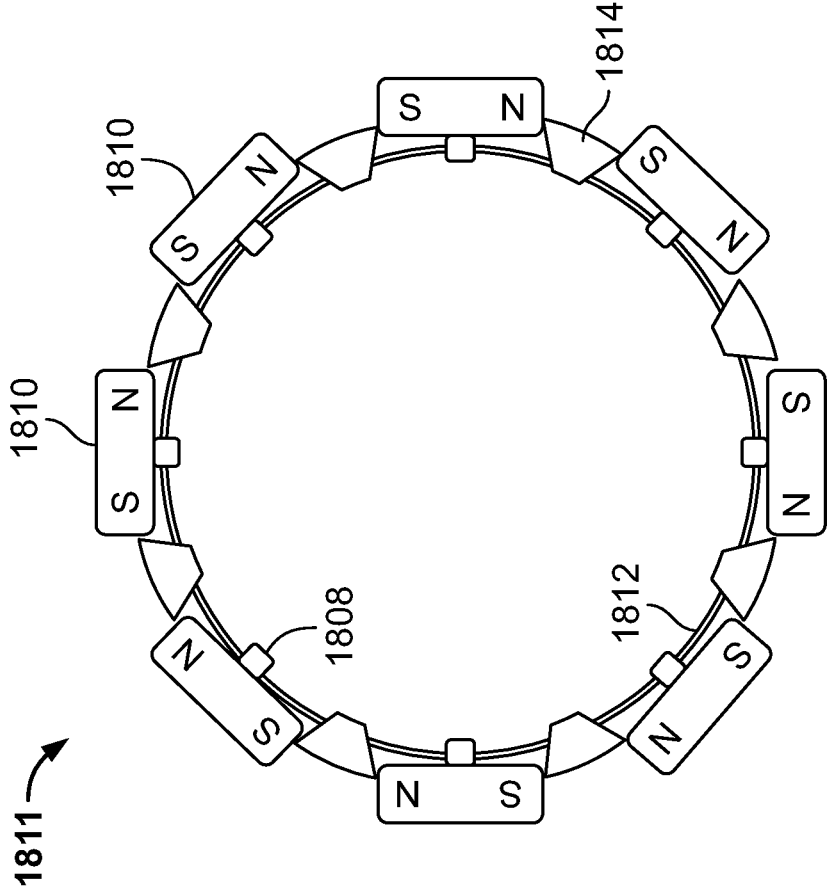
FIG. 18C illustrates a third configuration of a plurality of magnets arranged around a loop of a SMA wire coil separated by non-ferromagnetic spacers, for creating an anastomosis, in accordance with an embodiment of the present specification.

FIGS. 18C and 18D illustrate a plurality of magnets 1810, 1807 arranged around a loop 1812 of a SMA wire coil 1811, 1813 separated by non-ferromagnetic spacers 1814, for creating an anastomosis, in accordance with an embodiment of the present specification. As shown in FIG. 18C, rings 1808 of magnets 1810 are threaded through SMA coil loop 1812. The magnets 1810 are arranged such that opposite poles of adjacent magnets face each other, thereby creating an attractive force. Spacers 1814 made of a non-ferromagnetic material are placed between the magnets 1810 as shown, which keeps the magnets 1810 fixed in a desired position on the loop 1812, thereby ensuring that the magnets 1810 do not clump together on the loop 1812 and interfere with the shape-change from martensite shape to the austenite shape. In various embodiments, the spacers 1814 comprise silicone, Teflon, PTFE, or Nitinol tubes, O-rings or balls. In another embodiment, the spacers 1814 comprise only air, wherein each spacer 1814 is created by gluing or fixing each magnet 1810, 1807 onto the coil 1811, 1813 such that each magnet 1810, 1807 is positioned at a predefined distance from the next or previous magnet. In some embodiments, the predefined distance between adjacent magnets on a same loop of the coil is in a range of $1/128$ inch to 1 inch. In other embodiments, the predefined distance between adjacent magnets on a same loop of the coil is in a range of 0.1 mm to 1 cm. In some embodiments, a minimum predefined distance is defined as a distance between adjacent magnets on a same loop of the coil sufficient to ensure that the magnets do not physically interfere with the formation of coil loops to any significant degree. In some embodiments, a minimum predefined distance is defined as a distance between adjacent magnets on a same loop of the coil sufficient to ensure that the magnets do not physically touch each other until the coil loop is completely formed. In some embodiments, a maximum predefined distance between adjacent magnets on a same loop of the coil is no more than 10 times a length of the magnet. In another embodiment, the maximum predefined distance between adjacent magnets on a same loop of the coil is <50% of the circumference of the coil. Referring to FIG. 18D, magnets 1807 of coil 1813 comprise a hollow conduit through which the coil loop 1812 is threaded. Spacers 1814 made of a non-ferromagnetic material are placed between the magnets 1807 as shown, thereby ensuring that the magnets 1807 do not clump together on the loop 1812.

FIG. 18E illustrates an arrangement of magnets 1820, 1820a, 1820b, around a loop 1824 of a SMA coil 1821 for creating an anastomosis, in accordance with an embodiment of the present specification. Magnets 1820 are arranged by means of rings 1822 around a loop 1824 of a SMA coil 1821. A magnet 1826 of an adjacent loop 1828 is positioned, by means of magnetic attraction, proximate and between the magnetic poles of magnets 1820a and 1820b of the loop 1824. The magnet 1826 functions as a locking magnet, thereby locking each of the magnets 1820a and 1820b in their fixed respective positions on the coil loop 1824 forming a lasso. This allows for a fixed loop which can be used to pull the walls of the adjacent organ closer during deployment. This locking mechanism also prevents the loop from inadvertently slipping out of an organ during deployment.

FIG. 18F illustrates another arrangement of magnets 1830, 1830a, 1830b around a loop 1834 of a SMA coil 1835 for creating an anastomosis, in accordance with an embodiment of the present specification. Magnets 1830 are arranged around a loop 1834 of a SMA coil 1835. A magnet 1836 of an adjacent loop 1838 is positioned, by means of magnetic attraction, proximate and between the magnetic poles of magnets 1830*a* and 1830*b* of the loop 1834. The magnet 1836 functions as a locking magnet, thereby locking each of the magnets 1830*a* and 1830*b* in their fixed respective positions on the coil loop 1834. This allows for a fixed loop which can be used to pull the walls of the adjacent organ closer during deployment. This locking mechanism also prevents the loop from inadvertently slipping out of an organ during deployment as described above. Spacers 1840 made of a non-ferromagnetic material are also placed between the magnets 1830 as shown, thereby ensuring that the magnets 1830 do not clump together on the loop 1834. In various embodiments, the spacers 1840 comprise silicone, Teflon, PTFE, or Nitinol tubes.

FIGS. 19A, 19B and 19C illustrate steps of formation of an anastomosis between two organs in a human body, in accordance with an embodiment of the present specification. In order to form an anastomosis between a pancreatic pseudocyst 1902 and a stomach 1901 wall, firstly, a stomach or duodenal wall adjacent to a pseudocyst wall is identified by means of an endoscope 1906. Using the endoscope 1906, a hollow needle or a catheter 1910 having a lumen for carrying a SMA wire 1912, which may be coupled with magnets 1914, is delivered at the identified location. The needle or catheter 1910 is used to pierce the organ walls and deliver the SMA wire 1912 therein. During deployment, the SMA wire 1912 is passed through the lumen of the needle or catheter 1910 until approximately ½ of the wire along, with the magnets 1914, is deployed in the pseudocyst 1902. The adjacent loops of the wire in the pseudocyst may attract together as described in FIGS. 18E and 18F and the loop can be used to pull the pseudocyst wall proximate to the gastric wall. Then the needle or catheter 1910 is retracted back into the stomach 1901 with the endoscope 1906 and the remaining ½ of the wire 1912 and magnets 1914 are deployed such that a portion of the wire resides in each of the pseudocyst and the stomach. Upon coming in contact with body heat, the straight SMA wire 1912 coils up and compresses the adjacent organs (pseudocyst 1902 and stomach 1901) together and the loops of the coil 1912 slowly cut through the walls of the adjacent organs, forming an anastomosis as described above. The compressive force can be provided by the coil alone or in conjunction with the magnets. Once the coil 1912 has completely cut through the two walls forming a stable anastomosis 1920, the coil 1912 spontaneously falls off and is naturally passed through the body, or may be retrieved using an endoscope or any other minimally invasive technique.

Figure 20A:
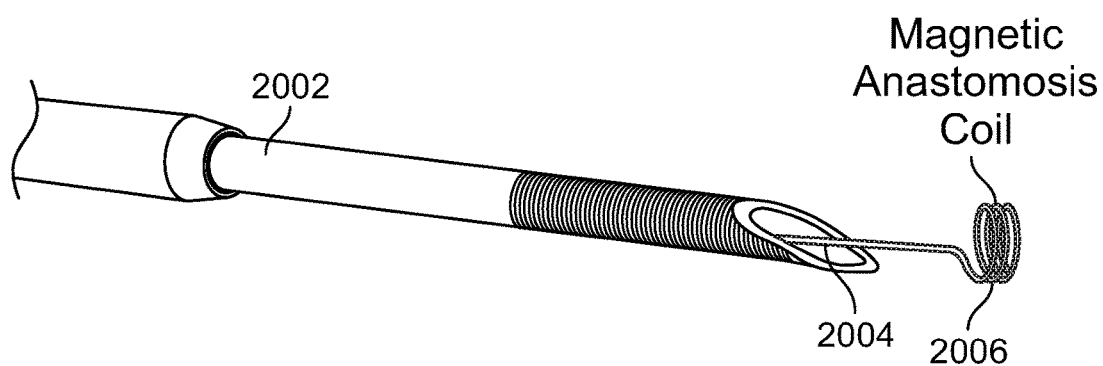
FIG. 20A illustrates a non-cautery needle that is used to deliver a SMA coil within a body, in accordance with an embodiment of the present specification.
Figure 20B:
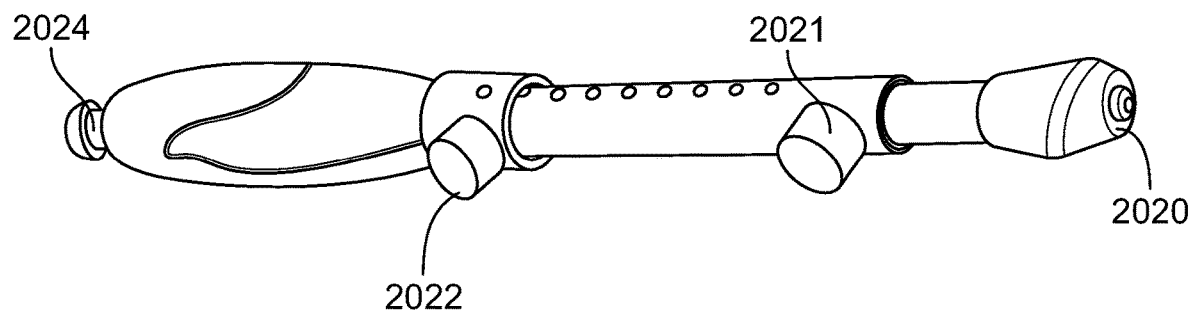
FIG. 20B illustrates the handle of the non-cautery needle shown in FIG. 20A, in accordance with an embodiment of the present specification.

FIG. 20A illustrates a non-cautery needle 2002 that is used to deliver a SMA coil 2006 within a body, in accordance with an embodiment of the present specification. Non-cautery hollow needle 2002 comprises a lumen 2004 in which a SMA anastomosis coil 2006 is placed for deployment via an endoscope into a human body. FIG. 20B illustrates the handle of the non-cautery needle shown in FIG. 20A. A tip portion 2020 engages with an endoscope. Knob 2021 controls the length of the catheter that can move in and out of the scope tip. Knob 2022 controls the length of the needle that can be withdrawn out of the catheter shaft at the needle tip. Port 24 allows for pushing cold saline into the needle lumen to help maintain the coil in the martensite shape and also accommodate the pusher catheter to push the coil out of the needle.

Figure 21:
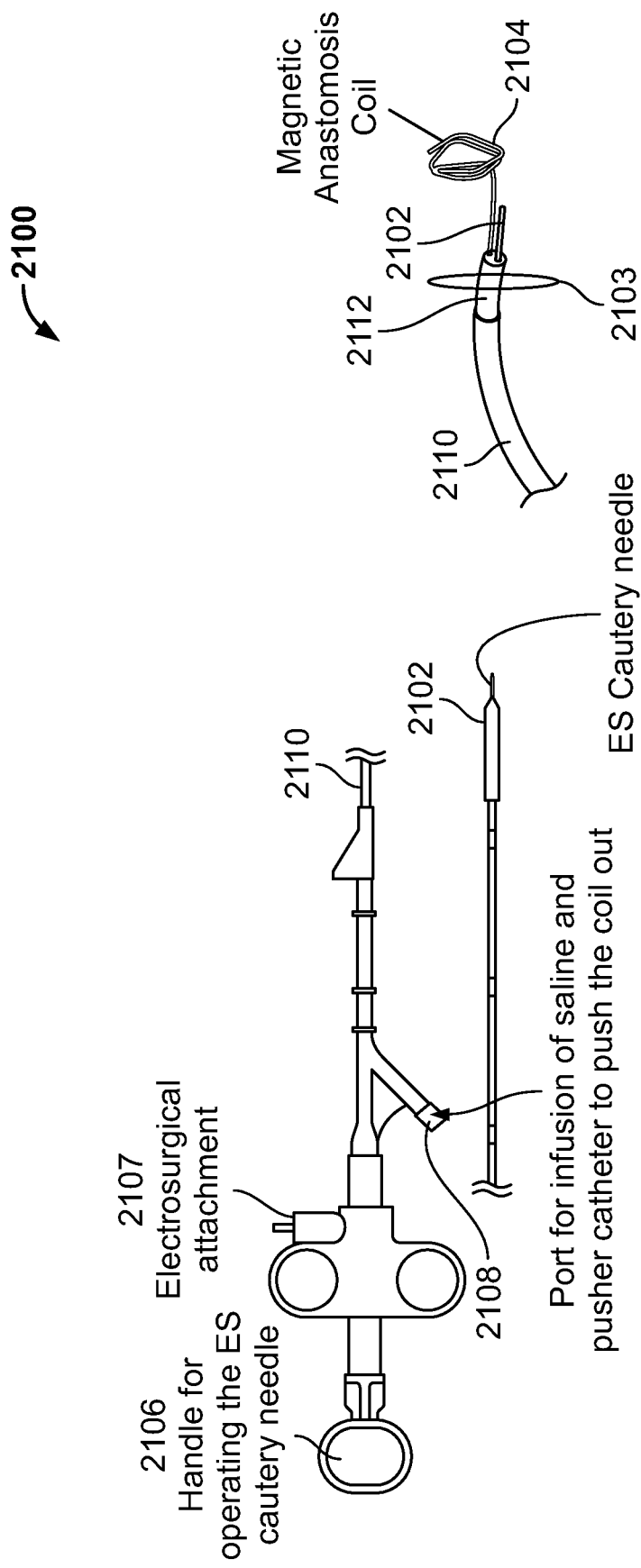
FIG. 21 illustrates a cautery needle device that is used to deliver a SMA coil within a body via an endoscope, in accordance with an embodiment of the present specification.

FIG. 21 illustrates a cautery needle device 2100 that is used to deliver a SMA coil 2104 within a body via an endoscope, in accordance with an embodiment of the present specification. The cautery needle device 2100 includes a port 2108, a body 2110, a handle 2106, a distal tip 2112, a needle 2102, and an electrosurgical attachment 2107 and is used to deliver a SMA anastomosis coil 2104 into a human body by means of an endoscope. The body 2110 of the needle device 2100 is inserted into a human body via an instrument channel of an endoscope such that the distal tip 2112 protrudes out of a distal end of the endoscope. The needle 2102 extends from the distal tip 2112 of the device 2100 via operation of handle 2106 for piercing a desired organ wall. The needle device 2100 includes a port 2108 for the infusion of cold saline into the needle lumen to help maintain the coil in the martensite shape and introduction of a pusher catheter. The SMA coil 2104 is delivered through the pierced site by means of the pusher catheter which is inserted into the port 2108 and pushes the coil 2104 out from the tip 2112 of the needle device 2100 and into the pierced organ wall. Optionally, in an embodiment, the device 2100 includes a balloon 2103 at its distal tip 2112 for positioning said tip 2112, approximating the two lumens proximate to each other and assisting with coil 2104 deployment. The pusher tube has marking or stopping mechanisms built into it assess the amount of coil that has been pushed out of the catheter.

Figure 22:
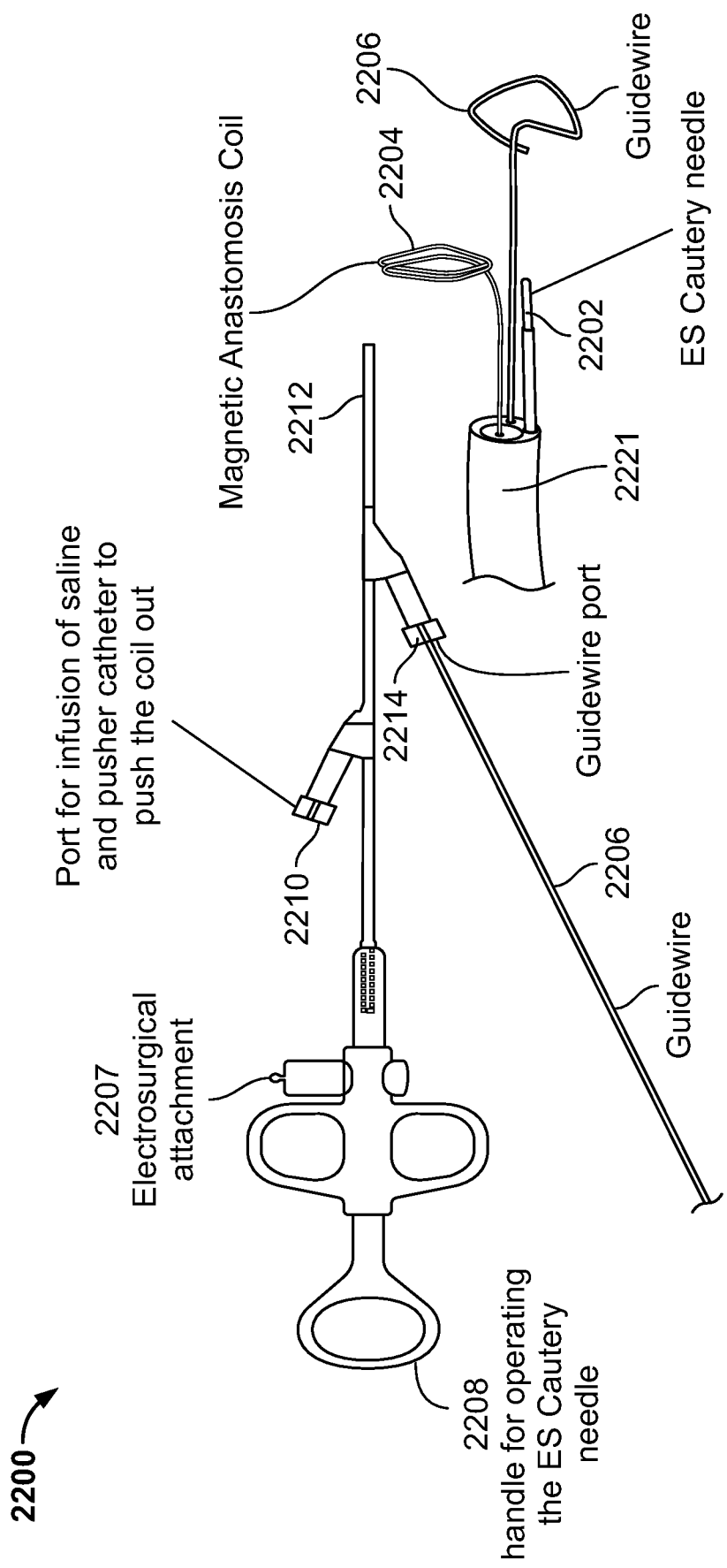
FIG. 22 illustrates a cautery needle device that is used to deliver a SMA coil within a body with the aid of a guidewire via an endoscope, in accordance with an embodiment of the present specification.

FIG. 22 illustrates a cautery needle device 2200 that is used to deliver a SMA coil 2204 within a body with the aid of a guidewire 2206 via an endoscope, in accordance with an embodiment of the present specification. A cautery needle device 2200, comprising a handle 2208, a body 2212, a first port 2210 for cold saline infusion, a second port 2214 for passage of a guidewire, a distal tip 2221, a needle 2202, and an electrosurgical attachment 2207, is used to deliver a SMA anastomosis coil 2204, with the help of a guide wire 2206, into a human body by means of an endoscope. The body 2212 of the needle device 2200 is inserted into a human body via a channel of an endoscope such that the distal tip 2221 protrudes out a distal end of the endoscope. The needle 2202 extends from distal tip 2221 via operation of handle 2208 to pierce a target tissue. Electrocautery is used to assist with the puncture. A guide wire 2206 is inserted via second port 2214 into the body 2212 of the needle device 2200 and extends from the distal tip 2221 into the punctured organ for maintaining position/access, for guiding placement of the catheter tip 2221 and the SMA coil 2204 in a desired location. The SMA coil 2204 is delivered into the lumen pierced by the needle 2202 by means of a pusher catheter which is introduced via the first port 2210 and pushes a portion of the coil 2204 out from the distal tip 2221 into the lumen of a second organ. The tip 2221 is retracted back into the lumen of a first organ and the remaining coil is deployed. The coil then changes shape and secures the two walls of the two organs together, fusing the two walls and then cutting out an anastomosis of a predetermined shape and dimension.

Figure 23A:
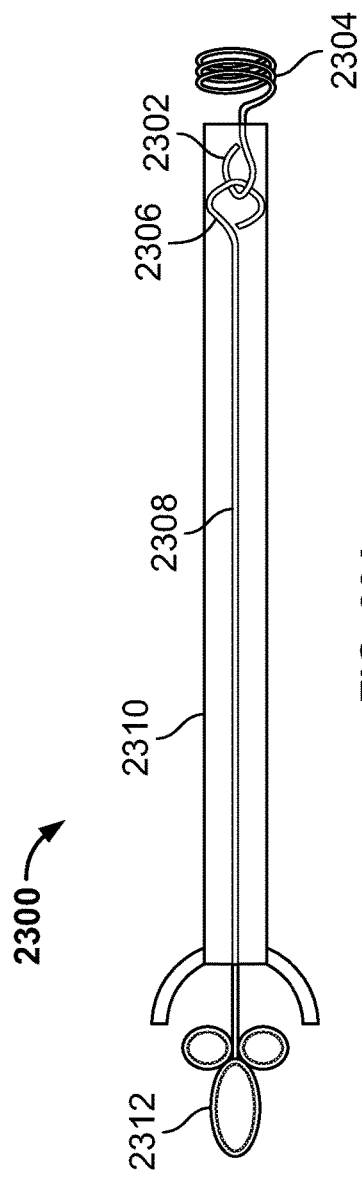
FIG. 23A illustrates a release mechanism of a SMA coil from a delivery catheter, in accordance with an embodiment of the present specification.
Figure 23B:
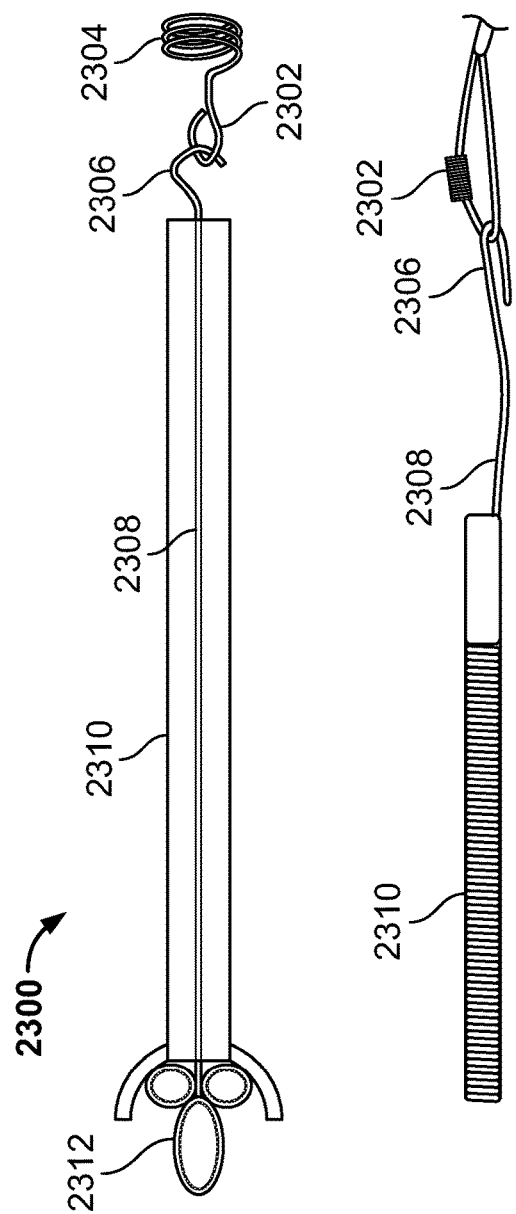
FIG. 23B illustrates the SMA coil being released from the delivery catheter shown in FIG. 23A, in accordance with an embodiment of the present specification.

FIG. 23A illustrates a release mechanism of a SMA coil 2304 from a delivery catheter 2300, in accordance with an embodiment of the present specification. A coil coupling member 2302 at the end of a SMA coil 2304 to be deployed is attached to a delivery coupling member 2306 on a pusher element 2308 to move the coil 2304 in and out of the delivery catheter sheath 2310. In some embodiments, the coil coupling member 2302 comprises a coil loop and the delivery coupling member 2306 comprises a delivery loop. In various embodiments, the one or both of the coil coupling member 2302 and delivery coupling member 2306 are configurable between a first open configuration and a second closed configuration. A handle 2312 is provided for pushing in or out the pusher element 2308. FIG. 23B illustrates the SMA coil 2304 being released from the delivery catheter 2300 shown in FIG. 23A, in accordance with an embodiment of the present specification. The handle 2312 is pushed forward while holding the sheath 2310. As shown, as the coil 2304 is pushed out of the catheter sheath 2310, the delivery coupling member 2306 on the pusher 2308 or the coil 2304, or both, open up, disengaging the coil 2304 from the pusher 2308 and the catheter 2300.

Figure 24A:
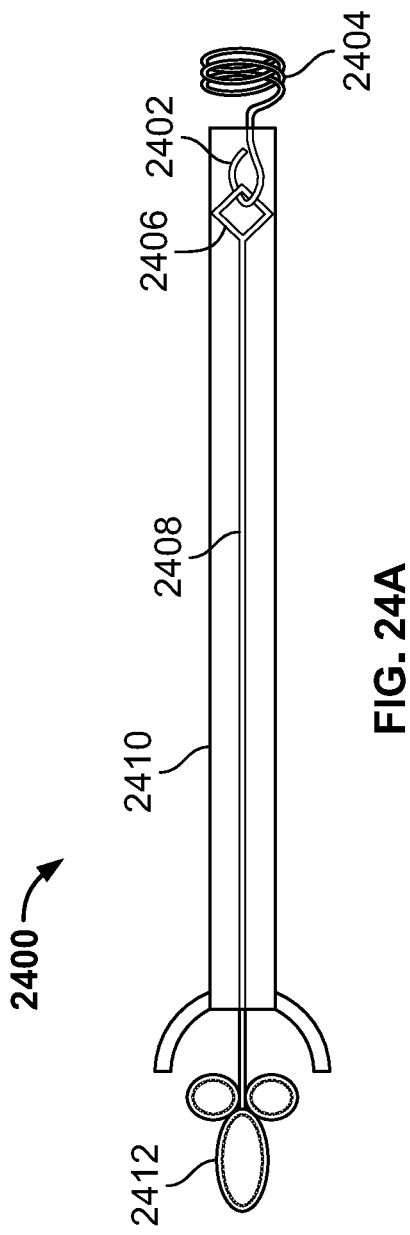
FIG. 24A illustrates a release mechanism of a SMA coil from a delivery catheter, in accordance with another embodiment of the present specification.
Figure 24B:
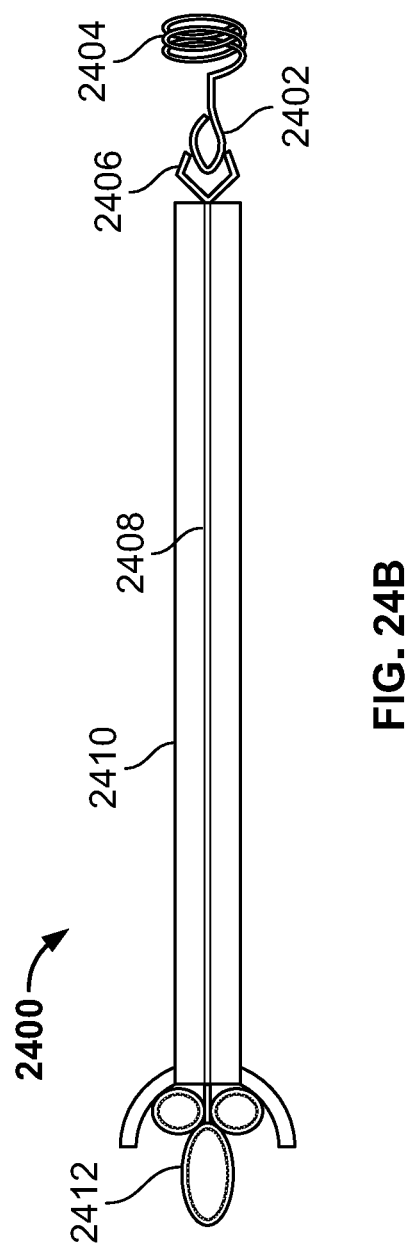
FIG. 24B illustrates the SMA coil being released from the delivery catheter shown in FIG. 24A, in accordance with an embodiment of the present specification.

FIG. 24A illustrates a release mechanism of a SMA coil 2404 from a delivery catheter 2400, in accordance with another embodiment of the present specification. A coil coupling member 2402 at the end of a SMA coil 2404 to be deployed is attached to a delivery coupling member 2406 on a pusher element 2408 to move the coil 2404 in and out of the delivery catheter sheath 2410. In some embodiments, the coil coupling member 2402 comprises a coil loop and the delivery coupling member 2406 comprises a delivery articulating grasper. In various embodiments, the one or both of the coil coupling member 2402 and delivery coupling member 2406 are configurable between a first open configuration and a second closed configuration. A handle 2412 is provided for pushing in or out the pusher element 2408. FIG. 24B illustrates the SMA coil 2404 being released from the delivery catheter 2400 shown in FIG. 24A, in accordance with an embodiment of the present specification. The handle 2412 is pushed forward while holding the sheath 2410. As shown, when the coil 2404 is pushed out of the catheter sheath 2410, the delivery coupling member 2406 on the pusher 2408 opens up disengaging the coil 2404 from the pusher 2408 and the catheter 2400. In an embodiment, the pusher 2408 comprises markings for alerting a user when a portion (less than the complete length) of the coil 2404 has been released from the catheter 2410. In another embodiment, the pusher 2408 comprises stopping mechanism for preventing a user from inadvertently deploying the complete length of the coil 2404 from the catheter 2410 at any one time.

Figure 25:
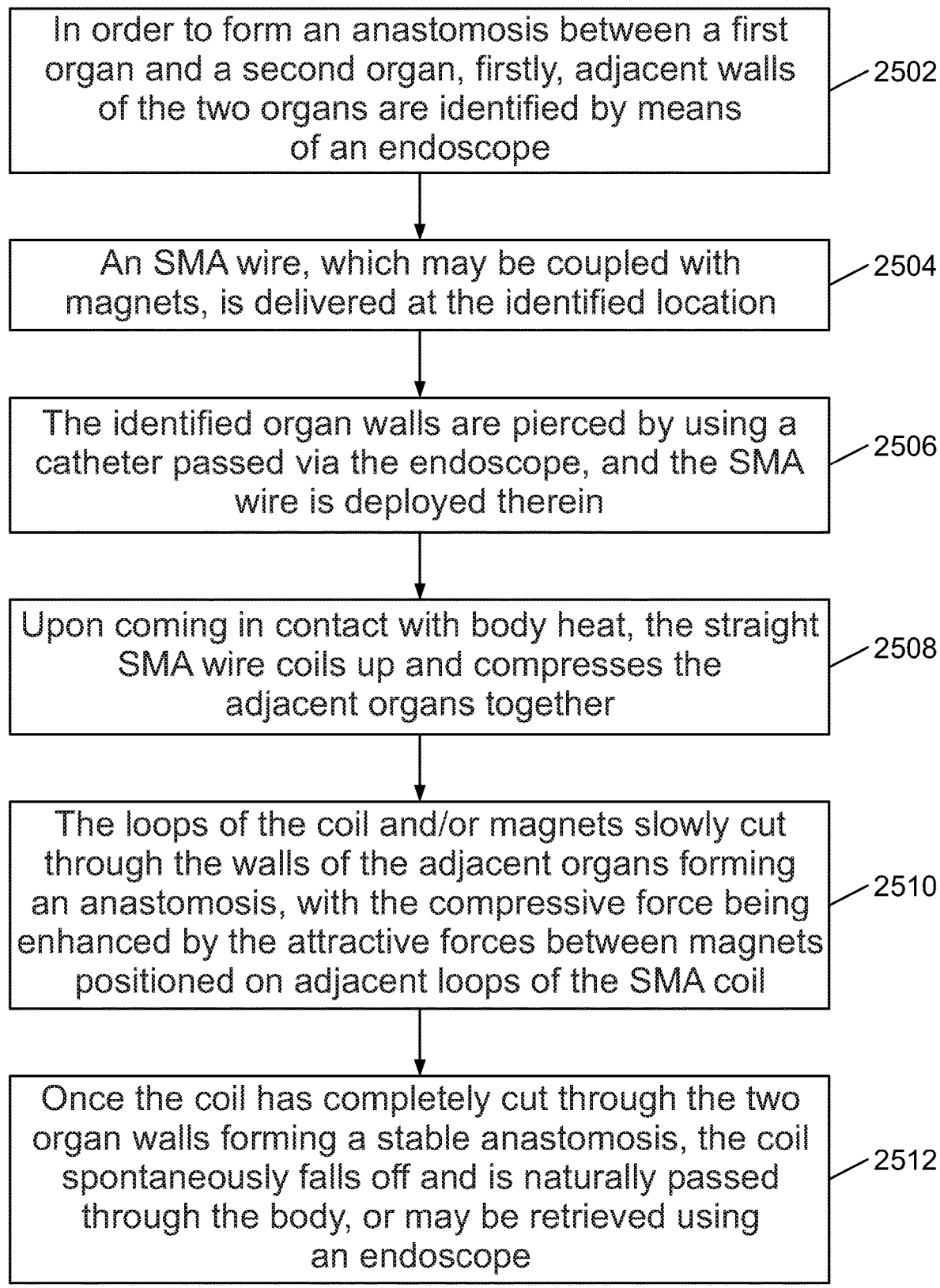
FIG. 25 is a flowchart illustrating the steps of creating an anastomosis by using an anastomosis instrument in accordance with an embodiment of the present specification.

FIG. 25 is a flowchart illustrating the steps of creating an anastomosis by using an anastomosis instrument in accordance with an embodiment of the present specification. At step 2502, in order to form an anastomosis between a first organ and a second organ, firstly, adjacent walls of the two organs are identified by means of an endoscope. Next, at step 2504, a SMA wire, which may be coupled with magnets, is delivered at the identified location. In an embodiment, the SMA coil is delivered using an endoscope via a hollow needle or catheter having a lumen for carrying the SMA wire which may be coupled with magnets. At step 2506 the identified organ walls are pierced and a portion of SMA wire is deployed in the lumen of the first organ and the remaining coil is deployed in the lumen of the second organ. At step 2508, upon coming in contact with body heat, the relatively straight SMA wire coils up to its predetermined austenite shape and compresses the adjacent organs together. At step 2510 the loops of the coil and/or magnets, if included, slowly cut through the walls of the walls of the two adjacent organs together forming an anastomosis over a period of time, with the compressive force being enhanced by the attractive forces between magnets positioned on adjacent loops of the SMA coil. The attractive forces increase over time as the loops of the coil and/or magnets cut through the walls of the two organs, thereby bringing the magnets closer to each other. At step 2512, once the coil has completely cut through the two organ walls forming a stable anastomosis, the coil spontaneously falls off and is naturally passed through the body, or may be retrieved using an endoscope or any other minimally invasive technique. In some embodiments, the coil is specifically shaped to promote its passage in a specific direction.

FIGS. 26A, 26B, and 26C illustrate first, second, and third views respectively, of an exemplary device 2600 for creating an anastomosis in a relatively straight pre-coiled configuration, in accordance with an embodiment of the present specification. The device comprises a shape memory alloy (SMA) wire 2602 with a plurality of magnets 2604 and spacers 2606 positioned coaxially about the wire 2602. In an embodiment, the wire 2602 is composed of Nitinol. In an embodiment, the spacers 2606 are composed of a non-ferromagnetic material. In various embodiments, the spacers 2606 comprise silicone, Teflon, PTFE, or Nitinol tubes or O-rings or circular balls. In various embodiments, each magnet 2604 is separated from an adjacent magnet 2604 by a set of spacers 2606. In an embodiment, each set of spacers 2606 comprises three spacers 2606. FIGS. 26A-26C depict the device 2600 is a pre-coiled or pre-deployment configuration. The device 2600 has a curved shape when unrestrained by a delivery catheter and at room temperature. The device 2600 has a nearly straight shape when restrained in a delivery catheter (for example, as seen with device 1500 in FIG. 15A).

Figure 26D:
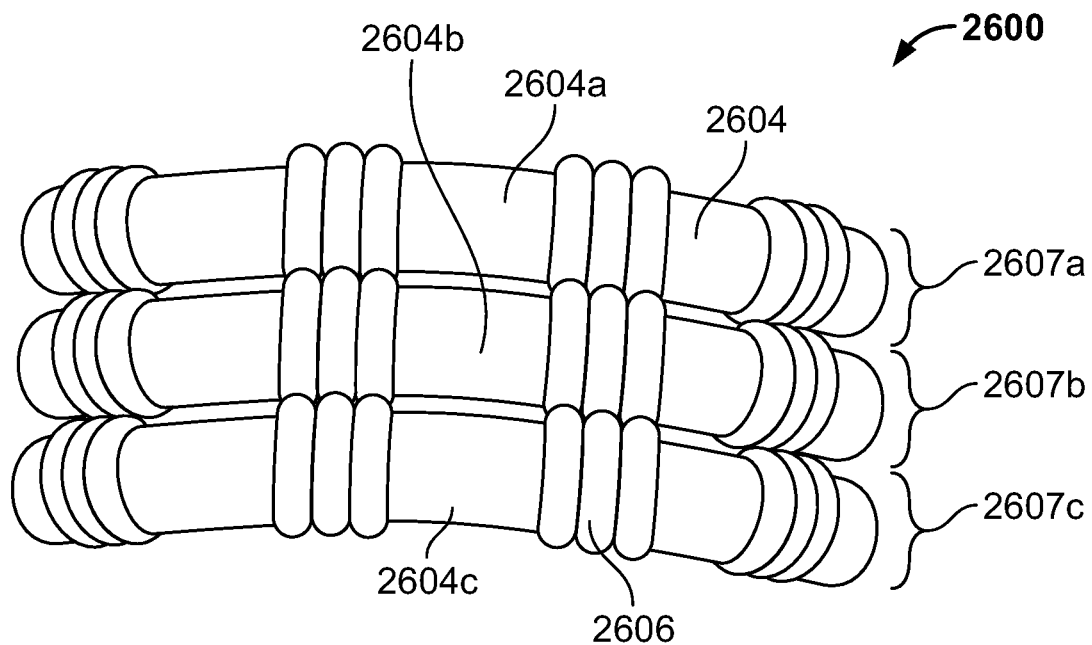
FIG. 26D illustrates a side view of the device for creating an anastomosis of FIG. 26A in a coiled configuration.
Figure 26E:
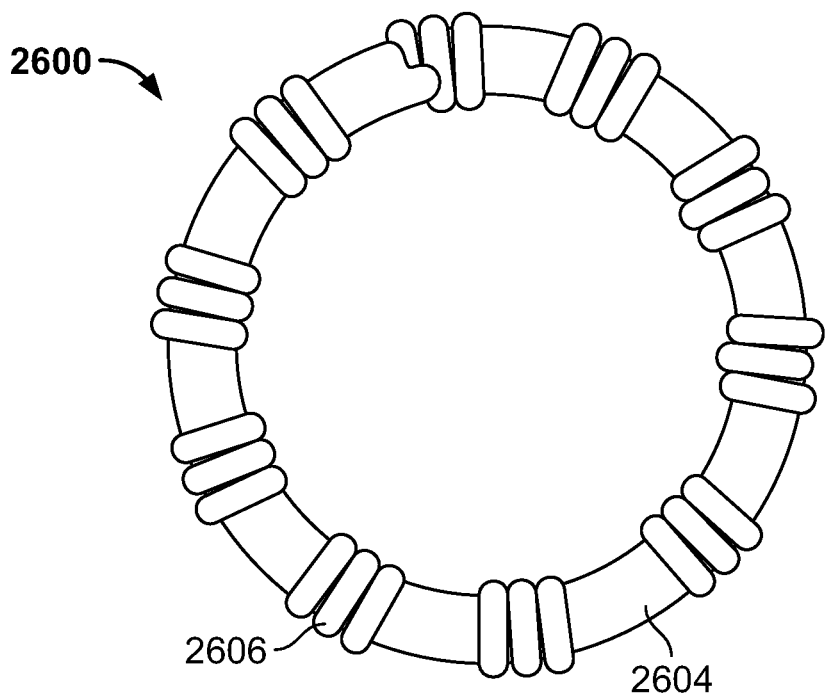
FIG. 26E illustrates an axial view of the device for creating an anastomosis of FIG. 26A in a coiled configuration.

FIGS. 26D and 26E illustrate side and axial views respectively, of the device 2600 for creating an anastomosis of FIG. 26A in a coiled configuration. After deployment, and when exposed to body temperature, the SMA wire coils to move the device 2600 from the curved configuration shown in FIGS. 26A-26C to the coiled configuration depicted in FIGS. 26D and 26E. The spacers 2606 ensure that the magnets 2604 do not clump together on the device 2600. Referring to FIG. 26D, magnetic force attraction between magnets 2604 on adjacent loops 2607a, 2607b, 2607c of the coiled device, for example, between magnets 2604a, 2604b, 2604c on adjacent loops 2607a, 2607b, 2607c, serves to pull the loops 2607a, 2607b, 2607c closer together and tighten the coil.

Figure 26F:
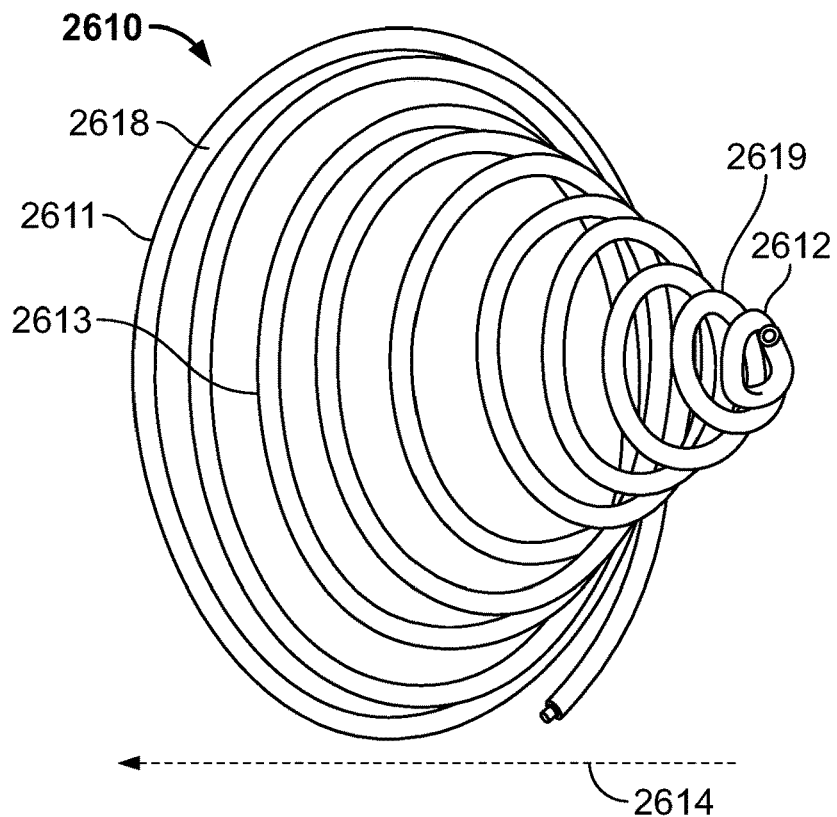
FIG. 26F illustrates a first exemplary device for creating an anastomosis in a post-deployment cone-shaped coil configuration, in accordance with one embodiment of the present specification.

FIG. 26F illustrates a first exemplary device 2610 for creating an anastomosis in a post-deployment cone-shaped coil configuration, in accordance with one embodiment of the present specification. The device 2610 is configured to pass from the tissue in only one direction following anastomosis formation. The device 2610 comprises a single shape memory wire which takes the shape of a coil 2613 once deployed. The device 2610 includes loops 2618 having a larger diameter at a first end 2611 of the coil 2613 compared with loops 2619 at a second, opposite end 2612 of the coil 2613. The diameter of the cutting loops 2618, 2619 of the coil 2613 determine the diameter of the anastomosis. Therefore, the resultant anastomosis will also have a cone or funnel shape, having a larger opening at a first end associated with the first end 2611 of the coil 2613 and a smaller opening at a second end associated with the second end 2612 of the coil 2613. Once the anastomosis has formed, the device 2610 will only be able to pass through the anastomosis in the direction indicated by arrow 2614, as the first end 2611 will be too large to pass through the anastomosis opening created by loops 2619 and device end 2612.

Figure 26G:
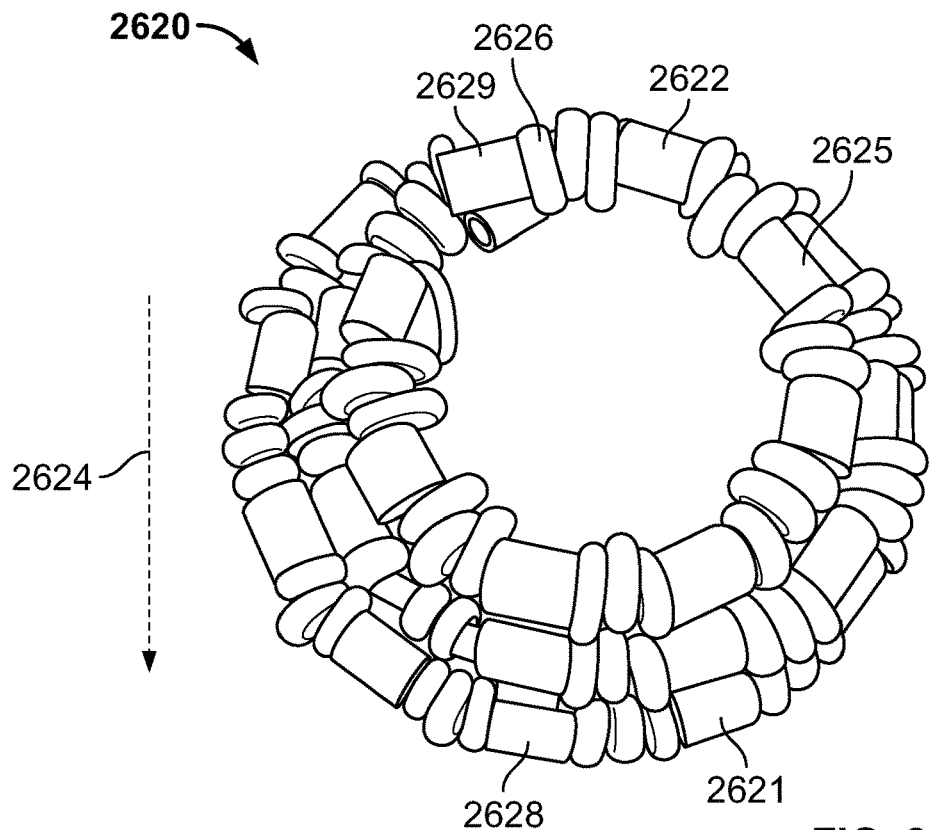
FIG. 26G illustrates a second exemplary device for creating an anastomosis in a post-deployment cone-shaped coil configuration, in accordance with one embodiment of the present specification.

FIG. 26G illustrates a second exemplary device 2620 for creating an anastomosis in a post-deployment cone-shaped coil configuration, in accordance with one embodiment of the present specification. The device 2620 is configured to pass from the tissue in only one direction following anastomosis formation. The device 2620 comprises a plurality of magnets 2625 separated by a plurality of spacers 2626 positioned on a shape memory wire. The device 2620 includes loops 2628 having a larger diameter at a first end 2621 of the device 2620 compared with loops 2629 at a second, opposite end 2622 of the device 2620. The diameter of the cutting loops 2628, 2629 of the device 2620 determine the diameter of the anastomosis. Therefore, the resultant anastomosis will also have a cone or funnel shape, having a larger opening at a first end associated with the first end 2621 of the device 2620 and a smaller opening at a second end associated with the second end 2622 of the device 2620. Once the anastomosis has formed, the device 2620 will only be able to pass through the anastomosis in the direction indicated by arrow 2624, as the first end 2621 will be too large to pass through the anastomosis opening created by loops 2629 and device end 2622.

Figure 26H:
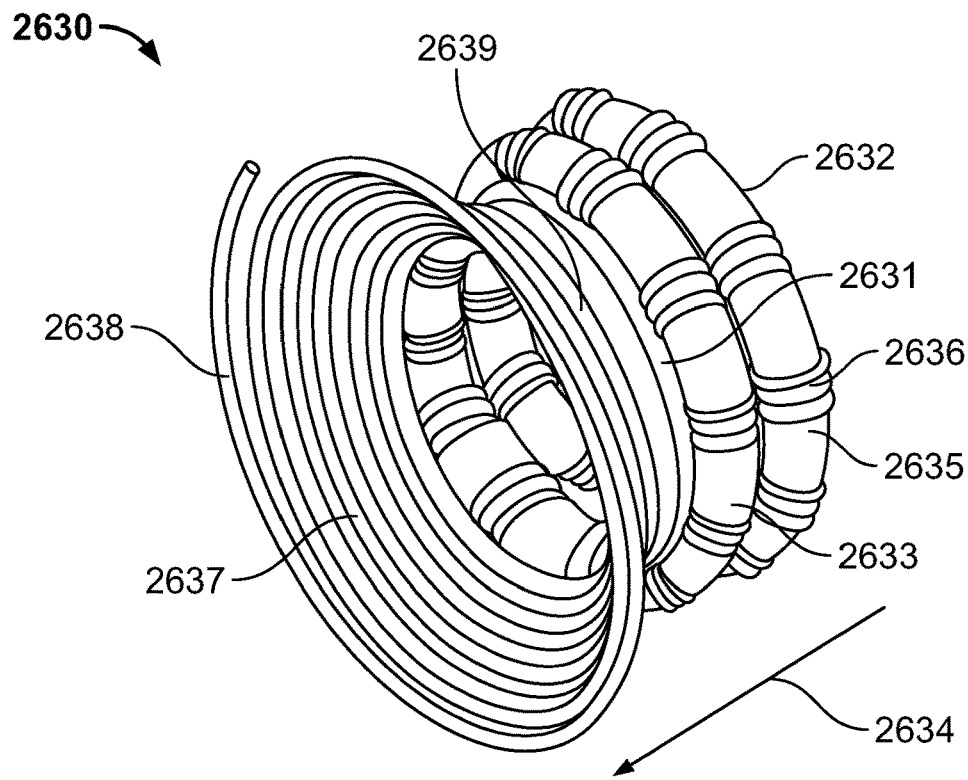
FIG. 26H illustrates an embodiment of a device for creating an anastomosis in a post-deployment coil configuration and comprising a single flange attached to one end of the coil.

FIG. 26H illustrates an embodiment of a device 2630 for creating an anastomosis in a post-deployment coil configuration and comprising a single flange 2637 attached to one end 2631 of the coil 2633. The device 2630 includes a coil 2633 having a first end 2631 and a second, opposite end 2632 and comprises a plurality of magnets 2635 separated by a plurality of spacers 2636 positioned on a shape memory wire. In an embodiment, a diameter of the first end 2631 of the coil 2633 is equal to a diameter of the second end 2632 of the coil 2633. The device 2630 further includes an extension or flange 2637 having a first end 2638 and a second end 2639. In an embodiment, the flange 2637 is cone shaped. The second end 2639 of the flange 2637 is attached to the first end 2631 of the coil 2633. The first end 2638 of the flange 2637 has a diameter that is greater than the diameter of the second end 2639 of the flange 2637 and greater than the diameters of both ends 2631, 2632 of the coil 2633. Once an anastomosis has formed, the device 2630 will pass only in the direction indicated by arrow 2634 (direction of the end including the flange), as the relatively larger diameter of the first end 2638 of the flange 2637 will prevent passage of the flange 2637 through the anastomosis formed by the relatively smaller diameter of the coil 2633.

Figure 26I:
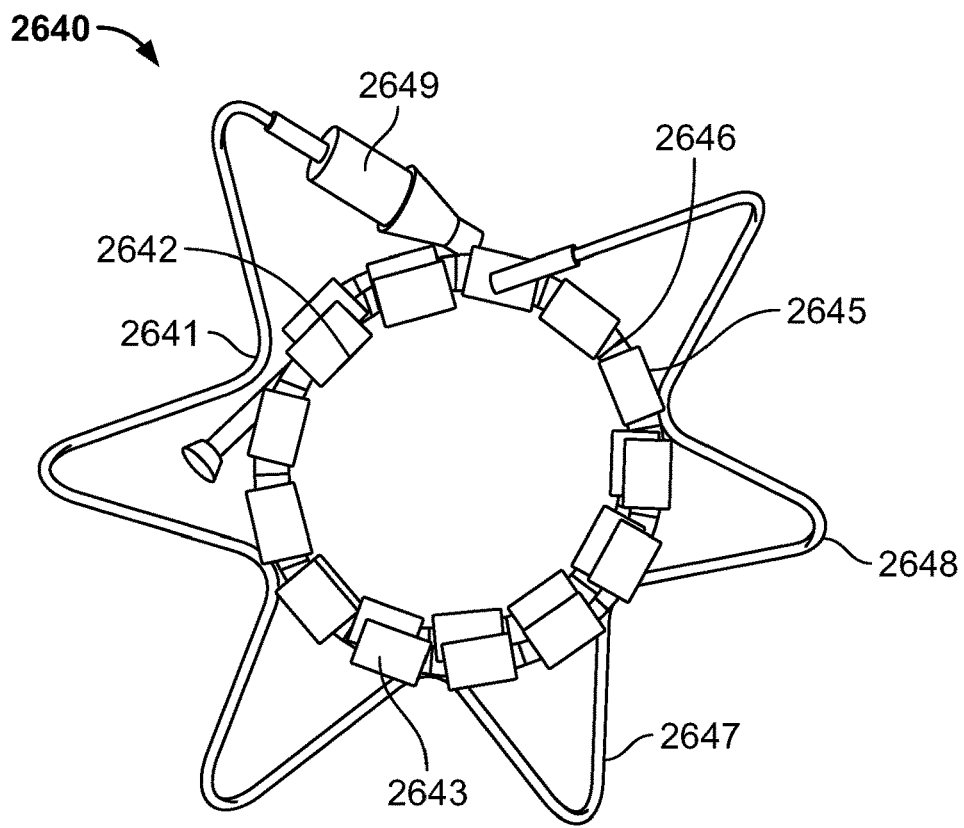
FIG. 26I illustrates another embodiment of a device for creating an anastomosis in a post-deployment coil configuration and comprising a single flange attached to one end of the coil.
Figure 26J:
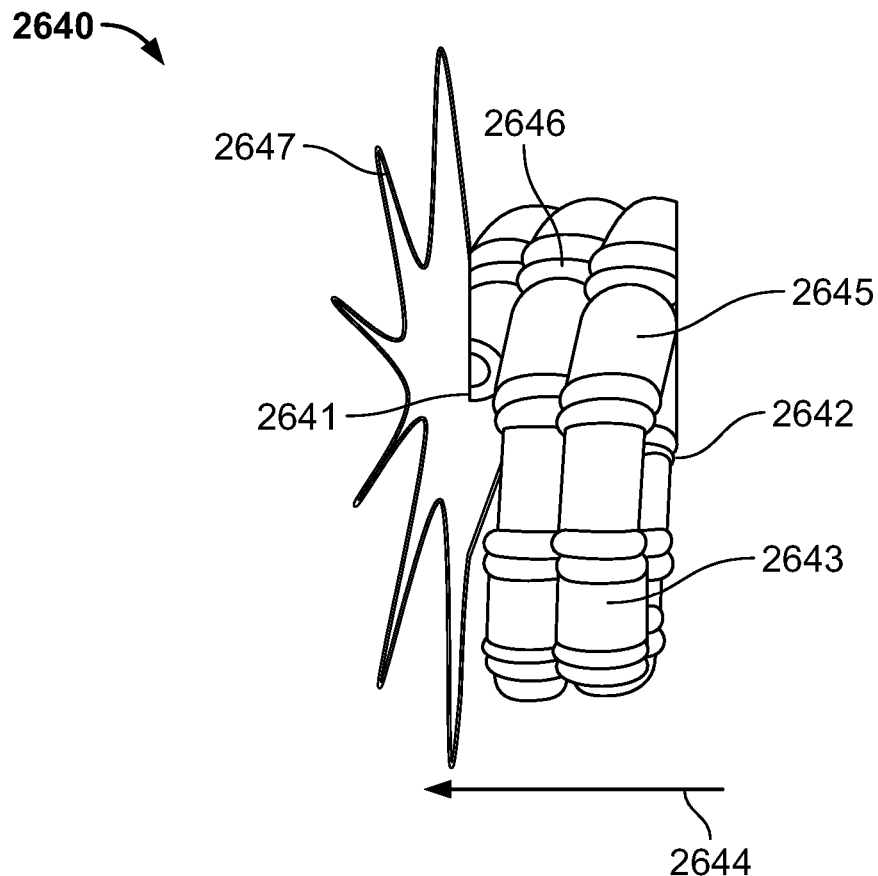
FIG. 26J illustrates a side view of the device for creating an anastomosis of FIG. 26I.

FIGS. 26I and 26J illustrate end and side views respectively, of another embodiment of a device 2640 for creating an anastomosis in a post-deployment coil configuration and comprising a single flange 2647 attached to one end 2641 of the coil 2643. The device 2640 includes a coil 2643 having a first end 2641 and a second, opposite end 2642 and comprises a plurality of magnets 2645 separated by a plurality of spacers 2646 positioned on a shape memory wire. In an embodiment, a diameter of the first end 2641 of the coil 2643 is equal to a diameter of the second end 2642 of the coil 2643. The device 2640 further includes a star or flower shaped extension or flange 2647 attached to the first end 2641 of the coil 2643. In an embodiment, the flange 2647 includes a cautery puncture component 2649 which is configured to receive an electrical current to generate heat and puncture a tissue to deliver the device 2640. The cautery puncture component 2649 is attached to an end of the flange 2647 via a screw connection. An opposite end of the flange 2647 includes another screw connection for attaching the flange 2647 to the coil 2643. The flange 2647 includes a plurality of angular protrusions 2648 which extend outwardly from a center of the device 2640 such that a diameter defined by the outer edges of the protrusions 2648 is greater than the diameters of both ends 2641, 2642 of the coil 2643. Once an anastomosis has formed, the device 2640 will pass only in the direction indicated by arrow 2644 (direction of the end including the flange), as the relatively larger diameter defined by the outer edges of the protrusions 2648 of the flange 2647 will prevent passage of the flange 2647 through the anastomosis formed by the relatively smaller diameter of the coil 2643.

Figure 26K:
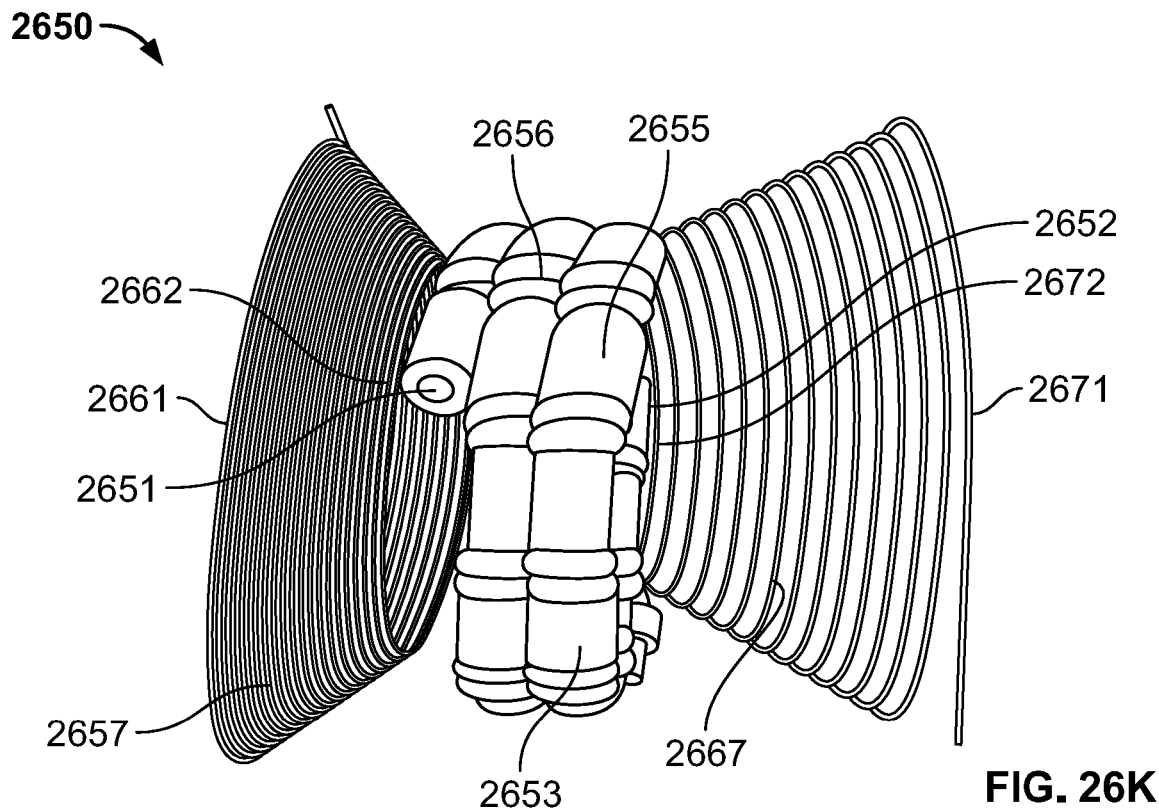
FIG. 26K illustrates an embodiment of a device for creating an anastomosis in a post-deployment coil configuration and comprising a flange attached to each end of the coil.

FIG. 26K illustrates an embodiment of a device 2650 for creating an anastomosis in a post-deployment coil configuration and comprising a flange 2657, 2667 attached to each end of the coil 2653. The device 2650 includes a coil 2653 having a first end 2651 and a second, opposite end 2652 and comprises a plurality of magnets 2655 separated by a plurality of spacers 2656 positioned on a shape memory wire. In an embodiment, a diameter of the first end 2651 of the coil 2653 is equal to a diameter of the second end 2652 of the coil 2653. The device 2650 further includes a first extension or flange 2657 and a second extension of flange 2667, each having a first end 2661, 2671 and a second end 2662, 2672. In an embodiment, each flange 2657, 2667 is cone shaped. The second end 2662 of the first flange 2657 is attached to the first end 2651 of the coil 2653 and the second end 2672 of the second flange 2667 is attached to the second end 2652 of the coil. The first ends 2661, 2671 of each flange 2657, 2667 each have a diameter that is greater than a diameter of each second end 2662, 2672 of the flanges 2657, 2667 and greater than the diameters of both ends 2651, 2652 of the coil 2653. Once an anastomosis has formed, the device 2650 will become fixed within the anastomosis and cannot be passed, as the relatively larger diameters of the first ends 2661, 2671 of the flanges 2657, 2667 will prevent passage of the device 2650 in either direction through the anastomosis formed by the relatively smaller diameter of the coil 2653. In this configuration, the diameter of the coil 2653 is smaller than the flanges 2657, 2667 on both ends and, after an anastomosis is formed, the coil 2653 would not spontaneously pass through the anastomosis as the flanges 2657, 2667 will become stuck.

Figure 26L:
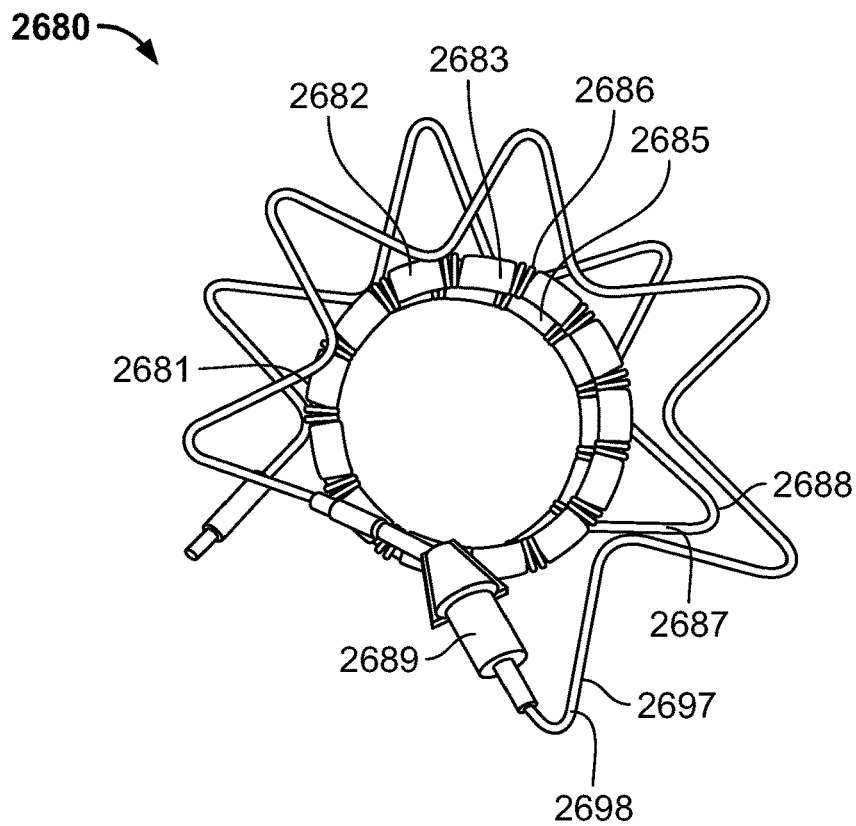
FIG. 26L illustrates another embodiment of a device for creating an anastomosis in a post-deployment coil configuration and comprising a flange attached to each end of the coil.
Figure 26M:
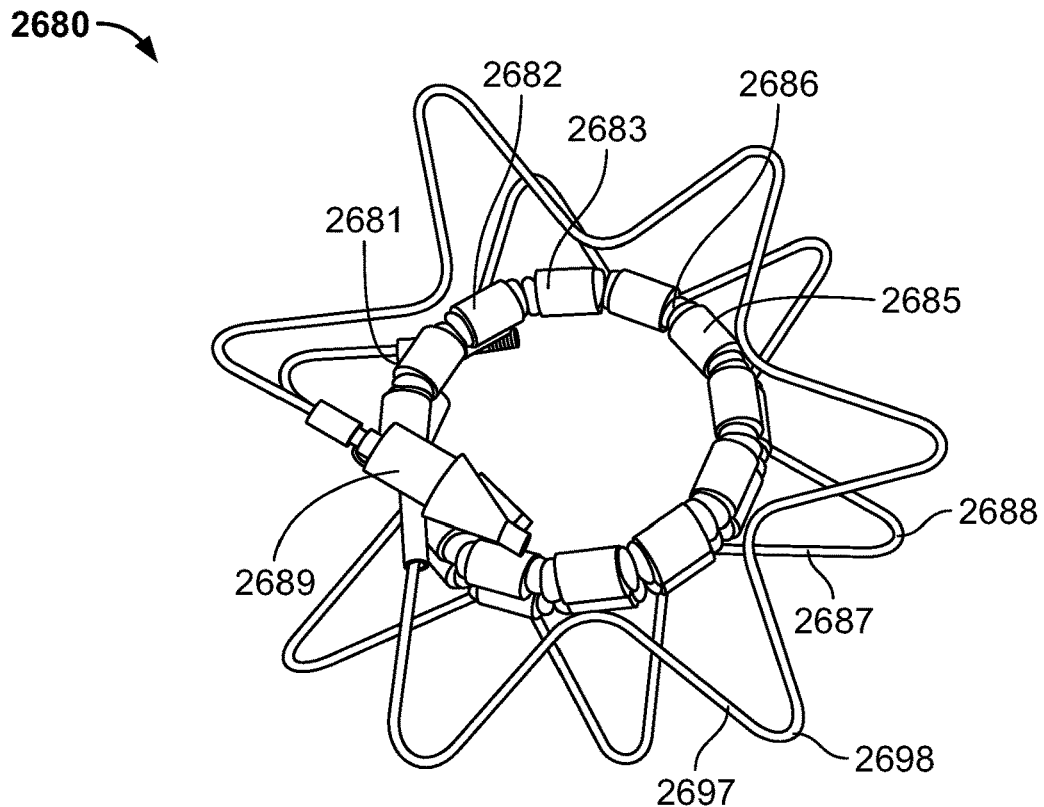
FIG. 26M illustrates an additional view of the device for creating an anastomosis of FIG. 26L.
Figure 26N:
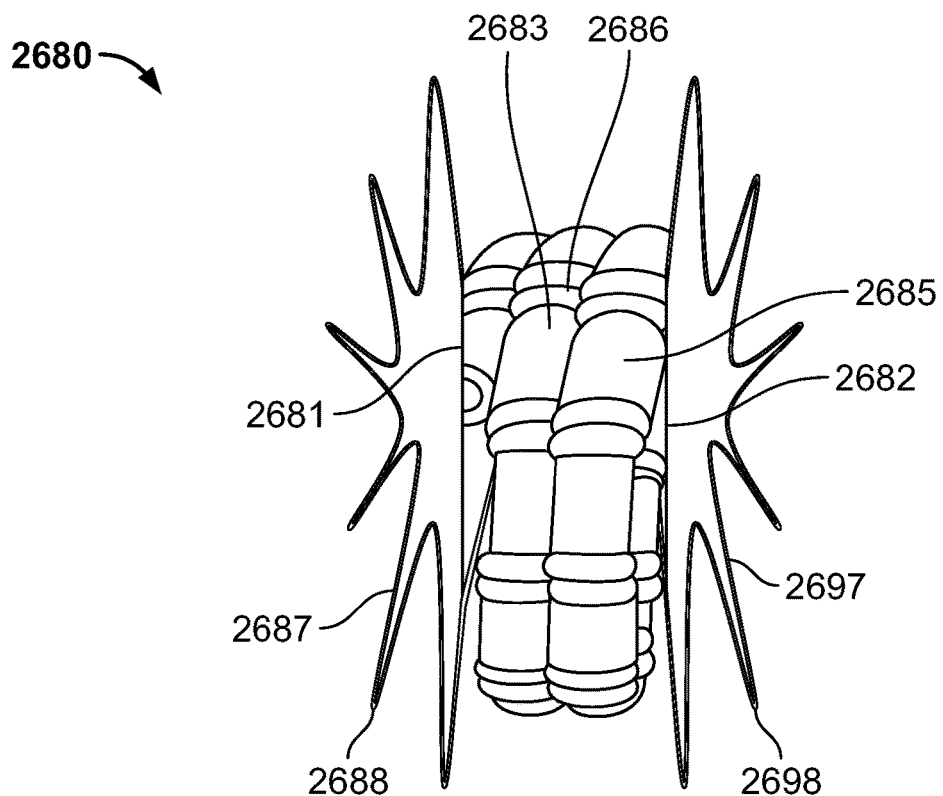
FIG. 26N illustrates a side view of the device for creating an anastomosis of FIG. 26L.

FIGS. 26L, 26M, and 26N illustrate end and side views of another embodiment of a device 2680 for creating an anastomosis in a post-deployment coil configuration and comprising a flange 2687, 2697 attached to each end of the coil 2683. The device 2680 includes a coil 2683 having a first end 2681 and a second, opposite end 2682 and comprises a plurality of magnets 2685 separated by a plurality of spacers 2686 positioned on a shape memory wire. In an embodiment, a diameter of the first end 2681 of the coil 2683 is equal to a diameter of the second end 2682 of the coil 2683. The device 2680 further includes a first star or flower shaped extension or flange 2687 attached to the first end 2681 of the coil 2683 and a second star or flower shaped extension or flange 2697 attached to the second end 2682 of the coil 2683. In an embodiment, one or each flange 2687, 2697 includes a cautery puncture component 2689 which is configured to receive an electrical current to generate heat and puncture a tissue to deliver the device 2680. A cautery puncture component 2689 is attached to an end of one or each flange 2687, 2697 via a screw connection. An opposite end of each flange 2687, 2697 includes another screw connection for attaching the flanges 2687, 2697 to the coil 2683. The flanges 2687, 2697 each include a plurality of angular protrusions 2688, 2698 which extend outwardly from a center of the device 2680 such that diameters defined by the outer edges of the protrusions 2688, 2698 are greater than the diameters of both ends 2681, 2682 of the coil 2683. Once an anastomosis has formed, the device 2680 will become fixed within the anastomosis and cannot be passed, as the relatively larger diameters defined by the protrusions 2688, 2698 of the flanges 2687, 2697 will prevent passage of the device 2680 in either direction through the anastomosis formed by the relatively smaller diameter of the coil 2683. The coil 2680 will not pass spontaneously after the anastomosis is formed.

Figure 26O:
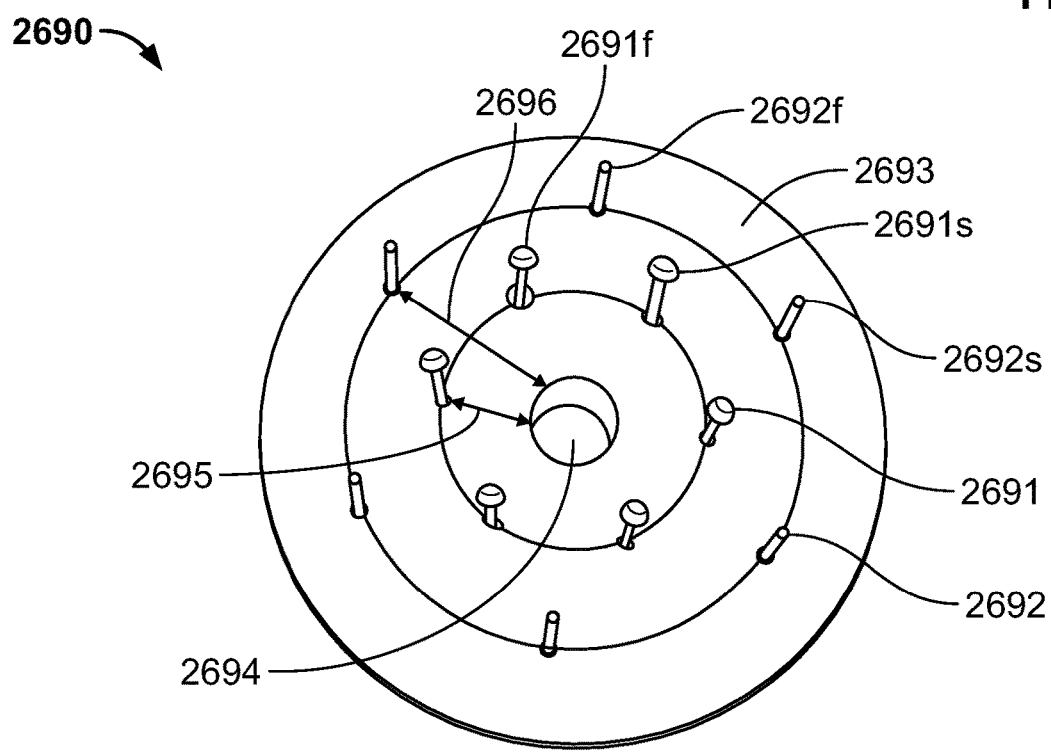
FIG. 26O illustrates a mold for creating the anastomosis device with flanges of FIG. 26L.
Figure 27:
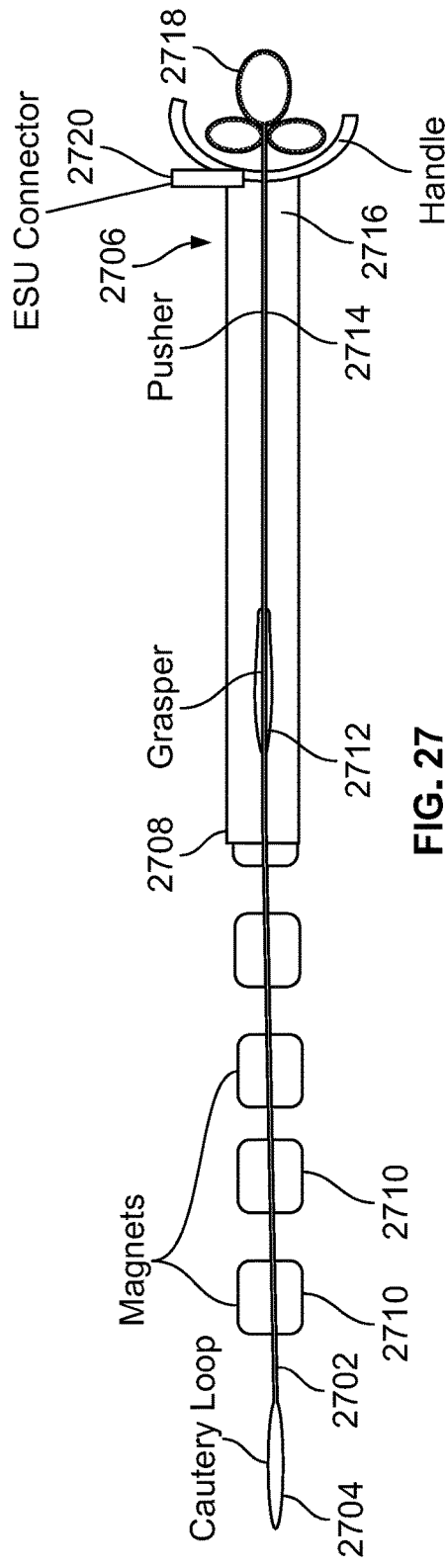
FIG. 27 illustrates a SMA coil device for creating an anastomosis in a pre-deployment configuration with delivery catheter, in accordance with an embodiment of the present specification.

FIG. 26O illustrates a mold 2690 for creating the anastomosis device 2680 with flanges of FIG. 26L. The mold 2690 includes a first plurality of pins 2691 and a second plurality of pins 2692 extending perpendicularly from a base 2693 of the mold 2690. The first plurality of pins 2691 is positioned at a first distance 2695 from a center 2694 of the mold 2693 and the second plurality of pins 2692 is positioned at a second distance 2696 from the center 2694 of the mold 2693, wherein the second distance 2696 is greater than the first distance 2695. Referring to FIGS. 26L through 26O simultaneously, a diameter defined by the first plurality of pins 2691 corresponds to the diameter of the coil 2683 and a diameter defined by the second plurality of pins 2692 corresponds to the diameter defined by the outer edges of the protrusions 2688, 2698 of the flanges 2687, 2697. The coil 2683 of the anastomosis device 2680 is wrapped about the first plurality of pins 2691 to give the coil 2683 its coil shape. Each flange 2687, 2697 is wrapped about a first pin 2691f of the first plurality of pins 2691, then an adjacent first pin 2692f of the second plurality of pins 2692, then an adjacent second pin 2691s of said first plurality of pins 2691, then an adjacent second pin 2692s of said second plurality of pins 2692, and so on, in a clockwise direction (or, in another embodiment, in a counter-clockwise direction) to form a star or flower shaped flange. FIG. 27 illustrates a SMA coil device 2702 for creating an anastomosis in a pre-deployment configuration with delivery catheter 2706, in accordance with an embodiment of the present specification. A cautery loop 2704 formed at a distal end of the SMA coil 2702 device is used to puncture a target tissue and cauterize the tissue as an opening is created for the anastomosis. A pusher delivery catheter 2706 pushes the coil 2702 out from a distal end of the catheter 2706. The SMA coil device 2702 comprises magnets 2710 which enable the coil to change shape and secure two walls of two organs together. The SMA coil device 2702 is attached to a loop/articulating grasper 2712 on a pusher element 2714 of the delivery catheter 2706 to move the coil device 2702 in and out of the delivery catheter sheath 2716. A handle 2718 is provided for pushing in or out the pusher element 2714. In an embodiment, an electrosurgical unit connector 2720 provides electrical contact for the pusher element 2714 and the SMA coil device 2702 with an electrosurgical generator.

Figure 28:
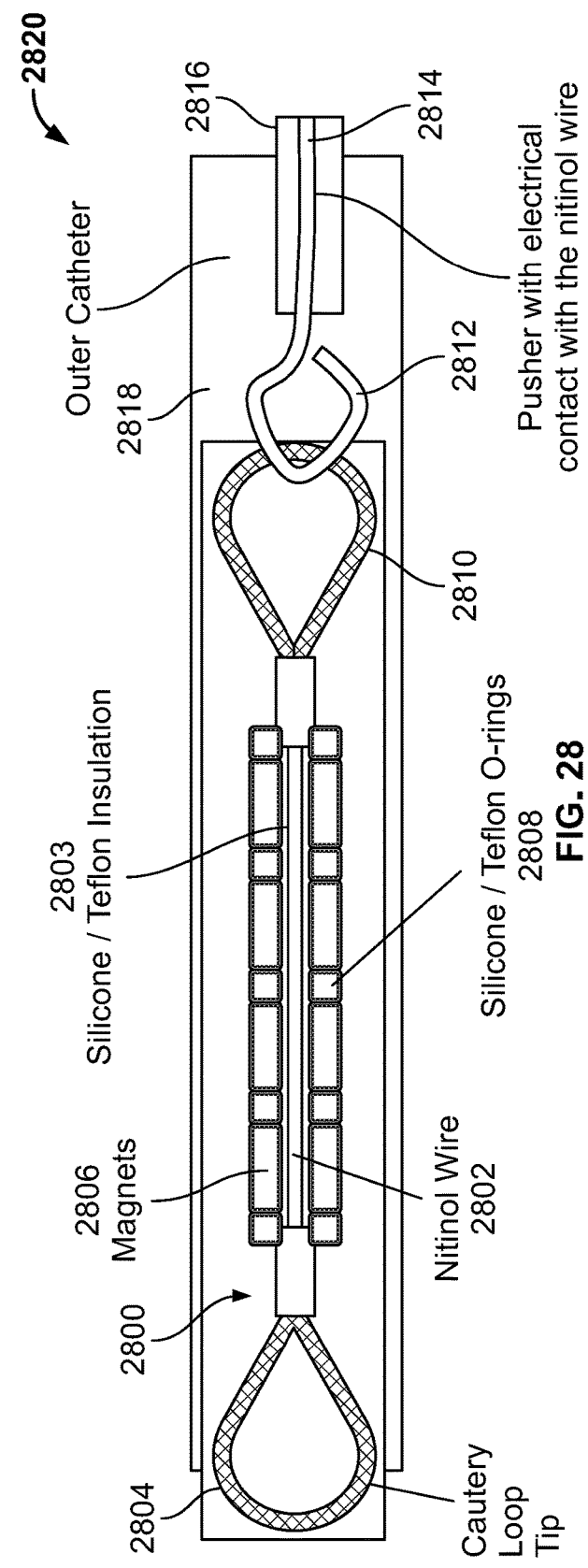
FIG. 28 illustrates a SMA coil device for creating an anastomosis in a pre-deployment configuration with delivery catheter, in accordance with another embodiment of the present specification.

FIG. 28 illustrates a SMA coil device 2800 for creating an anastomosis in a pre-deployment configuration with delivery catheter 2820, in accordance with another embodiment of the present specification. The SMA coil device 2800 includes a cautery loop 2804 formed at a distal end of a SMA wire 2802 and a plurality of magnets 2806 and spacers 2808 positioned coaxially about the SMA wire 2802. The cautery loop 2804 is used to puncture a target tissue and cauterize the tissue as an opening is created for the anastomosis. In an embodiment, the SMA wire 2802 is composed of Nitinol. In an embodiment, the spacers 2808 are composed of a non-ferromagnetic material. In various embodiments, the spacers 2808 comprise silicone or Nitinol tubes or O-rings or circular balls. A loop 2810 at a proximal end of the SMA wire 2802 is attached to a loop/articulating grasper 2812 on a pusher element 2814 to move the SMA wire 2802 in and out of a delivery catheter sheath 2816 of a delivery catheter 2820. In an embodiment, the SMA wire 2802 includes an insulation covering 2803. In various embodiments, the insulation covering 2803 is composed of silicone or Teflon. The insulation covering 2803 prevents the body of the SMA wire from transferring heat to the magnets 2806 and spacers 2808 as the cautery loop 2804 is heated via electrical current communicated to the SMA wire 2802 through the pusher element 2814 and loop/articulating grasper 2812. The SMA wire 2802 and the delivery catheter sheath 2816 are disposed within an outer catheter 2818 at a distal end of the delivery catheter 2820.

Figure 29A:
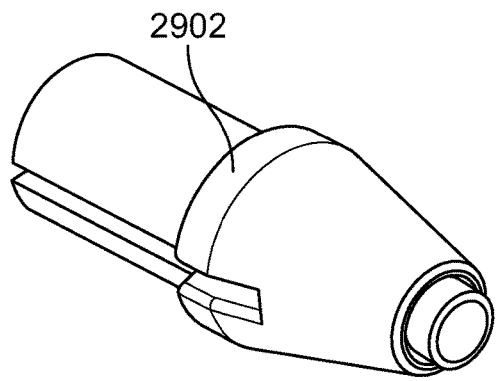
FIG. 29A illustrates a cautery tip for deployment with an anastomosis coil device, in accordance with various embodiments of the present specification.
Figure 29B:
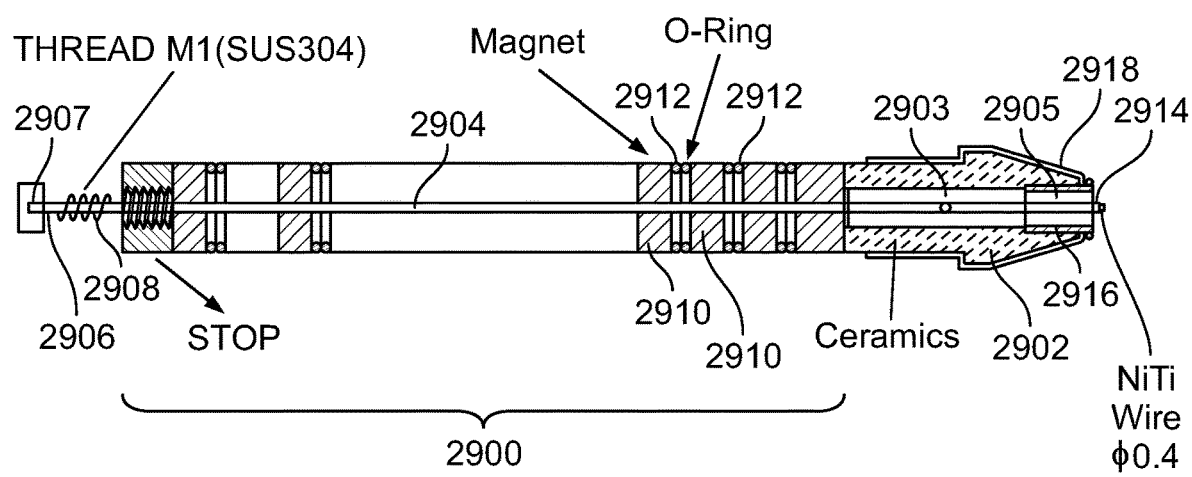
FIG. 29B illustrates an anastomosis coil device provided with a cautery tip in a pre-deployment configuration, in accordance with an embodiment of the present specification.

FIG. 29A illustrates a cautery tip 2902 for deployment with an anastomosis coil device, in accordance with various embodiments of the present specification. The cautery tip 2902 is configured to receive thermal energy from an electrical current source. As the cautery tip heats, it is advanced forward into a body tissue. The thermal energy cuts through the target tissue, creating an opening for creation of an anastomosis while simultaneously cauterizing and stopping blood loss from the tissue surrounding the newly formed opening. FIG. 29B illustrates an anastomosis coil device 2900 provided with a cautery tip 2902 in a pre-deployment configuration, in accordance with an embodiment of the present specification. Anastomosis coil device 2904 is detachably connected to a pusher 2907 comprising a cautery wire 2906 through thread connector 2908 at the proximal end of the anastomosis coil device 2904, which creates an electrical connection between the pusher 2907 with cautery wire 2906 and the anastomosis coil device 2904. The anastomosis coil device 2900 comprises an inner SMA wire 2904 with a plurality of magnets 2910 and spacers 2912 positioned coaxially thereabout. In an embodiment, the SMA wire 2904 is composed of Nitinol. The SMA wire 2904 extends distally through a lumen 2903 of the cautery tip 2902. A metal cylinder 2916 is positioned in the distal end of the lumen 2903 of the cautery tip 2902. The SMA wire 2904 further extends distally through a lumen 2905 of the metal cylinder 2916. A rivet 2914 connects the metal cylinder 2916 to the SMA wire 2904 at the distal end of the cautery tip 2902. An additional metal wire 2918 is connected to the rivet 2914 and, in various embodiments, extends along an outer surface of the cautery tip 2902. An electrical current is provided via the cautery wire 2906 and passes through the thread connector 2908, along the SMA wire 2904, and to the metal cylinder 2916 and metal wire 2918. The electrical current creates thermal energy in the metal cylinder 2916 and metal wire 2918 which is transferred to the cautery tip 2902 which, in various embodiments, is composed of ceramic or PEEK. The thermal energy heats the cautery tip 2902 which is used to puncture and cauterize tissue to create an opening for anastomosis creation. After deployment of the anastomosis coil device 2900, the pusher 2907 with cautery wire 2906 is disconnected from the SMA wire 2904.

Figure 30A:
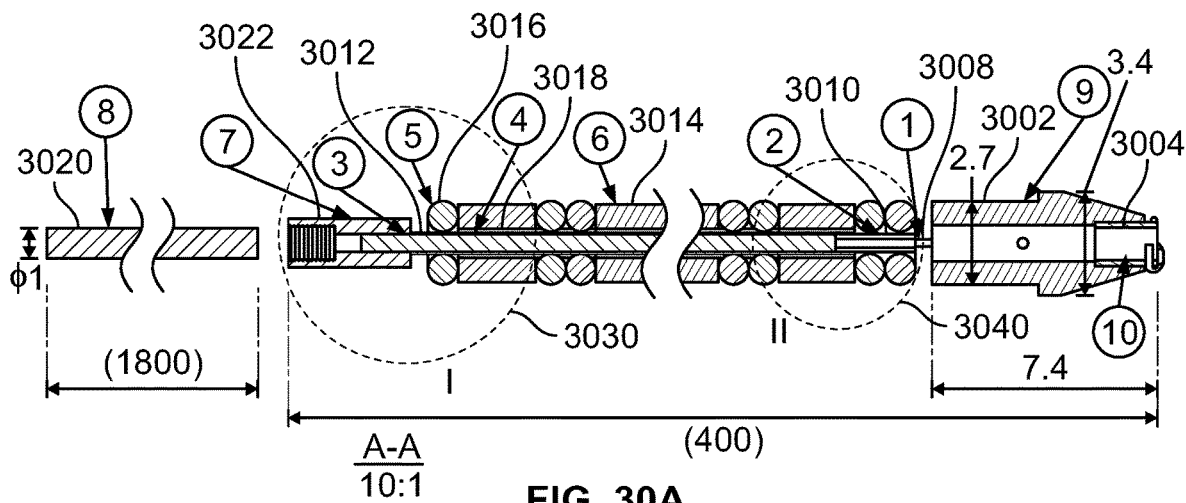
FIG. 30A illustrates a side cross sectional view of an anastomosis coil device with a distal cautery tip in a pre-deployment configuration, in accordance with an embodiment of the present specification.

FIG. 30A illustrates a side cross sectional view of an anastomosis coil device 3000 with a distal cautery tip 3002 in a pre-deployment configuration, in accordance with an embodiment of the present specification. In an embodiment, the cautery tip 3002 comprises a ceramic 'hot head' coupled with a cautery electrode 3004. The ceramic hot head design enables the catheter to puncture into the wall of an organ. In an embodiment, length of the ceramic head 3002 and the cautery electrode 3004 is approximately 7.4 mm. A stainless steel support wire 3008 and a clamping tube 3010 couple the cautery tip 3002 with a Nitinol wire 3012. A plurality of magnets 3014 and spacers 3016 are positioned coaxially about the Nitinol wire 3012. In an embodiment, the Nitinol wire 3012 is enveloped in an insulating PTFE, Teflon, or silicone sleeve 3018. The stainless steel wire 3008 couples the Nitinol wire 3012 to the cautery tip 3002 and a proximal stop 3022, attached to the proximal end of the Nitinol wire 3012, detachably couples with a steel pusher catheter 3020. Electrical current passes from the pusher catheter 3020 through the Nitinol wire 3012 and stainless steel wire 3008 and into the cautery tip 3002 and electrode 3004, heating up the cautery tip 3002 to enable electro-cautery puncture of a target tissue.

Figure 30B:
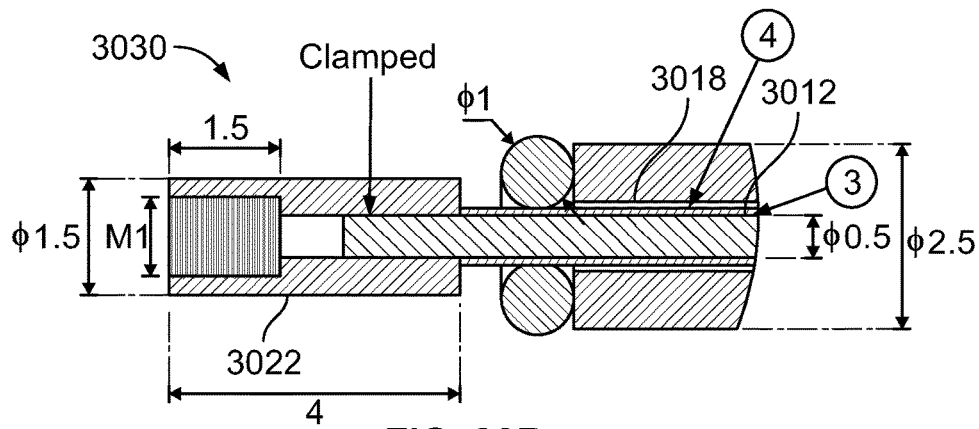
FIG. 30B illustrates a blown up view of the portion marked as 3030 in FIG. 30A.
Figure 30C:
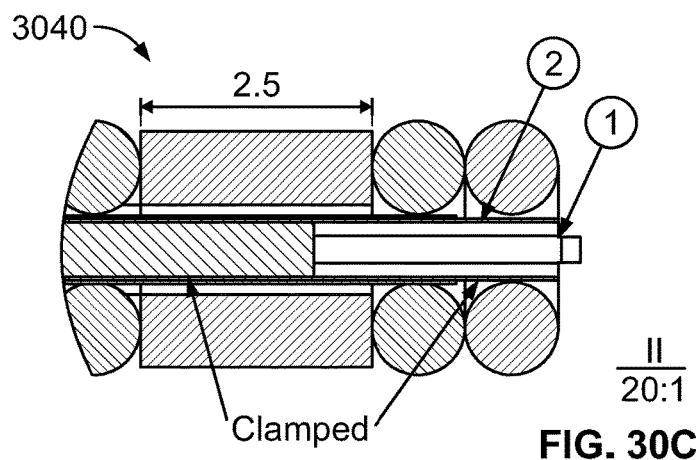
FIG. 30C illustrates a blown up view of the portion marked as 3040 in FIG. 30A.

FIG. 30B illustrates a blown up view of the portion marked as 3030 in FIG. 30A. In an embodiment, diameters of the Nitinol wire 3012 and each of the magnets 3014 are approximately 0.5 mm and 2.5 mm respectively, and a length and diameter of the proximal stop 3022 are approximately 4 mm and 1.5 mm respectively. FIG. 30C illustrates a blown up view of the portion marked as 3040 in FIG. 30A. In an embodiment, a length of each of the magnets 3014 is approximately 2.5 mm.

Figure 30D:
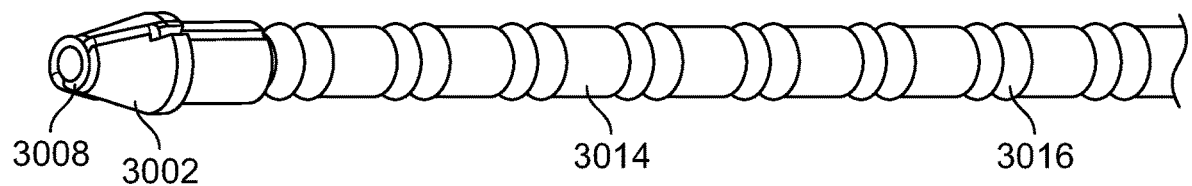
FIG. 30D illustrates another view of the cautery enabled anastomosis coil device with cautery tip shown in FIG. 30A.
Figure 30E:
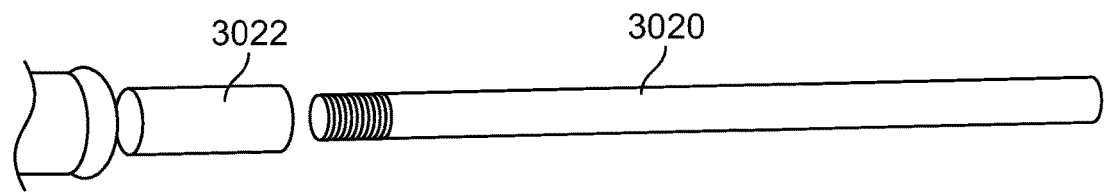
FIG. 30E illustrates a blown up view of the coupling mechanism of the proximal stop and pusher catheter of the anastomosis coil device shown in FIG. 30A.

FIG. 30D illustrates another view of the cautery enabled anastomosis coil device with cautery tip shown in FIG. 30A. The cautery tip 3002 is coupled to the Nitinol wire (not visible in the figure) covered with magnets 3014 and spacers 3016 via support wire 3008. FIG. 30E illustrates a blown up view of the coupling of the proximal stop 3022 and pusher catheter 3020 of the anastomosis coil device shown in FIG. 30A. The proximal stop 3022 is detachably coupled with the steel pusher catheter 3020 which allows electrical current to flow through the Nitinol wire all the way up to the cautery tip.

Figure 30F:
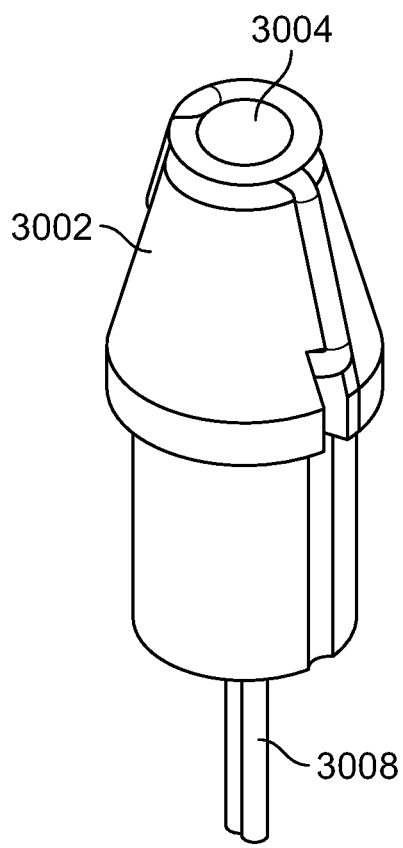
FIG. 30F illustrates a close up view of the cautery tip coupled with the cautery electrode of the anastomosis coil device shown in FIG. 30A.
Figure 30G:
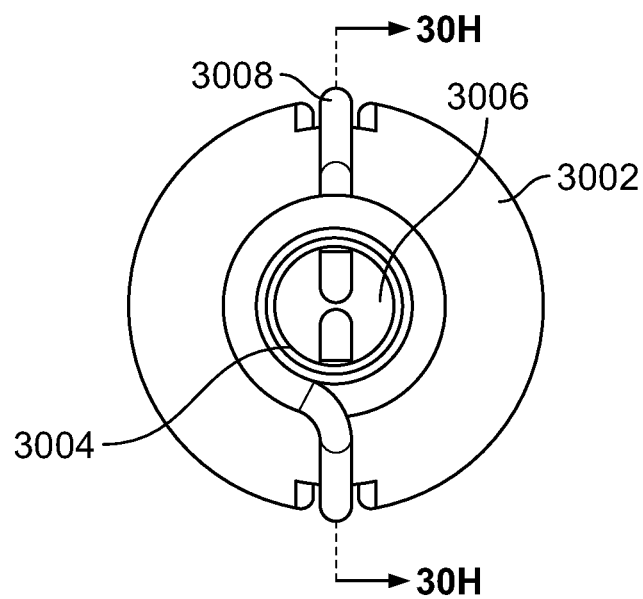
FIG. 30G illustrates a front on view of the cautery tip shown in FIG. 30F.
Figure 30H:
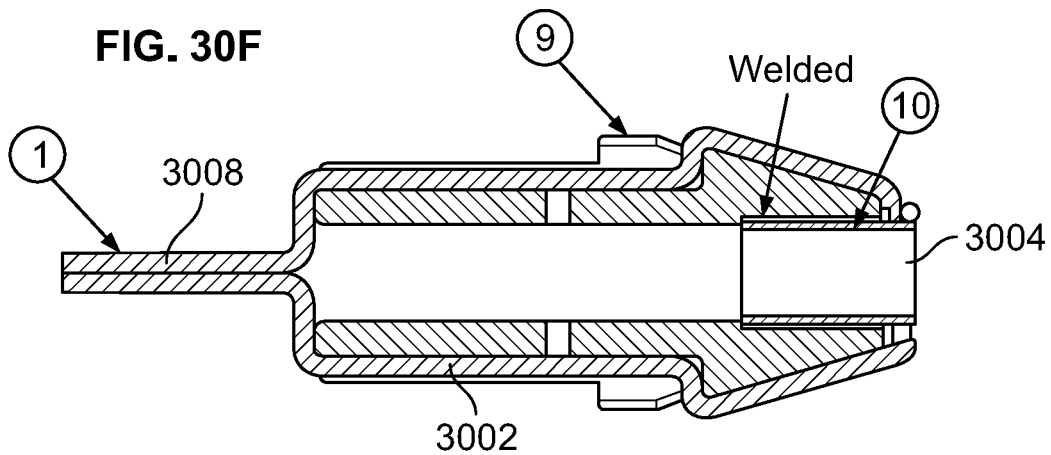
FIG. 30H illustrates a side cross sectional view of the cautery tip and cautery electrode shown in FIG. 30F.
Figure 30I:
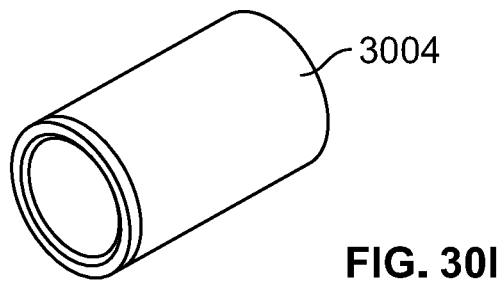
FIG. 30I illustrates the cautery electrode shown in FIG. 30F.

FIG. 30F illustrates a close up view of the cautery tip 3002 coupled with the cautery electrode 3004 of the anastomosis coil device shown in FIG. 30A. FIG. 30G illustrates a front on view of the cautery tip 3002 shown in FIG. 30F. As shown, the cautery tip 3002 has a substantially circular cross section with a circular opening 3006 in the center for accommodating the cautery electrode 3004. FIG. 30H illustrates a side cross sectional view of the cautery tip 3002 and cautery electrode 3004 shown in FIG. 30F. FIG. 30I illustrates the cautery electrode 3004 shown in FIG. 30F. As shown, the electrode 3004 is substantially cylindrical and fits into a circular opening 3006 provided at a distal end of the cautery tip 3002. In one embodiment, support wire 3008 forms a loop at a distal end of the cautery tip 3002 and assists with securing the electrode 3004 in place and with the electro-cautery puncture of an organ. An electrical current travels along wire 3008 to heat electrode 3004. Thermal energy is transferred to the cautery tip 3002 which is then used to puncture and cauterize a target tissue to create an opening for forming an anastomosis.

Figure 31A:
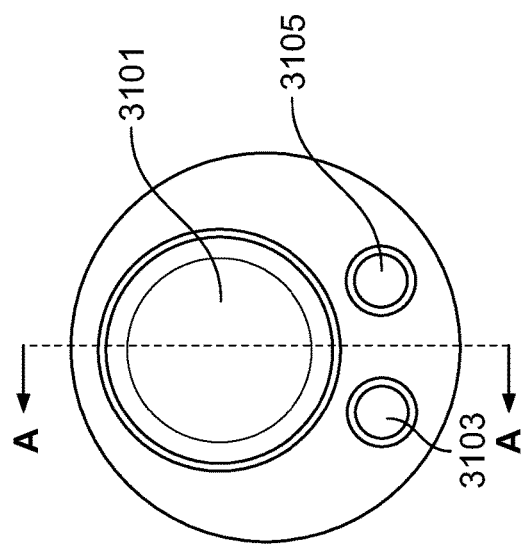
FIG. 31A illustrates a cross sectional view of a triple lumen catheter used for delivering an anastomosis coil device, in accordance with an embodiment of the present specification.
Figure 31B:
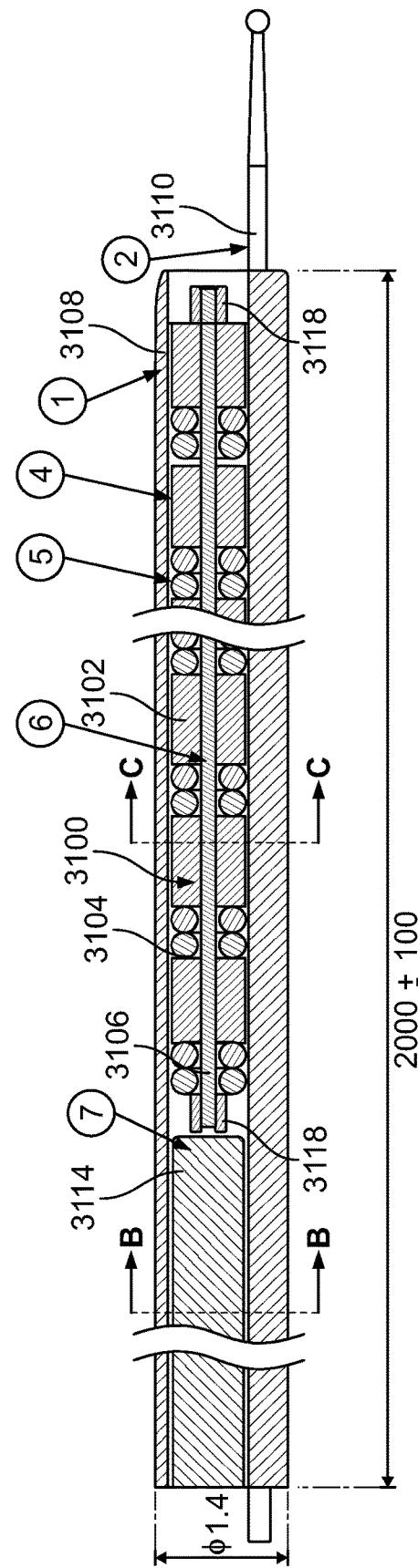
FIG. 31B illustrates a side cross sectional view of an anastomosis coil device in a pre-deployment configuration and a guide wire enveloped in a catheter for delivering the anastomosis coil device, in accordance with an embodiment of the present specification.
Figure 31C:
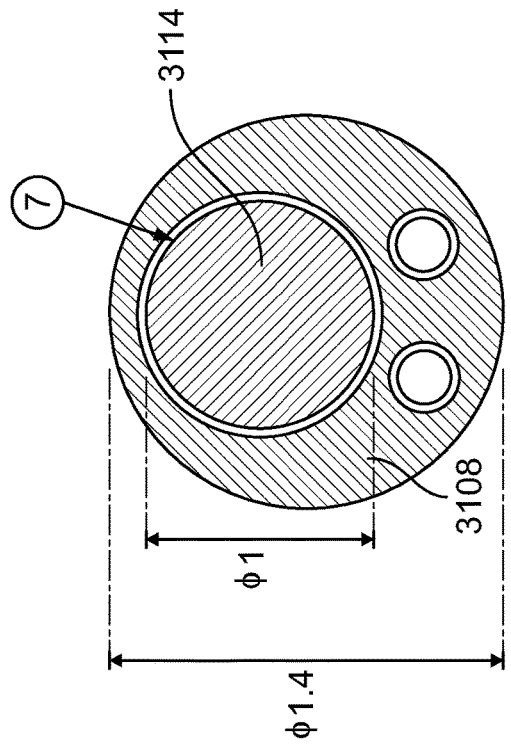
FIG. 31C illustrates a cross sectional view along the CC axis shown in FIG. 31B.
Figure 31D:
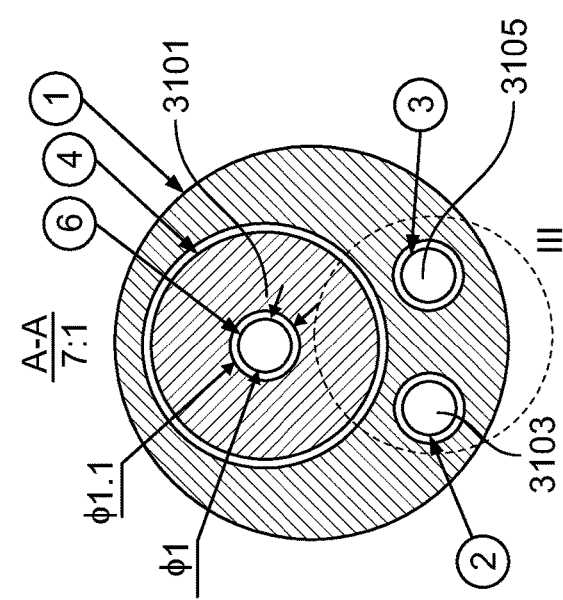
FIG. 31D illustrates a cross sectional view along the BB axis shown in FIG. 31B.
Figure 31E:
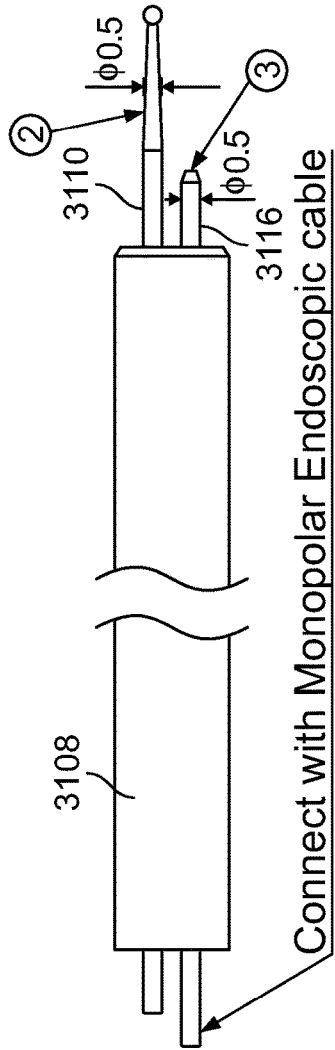
FIG. 31E illustrates another view of the catheter and a guide wire for delivering the anastomosis coil device shown in FIG. 31B.

FIG. 31A illustrates a triple lumen catheter used for delivering an anastomosis coil device, in accordance with an embodiment of the present specification. A first lumen 3101 is used for carrying the anastomosis coil device, a second lumen 3103 for carrying a guidewire and a third lumen 3105 is provided for optionally carrying a cautery wire for puncturing an organ. FIG. 31B illustrates a side cross sectional view of an anastomosis coil device 3100 in a pre-deployment configuration and a guide wire 3110 enveloped in a catheter 3108 for delivering the anastomosis coil device 3100, in accordance with an embodiment of the present specification. A plurality of magnets 3102 and spacers 3104 are positioned coaxially about a SMA wire 3106 as shown. In an embodiment, the wire 3106 is composed of Nitinol. In an embodiment, the spacers 3104 are composed of a non-ferromagnetic material. In various embodiments, the spacers 3104 comprise silicone or Nitinol tubes or O-rings or circular balls. Stop mechanisms 3118 are coupled to both ends of the wire 3106. In embodiments, the stop mechanisms 3118 are riveted or crimped to both ends of the wire 3106 after the magnets 3102 and spacers 3104 are assembled along the wire 3106. In an embodiment, a length of each of the stop mechanisms 3118 is 1 mm. A catheter 3108, similar to the triple lumen catheter depicted in FIG. 31A, delivers the anastomosis coil device 3100 through a first lumen in the catheter 3108 while a guidewire 3110 for guiding the placement of the anastomosis coil device 3100 at a desired location in a body is positioned within a second lumen of the catheter 3108. The anastomosis coil device 3100 is pushed out of catheter 3108 by a pusher tube 3114. A cautery wire (not shown in the figure) may optionally be passed through a third lumen, or keyhole (lumen 3105 in FIG. 31A) for heating a distal end of the anastomosis coil device 3100 to assist with puncturing and cauterizing a target tissue. FIG. 31C illustrates a cross sectional view along the CC axis shown in FIG. 31B. As shown, the first lumen 3101 for the anastomosis coil device, second lumen 3103 for the guidewire, and third lumen or keyhole 3105 for the cautery wire each have circular cross sections. In an embodiment, a diameter of the third lumen or keyhole 3105 is approximately 0.60 mm, a diameter of the second lumen 3103 is approximately 0.60 mm and a diameter of the first lumen 3101 is approximately 2.2 mm. FIG. 31D illustrates a cross sectional view along the BB axis shown in FIG. 31B. In an embodiment, a diameter of the pusher tube 3114 is approximately 2 mm and a diameter of catheter 3108 is approximately 3.5 mm. FIG. 31E illustrates another view of the catheter 3108 and a guide wire for delivering the anastomosis coil device shown in FIG. 31B. As shown, the catheter 3108 partially envelops the guidewire 3110 as well as a connector 3116 for connecting with a monopolar endoscopic cable, which is disposed within the third lumen or keyhole (lumen 3105 in FIG. 31C). In an embodiment, a diameter of the guidewire 3110 is approximately 0.5 mm and a diameter of the connector 3116 is approximately 0.5 mm.

FIG. 32A illustrates a cross sectional view of an anastomosis coil device 3200 in a pre-deployment configuration disposed in a delivery catheter 3208, in accordance with another embodiment of the present specification. The anastomosis coil device 3200 comprises a plurality of magnets 3202 and spacers 3204 positioned coaxially about a SMA wire 3206 as shown. In an embodiment, the wire 3206 is composed of Nitinol. In an embodiment, the spacers 3204 are composed of a non-ferromagnetic material. In various embodiments, the spacers 3204 comprise silicone or Nitinol tubes or O-rings or circular balls. A catheter 3208, in some embodiments made of PEEK or Teflon, envelops the anastomosis coil device 3200 and is coupled at a distal end with a conductor head 3210, in some embodiments made of ceramic or PEEK, for puncturing an organ by using electro-cautery action. At a proximal end, the anastomosis coil device 3200 is coupled with a pusher tube 3212 as shown. Stop mechanisms 3216 are applied to both ends of the wire 3206 preventing the magnets 3202 and spacers 3204 from sliding off the wire 3206. In embodiments, the stop mechanisms 3216 are crimped or riveted to both ends of the wire 3206 after the magnets 3202 and spacers 3204 are assembled along the stent. The rivet or crimp stop mechanism 3216 at the proximal end is detachably coupled with the pusher tube 3212 allowing for release of the anastomosis coil device 3200 from the catheter 3208. In an embodiment, a length of each of the stop mechanisms 3216 is 1.5 mm. FIG. 32B illustrates a cross sectional view along the BB axis shown in FIG. 32A. As shown, the outer catheter 3208 and the conductor head 3210 have circular cross sections and diameters of approximately 3.3 mm and 2.2 mm respectively. Further, a conductor wire 3214 runs through the length of the catheter 3208 and is positioned proximate the conductor head 3210. Electrical current supplied to the conductor wire 3214 is converted to heat energy in the conductor head 3210 which assists with electrocautery and puncturing of a target tissue by the conductor head 3210 for anastomosis formation. FIG. 32C illustrates a cross sectional view along the CC axis shown in FIG. 32A. As shown, the wire 3206 and each of the magnets 3202 have circular cross sections. In an embodiment, diameters of each of the magnets 3202 are 2 mm and a diameter of a first lumen 3201 containing the anastomosis coil device is 2.2 mm. The conductor wire 3214 is depicted extending through a second lumen 3203 in a wall of the catheter 3208. FIG. 32D illustrates a cross sectional view along the DD axis shown in FIG. 32A. As shown, the pusher tube 3212 has a circular diameter which is approximately 1.9 mm and is disposed within the first lumen 3201, in an embodiment. Also, in an embodiment, the conductor wire 3214 has a circular cross section and a diameter of approximately 0.25 mm and is disposed within the second lumen 3203 which, in an embodiment, has a diameter of 0.30 mm.

FIG. 32E illustrates a blown up view of the conductor head 3210 shown in FIG. 32A. Outer catheter 3208 partially envelops the conductor wire 3214 and conductor head 3210 as shown in FIG. 32E. In an embodiment, the conductor wire 3214 is welded with conductor head 3210. In an embodiment, the conductor head has a cylindrical portion 3220 with flanges 3222 approximately 2.5 mm long, protruding around the circular portion as shown. In an embodiment, inner and outer diameters of the conductor head 3210 are approximately 2.2 mm and 2.4 mm respectively. FIG. 32F illustrates the anastomosis coil device 3200 shown in FIG. 32A in a post-deployment configuration after being delivered within a body. As shown, after delivery, the wire 3206 coils up catching body tissue within the turns of wire and magnets 3202 for causing anastomosis. FIG. 32G illustrates a cross sectional view of the anastomosis coil device 3200 shown in FIG. 32F. In an embodiment, a diameter of the wire 3206 is 0.4 mm. The magnets 3202 are shown aligning along a like plane in the post-deployment configuration of the device 3200. FIG. 32H illustrates an O-ring being used as a spacer 3204 as shown in FIG. 32B. In an embodiment, an outer diameter of the O-ring is approximately 2.2 mm and a diameter of an inner circular opening 3209 is approximately 0.6 mm.

FIG. 33A illustrates a dual handle delivery device 3300 for delivering an anastomosis coil device 3308 provided with a cauterizing tip 3318, in accordance with an embodiment of the present specification. As shown, the dual handle delivery device 3300 comprises a first handle 3302 coupled with an outer catheter 3306. The device 3300 also includes a second handle 3310 coupled with an inner catheter 3312. The second handle 3310 includes an electrosurgical unit connector 3316 in electrical communication with the inner catheter 3312 for delivering electrical current to the cauterizing tip 3318 of the anastomosis coil device 3308. The anastomosis coil device 3308, with cauterizing tip 3318, is positioned within the inner catheter 3312. The first handle 3302 and second handle 3310 are manipulated relative to one another to deploy the anastomosis coil device 3308. FIG. 33B illustrates a blown up view of the second handle 3310 and electrosurgical connector 3316 shown in FIG. 33A.

FIG. 34A illustrates a sectional view of a dual handle delivery device 3400 for delivering an anastomosis coil device provided with a cauterizing tip 3402, in accordance with an embodiment of the present specification. Anastomosis coil device comprising a cauterizing tip portion 3402 is delivered via a distal end of the delivery device 3400, which also comprises a handle portion 3406 at a proximal end for pushing out the anastomosis coil device from the distal end of the delivery device 3400. FIG. 34B illustrates a blown up sectional view of the tip portion 3402 shown in FIG. 34A. Tip portion 3402 comprises a ceramic head 3408 enveloping a cauterizing electrode 3410. A guidewire 3412 passes through the ceramic head 3408 from its proximal end all the way through and protrudes out from the distal end of the ceramic head 3408 adjacent cauterizing electrode 3410. In an embodiment, the guidewire 3412 has a diameter of approximately 0.025 inches. Ceramic head 3408 partially covers a guidewire support 3414 enveloped within an inner tube 3416 made of PEEK material. In an embodiment, the guidewire support 3414 has a diameter of approximately 0.89 mm. In an embodiment, the guidewire 3412 is coupled with the ceramic head 3408 by using ultraviolet glue. In an embodiment, the inner tube 3416 is coupled with the guidewire support 3414 by using ultraviolet glue. FIG. 34C illustrates a cross sectional view of the tip portion 3402 shown in FIG. 34B. As shown, the ceramic head 3408, guidewire 3412, guidewire support 3414 and inner tube 3416 have a circular cross section.

In an embodiment, the cautery tip 3402 is a monopolar cautery tip to facilitate puncture of an organ such as a bowel wall. In an embodiment, a catheter carrying the anastomosis coil device is placed within a patient's bowel using a therapeutic endoscopic ultrasound (EUS). Under ultrasound guidance the cautery tip is used for transmural puncture through gastric wall into the adjacent lumen of small bowel or gallbladder. In another embodiment, a small enterotomy is performed close to the anti-mesenteric border of a loop of the patient's jejunum and the catheter carrying the anastomosis coil device is passed through the lumen across the bowel into the lumen of adjacent loop of jejunum or stomach.

FIG. 34D illustrates a blown up sectional view of the guidewire portion 3404 shown in FIG. 34A. FIG. 34E illustrates a cross sectional view of the guidewire portion 3404 shown in FIG. 34D. Referring to FIGS. 34D and 34E, the guidewire support 3414 is enveloped within an inner tube 3416, which in turn is surrounded by a double lumen tube 3418 made of a PEEK material. The guidewire 3412 is threaded through one lumen of the double lumen tube 3418, while the guidewire support 3414 passes through another lumen of the double lumen tube 3418 as shown in FIG. 34E. The double lumen tube 3418 is partially enveloped by an outer tube 3420 which in an embodiment, is made of a braided mesh material.

FIG. 34F illustrates a blown up sectional view of the handle portion 3406 shown in FIG. 34A. The handle portion 3406 comprises a conductive plug/pins 3422 and a transparent knob tail 3424. The conductive plug/pins 3422 are in electrical communication with the guidewire 3412 for delivering electrical current to the electrode 3410 of FIG. 34B.

FIG. 35 is a flowchart illustrating the steps of creating an anastomosis by using a shape memory wire and magnetic compression forces between adjacent organs or structures, in accordance with an embodiment of the present specification. At step 3502, in order to form an anastomosis between a first organ and a second organ, firstly, an endoscope is placed into the lumen of a first organ. At step 3504, an adjacent second organ is identified using endoscopy, fluoroscopy, or ultrasound imaging techniques. At step 3506, walls of the first and the second organs are punctured through by using a catheter passed through or alongside the endoscope to reach a lumen of the second organ. At step 3508, a portion of the shape memory wire comprising magnets is deployed in the lumen of the second organ and the wire transforms from a straight to a coiled shape. At step 3510, the catheter is pulled back into the lumen of the first organ and the remaining portion of the shape memory wire comprising magnets is deployed in the lumen of the first organ and the wire transforms from a straight to a coiled shape. At step 3512 the adjacent walls of the first and the second organs are compressed due to the compressive force created by the coil, the compressive force increases over time to cause compressive anastomosis.

FIG. 36 is a flowchart illustrating the steps of creating an anastomosis by using a shape memory coil with magnets between adjacent organs, in accordance with an embodiment of the present specification. At step 3602, in order to form an anastomosis between a first organ and a second organ, firstly, an endoscope is placed into the lumen of a first organ for inflating the lumen with a gas or fluid and allowing the gas or fluid to flow into the lumen of the adjacent second organ. At step 3604, an adjacent second organ is identified using endoscopy or ultrasound imaging techniques, wherein the gas or fluid assist in the identification. At 3606, walls of the first and the second organs are punctured through by using a catheter passed through or alongside the endoscope to reach a lumen of the second organ. At step 3608, a portion of the shape memory wire comprising magnets is deployed in the lumen of the second organ and the wire transforms from a straight to a coiled shape. At step 3610, the catheter is pulled back into the lumen of the first organ and the remaining portion of the shape memory wire comprising magnets is deployed in the lumen of the first organ and the wire transforms from a straight to a coiled shape. At step 3612 the adjacent walls of the first and the second organs are compressed due to the compressive force created by the coil, the compressive force increases over time to cause compressive anastomosis.

FIG. 37 is a flowchart illustrating the steps of creating an anastomosis by using a shape memory wire and magnetic compression forces between adjacent organs or structures, in accordance with an embodiment of the present specification. At step 3702, in order to form an anastomosis between a first organ and a second organ, firstly, an endoscope is placed into the lumen of a first organ. At step 3704, an adjacent second organ is identified using endoscopy or ultrasound imaging techniques. At 3706, walls of the first and the second organs are punctured through by using a catheter passed through or alongside the endoscope to reach a lumen of the second organ. At step 3708, a portion of the shape memory wire comprising magnets is deployed in the lumen of the second organ and the wire transforms from a straight to a coiled shape. At step 3710, the catheter is pulled back into the lumen of the first organ and the remaining portion of the shape memory wire comprising magnets is deployed in the lumen of the first organ and the wire transforms from a straight to a coiled shape. At step 3712 the adjacent walls of the first and the second organs are compressed due to the compressive force created by the coil, the compressive force increases over time to cause compressive anastomosis. At step 3714, once the anastomosis is formed, the shape memory coil falls off spontaneously and is eliminated naturally out of the body.

FIG. 38 is a flowchart illustrating the steps of creating an anastomosis by using a shape memory coil with magnets between adjacent organs, in accordance with an embodiment of the present specification. At step 3802, in order to form an anastomosis between a first organ and a second organ, firstly, an endoscope is placed into the lumen of a first organ for inflating the lumen with a gas or fluid and allowing the gas or fluid to flow into the lumen of the adjacent second organ. At step 3804, an adjacent second organ is identified using endoscopy or ultrasound imaging techniques, wherein the gas or fluid assist in the identification. At 3806, walls of the first and the second organs are punctured through by using a catheter passed through or alongside the endoscope to reach a lumen of the second organ. At step 3808, a portion of the shape memory wire comprising magnets is deployed in the lumen of the second organ and the wire transforms from a straight to a coiled shape. At step 3810, the catheter is pulled back into the lumen of the first organ and the remaining portion of the shape memory wire comprising magnets is deployed in the lumen of the first organ and the wire transforms from a straight to a coiled shape. At step 3812 the adjacent walls of the first and the second organs are compressed due to the compressive force created by the coil, the compressive force increases over time to cause compressive anastomosis. At step 3814, once the anastomosis is formed, the shape memory coil remains in the anastomosis, until removed out of the body by using an endoscope.

FIG. 39A illustrates an exemplary magnet 3902 used with a device for creating an anastomosis, in accordance with an embodiment of the present specification. As shown, force 3904 generated by the magnet 3902 and measured between two cylindrical outer surfaces 3902a, 3902b of the magnet 3902 is approximately 1.185 N. In various embodiments, the length, inner diameter and outer diameter of the magnet 3902 are 2.5 mm, 1.0 mm and 2.5 mm respectively. FIG. 39B illustrates an exemplary magnet 3906 used with a device for creating an anastomosis, in accordance with another embodiment of the present specification. As shown, force 3908 generated by the magnet 3906 and measured between two cylindrical outer surfaces 3906a, 3906b of the magnet 3906 is approximately 2.318 N. In various embodiments, the length, inner diameter and outer diameter of the magnet 3906 are 3 mm, 0.66 mm and 3 mm respectively. The force between the cylindrical surfaces 3906a, 3906b of the magnet 3906 is about 191% greater than the force between the cylindrical surfaces 3902a, 3902b of magnet 3902 of FIG. 39A.

As discussed above, the coil structure of the anastomosis devices of the present specification allows for the application of multiple magnetic layers (or coil loops), thereby increasing compressive force on a tissue surface, without increasing the complexity of a medical procedure. Magnetic anastomosis devices are subject to separation as a result of exposure to gastrointestinal forces. The likelihood of separation, defined by the distance between loops of a coiled device, is dependent upon the size of the magnets, number of coils or loops in the device, and the radius of the coil. Since embodiments of the anastomosis devices of the present specification include multiple coil loops on both sides of the anastomosis being formed, the coil loops are less likely to separate compared to the single loop, individual and physically separate devices of the prior art. In addition, since the embodiments of the present specification comprise a single integrated device, if, after the first magnetic element on a first coil loop attaches to a second magnetic element on a second coil loop, the two magnetic elements thereafter detach, the detachment will only be temporary and the two magnetic elements will automatically reattach over the target tissue region without requiring human intervention. In other words, the magnetic coil loops cannot travel away from one another since they are attached to a single device, and they will eventually reattach due to magnetic forces.

The following are case examples illustrating the effects of magnet size, number of coil loops, and coil radius on the distance between coil loops of deployed magnetic anastomosis devices of the present specification, and resultant likelihood of anastomosis separation (separation of two adjacent tissues). Operationally, the device, having a plurality of magnets in a fixed relation to each other, is endoscopically positioned proximate a tissue wall; the tissue wall is pierced with the device and a first set of the plurality of magnets is passed through the wall while concurrently a second set of the plurality of magnets is not passed through the tissue wall, thereby leaving some of the plurality of magnets on one side of the tissue wall and some of the plurality of magnets on the other side of the tissue wall; after the first set of the plurality of magnets form into at least one coil and the second set of the plurality of magnets form into at least one second coil, which occurs automatically and without further human intervention, one waits a period of time. When formed into coils, the first set and second set of the plurality of magnets, each of which has a diameter in a range of 1 mm to 4 mm, preferably 2 mm to 3 mm, are attracted to each other and automatically move toward each other, thereby compressing the tissue wall, which is approximately 10 to 15 mm thick, to a size of 2 mm to 8 mm thick, depending on the type of tissue being targeted.

In the case examples below, magnets having a maximum diameter up to 3 mm are used in order to accommodate endoscopic delivery. In other embodiments, anastomosis devices of the present specification have a maximum diameter of up to 7 mm. In some embodiments, the magnets are N52 magnets and each have a surface magnetic field in a range of 10,000 to 20,000 Gauss, preferably 14800 Gauss. In addition, several assumptions regarding the magnetic devices, human anatomy, and forces created by said devices and anatomy are made:

- The standard cumulative thickness of two walls to be anastomosed is assumed to be 8-10 mm.
- The ideal magnetic force for anastomosis formation is 0.1-0.3 N and the ideal pressure for anastomosis formation is 14.5-58 psi (0.1-0.4 MPa), although the disclosed range for applied pressure by the device is in a range of 1-145 psi (0.007-1 MPa).
- The average cumulative stress in a human stomach summed over a 30 minute period prior to gastric emptying is 160,000±70,000 dynes/cm$^2$ (0.016±0.007 MPa) fasted and 520,000±270,000 dynes/cm$^2$ (0.052±0.027 MPa) fed.
- The small intestine is capable of generating pressures greater than 1.93 psi (100 mm Hg; 0.013 MPa).
- The average normal stomach wall thickness is 5.1±1.1 mm, with a maximum thickness of 7 mm.
- The average normal small intestine wall thicknesses are as follows:
  - Duodenum: 1.53±0.58 mm.
  - Jejunum: 1.50±0.55 mm.
  - Ileum: 1.61±0.47 mm.
- The average normal gallbladder wall thickness is 2.6±1.6 mm, with a maximum thickness of 4 mm.
- The average gallstone thickness is 0.4±1.4 mm.
- The average gallbladder sludge thickness is 0.5±1.4 mm.
- The average wall thickness of a gallbladder with acute cholecystitis is 3.1±1.6 mm.
- The average common bile duct wall thickness is 0.8±0.4 mm.

CASE EXAMPLE 1

Devices Having One Coil Loop on Each Side of Anastomosis

FIG. 39C is a graph illustrating the relationship between compressive pressures and distances between coil loops provided by anastomosis devices having a single coil loop on each side of an anastomosis to be formed, in accordance with an embodiment of the present specification. In other words, each device represented in FIG. 39C includes a total of one pair of coil loops comprising a single coil loop on each side of an anastomosis to be formed. Curves 3910, 3911, and 3912 illustrate the relationship between pressure and distance between coil loops for devices having 1 pair of coil loops, an inner coil radius of 10 mm, and magnet widths or diameters of 2.0 mm, 2.5 mm, and 3.0 mm respectively. It is assumed that normal peristaltic motility of the gastrointestinal tract is capable of producing a maximum gastric pressure 3913 of approximately 7.25 psi (0.05 MPa) and a maximum small intestine pressure 3914 of approximately 1.88 psi (0.013 MPa). As can be seen in FIG. 39C, pressure (P) created by the anastomosis devices increases as the distance (d) between the coil loops decreases. In addition, the pressure created increases as the magnet width increases. For example, curve 3912 illustrates a pressure of approximately 7.25 psi (0.05 MPa) at a distance of approximately 0.36 cm for a device comprising magnets with a width of 3.0 mm compared to curve 3910 illustrating a pressure of approximately 3.63 psi (0.025 MPa) at the same distance for a device comprising magnets with a width of 2.0 mm.

To form a gastric anastomosis, devices comprising 2 mm or 3 mm diameter magnets will need to reach a distance of no more than 2 mm to 4 mm between loops, and hence magnets, respectively, such that gastric pressure cannot separate the loops. To form a small bowel anastomosis, devices comprising 2 mm or 3 mm magnets will need to reach a distance of no more than 6 mm to 8 mm between loops, and hence magnets, respectively, such that small intestinal pressure cannot separate the loops. Cumulative thickness of the organ walls is assumed to be greater than 10 mm.

As the distance between coil loops increases, the pressure created by the devices decreases and the risk of anastomosis separation increases. Box 3915 depicts the distances over which a gastric anastomosis formed by the devices represented in FIG. 39C is at risk for separation. Once each curve 3910, 3911, 3912 crosses below the assumed maximum gastric pressure 3913, each gastric anastomosis is at risk for separation. That is, each gastric anastomosis formed by the devices represented in FIG. 39C is at risk for separation at distances ranging from at least 0.36 cm to 1 cm as a result of exposure to gastric pressure. Box 3916 depicts the distances over which a small bowel anastomosis formed by the devices represented in FIG. 39C is at risk for separation. Once each curve 3910, 3911, 3912 crosses below the assumed maximum small intestinal pressure 3914, each small bowel anastomosis is at risk for separation. That is, each small bowel anastomosis formed by the devices represented in FIG. 39C is at risk for separation at distances ranging from at least 0.8 cm to 1 cm as a result of exposure to small intestinal pressure. Therefore, assuming the magnets are 3.0 mm in diameter and less than 3.6 mm apart, gastric peristalsis will not be sufficient to separate the magnets and/or dislodge them. Assuming the magnets are 3.0 mm in diameter and less than 8 mm apart, small bowel peristalsis will not be sufficient to separate the magnets and/or dislodge them. As noted earlier, the single device structure of the anastomosis devices of the present specification allows them to reattach automatically, and in the correct orientation, should separation occur. Since prior art devices require two separate devices for anastomosis formation, these devices are at risk for spontaneous separation, and resultant dislodgement without reattachment, at distances represented by boxes 3915 and 3916.

CASE EXAMPLE 2

Devices Having Two Coil Loops on Each Side of Anastomosis

FIG. 39D is a graph illustrating the relationship between compressive pressures and distances between coil loops provided by anastomosis devices having two coil loops on each side of an anastomosis to be formed, in accordance with an embodiment of the present specification. In other words, each device represented in FIG. 39D includes a total of two pairs of coil loops, with each pair comprising a single coil loop on each side of an anastomosis to be formed, for a total of 4 loops. Curves 3920, 3921, and 3922 illustrate the relationship between pressure and distance between coil loops for devices having 2 pairs of coil loops, an inner coil radius of 10 mm, and magnet widths or diameters of 2.0 mm, 2.5 mm, and 3.0 mm respectively. It is assumed that normal peristaltic motility of the gastrointestinal tract is capable of producing a maximum gastric pressure 3923 of approximately 7.25 psi (0.05 MPa) and a maximum small intestine pressure 3924 of approximately 1.88 psi (0.013 MPa). As can be seen in FIG. 39D, pressure (P) created by the anastomosis devices increases as the distance (d) between the coil loops decreases. In addition, the pressure created increases as the magnet width increases. For example, curve 3922 illustrates a pressure of approximately 7.25 psi (0.05 MPa) at a distance of approximately 0.55 cm for a device comprising magnets with a width of 3.0 mm compared to curve 3920 illustrating a pressure of approximately 3.63 psi (0.025 MPa) at the same distance for a device comprising magnets with a width of 2.0 mm. To form a gastric anastomosis, devices comprising 2 mm to 3 mm magnets will need to reach a distance of no more than 3.5 mm to 6 mm between loops, and hence magnets, respectively, such that gastric pressure cannot separate the loops. To form a small bowel anastomosis, devices comprising 2.5 mm to 3 mm magnets cannot be separated by small intestinal pressure, while devices comprising 2 mm magnets will need to reach a distance of no more 8 mm between loops, and hence magnets, such that small intestinal pressure cannot separate the loops. Cumulative thickness of the organ walls is assumed to be greater than 10 mm.

As the distance between coil loops increases, the pressure created by the devices decreases and the risk of anastomosis separation increases. Box 3925 depicts the distances over which a gastric anastomosis formed by the devices represented in FIG. 39D is at risk for separation. Once each curve 3920, 3921, 3922 crosses below the assumed maximum gastric pressure 3923, each gastric anastomosis is at risk for separation. That is, each gastric anastomosis formed by the devices represented in FIG. 39D is at risk for separation at distances ranging from at least 0.54 cm to 1 cm as a result of exposure to gastric pressure. Box 3926 depicts the distances over which a small bowel anastomosis formed by the devices represented in FIG. 39D is at risk for separation. Curves 3921 and 3922, representing devices having magnets with diameters of 2.5 mm and 3 mm respectively, do not cross under the assumed maximum small intestine pressure 3924 and, as such, these devices are not subject to separation. Once curve 3920 crosses below the assumed maximum small intestinal pressure 3914, the small bowel anastomosis formed by the device having magnets with a diameter of 2.0 mm is at risk for separation. That is, the small bowel anastomosis formed by the device having magnets with a diameter of 2.0 mm is at risk for separation at distances ranging from 0.8 cm to 1 cm as a result of exposure to small intestinal pressure. Therefore, assuming the magnets are 3.0 mm in diameter and less than 5.4 mm apart, gastric peristalsis will not be sufficient to separate the magnets and/or dislodge them. Assuming the magnets are 3.0 mm in diameter, no amount of normal small bowel peristalsis will be sufficient to separate the magnets and/or dislodge them. Therefore, increasing the coil pairs from 1 to 2 lowers the risk of anastomosis separation at greater distances for all the devices represented in FIG. 39D. As noted earlier, the single device structure of the anastomosis devices of the present specification allows them to reattach automatically, and in the correct orientation, should separation occur. Since prior art devices require two separate devices for anastomosis formation, these devices are at risk for spontaneous separation, and resultant dislodgement without reattachment, at distances represented by boxes 3925 and 3926.

CASE EXAMPLE 3

Devices Having Three Coil Loops on Each Side of Anastomosis

FIG. 39E is a graph illustrating the relationship between compressive pressures and distances between coil loops provided by anastomosis devices having three coil loops on each side of an anastomosis to be formed, in accordance with an embodiment of the present specification. In other words, each device represented in FIG. 39E includes a total of three pairs of coil loops, with each pair comprising a single coil loop on each side of an anastomosis to be formed, for a total of 6 loops. Curves 3930, 3931, and 3932 illustrate the relationship between pressure and distance between coil loops for devices having 3 pairs of coil loops, an inner coil radius of 10 mm, and magnet widths or diameters of 2.0 mm, 2.5 mm, and 3.0 mm respectively. It is assumed that normal peristaltic motility of the gastrointestinal tract is capable of producing a maximum gastric pressure 3933 of approximately 7.25 psi (0.05 MPa) and a maximum small intestine pressure 3934 of approximately 1.88 psi (0.013 MPa). As can be seen in FIG. 39E, pressure (P) created by the anastomosis devices increases as the distance (d) between the coil loops decreases. In addition, the pressure created increases as the magnet width increases. For example, curve 3932 illustrates a pressure of approximately 7.25 psi (0.05 MPa) at a distance of approximately 0.65 cm for a device comprising magnets with a width of 3.0 mm compared to curve 3930 illustrating a pressure of approximately 3.63 psi (0.025 MPa) at the same distance for a device comprising magnets with a width of 2.0 mm. To form a gastric anastomosis, devices comprising 2 mm to 3 mm magnets will need to reach a distance of no more than 4 mm to 7 mm between loops, and hence magnets, respectively, such that gastric pressure cannot separate the loops. Additional force from the coil and self-aligning feature may further prevent the coils from separating. All devices represented in FIG. 39E, comprising 2.0 mm, 2.5 mm, and 3 mm diameter magnets, cannot be separated by small intestinal pressure. Cumulative thickness of the organ walls is assumed to be greater than 10 mm.

As the distance between coil loops increases, the pressure created by the devices decreases and the risk of anastomosis separation increases. Box 3935 depicts the distances over which a gastric anastomosis formed by the devices represented in FIG. 39E is at risk for separation. Once each curve 3930, 3931, 3932 crosses below the assumed maximum gastric pressure 3933, each gastric anastomosis is at risk for separation. That is, each gastric anastomosis formed by the devices represented in FIG. 39E is at risk for separation at distances ranging from at least 0.65 cm to 1 cm as a result of exposure to gastric pressure. No devices are at risk for separation due to small intestinal pressure. Therefore, assuming the magnets are 3.0 mm in diameter and less than 6.5 mm apart, gastric peristalsis will not be sufficient to separate the magnets and/or dislodge them. Assuming the magnets are 3.0 mm in diameter, no amount of normal small bowel peristalsis will be sufficient to separate the magnets and/or dislodge them. Therefore, increasing the coil pairs from 1 to 3 further lowers the risk of anastomosis separation at greater distances for all the devices represented in FIG. 39E. As noted earlier, the single device structure of the anastomosis devices of the present specification allows them to reattach automatically, and in the correct orientation, should separation occur. Since prior art devices require two separate devices for anastomosis formation, these devices are at risk for spontaneous separation, and resultant dislodgement without reattachment, at distances represented by boxes 3935.

CASE EXAMPLE 4

Devices Having 2.0 mm Diameter Magnets and Varying Numbers of Coil Loops on Each Side of Anastomosis FIGS. 39F and 39G are graphs illustrating the relationship between compressive pressures and distances between coil loops and between force and distances between coil loops respectively, provided by anastomosis devices having 2.0 mm diameter magnets and varying numbers of coil loops on each side of an anastomosis to be formed, in accordance with embodiments of the present specification. As can be seen in FIGS. 39F and 39G, both pressure (P) and force (F) increase as the distance (d) between the coil loops decreases. Curves 3940 and 3950 represent devices having magnets with a width or diameter of 2.0, an inner coil radius of 10 mm, and one pair of coil loops (1 coil on each side of anastomosis to be formed). Curves 3941 and 3951 represent devices having magnets with a width or diameter of 2.0, an inner coil radius of 10 mm, and two pairs of coil loops (2 coils on each side of anastomosis to be formed). Curves 3942 and 3952 represent devices having magnets with a width or diameter of 2.0, an inner coil radius of 10 mm, and three pairs of coil loops (3 coils on each side of anastomosis to be formed). Curves 3943 and 3953 represent devices having magnets with a width or diameter of 2.0, an inner coil radius of 10 mm, and four pairs of coil loops (4 coils on each side of anastomosis to be formed). Increasing the number of coil loop pairs increases the pressure and force generated by the devices at the same distance. For example, a device having 4 coil loop pairs represented by curves 3943, 3953 generates a pressure of approximately 11.6 psi (0.08 MPa) and a force of approximately 16 N at a distance of approximately 0.6 cm between coil loops, while a device having only one pair of coil loop pairs represented by curves 3940, 3950 generates a pressure of approximately 2.9 psi (0.02 MPa) and a force of approximately 4 N at the same distance. Referring to FIG. 39F, spontaneous separation of a gastric anastomosis formed by all the devices represented in FIG. 39F can occur at distances ranging from 0.8 to 1.0 cm between coil loops, as depicted by box 3946, once the pressure generated by the devices drops below the assumed maximum gastric pressure 3944. Only the device having 1 pair of coil loops is susceptible to small bowel anastomosis separation, as depicted by curve 3940 dropping below the assumed maximum small intestinal pressure 3945. Therefore, assuming a 4 pair coil device includes magnets that are 2.0 mm in diameter and less than 8 mm apart, gastric peristalsis will not be sufficient to separate the magnets and/or dislodge them. Assuming a 4 pair coil device includes magnets that are 2.0 mm in diameter, no amount of normal small bowel peristalsis will be sufficient to separate the magnets and/or dislodge them.

CASE EXAMPLE 5

Devices Having 2.5 mm Diameter Magnets and Varying Numbers of Coil Loops on Each Side of Anastomosis FIGS. 39H and 39I are graphs illustrating the relationship between compressive pressures and distances between coil loops and between force and distances between coil loops respectively, provided by anastomosis devices having 2.5 mm diameter magnets and varying numbers of coil loops on each side of an anastomosis to be formed, in accordance with embodiments of the present specification. As can be seen in FIGS. 39H and 39I, both pressure (P) and force (F) increase as the distance (d) between the coil loops decreases. Curves 3960 and 3970 represent devices having magnets with a width or diameter of 2.5, an inner coil radius of 10 mm, and one pair of coil loops (1 coil on each side of anastomosis to be formed). Curves 3961 and 3971 represent devices having magnets with a width or diameter of 2.5, an inner coil radius of 10 mm, and two pairs of coil loops (2 coils on each side of anastomosis to be formed). Curves 3962 and 3972 represent devices having magnets with a width or diameter of 2.5, an inner coil radius of 10 mm, and three pairs of coil loops (3 coils on each side of anastomosis to be formed). Curves 3963 and 3973 represent devices having magnets with a width or diameter of 2.5, an inner coil radius of 10 mm, and four pairs of coil loops (4 coils on each side of anastomosis to be formed). Increasing the number of coil loop pairs increases the pressure and force generated by the devices at the same distance. For example, a device having 4 coil loop pairs represented by curves 3963, 3973 generates a pressure of approximately 11.6 psi (0.08 MPa) and a force of approximately 16 N at a distance of approximately 0.6 cm between coil loops, while a device having only one pair of coil loop pairs represented by curves 3960, 3970 generates a pressure of approximately 2.9 psi (0.02 MPa) and a force of approximately 4 N at the same distance. Referring to FIG. 39H, spontaneous separation of a gastric anastomosis formed by all the devices represented in FIG. 39H can occur at distances ranging from 0.8 to 1.0 cm between coil loops, as depicted by box 3966, once the pressure generated by the devices drops below the assumed maximum gastric pressure 3964. Only the device having 1 pair of coil loops is susceptible to small bowel anastomosis separation, as depicted by curve 3960 dropping below the assumed maximum small intestinal pressure 3965. Therefore, assuming a 4 pair coil device includes magnets that are 2.5 mm in diameter and less than 8 mm apart, gastric peristalsis will not be sufficient to separate the magnets and/or dislodge them. Assuming a 4 pair coil device includes magnets that are 2.5 mm in diameter, no amount of normal small bowel peristalsis will be sufficient to separate the magnets and/or dislodge them.

CASE EXAMPLE 6

Devices Having 3.0 mm Diameter Magnets and Varying Numbers of Coil Loops on Each Side of Anastomosis FIGS. 39K and 39J are graphs illustrating the relationship between compressive pressures and distances between coil loops and between force and distances between coil loops respectively, provided by anastomosis devices having 3.0 mm diameter magnets and varying numbers of coil loops on each side of an anastomosis to be formed, in accordance with embodiments of the present specification. As can be seen in FIGS. 39K and 39J, both pressure (P) and force (F) increase as the distance (d) between the coil loops decreases. Curves 3980 and 3990 represent devices having magnets with a width or diameter of 3.0, an inner coil radius of 10 mm, and one pair of coil loops (1 coil on each side of anastomosis to be formed). Curves 3981 and 3991 represent devices having magnets with a width or diameter of 3.0, an inner coil radius of 10 mm, and two pairs of coil loops (2 coils on each side of anastomosis to be formed). Curves 3982 and 3992 represent devices having magnets with a width or diameter of 3.0, an inner coil radius of 10 mm, and three pairs of coil loops (3 coils on each side of anastomosis to be formed). Curves 3983 and 3993 represent devices having magnets with a width or diameter of 3.0, an inner coil radius of 10 mm, and four pairs of coil loops (4 coils on each side of anastomosis to be formed). Increasing the number of coil loop pairs increases the pressure and force generated by the devices at the same distance. For example, a device having 4 coil loop pairs represented by curves 3983, 3993 generates a pressure of approximately 11.6 psi (0.08 MPa) and a force of approximately 16 N at a distance of approximately 0.6 cm between coil loops, while a device having only one pair of coil loop pairs represented by curves 3980, 3990 generates a pressure of approximately 2.9 psi (0.02 MPa) and a force of approximately 4 N at the same distance. Referring to FIG. 39K, spontaneous separation of a gastric anastomosis formed by all the devices represented in FIG. 39K can occur at distances ranging from 0.84 to 1.0 cm between coil loops, as depicted by box 3986, once the pressure generated by the devices drops below the assumed maximum gastric pressure 3984. No devices are susceptible to small bowel anastomosis separation, as no curve drops below the assumed maximum small intestinal pressure 3985. Therefore, assuming a 4 pair coil device includes magnets that are 3.0 mm in diameter and less than 8.4 mm apart, gastric peristalsis will not be sufficient to separate the magnets and/or dislodge them. Assuming a 4 pair coil device includes magnets that are 3.0 mm in diameter, no amount of normal small bowel peristalsis will be sufficient to separate the magnets and/or dislodge them.

FIG. 40A illustrates an exemplary device 4000 for creating an anastomosis in a pre-coiled configuration, in accordance with an embodiment of the present specification. The device 4000 comprises a shape memory alloy (SMA) wire 4002 with a plurality of magnets 4004 and spacers 4006 positioned alternately and coaxially about the wire 4002. In an embodiment, the wire 4002 is composed of Nitinol. In an embodiment, the spacers 4006 are composed of a non-ferromagnetic material. In various embodiments, the spacers 4006 comprise silicone or Nitinol tubes or O-rings or circular balls. In an embodiment, as shown, a length of the device 4000 for creating an anastomosis, while in a pre-coiled configuration, is in a range of 440 to 460 mm. In an embodiment, a proximal end 4000p of the device 4000 includes a device connector 4008 for attaching the device 4000 for creating an anastomosis to a delivery device. In an embodiment, the device connector 4001 is a thread nut and the device 4000 connects to a delivery device via a screw mechanism.

FIGS. 40B and 40C illustrate the device 4000 for creating an anastomosis of FIG. 40A in a coiled configuration. Referring to FIGS. 40A, 40B and 40C, after deployment, and when exposed to body temperature, the SMA wire 4002 coils to move the device 4000 from the uncoiled configuration shown in FIG. 40A to the coiled configuration depicted in FIGS. 40B and 40C. The spacers 4006 ensure that the magnets 4004 do not clump together on the device 4000. In an embodiment, the device 4000 is provided with a connector 4008 at the proximal end of the wire 4002 for connecting with a delivery device. In an embodiment, a length of the anastomosis device 4000 in a coiled state is in a range of approximately 22 to 23 mm.

FIG. 40D illustrates a delivery device 4010 for delivering the anastomosis device 4000 shown in FIGS. 40A, 40B, and 40C in a desired location within a body, in accordance with an embodiment of the present specification. The delivery device 4010 includes a handle 4016 comprising a first proximal portion 4017 and a second distal portion 4019 having a port 4012, a body 4014 comprising an outer tubular sheath 4013 positioned coaxially about an inner shaft 4015, and a distal tip 4018, and is used to deliver the SMA anastomosis coil 4000 into a human body by means of an endoscope (not shown). The first proximal portion 4017 of the handle 4016 is movable relative to the second distal portion 4019 which moves the inner shaft 4015 in and out of the outer tubular sheath 4015 at the distal end of the delivery device body 4014. During delivery, a warm liquid may be introduced via port 4012 which, when contacting the shape memory alloy of the anastomosis device 4000, assists in changing the anastomosis device 4000 from its linear pre-deployment configuration to its coiled post-deployment configuration. FIGS. 40E, 40F and 40G illustrate the delivery device 4010 shown in FIG. 40D connected to the coiled anastomosis device 4000 shown in FIGS. 40B and 40C, in accordance with an embodiment of the present specification. In some embodiments, the distal tip 4018 of the inner shaft 4015 is provided with a delivery connector 4020 for connecting with the anastomosis device 4000 by means of the device connector 4008. In an embodiment, the delivery connector 4020 comprises a screw mandrel, the device connector 4008 comprises a thread nut, and together the delivery connector 4020 and device connector 4008 comprise a screw mechanism for connecting the delivery device 4010 to the device 4000 for creating an anastomosis. In an embodiment, prior to deployment, the anastomosis device 4000, in a linear configuration as depicted in FIG. 40A, is positioned within the outer tubular sheath 4013 of the delivery device body 4014, which helps restrain the anastomosis device 4000 and prevent it from coiling before being delivered to the desired location within a patient's body. The body 4014 is long and tubular and is inserted into a human body via a channel of an endoscope such that the distal tip 4018 connected to the anastomosis device 4000 (in a non-coiled shape) protrudes out of a distal end of the endoscope. Referring to FIGS. 40D, 40E, 40F and 40G, once the delivery device 4010 is positioned at the desired location within a human body, the handle 4016 is actuated to extrude the anastomosis device 4000 out of the outer sheath 4013 and disengage the delivery connector 4020 from the device connector 4008, allowing the anastomosis device 4000 to be deployed and change to its coiled configuration.

FIG. 40H is a flowchart listing the steps involved in a method of deploying an anastomosis device using a delivery device in accordance with one embodiment of the present specification. At step 4021, an endoscope is inserted into a patient's body with a distal end of the endoscope positioned proximate a desired anastomosis creation location. At step 4022, an anastomosis device with a device connector at its proximal end, and in a linear, pre-deployment configuration, is connected to a delivery device via a delivery connector at a distal end of the delivery device and retracted, using the delivery device handle, into a tubular sheath of the delivery device. The distal end of the delivery device, with anastomosis device attached, is inserted into an instrument channel of the endoscope at step 4023. Then, at step 4024, the user manipulates a handle of delivery device to advance the delivery device beyond said distal end of the endoscope and extend the anastomosis device out of said tubular sheath, positioning the anastomosis device proximate the desired anastomosis creation location. Optionally, at step 4025, the user injects warm fluid through a port on the delivery device handle or provides electrical current to the device to heat the device to assist with transformation of the anastomosis device from a linear, pre-deployment configuration to a coiled, post-deployment configuration. At step 4026, the user actuates the handle to disengage the delivery connector from the device connector, allowing the anastomosis device to separate from the delivery device, coil into its post-deployment configuration, and create an anastomosis. The delivery device and endoscope are removed from the patient at step 4027.

Referring to FIG. 41, in another embodiment, a SMA wire 4100 is coupled with magnets 4108, 4108*a*, 4108*b*, 4108*c*, 4108*d* prior to deployment in a body for creating an anastomosis, in accordance with an embodiment of the present specification. Prior to deployment, SMA wire 4100 is relatively straight and divided into at least three sections 4102, 4104 and 4106. Sections 4102 and 4106 are coupled with a plurality of magnets 4108, 4108*a*, 4108*b*, 4108*c*, 4108*d* such that positions of first magnets 4108*a*, 4108*c* and last magnets 4108*b*, 4108*d* of sections 4102 and 4104 respectively, are fixed and immovable. In one embodiment, elements 4108*a*, 4108*b*, 4108*c* and 4108*d* are nonmagnetic fixed elements. Remaining magnets 4108 of each section may be fixed or may be movable/slidable in the space between the first and last magnets of each section. As shown, no magnets are provided on section 4104. Over section 4104 are a plurality of washers or rings or other space occupying elements 4152 made of biocompatible material, such as PTFE, wherein the rings 4152 comprise lumens through which the central wire 4190 passes. In another embodiment, section 4104 may have magnets, as provided in sections 4102 and 4106, and the rings 4152 may be placed between the magnets.

Referring to FIG. 42, in another embodiment, a SMA wire 4200 is coupled with magnets 4208, 4208*a*, 4208*b*, 4208*c*, 4208*d* prior to deployment in a body for creating an anastomosis, in accordance with an embodiment of the present specification. Prior to deployment, SMA wire 4200 is relatively straight and divided into at least three sections 4202, 4204 and 4206. Sections 4202 and 4206 are coupled with a plurality of magnets 4208, 4208*a*, 4208*b*, 4208*c*, 4208*d* such that positions of first magnets 4208*a*, 4208*c* and last magnets 4208*b*, 4208*d* of sections 4202 and 4204 respectively, are fixed and immovable. Remaining magnets 4208 of each section may be fixed or may be movable/slidable in the space between the first and last magnets of each section. As shown, no magnets are provided on section 4204. Over section 4204 is a mechanism 4253 to provide immediate drainage between two segments to be anastomosed. In one embodiment, mechanism 4253 is a stent comprising a wire mesh and a membrane of biocompatible material covering the wire mesh. The mechanism or stent 4253 is compressible and expandable, where, when expanded, the stent 4253 is a cylinder with a length and a constant radius over a portion of the length. Alternatively, the stent 4253 could be shaped like a barbell with a central cylindrical portion having a first radius and end cylindrical portions having a second radius, where the second radius is greater than the first radius. Alternatively, the stent 4253 is a cylinder with a length and a non-constant radius over the length. In each embodiment, the stent 4253 is positioned over the central wire 4290 which passes through a length of the stent 4253, is secured to the central wire 4290 or one or more magnets via a suture 4254 and expands from a compressed state pre-deployment to an expanded state post-deployment. In other embodiments, other securing mechanisms known in the art, such as crimping, gluing, or welding, are used to secure the mechanism 4253 over the central wire 4290.

FIG. 43A illustrates an image of a coiled device 4300 with a distal end (ceramic tip) 4302 bent inward to prevent a sharp edge or end, in accordance with one embodiment of the present specification. A proximal end (screw end) (not shown) may also be bent inward. In some embodiments, the ends are bent inward in a range of 0 to 180 degrees relative to a circular shape defined by the coils of the device, creating an atraumatic u-shape. This prevents the end from sticking out tangentially relative to the circular shape of the coil loops, eliminating rough or sharp edges. A distal end 4302 may, in some cases, point out away from coil of the device 4300, which is undesirable as it presents a sharp edge which could damage tissue inadvertently. Therefore, distal end 4302 may also be bent inwards. Referring to the figure, a first arrow 4304 represents a direction the distal end would extend in the absence of an inward bend. A second arrow 4303 indicates the location where an inward bend is introduced at the distal end. A third arrow 4306, pointing substantially horizontally, represents direction of the new positioning of distal end 4302, which, in some embodiments, is approximately 0-180 degrees, and more preferably, 15-20 degrees inward relative to the coil shape to eliminate potential distress due to the sharp end. In some embodiments, electro polishing is used during manufacture of coil 4300 to reduce sharp edges from laser cutting. Additionally, both coil 4300 and magnets have smooth/round edges. Sharp edges are avoided and/or eliminated through design. In embodiments, maximum magnet volume is accommodated within the space available in a delivery device. Pressure is created by virtue of the strength of the magnet, which causes a necrosis of the tissue that results in cleave. A sharp edge is also undesirable as it might force an anastomosis too soon versus the "natural" pressure occurrence. An ideal anastomosis is formed between Day 1 and Week 2. In some embodiments, a bevel is added to create a small, more rounded edge. In some embodiments, polishing is used to eliminate rough or sharp edges.

FIG. 43B illustrates a side view to scale of a coiled device 4310 with the distal end bent inward, in accordance with one embodiment of the present specification. FIG. 43C illustrates a rear view to scale of the coiled device 4310 of FIG. 43B with the distal end bent inward, in accordance with one embodiment of the present specification. In embodiments, a total length of coiled device 4310 is less than 650 mm, and a diameter of the cylinder formed by coiled device 4310 is up to 50 mm.

FIG. 43D illustrates a coil device 4320, in accordance with an alternative embodiment of the present specification. Coil device 4320 includes eight coil loops (four for each side of the anastomosis) that are formed during deployment. Coil device 4320 is similar to the coil devices described in the previous embodiments, but includes magnets that are relatively smaller compared to the magnets in coil devices of the previous embodiments. In an embodiment, the magnets of coil device 4320 have a diameter of 2.5 mm. In embodiments, a distal 1 cm of the coil of coil device 4320 is scored around an inner (inside) circumference of the coil to improve bending over an EUS elevator. Alternatively, in some embodiments, 1 cm spring tip coil is welded at the distal portion of the coil. In embodiments, the ends of the coil are bent inwards by 15-20 degrees during shape-setting to avoid sharp edges or to pre-set a bend to aid with puncture.

In one embodiment, a 30 degree bend is created at the ceramic tip, which includes 10 degrees from the EUS elevator and 20 degrees from the bend. In embodiments, outer diameter of magnets of various coil device ranges from 2 mm to 5 mm and a volume of 2 mm$^3$ to 400 mm$^3$. In embodiments, a coil length determines size of an anastomosis. In one example, a 2 cm diameter of coil creates approximately a 2 cm diameter hole for anastomosis. In alternative embodiments, less than eight loops of coil are configured.

FIGS. 44A, 44B, 44C, 44D, 44E, and 44F illustrate a double coil device 4400 with a PTFE wire with an optional electrical wire 4406 mechanically and/or electrically connecting two coils 4402 and 4404, in accordance with an embodiment of the present specification. In embodiments, the electrical wire 4406 provides electrical contact to a cautery tip 4403 at the distal end of the device 4400, which heats upon delivery of an electrical current to provide thermal energy to pierce a body tissue. The electrical wire 4406 also serves to mechanically connect the two coils 4402, 4404 of the device 4400. In embodiments, coil 4402 comprises distal coil stent loops. The figure illustrates two coil loops for coil 4402. Similarly, coil 4404 comprises proximal coil stent loops. The figure illustrates two coil loops for coil 4404. FIG. 44A illustrates a side horizontal view of coil device 4400, FIG. 44B illustrates a front view of coil device 4400 with distal coil 4402 facing forward and proximal coil 4404 facing back, FIG. 44C illustrates a cross-sectional view of coil device 4400, FIG. 44D illustrates a close-up view of the cross-section of proximal coil 4406, FIG. 44E illustrates a side vertical view of coil device 4400, and FIG. 44F illustrates a perspective view of FIG. 44E. Embodiments of coil device 4400 comprise a wire 4406 connecting distal coil 4402 and proximal coil 4404, configured to bring a puncture site in the middle of the coil loops of the two coils 4402 and 4404. In some embodiments, wire 4406 is a spring wire. Therefore, wire 4406 eliminates the chance of a leak at the puncture site.

In one embodiment of the present implementation, the two coil segments 4402 and 4404 are configured with magnets 4408 having opposing directionality, with one of the two coils having a clockwise direction and the other having an counterclockwise direction. The opposite directionalities of the two coils may ensure that proper deployment of the proximal coil 4404 is achieved during deployment without restriction due to torque which may otherwise build as distal coil 4402 is fixed in a distal organ and does not rotate freely. Additionally, the opposite directionality of the coil segments counters the strain in the opposite coil segment, minimizing the strain transmitted to the catheter in its pre-deployment position, resulting in twisting of a delivery catheter housing the coil. In alternative embodiments, this may be achieved with a flexible connection with a delivery catheter which allows for the coil to freely rotate as it is being deployed, hence releasing any built-up torsion in the coil and allowing the coil to deploy properly. In another embodiment, a counter rotation of the proximal half of the coil relative to a direction of torque generated during deployment allows for torsional energy to be relieved through an inner pusher of a handle of a delivery device. In another embodiment, unscrewing a release mechanism as the coil is being deployed relieves the torque in the coil. In this embodiment, a direction of the pitch of the screw is such that unscrewing the coil from the screw results in a relief of the torsion force.

FIG. 45 illustrates a scissor cutting action of a deployed coil device 4500, in accordance with an embodiment of the present specification. A scissor compression and cutting action is implemented post deployment of coil device 4500 comprising a distal coil segment 4504 and a proximal coil segment 4502, when at least two forces of attraction F1 4506 and F2 4508 are exerted between magnets of coils 4502 and 4504. Force 4506 and 4508 are the forces of attraction at different points of the circumference of loops of coil segments 4502 and 4504 that are adjacent to each other. Force 4506 is greater than force 4508. In some embodiments, adjacent loops of the two coils 4502 and 4504 have different circumferences. In embodiments, different circumferences are achieved by varying thickness of magnets in one loop of proximal coil 4504 compared to the other adjacent loop from distal coil 4502.

FIG. 46A is a diagrammatic representation of a device for creating an anastomosis comprising a bridging element, in accordance with an embodiment of the present specification. The device 4600 comprises two loops 4602, 4604 of an SMA wire with a bridging segment 4606 connecting the two loops. In various embodiments, loops 4602 and 4604 are coiled in opposing directions for reducing the torque experienced by the SMA wire when the straight wire changes shape to form loops 4602, 4604 after deployment. The reduction in torque causes the SMA wire to coil in a desired manner, as explained with reference to the embodiments of the anastomosis device described above. In embodiments, the overlap between the ends of the two loop segments 4602, 4604 ranges from 5% to 100% of the circumference of said loops. In an embodiment, the overlap between the ends of the two loop segments 4602, 4604 is 25 mm as shown in FIG. 46A. In various embodiments, the bridging element 4606 is made of the same SMA material as the loops 4602, 4604. In an embodiment the bridging element 4606 is made of a material different from the SMA material of the loops 4602, 4604.

FIG. 46B is a diagrammatic representation of another device for creating anastomosis comprising a bridging element, in accordance with another embodiment of the present specification. Anastomosis device 4610 comprises two loops 4612, 4614 of an SMA wire with an S' shaped bridging segment 4616 connecting the two loops. In various embodiments, loops 4612 and 4614 are coiled in opposing directions for reducing the torque experienced by the SMA wire when the straight wire changes shape to form loops 4612, 4614 after deployment. The bridging segment 4616 of device 4600 is shaped in a curve as compared to the straight bridging segment 4606 shown in FIG. 46A. The curved shape enables the SMA wire to coil easily in a desired manner upon deployment. In embodiments, the overlap between the ends of the two loop segments 4612, 4614 ranges from 5% to 100% of the circumference of said loops. In an embodiment, the overlap between the ends of the two loop segments 4612, 4614 is 25 mm as shown in FIG. 46B. In various embodiments, the bridging element 4616 is made of the same SMA material as the loops 4612, 4614. In an embodiment the bridging element 4616 is made of a material different from the SMA material of the loops 4612, 4614.

FIGS. 46C, 46D, 46E, 46F and 46G illustrate different views of the coiled anastomosis device shown in FIG. 46B with a tip covering, in accordance with an embodiment of the present specification. Anastomosis device 4620 comprises two loops, a first loop 4622 and a second loop 4624 of an SMA wire with an 'S' shaped bridging segment 4626 connecting the two loops. In various embodiments, the first loop 4622 and the second loop 4624 are coiled in opposing directions for reducing the torque experienced by the SMA wire/coils when the straight wire coils up after deployment. Additionally, the opposite direction of the two coils counterbalance the torsional potential energy in the coil in the straight position. A distal end of the first loop 4622 is bent inward to prevent a sharp edge or end and is capped using a ceramic tip 4628. A proximal end of the second loop 4624 is also bent inward and ends in a screw 4630 for attachment with a bolt connection on a delivery device during/after deployment. In some embodiments, the ends are bent inward by 10 to 90 degrees. In some embodiments, the distal tip can be bent up to 180°, creating an atraumatic U-curve at the tip. The ends of the first and the second loops may, in some cases, point out away from coil of the device 4620, which is undesirable as it presents a sharp edge which could damage tissue inadvertently. Therefore, the ends are bent inwards. Referring to FIGS. 46C, arrows 4632, 4634 represent a direction of the inwards bend in the end of the first loop 4622, and the second loop 4624 respectively, in order to eliminate potential mechanical trauma due to the sharp end. In an embodiment, a plurality of rings made of biocompatible material, such as PTFE, may be placed over the bridging segment 4626, wherein the rings comprise lumens through which the bridging segment passes. In another embodiment, a plurality of magnets may be placed over the bridging segment 4626 as explained with reference to FIG. 41A. In yet another embodiment, bridging segment 4626 may have magnets, and a PTFE film may be placed over the magnets. In another embodiment, a thin plastic, polymer or PTFE film can be placed over the entire device, from the distal ceramic tip to the proximal screw connection. In embodiments, a thin plastic layer of a biocompatible material, such as PTFE, is placed over 0%-100% of the device. In embodiments, the layer is positioned over certain components of the device, such as the magnets or spacers. In various embodiments, the diameter of each curve of the bridging segment ranges between 25% and 75% of the diameter of the loop of the coil.

FIGS. 47A-47M illustrate different views of a coiled compression/anastomosis device comprising a bridging segment, in accordance with an embodiment of the present specification. Device 4700 comprises a first set of loops 4702 and a second set of loops 4704 of an SMA wire, wherein the first and the second sets of loops are connected with a bridging segment 4706. In various embodiments, the first set of loops 4702 and the second set of loops 4704 are coiled in opposing directions for reducing the torque experienced by the SMA wire when the wire changes shape to form multiple loops 4702, 4704 after deployment. The reduction in torque causes the SMA wire to coil in a desired manner, as explained with reference to the embodiments of the anastomosis device described above. Additionally, the bridging segment counterbalances the torque in the two individual segments of the loop in the straight position, diminishing the distortion of a flexible catheter in the segment where the device is stored pre-deployment. The bridging segment 4706 is shaped in a curve forming an 'S' as shown in the FIGURES, and in an embodiment is connected to the ends of the first and the second loops via short PTFE tubes. In another embodiment, a thin plastic, polymer or PTFE film can be placed over the whole device, from the distal ceramic tip to the proximal screw connection. In various embodiment the diameter of each curve of the bridging segment ranges between 25% and 75% of the diameter of the loop of the coil. The curved shape enables the SMA wire to coil easily in a desired manner upon deployment.

The device 4700 comprises a shape memory alloy (SMA) wire 4701 shown in FIG. 47C, with a plurality of magnets 4708 and spacers 4710 positioned alternately and coaxially about the wire 4701. In an embodiment, the wire 4701 is composed of Nitinol. In an embodiment, the spacers 4710 are composed of a non-ferromagnetic material. In various embodiments, the spacers 4710 comprise silicone or Nitinol tubes or O-rings or spherical balls.

Referring to FIGS. 47A-47M, after deployment, and when exposed to body temperature, the SMA wire 4701 coils to form multiple loops, which can be classified into the first set of loops 4702 and the second set of loops 4704 connected by the bridging element 4706, wherein the first set of loops 4702 and the second set of loops 4704 are coiled in opposing directions. The spacers 4710 ensure that the magnets 4708 do not clump together on the device 4700 while in a straight pre-deployment shape. A distal end of the first set of loop 4702 is bent inward to prevent a sharp edge or end and is capped using a ceramic tip 4712, and a proximal end is connected to a first end of the 'S' shaped bridging segment 4706. A proximal end of the second set of loop 4704 is also bent inward and ends in a screw 4714 for attachment with an inner member of a delivery catheter, while a distal end of the second set of loop 4704 is connected to a second end of the 'S' shaped bridging segment 4706. In some embodiments, the ends are bent inward by 10 to 90 degrees. In one embodiment, the distal end is bent by 180° to make an atraumatic U-curve. The ends of the first and the second loops may, in some cases, point out away from coil of the device 4700, which is undesirable as it presents a sharp edge which could damage tissue inadvertently. Therefore, the ends are bent inwards, thereby preventing damage to tissue during and post deployment. The bending of the ends also creates a rounded knuckle 4716 (shown in FIG. 47A) in the coil 4701 which prevents the tips of the first and the second sets of loops 4702, 4704 not connected to the bridging element 4706 from scraping or catching tissue while the SMA wire is coiling and forming loops in the lumen of an organ after deployment.

FIGS. 47D-47H illustrate the device shown in FIGS. 47A-47C without the magnets and spacers placed around the SMA wire. FIGS. 47I-47M illustrate different views of the device 4700 shown in FIGS. 47A-47C wherein the magnets 4708 are plated with a corrosion-resistant material such as gold or titanium, or are coated with plastic or PTFE, and wherein the spacers 4710 are O-rings made of PTFE or another biocompatible non-ferromagnetic material. FIGS. 47N-47S illustrate the device shown in FIGS. 47A-47C with PTFE washers 4730 provided around the 'S' shaped bridging element 4706. The PTFE washer have a diameter similar to the magnets and function as a filler that prevents the flexible catheter housing the device from collapsing in the S-segment section, inadvertently trapping the device and interfering with its deployment. In an embodiment, the bridging element 4706 is threaded through approximately 20 to 25 PTFE washers 4730. In an embodiment, a diameter of the SMA wire 4701 threaded through magnets 4708 is approximately 0.75 mm while a diameter of the magnets 4708 is approximately 2.9 mm as shown in FIG. 47R. FIG. 47Q illustrates the different portions of the anastomosis device shown in FIG. 47N separately. In various embodiments, a nitinol tube with a central lumen to receive a guidewire can be used in place of a solid nitinol wire.

FIG. 47T illustrates another view of a coiled anastomosis device comprising a bridging segment, in accordance with an embodiment of the present specification. Device 4780 comprises a first set of loops 4782 of an SMA wire forming a proximal coil and a second set of loops 4784 of an SMA wire forming a distal coil, wherein the first and the second sets of loops are connected with a bridging segment or connecting member 4786. A plurality of magnets 4788 and spacers 4790 are positioned alternately and coaxially about the SMA wire. In an embodiment, the bridging segment 4786 is a 'S' shaped connecting member, which may include a drainage structure configured to provide immediate connectivity between two lumens joined by an anastomosis. The connecting member 4786 shown in FIG. 47T is shown without the drainage structured included with the 'S' shaped connector. In various embodiments, the connecting member 4786 is employed to provide connection between the proximal and distal coils. Further, the 'S' shaped connecting member 4786 provides a pulling force that pulls the two coil loops of the device 4780 together to assist with pulling the two body tissues with lumens to be anastomosed together. The pulling forces of the S-curve are greatest when the two device loops are farthest apart. As the loops are pulled together, the pulling force of the S-curve diminishes while the attracting force of the magnets take over, completing the anastomosis. In embodiments, a length of the connecting member 4786 is greater than the diameter of the SMA coil forming the loops 4782, 4784 but is less than or equal to the circumference of said coil, enabling the coils 4782, 4784 to come together and the magnets 4788 to align. The 'S' shape of the connecting member 4786 enables a piercing hole created by a tip 4792 of the SMA coil to lie inside the periphery of the two coils 4782, 4784.

FIGS. 48A and 48B illustrate an anastomosis device comprising a bridging segment with a drainage mechanism positioned thereon, in accordance with an embodiment of the present specification. Device 4800 is a coil and comprises a first set of loops 4802 and a second set of loops 4804 of an SMA wire, wherein the first and the second sets of loops are connected with an 'S' shaped bridging segment 4806. In various embodiments, the first set of loops 4802 and the second set of loops 4804 are coiled in opposing directions for reducing the torque experienced by the SMA wire upon deployment. In embodiments, as shown in FIGS. 48A, 48B an expandable wire mesh drainage mechanism 4808 with a biocompatible material covering the wire mesh is positioned around the bridging segment 4806. In some embodiments, the expandable wire mesh drainage mechanism 4808 is a stent. The wire mesh drainage mechanism 4808 is compressible and expandable, where, when expanded, the wire mesh drainage mechanism is a cylinder with a length and a constant radius over the length, and includes a lumen passing through, as shown in FIG. 48A. The wire mesh drainage mechanism in FIG. 48A is depicted in a compressed, pre-deployment configuration. Alternatively, the wire mesh drainage mechanism 4808 could be shaped like a barbell with a central cylindrical portion having a first radius and end cylindrical portions having a second radius, where the second radius is greater than the first radius, and a lumen passing through, as shown in FIG. 48B. Alternatively, the wire mesh drainage mechanism 4808 is a cylinder with a length and a non-constant radius over the length. In each embodiment, the wire mesh drainage mechanism 4808 is positioned over and secured to the bridging segment 4806, such that the bridging segment 4806 extends through the lumen of the wire mesh drainage mechanism 4808, and expands from a compressed state pre-deployment to an expanded state post-deployment. The use of the wire mesh drainage mechanism 4808 as shown in FIGS. 48A, 48B eliminates the need for PTFE tubes for covering the bridging element 4806.

The bridging segment extending through the lumen of the stent is preferably independent of, and separate from, an expandable housing that defines the exterior of the expandable wire mesh drainage mechanism or stent. The expandable housing that defines a cylinder through which fluid may drain may be tethered to the proximal or distal ends of the bridging segment, as shown in FIG. 50G. However, the wire mesh which defines the expandable housing is not integrated with, or interweaved with, the bridging segment itself. By not making the bridging segment part of the wire mesh or stent housing, one avoids unnecessarily interfering with the expansion and contraction of the wire mesh or stent, while still insuring the wire mesh drainage mechanism or stent remains in the proper location to facilitate drainage.

FIG. 48C illustrates a plurality of expandable wire mesh drainage mechanisms that can be employed with the anastomosis devices of FIGS. 48A and 48B, in accordance with some embodiments of the present specification. Wire mesh drainage mechanism 4820 is a lumen opposing metal stent having a cylindrical portion 4822 bounded by flanges 4824, 4826. Wire mesh drainage mechanism 4820 has an internal diameter ranging from 10 mm to 25 mm and a length of the cylinder 4822 between the flanges 4824, 4826 is approximately 5-15 mm. Wire mesh drainage mechanism 4830 is a lumen opposing metal stent having a cylindrical portion 4832 with an internal diameter ranging from 8 mm to 26 mm, and flanges 4834, 4836. A length of the cylinder 4832 between the flanges 4834, 4836 is approximately 5-15 mm. Wire mesh drainage mechanisms 4840, 4850 and 4860 are bi-flanged metal stents, each having a cylindrical portion having a first diameter, bounded by flanges having a diameter greater than the first diameter. Cylindrical portion 4842, of stent 4840 has a diameter ranging from 10 mm-26 mm and a length between flanges 4844, 4846 ranging from 10 mm to 30 mm. Cylindrical portion 4852, of wire mesh drainage mechanism 4850 has a diameter ranging from 8 mm to 25 mm and a length between flanges 4854, 4856 of approximately 30 mm. Cylindrical portion 4862 of wire mesh drainage mechanism 4860 has a diameter of approximately 14 mm and a length between flanges 4864, 4866 ranging from 10 mm to 30 mm.

FIGS. 49A-49D illustrate different views of an anastomosis device comprising a wire mesh drainage mechanism positioned over an 'S' shaped bridging element, in accordance with an embodiment of the present specification. Device 4900 comprises a first set of loops 4902 and a second set of loops 4904 of an SMA wire 4901, wherein the first and the second sets of loops are connected with an 'S' shaped bridging segment 4906. In various embodiments, the first set of loops 4902 and the second set of loops 4904 are coiled in opposing directions for reducing the torque experienced by the SMA wire 4901 when the wire changes shape to form multiple loops after deployment. A plurality of magnets 4908 and spacers 4910 are positioned alternately and coaxially about the wire 4901. In an embodiment, the SMA wire 4901 is composed of Nitinol. In an embodiment, the spacers 4910 are composed of a non-ferromagnetic material. In various embodiments, the spacers 4910 comprise silicone, PTFE, or Nitinol tubes or O-rings or circular balls. A distal end of the first loop 4902 is bent inward to prevent a sharp edge or end and is capped using a ceramic tip 4912. The ceramic tip may house cautery wire for electrocautery to puncture the wall of an organ. A proximal end of the second loop 4904 is also bent inward and ends in a screw 4914 for attachment with a delivery device during/after deployment. A drainage mechanism such as a stent 4916 made of a wire mesh and a biocompatible material covering the wire mesh is placed around the bridging segment 4906. The stent 4916 is compressible and expandable and is positioned over and secured to the bridging element 4806. The stent 4916 expands from a compressed state pre-deployment to an expanded state post-deployment.

FIGS. 50A-50D illustrate different views of an anastomosis device comprising a wire mesh drainage mechanism positioned over a bridging element, in a pre-deployment state, in accordance with an embodiment of the present specification. Device 5000 comprises an SMA wire 5001 with a plurality of magnets 5004 and spacers 5006 positioned alternately and coaxially about the wire 5001. A first portion 5008 of the wire 5001 is coupled to a second portion 5010 of the wire 5001 via a bridging segment 5012 which is at least partially covered by a wire mesh drainage mechanism 5014 as shown in the FIGURES. A distal tip of the portion 5010 is covered with an optional ceramic tip 5016. A proximal tip of the portion 5008 ends in an optional screw 5018. In an embodiment, a total length of the device 5000 is approximately 283 mm and ranges between 172 mm and 382 mm; a length of the bridging segment 5012 is approximately 44 mm and ranges between 31.3 mm and 127.3 mm; a length of the stent 5014 is approximately 15 mm and ranges between 10 mm and 25 mm.

FIG. 50E illustrates the device of FIGS. 50A-50D after deployment, in accordance with an embodiment of the present specification. After deployment, and when exposed to body temperature, the SMA wire 5001 coils to form multiple loops, wherein the first portion 5008 forms a first set of loops 5009 and the second portion 5010 forms a second set of loops 5011. The bridging segment 5012 curls into an 'S' shape with the wire mesh drainage mechanism 5014 positioned around it. FIG. 50F illustrates the device of FIG. 50E without the wire mesh drainage mechanism positioned over the bridging segment and deployed in a desired location, in accordance with an embodiment of the present specification.

FIGS. 50G and 50H illustrate the device shown in FIGS. 50A-50D along with means for attaching the wire mesh drainage mechanism to the bridging segment, in accordance with an embodiment of the present specification. In an embodiment, flexible attachments such as sutures 5013 are used to secure the wire mesh drainage mechanism 5014 to the bridging segment 5012 by using a crimp 5017. In embodiments, the crimp is comprised of a metal material. In various embodiments, the wire mesh drainage mechanism 5014 is attached to the bridging segment 5012 in a manner that allows expansion and sideways motion of the wire mesh drainage mechanism 5014 while still being secured at a desired position on the bridging segment 5012. In an embodiment, the compressed length of the wire mesh drainage mechanism 5014 is less than πr where r is the radius of the coil 5001. In an embodiment, the expanded diameter of the wire mesh drainage mechanism 5014 ranges between 3 mm and 30 mm.

FIG. 50I illustrates a view of an anastomosis device comprising a wire mesh drainage mechanism positioned over a bridging element, in a post-deployment state, in accordance with an embodiment of the present specification. After deployment, and when exposed to body temperature, the anastomosis device 5080 comprising an SMA wire with a plurality of magnets 5086 and spacers 5088 positioned alternately and coaxially about the SMA wire, coils to form multiple loops, wherein the first portion of the coil forms a first set of loops 5082 and a second portion of the coil forms a second set of loops 5084. A bridging segment 5090 connecting the first and second set of loops curls into an 'S' shape. As shown in the FIG. a wire mesh drainage mechanism 5092 is positioned over the connecting member 5090. The wire mesh drainage mechanism 5092 enables maintaining a hole in a patient's organ wall, having a diameter of at least 3 mm. The maintaining of the hole allows for fluid flow to occur through the organ wall reducing a buildup of pressure in the organ for a limited period of time, until the anastomosis device causes a larger, permanent anastomosis to form and then the entire device passes through the organ, such as a colon.

In one embodiment, the anastomosis device 5080 with the wire mesh drainage mechanism 5092 is deployed in a transected colon where a purse-string suturing technique using sutures or staples is used to close the mouth of the transected colon (described in FIG. 55), the wire mesh drainage mechanism 5092 extends between the colon proximal to the transected section to the colon distal to the transected section, allowing for immediate fluid connection and drainage from the colon proximal to the transected section to the colon distal to the transected section.

FIG. 50J illustrates a view of the anastomosis device of FIG. 50I in a pre-deployment configuration, in accordance with an embodiment of the present specification. Device 5080 comprises an SMA wire with a plurality of magnets 5086 and spacers 5088 positioned alternately and coaxially about the wire. A first portion 5082 of the wire is coupled to a second portion 5084 of the wire via a bridging segment 5090 which is at least partially covered by a wire mesh drainage mechanism 5092 as shown in the FIGS. 50I, 50J. For illustrative purposes, in FIG. 50J the first and the second portions 5082, 5084 of the wire are pulled straight, from their coiled up post-deployment state shown in FIG. 50I. The wire mesh drainage mechanism 5092 is made of a wire mesh and a biocompatible material covering the wire mesh. The wire mesh drainage mechanism 5092 is compressible and expandable and is positioned over and secured to the bridging element 5090 by using sutures 5094. The wire mesh drainage mechanism 5092 expands from the compressed state pre-deployment to an expanded state post-deployment. In an embodiment, the device 5080 is covered by a material such as, but not limited to PTFE to make it easier to insert into a patient's body without catching tissue (on edges). In an embodiment, only the magnets are either rounded or covered by a material such as, but not limited to PTFE, fluorinated ethylene propylene (FEP), or perfluoroalkoxy (PFA), for enabling easy insertion into a patient's body. Materials that can be shrink-wrapped at temperatures less than 80° C., and more preferably less than 60° C., may be used to cover the magnets.

FIG. 50K illustrates the anastomosis device comprising a wire mesh drainage mechanism 5014 provided over the bridging element 5012 in a pre-deployment state, as shown in FIGS. 50A-50D. The wire mesh drainage mechanism 5014 is shown in an expanded state and is shaped as a barbell with a central cylindrical portion having a first radius, a first end cylindrical portion 5015a and a second end cylindrical portion 5015b wherein the first and the second end cylindrical portions 5015a, 5015b have a second radius, where the second radius is greater than the first radius. The device 5000 is deployed within a lumen of an organ in proximity to and encircling a puncture in two adjacent organ walls, created by means of a delivery catheter. The wire mesh drainage mechanism is compressed when the device 5000 is loaded into the catheter for delivery. The device is deployed in a manner such that the wire mesh drainage mechanism 5014 plugs the puncture in the organ walls and provides fluid communication between the lumens of the two adjacent organs. Upon deployment, the first portion 5008 of the device 5000 and the first end cylindrical portion 5015a remains on one side of the puncture in the organ walls while the second portion 5010 and the second end cylindrical portion 5015b are deployed on the other side of the puncture in the organ walls, while the two loops of the coil encircle the puncture in each of the organ walls. FIGS. 50L and 50M illustrate the device of FIG. 50K in a post deployment state. A plastic sheet 5020 comprising on opening 5022 represents the adjacent organ walls with a puncture through them. As shown in the FIGS., the wire mesh drainage mechanism 5012 becomes positioned in the opening 5022, such that the first portion 5008 and the first end cylindrical portion 5015a remains on a left side of the opening 5022 while the second portion 5010, the second end cylindrical portion 5015b along with a substantial portion of the bridging segment 5012 are passed through and deployed on the right side of the opening 5022 in the plastic sheet 5020, thereby positioning the wire mesh drainage mechanism in the opening 5022 while providing a fluid communication from the right side to the left side through the wire mesh drainage mechanism. The magnets 5004 on the first and the second portions 5008, 5010 attract each other, causing the device 5000 to stay in place. The spacers 5006 ensure that the magnets 5004 do not clump together on the device 5000, particularly in the pre-deployment straight configuration of the device.

FIGS. 50N and 50O illustrate perspective and side views of an anastomosis device 5091 including a wire mesh drainage element 5099, in accordance with some embodiments of the present specification. The anastomosis device 5091 is similar to the device shown in FIG. 47T and comprises a bridging segment 5087, in accordance with an embodiment of the present specification. Device 5091 comprises a first set of loops 5093 of an SMA wire forming a distal coil and a second set of loops 5095 of an SMA wire forming a proximal coil, wherein the first and the second sets of loops are connected with a bridging segment or connecting member 5087. A plurality of magnets 5097 and spacers 5098 are positioned alternately and coaxially about the SMA wire. In an embodiment, the bridging segment 5087 is a 'S' shaped connecting member, which is covered by a wire mesh drainage element 5099 configured to provide immediate connectivity between the two lumens joined in the anastomosis. In various embodiments, the connecting member 5087 is employed to provide electrical and mechanical connection between the proximal and distal coils. The electrical connection provides electrical current to the cautery tip 5096 for piercing body tissues. Further, the 'S' shaped connecting member 5087 provides a pulling force that pulls the two loops of the device 5091 together to assist with pulling the two body tissues with lumens to be anastomosed together. The pulling forces of the S-curve are greatest when the two device loops are farthest apart. As the loops are pulled together, the pulling force of the S-curve diminishes while the attracting force of the magnets take over, completing the anastomosis. In embodiments, a length of the connecting member 5087 is greater than the diameter of the SMA coil forming the loops 5093, 5095 but is less than the circumference of said coil, enabling the coils 5093, 5095 to come together and the magnets 5097 to align. The 'S' shape of the connecting member 5087 enables a piercing hole created by the tip 5096 of the SMA coil to lie inside the periphery of the two coils 5093, 5095. In embodiments, a proximal end of the device 5091 includes a screw tip 5089 for connecting to a delivery device.

FIG. 51A illustrates a handle of a delivery device for an anastomosis device, such as the device shown in FIG. 47A, connected to a pusher catheter for delivering the anastomosis device in a desired location within a body, in accordance with an embodiment of the present specification. The delivery device 5100 includes a catheter 5116 comprising an outer catheter portion 5117 attached to a proximal handle 5119 having a port 5112. The device also comprises an inner pusher catheter 5113 comprising a first portion 5113a, a second portion 5113b, and a stopping mechanism 5115, attached to a distal handle 5118. The delivery device is used to deliver the SMA anastomosis device such as the device 5000 of FIG. 50D into a human body by any means including, but not limited to, endoscopy, laparoscopy, and open surgery. Inner pusher catheter 5113 is movable coaxially within outer catheter portion 5117 using distal handle 5118.

The tip of the catheter is used to puncture across the walls of adjacent organs and the tip of the catheter is placed in a first lumen of a first organ. The first portion 5113a of the inner pusher catheter 5113 is pushed to deploy a first segment of the coil and a portion of the S-connector into the first lumen. The stopping mechanism 5115 marks the end of a first step of deployment and prevents the user from deploying too much of the device. The position and adequacy of deployment could be verified using various imaging techniques. After verifying accurate placement and adequate deployment, the catheter is withdrawn and the catheter tip is positioned in a second lumen of a second organ with the deployed portion of the catheter still in the first lumen. The second portion 5113b of the inner pusher catheter 5113 is pushed after disengaging the stopping mechanism 5115 and the remaining portion of the anastomosis device is deployed in the second lumen. The anastomosis device is than disengaged from the inner pusher catheter 5113 and the entire catheter is removed. In certain embodiments, the second section 5113b of the inner pusher catheter 5113 may telescope within the first section 5113a to shorten the length of the pusher catheter 5113. In another embodiment, the inner pusher catheter 5113 comprises three distinct portions separated by two discrete stopping mechanisms. In this embodiment, the three portions separately control deployment of the distal coil loop, 's' shaped connecting segment, and the proximal coil loop of the anastomosis device. The three portions can telescope into each other to diminish the pusher catheter length. During delivery, a warm liquid may be introduced via port 5112 which, when contacting the shape memory alloy of the anastomosis device, assists in changing the anastomosis device from its linear pre-deployment configuration to its coiled post-deployment configuration. In an embodiment, as shown in FIG. 51B, a proximal portion of the proximal handle 5116 comprises an inner shaft 5155 which is coaxially surrounded by an outer shaft/barrel 5120. In an embodiment, the inner shaft 5155 comprises grooves/screw pitch on the surface for controlling a movement of the inner shaft 5155 within the outer shaft/barrel 5120 of the proximal handle 5116. The inner shaft 5155 is configured to be pushed into and rotated with respect to the outer sheath/barrel 5120 to deploy the anastomosis device, such that the inner shaft 5155 moves inside the barrel 5120 until only the screw pitches 5123 are visible outside the barrel, at which point the inner shaft 5155 is rotated in a counterclockwise direction (unspooled) to disengage the anastomosis device from the delivery device. In the embodiment shown in FIGS. 51A and 51B, screw pitch 5124 provided on the outer shaft 5120 engages with a screw pitch 5122 on the inner shaft 5155, while the screw pitch 5122 provided on the inner shaft 5155 relieves any tension on the anastomosis device held within the delivery device 5100. In an embodiment, optional screw pitches 5126, 5123, positioned at the distal handle 5118 of the delivery device body 5114 and the proximal end of the inner shaft 5155 respectively, are included for disengaging the delivery device from the anastomosis device. Referring to FIG. 51B, in embodiments, the length of groove 5121 equals the length of the distal coil loop segment and the 's' shaped connector of the anastomosis device, the length of following pitch groove 5129 equals the length of the proximal coil loop segment of the anastomosis device, and the rotating motion assists in relieving torque of the proximal coil loop segment post deployment. In embodiments, the groove segment 5123 corresponds to the screw connection that disconnects the anastomosis device from the delivery device.

FIG. 51C illustrates an anastomosis device 5170 including a wire mesh drainage element 5171 attached to a delivery device 5175, in accordance with some embodiments of the present specification. The anastomosis device 5170 is shown in a post-deployment configuration at a distal end of the delivery device 5175, just prior to being disengaged from the delivery device 5175.

In various embodiments, the anastomosis device or magnetic compression device of the present specification may be used for treating a plurality of sphincter dysfunctions by creating a partial myotomy. FIGS. 52A and 52B illustrate the anastomosis device being used to treat an achalasia dysfunction in a lower esophageal sphincter (LES) of a patient, in accordance with an embodiment of the present specification. Achalasia is a medical condition in which the muscles of the lower part of the esophagus fail to relax, preventing food from passing into the stomach. As shown in FIGS. 52A, a magnetic compression device 5200 comprising a first coil loop 5202 and a second coil loop 5204 is endoscopically inserted into a patient diagnosed with achalasia proximate. The second coil loop 5204 is placed distal to an LES 5208 while the first coil 5202 is placed proximal to the LES 5208. The coils 5202, 5204 apply pressure to the LES 5208, resulting in compressive resection of a portion of the sphincter thereby creating a compressive myotomy or an opening 5209 in the LES 5208 to allow easier passage of food from esophagus 5210 into the stomach 5206, as shown in FIG. 52B. The device 5200 falls away and may be removed or may pass naturally.

FIGS. 53A and 53B illustrate a magnetic compression device being used to treat a gastroparesis dysfunction by creating a myotomy in a pyloric sphincter of a patient, in accordance with an embodiment of the present specification. The pyloric sphincter acts as a valve to controls the flow of partially digested food from the patient's stomach to the small intestine. As shown in FIGS. 53A, 53B a magnetic compression device 5300 comprising a first coil loop 5302 and a second coil loop 5304 is endoscopically inserted into a pyloric sphincter 5308 of a patient diagnosed with gastroparesis as a result of the pyloric sphincter 5308 failing to open fully. The second coil loop 5304 is placed distal to the pyloric sphincter 5308, such that the second coil loop 5304 lies in a duodenum 5306, as shown in FIG. 53A, while the first coil 5302 is placed proximal to the pyloric sphincter 5308, such that the first coil loop 5302 lies in a stomach. The coils 5302, 5304 apply pressure to the pyloric sphincter 5308, resulting in compressive resection of a portion of the sphincter 5308, thereby creating a myotomy or an opening 5309 as shown in FIG. 53B, allowing the flow of contents from the stomach 5307 to the duodenum 5306. The device 5300 falls away and may be removed endoscopically or pass naturally.

FIGS. 54A and 54B illustrate a magnetic compression device being used to treat a gastrointestinal stricture in an esophagus of a patient, in accordance with an embodiment of the present specification. A gastrointestinal stricture in the esophagus may be formed by narrowing of the esophageal passage, restricting passage of food from the esophagus to the stomach of a patient. As shown in FIGS. 54A, 54B a magnetic compression device 5400 comprising a first coil loop 5402 and a second coil loop 5404 is endoscopically inserted into an esophagus 5410 of a patient diagnosed with an esophageal stricture 5408. A portion 5412 of the esophagus 5410 proximal to the stricture 5408 is dilated. The first coil loop 5402 is placed proximal to the stricture 5408 while the second coil loop 5404 is placed distal to the stricture 5408 as shown in FIG. 54A. The coils 5402, 5404 apply pressure to the stricture 5408, resulting in circumferential compressive resection of a portion of the stricture 5408, creating an opening 5409 and eliminating the stricture 5408. This allows for normal passage of contents through the esophagus 5410 and, after time, the dilated portion 5412 of the esophagus may resolve. The device 5400 falls away and may be removed or pass naturally.

In various embodiments the present specification provides a novel, flexible catheter based magnetic compression anastomosis deice and delivery system that has been able to safely create gastro-jejunal and jejunojejunal anastomosis. The anastomosis device may be used to perform procedures such as, but not limited to, end-to-end colo-colic anastomosis, and creation of a cholecysto-jejunostomy and cyst-gastrectomy for pseudocyst drainage. By reducing or eliminating the risk of anastomotic leaks, the device offers potential advantages over traditional anastomotic techniques.

FIG. 55 is a flowchart illustrating a method of performing a colorectal surgery for deploying the anastomosis device, in accordance with an embodiment of the present specification. At step 5502 a peritoneal inflection in a patient is located and a point approximately 15 cm above the inflection is marked on the patient's colon. At step 5504, the patient's colon is transected at the marked point. At step 5506 a distal end of the transected colon is partially closed by using sutures or staples. In an embodiment, a purse-string suturing technique using V-lock sutures is used to close the mouth of the transected colon. At step 5508 a proximal portion of the colon is clamped to allow for insufflation. The resection of the colon creates a proximal colon segment which is not in a fluid communication with a distal colon segment. At step 5510, an endoscope is inserted into the patient's distal colon segment trans-anally. At step 5512, an anastomosis delivery device carrying the magnetic anastomosis device is inserted into the patient's distal colon segment alongside or through the endoscope. In embodiments, the delivery device is such as shown in FIG. 51A. At step 5514, the delivery device is inserted into the proximal colon segment by exiting the distal colon segment proximate staple lines/purse strings of a suture. At step 5516, air is injected via the delivery device into the proximal colon segment in order to insufflate/distend the proximal colon segment. In another embodiment, air is injected via laparoscopic needle. At step 5518, a first coil of the anastomosis device is deployed free and clear in the distended proximal colon lumen. In embodiments, care is taken that the coil tip doesn't "catch" on the colon wall. At step 5520, the delivery device is pulled back until an 's' shaped segment of the anastomosis device connecting the first coil loop to a second coil loop is at least partially visible outside the proximal colon segment. In an embodiment, the delivery device is pulled back until ¾ of the 's' shaped coil segment is visible inside the distal colon lumen. At step 5522, the second coil of the anastomosis device is deployed in the distal end of the colon. At step 5524, the delivery device is detached from the anastomosis device and the delivery device is pulled out of the patient's body along with the endoscope. Attention is paid during the deployment that an entirety or a part of the suture/staple line is captured inside the loops of coils so as an entirety or a part of the suture/staple line is resected by the magnetic compression anastomosis device, leaving minimum foreign material in or around the anastomosis.

FIG. 56 is a flowchart illustrating a method of performing a gastrojejunostomy surgery for deploying the magnetic compression anastomosis device, in accordance with an embodiment of the present specification. Gastrojejunostomy is a surgical procedure in which an anastomosis is created between a patient's stomach and a proximal loop of the patient's jejunum. This is usually done either for the purpose of draining the contents of the stomach or to provide a bypass for the gastric contents. At step 5602 the patient's ligament of Treitz (a band of smooth muscle extending from the junction of the duodenum and jejunum to the left crus of the diaphragm and functioning as a suspensory ligament) is located and a point approximately 100-200 cm below the ligament is marked on the patient's abdomen. At step 5604 a enterotomy, which comprises opening the patient's small bowel surgically, is performed at a distance greater than approximately 10 cm from a targeted deployment site. In an embodiment, the enterotomy is performed by using a cautery device and a cauterized delivery system. In another embodiment, the enterotomy is performed by using surgical tools. In embodiments, the enterotomy is performed half way between mesentery and anti-mesentery side of the patients colon. At step 5606 an endoscope is inserted into the patient's stomach via the patient's mouth. In embodiments, the operator is provided with tools to perform fluoroscopy in order to obtain a view of the patient's internal organs. At step 5608, air is inserted into the patient's stomach via the endoscope to distend the stomach to create an air-filled volume, allowing for the coil to freely deploy without catching a gastric wall. In embodiments, air may be inserted into the patient's distended stomach via other means, such as but not limited to an NG (nasogastric) tube, or a laparoscopic needle. At step 5610 a catheter coupled with a magnetic compression anastomosis device is inserted through the enterotomy and exits via the anti-mesentery side of the patient's jejunum. At step 5612 the catheter coupled with an anastomosis delivery device carrying the anastomosis device is inserted into the patient's stomach via an opening created by a cautery tip of the anastomosis device or by another surgical tool. In embodiments, the delivery device is such as shown in FIG. 51A. At step 5614, it is confirmed by using endoscopic view that a tip of the delivery device is located within the patient's stomach.

At step 5616, a first coil loop of the anastomosis device is deployed free and clear in the distended stomach. In embodiments, care is taken that the coil tip doesn't "catch" on the stomach wall. At step 5618, the delivery device is pulled back until an 's' shaped segment of the anastomosis device connecting the first coil loop to a second coil loop is at least partially visible outside the stomach. In an embodiment, the delivery device is pulled back until ¼ to ¾ of the 's' shaped coil segment is visible. At step 5620, the small bowl of the patient is pulled up over the delivery device proximate the patient's stomach so the opening in the jejunum aligns with the opening in the stomach wall in order to cause the catheter tip and a proximal end of the second coil loop to be positioned in the patient's small bowel. In embodiments, a technician is required to hold the delivery system steady/still, while an operating surgeon uses graspers to "pull" the small bowel over the delivery system up to the stomach. At step 5622, the second coil loop of the anastomosis device is deployed in the patient's small bowel. In embodiments, care is taken that the small bowel doesn't twist when the coils are deployed. At step 5624, the delivery catheter is detached from the anastomosis device and the delivery device is pulled out of the patient's body and the endoscope is removed from the patient's stomach. At step 5626, the first opening in the jejunum created by the enterotomy is closed with sutures or staples.

FIG. 57A illustrates a human colon which may be resected to remove diseased portions, in accordance with an embodiment of the present specification. Colon 5700 comprises an ascending colon 5702, a transverse colon 5704, a descending colon 5706, and a sigmoid colon 5708 ending in a rectum 5710. Appendix 5712 is located at a proximal end of the ascending colon 5702. Various growths such as polyps 5714, or cancerous tumor 5716 may necessitate resection of a portion of the colon 5700 to remove a diseased portion. Once the diseased portion is removed, two ends of the resected colon are required to be fused together. In embodiments, the anastomosis device of the present specification may be used to fuse two ends of a colon resected at for example cut line 5718 and 5720 as shown in the FIGURE, while maintaining a central flow path between the proximal and distal parts of the colon, till the anastomosis is completed. FIG. 57B illustrates a human colon 5720 with a diseased portion 5722 being removed and the resultant ends 5724, 5726 of the colon anastomosed together. The two ends 5724, 5726 fuse after time and an anastomosis 5728 is formed.

A known method of fusing two ends of a resected colon comprises stapling the two ends together. The ECHELON CIRCULAR™ Powered Stapler produced by Johnson & Johnson Medical Devices Company is widely used for stapling open ends of a resected colon together.

Known methods of fusing two ends of a resected colon also include using an anastomosis device comprising a plunger end and a receiver end for fusing two cut ends of a colon. Said method comprises suturing a first end and a second end of the resected colon and using a handle having a control mechanism to insert a device similar to a plunger (through a hole made in the patient's organ) into the purse stringed first end. Next, the purse strings are tightened around the plunger device. Then a device similar to a plunger receiver is passed through the purse stringed second end of the colon and attached to the plunger device protruding from the first end of the resected colon. The control mechanism on the handle is turned to click the plunger end into the receiver until the plunger top presses against the receiver, causing the two ends to be pulled together and, fuse together. Over a period of time, anastomosis is formed between the first and second fused ends of the colon allowing fluid to pass through. However, in this method, there is no fluid flow possible through the colon until the anastomosis is complete.

Hence, known methods of fusing two ends of a resected colon do not fuse the two ends of the colon first and then achieve anastomosis. Cutting the anastomosis first and then fusing the colon ends may lead to profuse bleeding and leakage in the colon. Also, known methods do not provide a mechanism by which the anastomosis device may be delivered to the patient's colon via the GI tract without requiring for an additional hole to be made in the patient's organ walls. Circular staplers can be delivered via the GI tract trans-anally to the patient's rectum, sigmoid and descending colon but cannot be delivered into the colon via the GI tract without requiring for an additional hole for transverse colon and the ascending colon. Yet further, known methods of fusing two ends of a resected colon do not provide a continual fluid path through the colon ends throughout the fusion and anastomosis process.

In embodiments, the present specification provides an anastomosis device, a delivery handle, and a method for fusing two ends of a resected colon such that the device is delivered to the resected ends of the colon via the GI tract of a patient, without having to make an additional cut in the patient's organs. The method of the present specification allows fluid to pass through the colon ends throughout the fusion and anastomosis process, while minimizing bleeding and leakage.

FIG. 57C illustrates a human colon 5730 with a diseased portion 5732 being removed and the resultant ends 5734, 5736 of the colon anastomosed together using a magnetic compression anastomosis device 5735 in accordance with embodiments of the present specification. The anastomosis device 5735 falls away and may be removed for pass naturally, leaving behind a complete anastomosis 5738. The drainage mechanism 5737 of the anastomosis device 5735 provides immediate fluid patency from one end 5734 of the resected colon to the other end 5736 of the resected colon as the anastomosis is forming. In some embodiments, the anastomosis 5738 is fully formed and the anastomosis device 5735 falls away after approximately 6-8 days after implantation.

FIG. 57D illustrates different types of anastomoses using a magnetic compression anastomosis device 5745 in accordance with embodiments of the present specification. In various embodiments, end-to-end colo-colic anastomoses 5741, side-to-side colo-colic anastomoses 5743, and side-to-end colo-colic anastomoses 5747 may be formed.

FIG. 57E illustrates a side-to-side colo-colic anastomosis created using a magnetic compression anastomosis device in accordance with embodiments of the present specification. The anastomosis device 5755 is depicted being deployed 5751 and then depicted implanted 5759 in a colonic wall 5753 to create a side-to-side colo-colic anastomosis between two segments of a colon 5750. In embodiments, the anastomosis device 5755 includes a drainage mechanism 5756, such as a stent, to allow immediate fluid flow between adjacent lumens of the two segments of the colon as the anastomosis forms.

FIG. 57F illustrates an anastomosis created between a gall bladder 5760 and a duodenum 5762 using a magnetic compression anastomosis device 5765 in accordance with embodiments of the present specification. The anastomosis device 5765 is depicted being deployed 5761 and then depicted implanted 5769 in a duodenal wall 5767 to create an anastomosis between the gall bladder 5760 and the duodenum 5762. In embodiments, the anastomosis device 5765 includes a drainage mechanism 5766, such as a stent, to allow immediate fluid flow between adjacent the lumens gall bladder 5760 and the duodenum 5762 as the anastomosis forms.

FIG. 58 is a flowchart illustrating a method of fusing two ends of a resected colon, in accordance with an embodiment of the present specification. At step 5802 a diseased portion of a patient's colon is resected. At step 5804 the ends of the proximal colon segment and distal colon segment are sutured using a purse string suture technique or are stapled together using a stapler. At step 5806, the proximal and distal purse stringed sutured/stapled ends of the colon are brought close together. At step 5808 a magnetic compression anastomosis device coupled to a delivery catheter of a delivery device is delivered through an enterotomy in the colon and positioned at one of the proximal and distal purse stringed ends of the colon. In an embodiment, a catheter or an endoscope is used to navigate the delivery device through the patient's distal colon instead of using an enterotomy for access. In embodiments, the anastomosis device comprises at least a first coil loop and a second coil loop made of an SMA wire and threaded with magnets and spacers, with a drainage mechanism positioned about or proximate an 's' shape connector connecting the first and the second coil loops, as described in the various embodiments/drawings of the present specification. At step 5810, an end of a first coil loop of the anastomosis device is passed, through a first lumen, through the first purse stringed end of the colon. At step 5812, the end of the first coil loop of the anastomosis device is extended from the first purse stringed sutured end to pierce proximate the second purse stringed sutured end of the colon and extend into a second lumen. Inside the second lumen, the device is deployed out of the delivery catheter causing the first loop to coil up in the second lumen of the colon. At step 5814, the anastomosis device is released from the delivery device causing the second coil to curl up within the first lumen, with the drainage mechanism extending between the first and second lumens of the colon. At step 5816, the first and the second coils attract each other, creating a pressure on the colon tissue and causing the tissue to fuse around the coil circumference for creating an anastomosis. At step 5818, while the anastomosis is being created, the drainage mechanism of the anastomosis device, at least partially, maintains a fluid pathway flowing between the first and second lumens and proximal and distal segments of the colon. The drainage mechanism creates an initial, or first, opening permitting fluid flow and having a first diameter and a first surface area. Next at step 5820, after a predefined period of time, a compression anastomosis is formed between the two segments of the colon and the anastomosis device is naturally eliminated from the colon. After formation of the anastomosis, a second opening is formed in the colon, wherein the second opening has a second diameter and a second surface area; and wherein the first diameter and/or the first surface area is 5% to 95% of the second diameter and/or second surface area. In an embodiment of the present specification the drainage mechanism automatically deploys, joining the proximal and distal segments of the resected colon, once the anastomosis device is released by the delivery device. In another embodiment, a physician manually implants a separate drainage mechanism between the proximal and distal segments of the resected colon after placing the anastomosis device comprising SMA wire and magnets at a desired location in the colon. The separate drainage mechanism could be a stent or a plastic catheter and is ideally placed through the tissue encircled by the Nitinol coil.

In an embodiment, the delivery device for delivering an anastomosis device comprises a handle provided with a control mechanism for guiding a user to correctly position the stent of the anastomosis device at a desired location within a patient's body. The anastomosis device may be such as that shown in FIGS. 48A, and 48B, comprising a first and a second set of loops of an SMA wire, wherein the first and the second sets of loops are connected with an 'S' shaped bridging segment and wherein a stent made of a wire mesh and a biocompatible material covering the wire mesh material is placed around the bridging segment. In various embodiments, the handle control mechanism provides feedback to a user/physician that the first set of loops of the anastomosis device has been deployed, then the first half of the stent/'S' shaped bridging segment has been deployed, after which the second half of the stent/'S' shaped bridging segment has been deployed and finally the second set of loops of the anastomosis device has been deployed.

FIG. 59 is a block diagram of a handle of an anastomosis delivery device comprising a control mechanism, in accordance with an embodiment of the present specification. In an embodiment, handle 5900 is coupled with an endoscope and a display device for inserting the anastomosis device at a desired location within a patient's body. Handle 5900 comprises a shaft 5902 and a catheter lock 5904 which when opened allows movement of the shaft 5902 causing insertion of a catheter carrying the anastomosis device into an organ of the patient. Once the catheter has entered a desired tissue region, the catheter lock 5902 is locked to prevent inadvertent advancing of the inner pusher catheter (5113 of FIG. 51A) out of the outer shaft/barrel (5120 of FIG. 51A) of a coaxial catheter. The handle also comprises a stent deployment hub 5906 coupled with a stent lock, which when unlocked, enables the stent deployment hub 5906 to move up the shaft 5902 to a first pre-marked location 5908 on the handle which causes deployment of a first flange of a stent covering a connecting member of the anastomosis device. In embodiments, the stent deployment hub 5906 and catheter lock 5902 are separate components. In other embodiments, the stent deployment hub 5906 and catheter lock are the same structure. Hence, the stent deployment hub 5906 aligning with first pre-marked location 5908 provides a feedback to the user that the first half of the stent/'S' shaped bridging segment has been deployed. The catheter lock 5904 may be again opened and the shaft 5902 may be adjusted for ensuring deployment of the second set of loops or distal loop at a desired location within the organ. For deploying the second flange of the stent covering the connecting member of the anastomosis device, the stent deployment hub 5906 is unlocked and moved up the shaft 5902 to a second pre-marked location 5910 on the handle. The stent deployment hub 5904 aligning with second pre-marked location 5910 provides a feedback to the user that the second half of the stent/'S' shaped bridging segment has been deployed.

FIG. 60 is a flowchart listing the steps in a method of creating a side-to-side anastomosis using a magnetic compression anastomosis device, in accordance with embodiments of the present specification. At step 6002, a first lumen of bowel is accessed endoscopically or surgically. At step 6004, a delivery catheter with the anastomosis device connected thereto is passed into the first lumen and through bowel walls into a second lumen. At step 6006, distal loops of a first coil loop are deployed in the second lumen and the catheter is withdrawn back into the first lumen. At step 6008, proximal loops of the second coil loop are deployed in the first lumen and the s-shaped connector with drainage mechanism positioned thereover deploys, crossing the bowel walls so that the first lumen is in fluid communication with the second lumen. At step 6010, the catheter is withdrawn from the patient. At step 6012, a compression anastomosis is formed in 2-20 days and the magnetic anastomosis device is passed naturally.

FIG. 61 is a flowchart listing the steps in a method of creating a side-to-side anastomosis using a magnetic compression anastomosis device, in accordance with embodiments of the present specification. At step 6102, a diseased section of bowel is resected and ends of the resected bowel closed using sutures or staples. At step 6104, a first lumen within a first segment of remaining bowel, is accessed endoscopically or surgically. At step 62 a delivery catheter with the anastomosis device attached thereto is passed into the first lumen and through the bowel walls proximate the suture or stable line into a second lumen within a second segment of remaining bowel, separate and distinct from the first segment of remaining bowel, proximate its suture or staple line. At step 6108, distal loops of the of a first coil loop are deployed in the second lumen and the catheter withdrawn back into the first lumen. At step 6110, proximal loops of the coil are deployed in the first lumen and the s-shaped connector with drainage mechanism positioned thereover deploys, crossing the bowel walls so that the first lumen is in fluid communication with the second lumen. At step 6112, the catheter is withdrawn from the patient. At step 6114, a compression anastomosis is formed in 2-20 days and the magnetic anastomosis device is passed naturally.

FIG. 62 is a flowchart listing the steps in a method of creating an anastomosis with immediate fluid patency and delayed fluid patency, using a magnetic compression anastomosis device, in accordance with embodiments of the present specification. At step 6202, a magnetic anastomosis device with a drainage mechanism is deployed across the walls of two adjacent organs with distal loops of the coil of the device in a first lumen of the first organ and proximal loops in a second lumen of the second organ. At step 6404, an s-shape connector connecting the two loops of coil and including an expandable drainage mechanism positioned thereover crosses from the first lumen to the second lumen. At step 6206, the expandable drainage mechanism expands, creating a first fluid connection between the first lumen and the second lumen, wherein the first fluid connection has a first diameter D1. At step 6208, a compression anastomosis is formed and the magnetic anastomosis device is passed naturally, creating a second fluid connection between the first lumen and the second lumen, wherein the second fluid connection has a second diameter D2 and wherein D2 is at least 5% greater than D1.

FIG. 63 is a flowchart listing the steps in a method of creating an anastomosis with immediate fluid patency and delayed fluid patency, using a magnetic compression anastomosis device, in accordance with other embodiments of the present specification. At step 6302, a magnetic anastomosis device with a drainage mechanism is deployed across the walls of two adjacent organs with distal loops of the coil of the device in a first lumen of the first organ and proximal loops in a second lumen of the second organ. At step 6304, an s-shape connector connecting the two loops of coil and including an expandable drainage mechanism positioned thereover crosses from the first lumen to the second lumen.

At step 6306, the expandable drainage mechanism expands, creating a first fluid connection between the first lumen and the second lumen, wherein the first fluid connection has a first cross-sectional area A1. At step 6308, a compression anastomosis is formed and the magnetic anastomosis device is passed naturally, creating a second fluid connection between the first lumen and the second lumen, wherein the second fluid connection has a second cross-sectional area A2 and wherein A2 is at least 5% greater than A1.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

What is claimed is:

1. An anastomosis device comprising:
    a sheath having a lumen;
    a wire, wherein said wire has a first state and a second state, wherein, in said first state, the wire is positioned within the lumen of the sheath and has a substantially linear form, wherein, in said second state, the wire is positioned outside the lumen of the sheath and forms a coil having at least a first loop and a second loop, and wherein said wire is adapted to transform from the first state to the second state after being deployed outside said sheath, and wherein the first loop is connected to the second loop by means of a bridging segment comprising a predefined length of the wire, wherein the bridging segment is adapted to enable the wire, upon changing from the first state to the second state, to coil into the first loop having a first coil directionality and to coil into the second loop having a second coil directionality, wherein the first coil directionality is either clockwise or counterclockwise, and wherein the second coil directionality is either counterclockwise or clockwise and is opposite of the first coil directionality;
    a plurality of magnets positioned over the first loop and the second loop, wherein each of said plurality of magnets has a second lumen through which said wire extends, wherein, in each of said first loop and second loop, a portion of adjacent magnets of said plurality of magnets are configured to not attach to each other, and wherein a portion of said plurality of magnets in the first loop are configured to attract a portion of said plurality of magnets in the second loop; and
    a drainage element, wherein the drainage element has a first end connected to a first portion of the wire and a second end connected to a second portion of the wire, wherein the drainage element is configured to be positioned in the sheath and have a compressed linear form when the wire is in the first state, wherein the drainage element is configured to have an expanded form when the wire is deployed outside the sheath, and wherein, when the drainage element is in the expanded form, an internal volume of the drainage element is configured to form a passageway between a first area in physical contact with the first loop and a second area in physical contact with the second loop.

2. The anastomosis device of claim 1, wherein the bridging segment over which the drainage element is positioned is not coiled.

3. The anastomosis device of claim 1 wherein a tip of the wire is coupled with a cautery tip made of a ceramic material and configured to pierce body tissues.

4. The anastomosis device of claim 1 wherein in said second state, the wire forms a coil having at least four coil loops.

5. The anastomosis device of claim 1 wherein the coil has a proximal end comprising a threaded connector adapted to couple to a catheter and a distal end having a tip configured to pierce tissue, and wherein the proximal end and the distal ends are bent towards a center of the first loop and the second loop by an angle ranging from 15 degrees to 20 degrees.

6. The anastomosis device of claim 1 wherein said wire is caused to transform from the first state to the second state by exposing said wire to a temperature greater than 37° Celsius.

7. The anastomosis device of claim 1 wherein the bridging segment coils into an 'S' shape when the wire changes from the first state to the second state.

8. The anastomosis device of claim 1 wherein an end of the first loop not connected to the bridging segment is turned inwards towards a center of the first loop.

9. The anastomosis device of claim 1 wherein an end of the second loop not connected to the bridging segment is turned inwards towards a center of the second loop.

10. The anastomosis device of claim 1 further comprises non-ferromagnetic spacers positioned between adjacent magnets of said plurality of magnets.

11. The anastomosis device of claim 1, wherein said wire comprises a shape memory alloy.

12. The anastomosis device of claim 1, wherein the drainage element is a stent comprising a wire mesh and wherein the wire mesh is covered by a biocompatible material.

13. The anastomosis device of claim 1, wherein the first portion of the wire is proximate to a first end of the bridging segment and wherein the second portion of the wire is proximate to a second end of the bridging segment opposing the first end of the bridging segment.

14. The anastomosis device of claim 1, wherein the drainage element comprises wire mesh.

15. An anastomosis device comprising:
    a sheath having a lumen;
    a wire comprising a first section and a second section and a connecting section between the first section and the second section wherein, when positioned in the lumen of the sheath, the wire has a substantially linear form, and, when deployed outside the lumen of the sheath, the wire forms a coil having at least a first loop formed from the first section and at least a second loop formed from the second section, and wherein the first section is configured to coil into the at least one first loop having a first coil directionality and the second section is configured to coil into the at least one second loop having a second coil directionality, wherein the first coil directionality is either clockwise or counterclockwise, and wherein the second coil directionality is either counterclockwise or clockwise and is opposite of the first coil directionality;
    a first plurality of magnets positioned over the first section of the wire;
    a second plurality of magnets positioned over the second section of the wire; and
    a drainage element, wherein the drainage element is physically coupled to the wire and positioned over the connecting section, wherein the drainage element is configured to have a compressed linear form when the wire is in the lumen of the sheath, wherein the drainage element is configured to have an expanded cylindrical form when the wire is deployed outside the sheath, and wherein, when the drainage element is in the expanded cylindrical form, an internal volume of the drainage element is configured to form a passageway between a first anatomical area in physical contact with the first loop and a second anatomical area in physical contact with the second loop.

16. The device of claim 15 further comprises non-ferromagnetic spacers positioned between adjacent magnets of said first plurality of magnets and said second plurality of magnets.

17. The device of claim 15, wherein said wire comprises a shape memory alloy.

18. The device of claim 15, wherein, when deployed outside the lumen of the sheath, said connecting section of said wire forms an 'S' shape, and wherein said first section, second section, and connecting section of the wire are adapted to transform from the substantially linear form state to the coil form when exposed to a temperature greater than a threshold value.

19. The device of claim 15 wherein said first section, second section, and connecting section of the wire are caused to transform from the substantially linear form state to the coil form by exposing said wire to a temperature greater than 37° Celsius.

20. The device of claim 15, wherein the drainage element is a stent comprising a wire mesh and wherein the wire mesh is covered by a biocompatible material.

21. The device of claim 15, wherein the first plurality of magnets and the second plurality of magnets are covered with a PTFE material.

22. The device of claim 15, wherein a tip of the wire is coupled with a cautery tip made of a ceramic material for piercing body tissues.

* * * * *